US007524927B2

(12) United States Patent
Hoxie et al.

(10) Patent No.: US 7,524,927 B2
(45) Date of Patent: Apr. 28, 2009

(54) COMPOSITIONS, METHOD AND KITS RELATING TO DELETION MUTATIONS OF IMMUNODEFICIENCY VIRUS GP120 HYPERVARIABLE REGIONS

(75) Inventors: James A. Hoxie, Berwyn, PA (US); George Lin, Voorhees, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 73 days.

(21) Appl. No.: 10/767,648

(22) Filed: Jan. 29, 2004

(65) Prior Publication Data

US 2005/0064392 A1 Mar. 24, 2005

Related U.S. Application Data

(60) Provisional application No. 60/443,364, filed on Jan. 29, 2003.

(51) Int. Cl.
*C07K 14/00* (2006.01)
*A61K 38/10* (2006.01)
*C07H 21/04* (2006.01)

(52) U.S. Cl. .................... 530/350; 424/208.1; 536/23.1

(58) Field of Classification Search ....................... None
See application file for complete search history.

(56) References Cited

U.S. PATENT DOCUMENTS 5,886,163 A * 3/1999 Hasel et al. ................ 536/23.1

OTHER PUBLICATIONS

Aguilar, H. C. et al., "Cytoplasmic Tail of Moloney Murine Leukemia Virus Envelope Protein Influences the Conformation of the Extracellular Domain: Implications for Mechanism of Action of the R Peptide," *Journal of Virology*, vol. 77, pp. 1281-1291, 2003.

Allan, J. S. et al., "Major Glycoprotein Antigens That Induce Antibodies in AIDS Patients are Encoded by HTLV-III," *Science*, vol. 228, pp. 1091-1094, 1985.

Alkhatib, G. et al., "CC CKR5: a RANTES, MIP-1α, MIP-1β Receptor as a Fusion Cofactor for Macrophage-Tropic HIF-1," *Science* vol. 272, pp. 1955-1958, 1996.

Andreassen, H. et al., "Analysis of the Secondary Structure of the Human Immunodeficiency Virus (HIV) Proteins p17, gp120, and gp41 by Computer Modeling Based on Neural Network Methods," *J. Acquired Immune. Deficiency Syndrome*, vol. 3; pp. 615-622, 1990.

Baba, T. W. et al, "Human Neutralizing Monoclonal Antibodies of the igG1 Subtype Protect Against Mucosal Simian-Human Immunodeficiency Virus Infection," *Nature Med.* vol. 6, p. 200-206, 2000.

Barnett, S. W., et al., "The Ability of an Oligomeric Human Immunodeficiency Virus Type 1 (HIV-1) Envelope Antigen to Elicit Neutralizing Antibodies Against Primary HIV-2 Isolates is Improved Following Partial Deletion of the Second Hypervariable Region," *Journal of Virology*, vol. 75, pp. 5526-5540, 2001.

Basmaciogullari, S. et al., "Identification of Conserved and Variable Structures in the Human Immunodeficiency Virus gp120 Glycoprotein of Importance for CXCR4 Binding," *Journal of Virology*, vol. 76, pp. 10791-10800, 2002.

Berger, E. A. et al., "HIV Entry and Tropism: The Chemokine Receptor Connection," *AIDS*, vol. 11, pp. S3-S16, 1997.

Binley, J. M. et al., "A Recombinant Human Immunodeficiency Virus Type 1 Envelope Glycoprotein Complex Stabilized by an Intermolecular Disulfide Bond Between the gp120 and gp41 Subunits is an Antigenic Mimic of the Trimeric Virion-Associated Structure," *Journal of Virology*, vol. 74, pp. 627-643, 2000.

Bolmstedt, A. et al., "Enhanced Immunogenicity of a Human Immunodeficiency Virus Type 1 env DNA Vaccine by Manipulating N-Glycosylation Signals. Effects of Elimination of the V3 N306 Glycan," *Vaccine*, vol. 20:, pp. 397-405, 2002.

Calarese, D. A. et al., "Antibody Domain Exchange is an Immunological Solution to Carbohydrate Cluster Recognition" *Science*, vol. 300, pp. 2065-2071, 2003.

Chan, D. C. et al., "Core Structure of gp41 From the HIV Envelope Glycoprotein," *Cell*, vol. 89, pp. 263-273, 1997.

Chertova, E. et al., "Envelope Glycoprotein Incorporation, Not Shedding of Surface Envelope Glycoprotein (gp120/SU), Is the Primary Determinant of SU Content of Purified Human Immunodeficiency Virus Type 1 and Simian Immunodeficiency Virus," *Journal of Virology*, vol. 76, pp. 5315-5325, 2002.

Chertova, et al., "Sites, Mechanism of Action and Lack of Reversibility of Primate Lentivirus Inactivation by Preferential Covalent Modification of Virton Internal Proteins," *Curr. Mol. Med.*, vol. 3, pp. 265-272, 2003.

Choe, H. et al., "The β-Chemokine Receptors CCR3 and CCR5 Facilitate Infection by Primary HIV-1 Isolates," *Cell*, vol. 85, pp. 1135-1148, 1996.

Choe, H. et al., "Tyrosine Sulfation of Human Antibodies Contributes to Recognition of the CCR5 Binding Region of HIV-1 gp120," *Cell*, vol. 114, pp. 161-170, 2003.

Connor, R. et al., "Change in Coreceptor use Coreceptor use Correlates With Disease Progression in HIV-I-Infected Individuals," *Journal Exp. Med.*, vol. 185, pp. 621-628, 1997.

Cormier, E.G. et al., "The Crown and Stem of the V3 Loop Play Distinct Roles in Human Immunodeficiency Virus Type 1 Envelope Glycoprotein Interactions with the CCR5 Coreceptor," *Journal of Virology*, vol. 76, pp. 8953-8957, 2002.

Deng, H. et al., "Expression Cloning of New Receptors Used by Simian and Human Immunodeficiency Viruses," *Nature*, vol. 388, pp. 296-300, 1997.

Deng, H. et al., "Identification of a Major Co-Receptor for Primary Isolates of HIV-1," *Nature*, vol. 381, pp. 661-666, 1996.

(Continued)

*Primary Examiner*—Bruce Campell
*Assistant Examiner*—Agnieszka Boesen
(74) *Attorney, Agent, or Firm*—Drinker Biddle & Reath

(57) ABSTRACT

The present invention relates to replication competent variants of mammalian immunodeficiency virus comprising mutations and/or deletions of the V3 hypervariable loop and compensatory mutations, as well as methods for producing such variants. The invention also relates to V3-loop deletion mammalian immunodeficiency virus mutants that have compensatory mutations, deletions of the V1/V2 loops, or both. The invention further relates to isolated Env, gp120 polypeptides, and gp41 polypeptides comprising novel mutations useful in conjunction with, or separate from, a virus of the invention, as well as nucleic acids encoding the same.

7 Claims, 50 Drawing Sheets

OTHER PUBLICATIONS

Dey, B. et al., "Neutralization of Human Immunodeficiency Virus Type 1 by sCD4-17b, a Single-Chain Chimeric Protein, Based on Sequential Interaction of gp120 with CD4 and Coreceptor," *Journal of Virology*, vol. 77, 2859-2865, 2003.

Doranz, B. et al., A Dual Tropic Primary HIV-1 Isolate That Uses Fusion and the β-Chemokine Receptors CKR-5, CKR-3 and CKR-2b as Fusion Cofactors., *Cell*, vol. 85, pp. 1149-1158, 1996.

Dragic, T. et al., "HIV-1 Entry Into CD4+ Cells is Mediated by the Chemokine Receptor CC-CKR-5," *Nature*, vol. 381, pp. 667-673, 1996.

Dragic, T. et al., "An Overview of the Determinants of CCR5 and CXCR4 Co-Receptor Function," *Journal of General Virology*, vol. 82, pp. 1807-1814, 2001.

Earl, P. L. et al., "Oligomeric Structure of the Human Immunodeficiency Virus Type 1 Envelope Glycoprotein," *Proc. Nat. Acad. Sci. USA*, vol. 87, pp. 648-652, 1990.

Edinger, A. L. et al., "CD4-Independent, CCR5-Dependent Infection of Brain Capillary Endothelial Cells by a Neurovirulent SIV Strain," *Proc. Natl. Acad. Sci.,* USA, vol. 94, pp. 14742-14747, 1997.

Edwards, T. G. et al., "Relationships Between CD4 Independence, Neutralization Sensitivity, and Exposure of a CD4-Induced Epitope in a Human Immunodeficiency Virus Type 1 Envelope Protein," *Journal of Virology*, vol. 75, pp. 5230-5239, 2001.

Edwards, T. G. et al., "Truncation of the Cytoplasmic Domain Induces Exposure of Conserved Regions in the Ectodomain of Human Immunodeficiency Virus Type 1 Envelope Protein," *Journal of Virology*, vol. 76, pp. 2683-2691, 2002.

Eisenberg, D. et al., "The Most Highly Amphiphilic Alpha-Helices Include Two Amino Acid Segments in Human Immunodeficiency Virus Glycoprotein 41," *Biopolymers*, vol. 29, pp. 171-177, 1990.

Endres, M. J. et al., "CD4-Independent Infection by HIV-2 is Mediated by Fusion/CXCR4," *Cell*, vol. 87, pp. 745-756, 1996.

Farzan, M. et al., "Tyrosine-Sulfated Peptides Functionally Reconstitute a CCR5 Variant Lacking a Critical Amino-Terminal Region*," *The Journal of Biological Chemistry*, vol. 277, pp. 40397-40402, 2002.

Farzan, M. et al., "A Tyrosine-Sulfated Peptide Based on the N Terminus of CCR5 Interacts With a CD4-Enhanced Epitope of the HIV-1 gp120 Envelope Glycoprotein and Inhibits HIV-1 Entry," *The Journal of Biological Chemistry*, vol. 275, pp. 33516-33521, 2000.

Farzan, M. et al., "Tyrosine Sulfation of the Amino Terminus of CCR5 Faciloitates HIV-1 Entry," *Cell*, vol. 96, pp. 667-676, 1999.

Farzan, M. et al., "Two Orphan Seven-Transmembrane Segment Receptors Which are Expressed in CD-4-Positive Cells Support Simian Immunodeficiency Virus Infection," *Journal Exp. Medicine*, vol. 186, pp. 405-411, 1997.

Feng, Y. et al., "HIV-1 Entry Cofactor: Functional cDNA Cloning of a Seven-Transmembrane, G Protein-Coupled Receptor," *Science*, vol. 272, pp. 872-876, 1996.

Fouts, T. R. et al., "Neutralization of the Human Immunodeficiency Virus Type 1 Primary Isolate JR-FL by Human Monoclonal Antibodies Correlates With Antibody Binding to the Oligomeric Form of the Envelope Glycoprotein Complex," *Journal of Virology*, vol. 71, pp. 2779-2285, 1997.

Fouts, T. et al., "Crosslinked HIV-1 Envelope-CD4 Receptor Complexes Elicit Broadly Cross-Reactive Neutralizing Antibodies in *Rhesus macques," Proc. Natl. Acad. Sci. USA*, vol. 99, pp. 11842-11847, 2002.

Gallo, S. A. et al., "HIV-1 gp41 Six-Helix Bundle formation Occurs Rapidly After the Engagement of gp120 by CXCR4 in the HIV-1 Env-Mediated Fusion Process," *Biochemistry*, vol. 40, pp. 12231-12236, 2001.

Grundner, C. et al., "Solid-Phase Proteoliposomes Containing Human Immunodeficiency Virus Envelope Glycoproteins," *Journal of Virology*, vol. 76, pp. 3511-3521, 2002.

Ho, D.D. et al., "Conformational Epitope on gp120 Important in CD4 Binding and Human Immunodeficiency Virus Type 1 Neutralization Identified by a Human Monoclonal Antibody," *Journal of Virology*, vol. 65, pp. 489-493, 1991.

Hoffman, T. L., et al., "Chemokines and Coreceptors in HIV/SIV-Host Interactions," *AIDS*, vol. 12, pp. S17-S26, 1998.

Hoffman, T. L. et al., "A Biosensor Assay for Studying Ligand-Membrane Receptor Interactions: Binding of Antibodies and HIV-1 Env to Chemokine Receptors," *Proc. Natl. Acad. Sci. USA*, vol. 97, pp. 11215-11220, 2000.

Hoxie, J. A., "Hypothetical Assignment of Intrachain Disulfide Bonds for HIV-2 and SIV Envelope Glycoproteins," *AIDS Res. Hum. Retroviruses*, vol. 7, pp. 495-499, 1991.

Jones, P. L. et al., "Conformation Changes in Cell Surface HIV-1 Envelope Glycoproteins are Triggered by Cooperation Between Cell Surface CD4 and Co-Receptors," *The Journal of Biological Chemistry*, vol. 273, pp. 404-409, 1998.

Johnson, W. E. et al., "Importance of B-Cell Responses for Immunological Control of Variant Strains of Simian Immunodeficiency Virus," *Journal of Virology*, vol. 77, pp. 375-381, 2003.

Kalia, V. et al, "Rational Site-Directed Mutations of the LLP-1 and LLP-2 Lentivirus Lytic Peptide Domains in the Intracytoplasmic Tail of Human Immunodeficiency Virus Type 1 gp41 Indicate Common Functions in Cell-Cell Fusion by Distinct Roles in Virion Envelope Incorporation," *Journal of Virology*, vol. 77, pp. 3634-3646, 2003.

Kessler, J. A. et al., "Recombinant Human Monoclonal Antibody igG1b12 Neutralizes Diverse Human Immunodeficiency Virus Type 1 Primary Isolates," *AIDS Res. Hum. Retroviruses*, vol. 13, pp. 575-582, 1997.

Kim, Y. et al., "Immunogenicity and Ability of Variable Loop-Deleted Human Immunodeficiency Virus Type 1 Envelope Glycoproteins to Elicit Neutralizing Antibodies," *Virology*, vol. 305, pp. 124-137, 2003.

Kliger, P. D. et al., "A Leucine Zipper-Like Sequence from the Cytoplasmic Tail of the HIV-1 Envelope Glycoprotein Binds and Perturbs Lipid Bilayers," *Biochemistry*, vol. 36, pp. 5157-5169, 1997.

Kwong, P. D. et al., Structure of an HIV gp120 Envelope Glycoproteins in Complex With the CD4 Receptor and a Neutralizing Human Antibody, Nature, vol. 393, pp. 648-659, 1998.

Kwong et al., Structure of an HIV gp120 Envelope Glycoproteins From Laboratory-Adapted and Primary Isolates, *Structure Fold Des.*, vol. 8, pp. 1329-1339, 2000.

Kwong, P. D. et al., "Oligomeric Modeling and Electrostatic Analysis of the gp120 Envelope Glycoprotein of Human Immunodeficiency Virus," *Journal of Virology*, vol. 74, pp. 1961-1972, 2000.

Kwong, P. D. et al., HIV-1 Evades Antibody-Mediated Neutralization Through conformational Masking of Receptor-Binding Sites, *Nature*, vol. 420, pp. 678-682, 2002.

Labrijn, A. F. et al., "Access of Antibody Molecules to the Conserved Coreceptor Binding Site on Glycoprotein gp120 is Sterically Restricted on Primary Human Immunodeficiency Virus Type 1," *Journal of Virology*, vol. 77, pp. 10557-10565, 2003.

Lee, B. et al. "Epitope Mapping of CCR5 Reveals Multiple Conformational States and Distinct but Overlapping Structures Involved in Chemokine and Coreceptor Function," *The Journal of Biological Chemistry*, vol. 274, pp. 9617-9626, 1999.

Liao, F. et al., "A Novel Chemokine Receptor-Like Protein, Functions as a Fusion Cofactor for Both Macrophage-Tropic and T Cell Line-/Tropic HIV-1," *Journal Exp. Med.*, vol. 185, pp. 2015-2023, 1997.

Lifson, J. D. et al., "Whole Inactivated SIV Virion Vaccines With Functional Envelope Glycoproteins: Safety, Immunogenicity, and Activity Against Intrarectal Challenge," *J. Med. Primatol.*, vol. 31, pp. 205-216, 2002.

Lin, G. et al., "CD4-Independent use of *Rhesus* CR5 by Human Immunodeficiency Virus Type 2 Implicates an Electrostatic Interaction Between the CCR5 N Terminus and the gp120 C4 Domain," *Journal of Virology*, vol. 75, pp. 10766-10778, 2001.

Lin, G. et al., "Identification of gp120 Binding Sites on CXCR4 by Using CD4-Independent Human Immunodeficiency Virus Type 2 Env Proteins," *Journal of Virology*, vol. 77, pp. 931-942, 2003.

Lu, S. et al., Immunogenicity of DNA Vaccines Expressing Human Immunodeficiency Virus Type 1 Envelope Glycoprotein With and Without Deletions in the V1/2 and V3 Regions, *AIDS Res. Hum. Retroviruses*, vol. 14, pp. 151-155, 1998.

Martin, I. et al., "Lipid Membrane Fusion Induced by the Human Immunodeficiency Virus Type 1 gp41 N-Terminal Extremity is Determined by its Orientation in the Lipid Bilayer," *Journal of Virology*, vol. 70, pp. 298-304, 1996.

Mascola, J. R. et al., "Protection of Macaques against Pathogenic Simian/Human Immunodeficiency Virus 89.6PD by Passive Transfer of Neutralizing Antibodies," *Journal of Virology*, vol. 73, pp. 4009-4018, 1999.

Mascola, J. R. et al., "Protection of Macaques Against Vaginal transmission of a Pathogenic HIV-1/SIV Chimeric Virus by Passive Infusion of Neutralizing Antibodies," *Nat. Med.*, vol. 6:, pp. 207-210, 2000.

McMichael, A. J. et al., HIV Vaccines 1983-2003, *Nature Med.*, vol. 9, pp. 874-880, 2003.

Melikyan, G.B. et al., "Evidence that the Transition of HIV-1 gp41 into a Six-Helix Bundle, Not the Bundle Configuration, Induces Membrane Fusion," *The Journal of Cell Biology*, vol. 151, pp. 413-423, 2000.

Melikyan, G.B. et al., "Role of the Cytoplasmic Tail of Ecotropic Moloney Murine Leukemia Virus Env Protein in Fusion Pore Formation," *Journal of Virology*, vol. 74, pp. 447-455, 2000.

Miller, M. A. et al., "Alterations in Cell Membrane Permeability by the Lentivirus Lytic Peptide (LLP-1) of HIV-1 Transmembrane Protein," *Virology*, vol. 196, pp. 89-100, 1993.

Miller, M. A. et al., "Identification of a Calmodulin-Binding and Inhibitory Peptide Domain in the HIV-1 Transmembrane Glycoprotein," *AIDS Research and Human Retroviruses*, vol. 9, pp. 1057-1066, 1993.

Modrow, S. et al., "Computer-Assisted Analysis of Envelope Protein Sequences of Seven Human Immunodeficiency Virus Isolates: Prediction of Antigenic Epitopes in Conserved and Variable Regions," *Journal of Virology*, vol. 61, pp. 570-578, 1987.

Moore, J.P. et al., "Probing the Structure of the V2 Domain of Human Immunodeficiency Virus Type 1 Surface Glycoprotein gp120 with a Panel of Eight Monoclonal Antibodies: Human Immune Response to the V1 and V2 Domains," *Journal of Virology*, vol. 67, pp. 6136-6151, 1993.

Moore, J. P. et al., "Probing the Structure of the Human Immunodeficiency Virus Surface Glycoprotein gp120 with a Panel of Monoclonal Antibodies," *Journal of Virology*, vol. 68, pp. 469-484, 1994.

Moulard, M. et al., "Broadly Cross-Reactive HIV-1-Neutralizing Human Monoclonal Fab Selected for Binding to gp120-CD4-CCR5 Complexes," *Proc. Natl. Acad. Sci USA*, vol. 99, pp. 6913-6918, 2002.

Muster, T. et al., "A Conserved Neutralizing Epitope on gp41 of Human Immunodeficiency Virus Type 1," *Journal of Virology*, vol. 67, pp. 6642-6647, 1993.

Myszka, D.G. et al., "Energetics of the HIV gp120-CD4 Binding Reaction," *Proc. Natl. Acad. Sci. USA*, vol. 97, pp. 9026-9031, 2000.

Olson, W. C. et al., "Differential Inhibition of Human Immunodeficiency Virus Type 1 Fusion, gp120 Binding, and CC-Chemokine Activity by Monoclonal Antibodies to CCR5," *Journal of Virology*, vol. 73, pp. 4145-4155, 1999.

Olson, K. E .P. et al., "Palmitoylation of the Intracytoplasmic R Peptide of the Transmembrane Envelope Protein in Moloney Murine Leukemia Virus," *Journal of Virology*, vol. 73, pp. 8975-8981, 1999.

Parker, C. E. et al., "Fine Definition of the Epitope on the gp41 Glycoprotein of Human Immunodeficiency Virus Type 1 for the Neutralizing Monoclonal Antibody 2F5," *Journal of Virology*, vol. 75, pp. 10906-10911, 2001.

Parren, P. W. et al., "The Neutralizing Antibody Response to HIV-1: Viral Evasion and Escape From Humoral Immunity," *AIDS*, vol. 13, pp. S137-S162, 1993.

Pereira, F. B. et al., "Permeabilization and Fusion of Uncharged Lipid Vesicles Induced by the HIV-1 Fusion Peptide Adopting an Extended Conformation: Dose and Sequence Effects," *Biophys. J.*, vol. 73, pp. 1977-1986, 1997.

Pinter, A. et al., "Oligomeric Structure of gp41, the Transmembrane Protein of Human Immunodeficiency Virus Type 1," *Journal of Virology*, vol. 63, pp. 2674-2679, 1989.

Posner, M. R. et al., "An IgG Human Monoclonal Antibody That Reacts With HIV-1/GP120, Inhibits Virus Binding to Cells, and Neutralizes Infection," *J. Immunol.*, vol. 146, pp. 4325-4332, 1991.

Puffer, B.A. et al., "CD4 Independence of Simian Immunodeficiency Virus Envs is Associated with Macrophage Tropism, Neutralization Sensitivity, and Attenuated Pathogenicity," *Journal of Virology*, vol. 76, pp. 2595-2605, 2002.

Reitter, J. N. et al, "A Role for Carbohydrates in Immune Evasion in AIDS," *Nat. Med.*, vol. 4, pp. 679-684, 1998.

Richman, D. D. et al., "Rapid Evolution of the Neutralizing Antibody Response to HIV Type 1 infection," *Proc. Nat. Acad. Sci. USA*, vol. 100, pp. 4144-4149, 2003.

Rizzuto, C.D. et al., "A Conserved HIV gp120 Glycoprotein Structure Involved in Chemokine Receptor Binding," *Science*, vol. 280, pp. 1949-1953, 1998.

Rizzuto, C. et al., "Fine Definition of a conserved CCR-5-Binding Region on the Human Immunodeficiency Virus type 1 Glycoprotein 120," *AIDS Res. Hum. Retroviruses*, vol. 16, pp. 741-749, 2000.

Robey, W. G. et al., "Characterization of Envelope and Core Structural Gene Products of HTLV-III With Sera From AIDS Patients," *Science*, vol. 228, pp. 593-595, 1985.

Rousso, I. et al., "Palmitoylation of the HIV-1 Envelope Glycoprotein is Critical for Viral Infectivity," *Proc. Natl. Acad. Sci. USA*, vol. 97, No. 25, pp. 13523-13525, 2000.

Rucker, J. et al., "Utilization of Chemokine Receptors, Orphan Receptors and Herpesvirus-Encoded Receptors by Diverse Human and Simian Immunodeficiency Viruses," *Journal of Virology*, vol. 71, pp. 8999-9007, 1997.

Ruprecht, R. M. et al., "Antibody Protection: Passive Immunization of Neonates Against Oral AIDS Virus Challenge," *Vaccine*, vol. 21, pp. 3370-3373, 2003.

Sanders, R. W. et al., "Variable-Loop-Deleted Variants of the Human Immunodeficiency Virus Type 1 Envelope Glycoprotein can by Stabilized by an Intermolecular Disulfide Bond Between the gp120 and gp41 Subunits," *Journal of Virology*, vol. 74, pp. 5091-5100, 2000.

Saphire, E. O. et al., "Crystallization and Preliminary Structure Determination of an Intact Human Immunoglobulin, b12: An Antibody That Broadly Neutralizes Primary Isolates of HIV-1," *Acta. Crystal. D. Biol. Crystal.*, vol. 57, pp. 168-171, 2001.

Sattentau, Q. J. et al., "Conformational Changes Induced in the Envelope Glycoproteins of the Human and Simian Immunodeficiency Viruses by Soluble Receptor Binding," *Journal of Virology*, vol. 67, pp. 7383-7393, 1993.

Srivastava, I. K. et al., "Changes in the Immunogenic Properties of Soluble gp140 Human Immunodeficiency Virus Envelope Constructs Upon Partial Deletion of the Second Hypervariable Region," *Journal of Virology*, vol. 77, pp. 2310-2320, 2003.

Stamatatos, L. et al., "An Envelope Modification That Renders a Primary, Neutralization-Resistant Clade B Human Immunodeficiency Virus Type 1 Isolate Highly Susceptible to Neutralization by Sera From Other Clades," *Journal of Virology*, vol. 72, pp. 7840-7845, 1998.

Stamatatos, L. et al., "Effect of Major Deletions in the V1 and V2 Loops of a Macrophage-Tropic HIV Type 1 Isolate on Viral Envelope Structure, Cell Entry, and Replication," *AIDS Res. Hum. Retroviruses*, vol. 14, pp. 1129-1139, 1998.

Starcich, B. R. et al., "Identification and Characterization of Conserved and Variable Regions in the Envelope Gene of HTLV-III/LAV, the Retroviruses of AIDS," *Cell*, vol. 45, pp. 637-664, 1986.

Sullivan, N. et al., "Determinants of Human Immunodeficiency Virus Type 1 Envelope Glycoprotein Activation by Soluble CD4 and Monoclonal Antibodies," *Journal of Virology*, vol. 72, 6332-6338, 1998.

Thali, M. et al., "Discontinuous, Conserved Neutralization Epitopes Overlapping the CD4-Binding Region of Human Immunodeficiency Virus Type 1 gp120 Envelope Glycoprotein," *Journal of Virology*, vol. 66, pp. 5635-5641, 1992.

Trkola, A. et al., "CD4-Dependent, Antibody-Sensitive Interactions Between HIV-1 and its Co-Receptor CC4-5," *Nature*, vol. 384, pp. 184-187, 1996.

Trkola, A. et al., "Human Monoclonal Antibody 2G12 Defines a Distinctive Neutralization Epitope on the gp120 Glycoprotein of Human Immunodeficiency Virus Type 1," *Journal of Virology*, vol. 70, pp. 1100-1108, 1996.

Wei, X. et al., "Antibody Neutralization and Escape by HIV-1," *Nature*, vol. 422, pp. 307-312, 2003.

Weng, Y. et al., "Structure-Function Studies on the Self-Assembly Domain of the Human Immunodeficiency Virus Type 1 Transmembrane Protein gp41," *Journal of Virology*, vol. 74, pp. 5368-5372, 2000.

Wild, C. T. et al., "Peptides Corresponding to a Predictive α-Helical Domain of Human Immunodeficiency Virus Type 1 gp41 are Potent Inhibitors of Virus Infection," *Proc. Natl. Acad. Sci. USA*, vol. 91, pp. 9770-9774, 1994.

Willey, R. L. et al., "Control of Viremia and Prevention of Simian-Human Immunodeficiency Virus-Induced Disease in *Rheus macaques* Immunized with Recombinant Vaccinia Viruses Plus Inactivated Simian Immunodeficiency Virus and Human Immunodeficiency Virus Type 1 Particles," *Journal of Virology*, vol. 77, pp. 1163-1174, 2003.

Wu, L. et al., "CD4-Induced Interaction of Primary HIV-1 gp120 Glycoproteins With the Chemokine Receptor CCR-5," *Nature*, vol. 384, pp. 179-183, 1996.

Wu et al., "Interaction of Chemokine Receptor CCR5 With its Ligands: Multiple Domains for HIV-1 gp120 Binding and a Single Domain for Chemokine Binding," *J. Exp. Med.*, vol. 186, pp. 1373-1381, 1997.

Wyatt, R. et al., "Functional and Immunologic Characterization of Human Immunodeficiency Virus Type 1 Envelope Glycoproteins Containing Deletions of the Major Variable Regions," *Journal of Virology*, vol. 67, pp. 4557-4565, 1993.

Wyatt, R. et al., "Relationship of the Human Immunodeficiency Virus Type I gp120 Third Variable Loop to a Component of the CD4 Binding Site in the Fourth Conserved Region," *Journal of Virology*, vol. 66, pp. 6997-7004, 1992.

Wyatt, R. et al., "The Antigenic Structure of the HIV gp120 Envelope Glycoprotein," *Nature*, vol. 393, pp. 705-710, 1998.

Wyatt, R. et al., "Involvement of the V1/V2 Variable Loop Structure in the Exposure of Human Immunodeficiency Virus Type 1 gp120 Epitopes Induced by Receptor Binding," *Journal of Virology*, vol. 69, pp. 5723-5733, 1995.

Xiang, S. H. et al., "Mutagenic Stabilization and/or Disruption of a CD4-Bound State Reveals Distinct Conformations of the Human Immunodeficiency Virus Type 1 gp120 Envelope Glycoprotein," *Journal of Virology*, vol. 76, pp. 9888-9899, 2002.

Xiang, S. H. et al., "Characterization of CD4-Induced Epitopes on the HIV Type 1 gp120 Envelope Glycoprotein Recognized by Neutralizing Human Monoclonal Antibodies," *AIDS Res. Hum. Retroviruses*, vol. 18, pp. 1207-1217, 2002.

Yang, C. et al., "Analysis of the Murine Leukemia Virus R Peptide: Delineation of the Molecular Determinants Which are Important to Its Fusion Inhibition Activity," *Journal of Virology*, vol. 71, pp. 8490-8496, 1997.

Yang, X. et al., "Characterization of Stable, Soluble Trimers Containing Complete Ectodomains of Human Immunodeficiency Virus Type 1 Envelope Glycoproteins," *Journal of Virology*, vol. 74, pp. 5716-5725, 2000.

Yang, X. et al., "Highly Stable Trimers Formed by Human Immunodeficiency Virus Type 1 Envelope Glycoproteins Fused with the Trimeric Motif of T4 Bacteriophage Fibritin," *Journal of Virology*, vol. 76, p. 4634-4642, 2002.

Zhang, Y. et al., "Use of Coreceptors Other than CCR5 by Non-Syncytium-Inducing Adult and Pediatric Isolates of Human Immunodeficiency Virus Type 1 is Rare in Vitro," *Journal of Virology*, vol. 72, pp. 9337-9344, 1998.

Zhou, N. et al., "Exploring the Stereochemistry of CXCR4-Peptide Recognition and Inhibition HIV-1 Entry With D-Peptides Derived from Chemokines," *J. Biol. Chem.*, vol. 277, pp. 17476-17485, 2002.

Zwick, M .B. et al., "Broadly Neutralizing Antibodies Targeted to the Membrane-Proximal External Region of Human Immunodeficiency Virus Type 1 Glycoprotein gp41," *Journal of Virology*, vol. 75, pp. 10892-10905, 2001.

Zwick, M. B., et al., "A Novel Human Antibody against Human Immunodeficiency Virus Type 1 gp120 is V1, V2, and V3 Loop Dependent and Helps Delimit the Epitope of the Broadly Neutralizing Antibody Immunoglobulin G1 b12," *Journal of Virology*, vol. 77, pp. 6965-6978, 2003.

* cited by examiner

① HIV-2 VCP parental
  Mutagenesis ↓
   VCP² V3(6,6)
     ↓ Serial Passage
② VCP² V3(6,6)*adapted*
  Mutagenesis ↓
   VCP² V3(1,1)
     ↓ Serial Passage
③ VCP² V3(1,1)*adapted*
  Mutagenesis ↓
   VCP² V1/V2,² V3(1,1)
     ↓ Serial Passage
④ VCP² V1/V2,² V3(1,1)*adapted*

FIG. 19A

MKGSKNQLLIAIILASAYLTHCKQFVTVFYGIPAWRNASIPLFCATKNRDTWGTIQCLPDND
DYQEIALNVTEAFDAWNNTVTEQAVEDVWNLFETSIKPCVKLTPLCVAMNCTRNMTTSTGTT
DTQNITIINDTSPCVRADNCTGLKEEEMVDCQFNMTGLERDKRKQYTGTWYSKDVICDNNTS
SRSKCYMNHCNTSVITKSCDKHYWDAMRFRYCAPPGFALLRCNDTNYSGFAPNCSKVVAATC
TRMMETQSSTWFGFNGTRAENRTYIYWHGKNNRTIISLNNFYNLTMHCKGAGWCWFKGEWKE
AMQEVKETLAKHPRYKGNRSRTENIKFKAPGRGSDPEAAYMWTNCRGEFLYCNMAWFLNWVD
NRTGRKQRNYAPCHIRQIINTWHRVGKNIYLPPREGELACNSTVTSIIANIDTGDQTDITFS
AEVAELYRLELGDYKLVEITPIGFAPTSVKRYSSAHQRHTRGVFVLGFLGFLATAGSAMGAA
SVTLTAQSRTSLAGIVQQQQQLLDVVKKQQEMLRLTVWGTKNLQTRVTAIEKYLKDQAQLNS
WGCAFRQVCHTSVPWVNDSLTPDWNNMTWQEWEQKVRYWEANISQSLEQAQIQQEKNLYELQ
KLNSWGVFTNWLDFTSWVRYIQYGAYVVVGIVTLRIVIYIVQMLSRLRKGYRPVFSSPPGYI
QQIHIHKDQEQPAREETEEDVGSNGGDRSWL

FIG. 19B

ATGAAGGGTAGTAAGAATCAACTGCTGATTGCTATTATACTAGCTAGTGCTTACCTAACACA
TTGCAAGCAATTTGTGACTGTTTTCTATGGCATACCCGCGTGGAGGAATGCATCCATTCCCC
TGTTTTGTGCAACCAAAAATAGAGATACTTGGGGAACCATACAGTGCTTGCCAGACAATGAT
GATTATCAGGAAATAGCTCTAAATGTAACAGAGGCTTTCGATGCATGGAATAATACAGTAAC
AGAACAAGCAGTGGAGGATGTCTGGAATCTATTTGAGACATCAATAAAACCATGTGTCAAAT
TAACACCCTTATGTGTAGCAATGAACTGTACAAGGAACATGACCACATCCACAGGGACCACA
GACACCCAAAATATCACAATTATAAATGACACTTCGCCATGCGTACGTGCAGACAACTGCAC
AGGATTAAAGGAGGAAGAAATGGTCGACTGTCAGTTTAATATGACAGGATTAGAGAGAGACA
AGAGAAAACAGTATACTGGAACATGGTACTCAAAAGATGTGATTTGTGACAATAACACCTCA
AGTCGGAGCAAGTGTTACATGAACCATTGCAATACATCAGTCATCACAAAGTCATGTGATAA
GCACTATTGGGATGCTATGAGGTTTAGATACTGTGCACCACCGGGTTTTGCCCTACTAAGAT
GCAATGATACTAATTATTCAGGCTTTGCACCTAATTGCTCTAAAGTAGTAGCTGCTACATGC
ACCAGAATGATGGAAACGCAATCTTCTACATGGTTTGGATTTAATGGCACTAGAGCAGAAAA
TAGAACATATATATATTGGCATGGTAAAAATAACAGAACTATTATCAGCTTAAATAACTTTT
ATAATCTCACTATGCATTGTAAGGGTGCCGGCTGGTGTTGGTTCAAAGGCGAATGGAAGGAA
GCCATGCAGGAGGTGAAGGAGACCCTTGCGAAACATCCCAGATATAAAGGGAACAGGAGCCG
CACAGAGAATATTAAATTTAAAGCACCAGGAAGAGGCTCAGACCCAGAAGCAGCATACATGT
GGACTAACTGCAGAGGGGAATTTCTCTACTGCAACATGGCTTGGTTCCTCAACTGGGTAGAT
AACAGGACGGGTCGGAAACAGCGCAATTATGCACCGTGCCATATAAGGCAAATAATTAATAC
TTGGCACAGGGTAGGGAAAAACATATATTTGCCTCCCAGGGAAGGGGAGTTGGCCTGCAACT
CAACAGTGACCAGCATAATTGCCAACATTGATACGGGAGATCAAACAGATATTACCTTTAGT
GCAGAGGTGGCAGAACTATACCGATTGGAATTGGGAGATTACAAATTAGTAGAAATCACACC
AATTGGCTTCGCACCTACATCAGTAAAGAGATACTCCTCTGCTCACCAGAGACATACAAGAG
GTGTGTTCGTGCTAGGGTTCTTGGGTTTTCTCGCAACGGCAGGTTCTGCAATGGGCGCGGCG
TCGGTGACGCTGACCGCCCAGTCCCGGACTTCATTGGCTGGGATAGTGCAGCAACAGCAACA
GCTGTTGGACGTGGTCAAGAAACAACAAGAAATGTTGCGACTGACCGTCTGGGGAACTAAAA
ATCTCCAGACAAGAGTCACTGCTATAGAGAAATACCTAAAGGACCAGGCGCAGTTAAATTCA
TGGGGATGTGCGTTTAGACAAGTCTGCCACACTTCTGTACCATGGGTAAATGATAGCTTGAC
ACCTGATTGGAACAATATGACGTGGCAGGAATGGGAACAGAAAGTCCGCTACTGGAGGCAA
ATATCAGTCAAAGTCTAGAACAAGCACAAATTCAGCAAGAAAAGAATTTGTATGAGCTGCAA
AAATTAAATAGCTGGGGTGTTTTTACCAATTGGCTTGACTTCACCTCCTGGGTCAGGTATAT
TCAATATGGAGCATATGTAGTAGTAGGAATAGTAACTTTAAGAATAGTAATATATATAGTAC
AGATGTTAAGTAGACTTAGGAAGGGCTATAGGCCTGTTTTCTCCTCCCCCCCCGGTTATATC
CAACAGATCCATATCCACAAGGACCAGGAACAGCCAGCCAGAGAAGAAACAGAAGAAGACGT
TGGAAGCAACGGTGGAGACAGATCTTGGCTTTAG

FIG. 19C

MKGSKNQLLIAIILASAYLTHCKQFVTVFYGIPAWRNASIPLFCATKNRDTWGTIQCLPDND
DYQEIALNVTEAFDAWNNTVTEQAVEDVWNLFETSIKPCVKLTPLCVAMNCTRNMTTSTGTT
DTQNITIINDTSPCVRADNCTGLKEEEMVDCQFNMTGLERDKRKQYTGTWYSKDVICDNNTS
SRSKCYMNHCNTSVITKSCDKHYWDAMRFRYCAPPGFALLRCNDTNYSGFAPNCSKVVAATC
TRMMETQSSTWFGFNGTRAENRTYIYWHGKNNRTIISLNNFYNLTMHCKGAGWCWFKGEWKE
AMQEVKETLAKHPRYKGNRSRTENIKFKAPGRGSDPEAAYMWTNCRGEFLYCNMAWFLNWVD
NRTGRKQRNYAPCHIRQIINTWHRVGKNIYLPPREGELACNSTVTSIIANIDTGDQTDITFS
AEVAELYRLELGDYKLVEITPIGFAPTSVKRYSSAHQRHTR

FIG. 19D

ATGAAGGGTAGTAAGAATCAACTGCTGATTGCTATTATACTAGCTAGTGCTTACCTAACACA
TTGCAAGCAATTTGTGACTGTTTTCTATGGCATACCCGCGTGGAGGAATGCATCCATTCCCC
TGTTTTGTGCAACCAAAAATAGAGATACTTGGGGAACCATACAGTGCTTGCCAGACAATGAT
GATTATCAGGAAATAGCTCTAAATGTAACAGAGGCTTTCGATGCATGGAATAATACAGTAAC
AGAACAAGCAGTGGAGGATGTCTGGAATCTATTTGAGACATCAATAAAACCATGTGTCAAAT
TAACACCCTTATGTGTAGCAATGAACTGTACAAGGAACATGACCACATCCACAGGGACCACA
GACACCCAAAATATCACAATTATAAATGACACTTCGCCATGCGTACGTGCAGACAACTGCAC
AGGATTAAAGGAGGAAGAAATGGTCGACTGTCAGTTTAATATGACAGGATTAGAGAGAGACA
AGAGAAAACAGTATACTGGAACATGGTACTCAAAAGATGTGATTTGTGACAATAACACCTCA
AGTCGGAGCAAGTGTTACATGAACCATTGCAATACATCAGTCATCACAAAGTCATGTGATAA
GCACTATTGGGATGCTATGAGGTTTAGATACTGTGCACCACCGGGTTTTGCCCTACTAAGAT
GCAATGATACTAATTATTCAGGCTTTGCACCTAATTGCTCTAAAGTAGTAGCTGCTACATGC
ACCAGAATGATGGAAACGCAATCTTCTACATGGTTTGGATTTAATGGCACTAGAGCAGAAAA
TAGAACATATATATATTGGCATGGTAAAAATAACAGAACTATTATCAGCTTAAATAACTTTT
ATAATCTCACTATGCATTGTAAGGGTGCCGGCTGGTGTTGGTTCAAAGGCGAATGGAAGGAA
GCCATGCAGGAGGTGAAGGAGACCCTTGCGAAACATCCCAGATATAAAGGGAACAGGAGCCG
CACAGAGAATATTAAATTTAAAGCACCAGGAAGAGGCTCAGACCCAGAAGCAGCATACATGT
GGACTAACTGCAGAGGGGAATTTCTCTACTGCAACATGGCTTGGTTCCTCAACTGGGTAGAT
AACAGGACGGGTCGGAAACAGCGCAATTATGCACCGTGCCATATAAGGCAAATAATTAATAC
TTGGCACAGGGTAGGGAAAAACATATATTTGCCTCCCAGGGAAGGGGAGTTGGCCTGCAACT
CAACAGTGACCAGCATAATTGCCAACATTGATACGGGAGATCAAACAGATATTACCTTTAGT
GCAGAGGTGGCAGAACTATACCGATTGGAATTGGGAGATTACAAATTAGTAGAAATCACACC
AATTGGCTTCGCACCTACATCAGTAAAGAGATACTCCTCTGCTCACCAGAGACATACAAGA

FIG. 19E

GVFVLGFLGFLATAGSAMGAASVTLTAQSRTSLAGIVQQQQLLDVVKKQQEMLRLTVWGTK
NLQTRVTAIEKYLKDQAQLNSWGCAFRQVCHTSVPWVNDSLTPDWNNMTWQEWEQKVRYWEA
NISQSLEQAQIQQEKNLYELQKLNSWGVFTNWLDFTSWVRYIQYGAYVVVGIVTLRIVIYIV
QMLSRLRKGYRPVFSSPPGYIQQIHIHKDQEQPAREETEEDVGSNGGDRSWL

FIG. 19F

GGTGTGTTCGTGCTAGGGTTCTTGGGTTTTCTCGCAACGGCAGGTTCTGCAATGGGCGCGGC
GTCGGTGACGCTGACCGCCCAGTCCCGGACTTCATTGGCTGGGATAGTGCAGCAACAGCAAC
AGCTGTTGGACGTGGTCAAGAAACAACAAGAAATGTTGCGACTGACCGTCTGGGGAACTAAA
AATCTCCAGACAAGAGTCACTGCTATAGAGAAATACCTAAAGGACCAGGCGCAGTTAAATTC
ATGGGGATGTGCGTTTAGACAAGTCTGCCACACTTCTGTACCATGGGTAAATGATAGCTTGA
CACCTGATTGGAACAATATGACGTGGCAGGAATGGGAACAGAAAGTCCGCTACTGGGAGGCA
AATATCAGTCAAAGTCTAGAACAAGCACAAATTCAGCAAGAAAAGAATTTGTATGAGCTGCA
AAAATTAAATAGCTGGGGTGTTTTTACCAATTGGCTTGACTTCACCTCCTGGGTCAGGTATA
TTCAATATGGAGCATATGTAGTAGTAGGAATAGTAACTTTAAGAATAGTAATATATATAGTA
CAGATGTTAAGTAGACTTAGGAAGGGCTATAGGCCTGTTTTCTCCTCCCCCCCCGGTTATAT
CCAACAGATCCATATCCACAAGGACCAGGAACAGCCAGCCAGAGAAGAAACAGAAGAAGACG
TTGGAAGCAACGGTGGAGACAGATCTTGGCTTTAG

FIG. 21A

MKGSKNQLLIAIVLASAYLTHCKQFVTVFYGIPAWRNASIPLFCATKNRDTWGTIQC
LPDNDDYQEIALNVTEAFDAWNNTVTEQAVEDVWNLFETSIKPCVKLTPLCVAMNCT
RNMTTSTGTTDTQNITIINDTSPCVRADNCTGLKEEEMVDCQFNMTGLERDKRKQYT
EAWYSKDVICDNNTSSRSKCYMNHCNTSVITESCDKHYWDAMRFRYCAPPGFALLRC
NDTNYSGFAPNCSKVVAATCTRMMETQSSTWFGFNGTRAENRTYIYWHGKNNRTIIS
LNNFYNLTMHCKRPGNKTVLPIMSGFKFHSKPVINKKPRQAWCWFKGEWKEAMQEVK
ETLAKHPRYKGNRSRTENIKFKAPGRGSDPEAAYMWTNCRGEFLYCNMTWFLNWVDN
RTGQKQRNYAPCHIRQIINTWHRVGKNVYLPPREGELTCNSTVTSIIANIDTGDQTD
ITFSAEVAELYRLELGDYKLVEITPIGFAPTSVKRYSSAHQRHTRGVFVLGFLGFLA
TAGSAMGAASLTLTAQSRTSLAGIVQQQQQLLDVVKKQQEMLRLTVWGTKNLQARVT
AIEKYLKDQAQLNSWGCAFRQVCHTSVPWVNDSLTPDWNNMTWQEWEQKVRYWEANI
SQSLEQAQIQQEKNLYELQKLNSWGVFTNWLDFTSWVRYIQYGVYVVVGIVALRIVI
YIVQMLSRLRKGYRPVFSSPPGYIQQIHIHKDQEQPAREETEEDVGSNGGDRSWL

FIG. 21B

ATGAAGGGTAGTAAGAATCAACTGCTGATTGCTATTGTACTAGCTAGTGCTTACCTA
ACACATTGCAAGCAATTTGTGACTGTTTCTATGGCATACCCGCGTGGAGGAATGCA
TCCATTCCCCTGTTTGTGCAACCAAAAATAGAGATACTTGGGGAACCATACAGTGC
TTGCCAGACAATGATGATTATCAGGAAATAGCTCTAAATGTAACAGAGGCTTTCGAT
GCATGGAATAATACAGTAACAGAACAAGCAGTGGAGGATGTCTGGAATCTATTTGAG
ACATCAATAAAACCATGTGTCAAATTAACACCCTTATGTGTAGCAATGAACTGTACA
AGGAACATGACCACATCCACAGGGACCACAGACACCCAAAATATCACAATTATAAAT
GACACTTCGCCATGCGTACGTGCAGACAACTGCACAGGATTAAAGGAGGAAGAAATG
GTCGACTGTCAGTTTAATATGACAGGATTAGAGAGAGACAAGAGAAAACAGTATACT
GAAGCATGGTACTCAAAAGATGTGATTTGTGACAATAACACCTCAAGTCGGAGCAAG
TGTTACATGAACCATTGCAATACATCAGTCATCACAGAGTCATGTGATAAGCACTAT
TGGGATGCTATGAGGTTTAGATACTGTGCACCACCGGGTTTTGCCCTACTAAGATGC
AATGATACTAATTATTCAGGCTTTGCACCTAATTGCTCTAAAGTAGTAGCTGCTACA
TGCACCAGAATGATGGAAACGCAATCTTCTACATGGTTTGGCTTTAATGGCACTAGA
GCAGAAAATAGAACATATATCTATTGGCATGGTAAAAATAACAGAACTATTATCAGC
TTAAATAACTTTTATAATCTCACTATGCATTGTAAGAGGCCGGGAAATAAGACAGTG
TTACCAATAATGTCAGGGTTTAAGTTTCACTCCAAGCCGGTCATCAATAAAAAACCC
AGGCAAGCATGGTGTTGGTTCAAAGGCGAATGGAAGGAAGCCATGCAGGAGGTGAAG
GAGACCCTTGCGAAACATCCCAGATATAAAGGGAACAGGAGCCGCACAGAGAATATT
AAATTTAAAGCACCAGGAAGAGGCTCAGACCCAGAAGCAGCATACATGTGGACTAAC
TGCAGAGGGGAATTTCTCTACTGCAACATGACTTGGTTCCTCAATTGGGTAGATAAC
AGGACGGGTCAGAAACAGCGCAATTATGCACCGTGCCATATAAGGCAAATAATTAAT
ACTTGGCACAGGGTAGGGAAAAACGTATATTTGCCTCCCAGGGAAGGGGAGTTGACC
TGCAACTCAACAGTGACCAGCATAATTGCCAACATTGATACGGGAGATCAAACAGAT
ATTACCTTTAGTGCAGAGGTGGCAGAACTATACCGATTGGAATTGGGAGATTACAAA
TTAGTAGAAATCACACCAATTGGCTTCGCACCTACATCAGTAAAGAGATACTCCTCT
GCTCACCAGAGACATACAAGAGGTGTGTTCGTGCTAGGGTTCTTGGGTTTTCTCGCA
ACGGCAGGTTCTGCAATGGGCGCGGCGTCGTTGACGCTGACCGCTCAGTCCCGGACT
TCATTGGCTGGGATAGTGCAGCAACAGCAACAGCTGTTGGATGTGGTCAAGAAACAA
CAAGAAATGTTGCGACTGACCGTCTGGGGAACTAAAAATCTCCAGGCAAGAGTCACT
GCTATAGAGAAATACCTAAAGGACCAGGCGCAGCTAAATTCATGGGGATGTGCGTTT
AGACAAGTCTGCCACACTTCTGTACCATGGGTAAATGATAGCTTGACACCTGATTGG
AACAATATGACGTGGCAGGAATGGGAACAAAAAGTCCGCTACTGGGAGGCAAATATC
AGTCAAAGTCTAGAACAAGCACAAATTCAGCAAGAAAAGAATTTGTATGAGCTGCAA
AAATTAAATAGCTGGGGTGTTTTTACCAATTGGCTTGACTTCACCTCCTGGGTCAGG
TATATTCAATATGGAGTTTATGTAGTAGTAGGAATAGTAGCTTTAAGAATAGTAATA
TATATAGTACAGATGTTAAGTAGACTTAGGAAGGGCTATAGGCCTGTTTTCTCCTCC
CCCCCCGGTTATATCCAACAGATCCATATCCACAAGGACCAGGAACAGCCAGCCAGA
GAAGAAACAGAAGAAGACGTTGGAAGCAACGGTGGAGACAGATCTTGGCTTTAGCCG
ATAGCATATATTCATTTCCTGATCCGCCTGCTGATTCGCCTCTTGATCGGGCTATAC
AACATCTGCAGAGACTTACTATCCAGGATCTCCCCGATCCTCCAACCAATCTTCCAG
AGTCTCCAGAGAGCACTAACAGCAATCAGAGACTGGCTGAGGCTTAAAGCAGCCTAC
CTGCAGTATGGGTGCGAGTGGATCCAAGAAGCGTTCCAAGCCCTTGCAAGGACTACA
AGAGAGACTCTTGCAGGCGCGGGG

FIG. 21C

MKGSKNQLLIAIVLASAYLTHCKQFVTVFYGIPAWRNASIPLFCATKNRDTWGTIQC
LPDNDDYQEIALNVTEAFDAWNNTVTEQAVEDVWNLFETSIKPCVKLTPLCVAMNCT
RNMTTSTGTTDTQNITIINDTSPCVRADNCTGLKEEEMVDCQFNMTGLERDKRKQYT
EAWYSKDVICDNNTSSRSKCYMNHCNTSVITESCDKHYWDAMRFRYCAPPGFALLRC
NDTNYSGFAPNCSKVVAATCTRMMETQSSTWFGFNGTRAENRTYIYWHGKNNRTIIS
LNNFYNLTMHCKRPGNKTVLPIMSGFKFHSKPVINKKPRQAWCWFKGEWKEAMQEVK
ETLAKHPRYKGNRSRTENIKFKAPGRGSDPEAAYMWTNCRGEFLYCNMTWFLNWVDN
RTGQKQRNYAPCHIRQIINTWHRVGKNVYLPPREGELTCNSTVTSIIANIDTGDQTD
ITFSAEVAELYRLELGDYKLVEITPIGFAPTSVKRYSSAHQRHTR

FIG. 21D

ATGAAGGGTAGTAAGAATCAACTGCTGATTGCTATTGTACTAGCTAGTGCTTACCTA
ACACATTGCAAGCAATTTGTGACTGTTTTCTATGGCATACCCGCGTGGAGGAATGCA
TCCATTCCCCTGTTTTGTGCAACCAAAAATAGAGATACTTGGGGAACCATACAGTGC
TTGCCAGACAATGATGATTATCAGGAAATAGCTCTAAATGTAACAGAGGCTTTCGAT
GCATGGAATAATACAGTAACAGAACAAGCAGTGGAGGATGTCTGGAATCTATTTGAG
ACATCAATAAAACCATGTGTCAAATTAACACCCTTATGTGTAGCAATGAACTGTACA
AGGAACATGACCACATCCACAGGGACCACAGACACCCAAAATATCACAATTATAAAT
GACACTTCGCCATGCGTACGTGCAGACAACTGCACAGGATTAAAGGAGGAAGAAATG
GTCGACTGTCAGTTTAATATGACAGGATTAGAGAGAGACAAGAGAAAACAGTATACT
GAAGCATGGTACTCAAAAGATGTGATTTGTGACAATAACACCTCAAGTCGGAGCAAG
TGTTACATGAACCATTGCAATACATCAGTCATCACAGAGTCATGTGATAAGCACTAT
TGGGATGCTATGAGGTTTAGATACTGTGCACCACCGGGTTTTGCCCTACTAAGATGC
AATGATACTAATTATTCAGGCTTTGCACCTAATTGCTCTAAAGTAGTAGCTGCTACA
TGCACCAGAATGATGGAAACGCAATCTTCTACATGGTTTGGCTTTAATGGCACTAGA
GCAGAAAATAGAACATATATCTATTGGCATGGTAAAAATAACAGAACTATTATCAGC
TTAAATAACTTTTATAATCTCACTATGCATTGTAAGAGGCCGGGAAATAAGACAGTG
TTACCAATAATGTCAGGGTTTAAGTTTCACTCCAAGCCGGTCATCAATAAAAAACCC
AGGCAAGCATGGTGTTGGTTCAAAGGCGAATGGAAGGAAGCCATGCAGGAGGTGAAG
GAGACCCTTGCGAAACATCCCAGATATAAAGGGAACAGGAGCCGCACAGAGAATATT
AAATTTAAAGCACCAGGAAGAGGCTCAGACCCAGAAGCAGCATACATGTGGACTAAC
TGCAGAGGGGAATTTCTCTACTGCAACATGACTTGGTTCCTCAATTGGGTAGATAAC
AGGACGGGTCAGAAACAGCGCAATTATGCACCGTGCCATATAAGGCAAATAATTAAT
ACTTGGCACAGGGTAGGGAAAAACGTATATTTGCCTCCCAGGGAAGGGGAGTTGACC
TGCAACTCAACAGTGACCAGCATAATTGCCAACATTGATACGGGAGATCAAACAGAT
ATTACCTTTAGTGCAGAGGTGGCAGAACTATACCGATTGGAATTGGGAGATTACAAA
TTAGTAGAAATCACACCAATTGGCTTCGCACCTACATCAGTAAAGAGATACTCCTCT
GCTCACCAGAGACATACAAGA

FIG. 21E

GVFVLGFLGFLATAGSAMGAASLTLTAQSRTSLAGIVQQQQLLDVVKKQQEMLRLT
VWGTKNLQARVTAIEKYLKDQAQLNSWGCAFRQVCHTSVPWVNDSLTPDWNNMTWQE
WEQKVRYWEANISQSLEQAQIQQEKNLYELQKLNSWGVFTNWLDFTSWVRYIQYGVY
VVVGIVALRIVIYIVQMLSRLRKGYRPVFSSPPGYIQQIHIHKDQEQPAREETEEDV
GSNGGDRSWL*PIAYIHFLIRLLIRLLIGLYNICRDLLSRISPILQPIFQSLQRALT
AIRDWLRLKAAYLQYGCEWIQEAFQALARTTRETLAGAG

FIG. 21F

GGTGTGTTCGTGCTAGGGTTCTTGGGTTTTCTCGCAACGGCAGGTTCTGCAATGGGC
GCGGCGTCGTTGACGCTGACCGCTCAGTCCCGGACTTCATTGGCTGGGATAGTGCAG
CAACAGCAACAGCTGTTGGATGTGGTCAAGAAACAACAAGAAATGTTGCGACTGACC
GTCTGGGGAACTAAAAATCTCCAGGCAAGAGTCACTGCTATAGAGAAATACCTAAAG
GACCAGGCGCAGCTAAATTCATGGGGATGTGCGTTTAGACAAGTCTGCCACACTTCT
GTACCATGGGTAAATGATAGCTTGACACCTGATTGGAACAATATGACGTGGCAGGAA
TGGGAACAAAAAGTCCGCTACTGGGAGGCAAATATCAGTCAAAGTCTAGAACAAGCA
CAAATTCAGCAAGAAAAGAATTTGTATGAGCTGCAAAAATTAAATAGCTGGGGTGTT
TTTACCAATTGGCTTGACTTCACCTCCTGGGTCAGGTATATTCAATATGGAGTTTAT
GTAGTAGTAGGAATAGTAGCTTTAAGAATAGTAATATATATAGTACAGATGTTAAGT
AGACTTAGGAAGGGCTATAGGCCTGTTTTCTCCTCCCCCCCCGGTTATATCCAACAG
ATCCATATCCACAAGGACCAGGAACAGCCAGCCAGAGAAGAAACAGAAGAAGACGTT
GGAAGCAACGGTGGAGACAGATCTTGGCTTTAGCCGATAGCATATATTCATTTCCTG
ATCCGCCTGCTGATTCGCCTCTTGATCGGGCTATACAACATCTGCAGAGACTTACTA
TCCAGGATCTCCCCGATCCTCCAACCAATCTTCCAGAGTCTCCAGAGAGCACTAACA
GCAATCAGAGACTGGCTGAGGCTTAAAGCAGCCTACCTGCAGTATGGGTGCGAGTGG
ATCCAAGAAGCGTTCCAAGCCCTTGCAAGGACTACAAGAGAGACTCTTGCAGGCGCG
GGG

FIG. 22A

MKGSKNQLLIAIVLASAYLTHCKQFVTVFYGIPAWRNASIPLFCATKNRDTWGTVQCLPDND
DYQEIALNVTEAFDAWDNTVTEQAVEDVWNLFETSIKPCVKLTPLCVGAGHCNTSVIKESCD
KHYWDAMRFRYCAPPGFALLRCNDINYSGFAPNCSKVVAATCTRMMETQSSTWFGFNGTRTE
NRTYIYWHGKNNRTIISLNNFYNLTMHCKRPGNKGAGKPRQAWCWFKGEWKEAMQEVKETLA
KHPRYKGNRSRTENIKFKAPGRGSDPEAAYMWTNCRGEFLYCDMTWFLNWVDNRTGQKQRNY
APCHIRQIINTWHRVGKNVYLPPREGELTCNSTVTSIIANIDTGDQTDITFSAEVAELYRLE
LGDYKLVEITPIGFAPTSVKRYSSAHQRHTRGVFVLGFLGFLATAGSAMGAASVTLTAQSRT
SLTGIVQQQQLLDVVKKQQEMLRLTVWGTKNLQARVTAIEKYLKDQAQLNSWGCAFRQVCH
TSVPWVNDSLTPDWNNMTWQEWEQKVRYWEANISQSLEQAQIQQEKNLYELQKLNSWGVFTN
WLDFTSWVRYIQYGVYVVVGIVALRIVIYIVQMLSRLRKGYRPVFSSPPGYIQQIHIHKDQE
QPAREETEEDVGSNGGDRSWL*PIAYIHFLIRLLIRLLIGLYNICRDLLSRISPILQPIFQS
LQRALTAIRDWLRLKAAYLQYGCEWIQEAFQALARTTRETLAGAG

FIG. 22B

ATGAAGGGTAGTAAGAATCAACTGCTGATTGCTATTGTACTAGCTAGTGCTTACCTAACACA
TTGCAAGCAATTTGTGACTGTTTTCTATGGCATACCCGCGTGGAGGAATGCATCCATTCCCC
TGTTTTGTGCAACCAAAAATAGAGATACTTGGGGAACTGTACAGTGCTTGCCAGACAATGAT
GATTATCAGGAAATAGCTTTAAATGTAACAGAGGCTTTCGATGCATGGGATAATACAGTAAC
AGAACAAGCAGTGGAGGATGTCTGGAATCTATTTGAGACATCAATAAAACCATGTGTCAAAT
TAACACCCTTATGTGTAGGTGCCGGCCATTGCAATACATCAGTCATCAAAGAGTCATGTGAT
AAGCACTATTGGGATGCTATGAGGTTTAGATACTGTGCACCACCGGGTTTTGCCCTACTAAG
ATGCAATGATATTAATTATTCAGGCTTTGCACCTAATTGCTCTAAAGTAGTAGCTGCTACAT
GCACCAGAATGATGGAAACGCAATCTTCTACATGGTTTGGCTTTAATGGCACTAGAACAGAA
AATAGAACATATATCTATTGGCATGGTAAAAATAACAGAACTATTATCAGCTTAAATAACTT
TTATAATCTCACTATGCATTGTAAGAGGCCGGGAAATAAGGGTGCCGGCAAACCCAGGCAAG
CATGGTGTTGGTTCAAAGGCGAATGGAAGGAAGCCATGCAGGAGGTGAAGGAGACCCTTGCG
AAACATCCCAGATATAAAGGGAACAGGAGCCGCACAGAGAATATTAAATTTAAAGCACCAGG
AAGAGGCTCAGACCCAGAAGCAGCATACATGTGGACTAACTGCAGAGGGGAATTTCTCTACT
GCGACATGACTTGGTTCCTCAATTGGGTAGATAACAGGACGGGTCAGAAACAGCGCAATTAT
GCACCGTGCCATATAAGACAAATAATTAATACTTGGCACAGGGTAGGGAAAAACGTATATTT
GCCTCCCAGGGAAGGGGAGTTGACCTGCAACTCAACAGTGACCAGCATAATTGCCAACATTG
ATACGGGAGATCAAACAGATATTACCTTTAGTGCAGAGGTGGCAGAACTATACCGATTGGAA
TTGGGAGATTACAAATTAGTAGAAATCACACCAATTGGCTTCGCACCTACATCAGTAAAGAG
ATACTCCTCTGCTCACCAGAGACATACAAGAGGTGTGTTCGTGCTAGGGTTCTTGGGTTTTC
TCGCAACGGCAGGTTCTGCAATGGGCGCGGCGTCGGTGACGCTGACCGCTCAGTCCCGGACT
TCATTGACTGGGATAGTGCAGCAACAGCAACAGCTGTTGGATGTGGTCAAGAAACAACAAGA
AATGTTGCGACTGACCGTCTGGGGAACTAAAAATCTCCAGGCAAGAGTCACTGCTATAGAGA
AATACCTAAAGGACCAGGCGCAGCTAAATTCATGGGGATGTGCGTTTAGACAAGTCTGCCAC
ACTTCTGTACCATGGGTAAATGATAGCTTGACACCTGATTGGAACAATATGACGTGGCAGGA
ATGGGAACAAAAAGTCCGCTACTGGGAGGCAAATATCAGTCAAAGTCTAGAACAAGCACAAA
TTCAGCAAGAAAAGAATTTGTATGAGCTGCAAAAATTAAATAGCTGGGGTGTTTTTACCAAT
TGGCTTGACTTCACCTCCTGGGTCAGGTATATTCAATATGGAGTTTACGTAGTAGTAGGAAT
AGTAGCTTTAAGAATAGTAATATATATAGTACAGATGTTAAGTAGACTTAGGAAGGGCTATA
GGCCTGTTTTCTCCTCCCCCCCCGGTTATATCCAACAGATCCATATCCACAAGGACCAGGAA
CAGCCAGCCAGAGAAGAAACAGAAGAAGACGTTGGAAGCAACGGTGGAGACAGATCTTGGCT
TTAGCCGATAGCATATATTCATTTCCTGATCCGCCTGCTGATTCGCCTCTTGATCGGGCTAT
ACAACATCTGCAGAGACTTACTATCCAGGATCTCCCCGATCCTCCAACCAATCTTCCAGAGT
CTCCAGAGAGCACTAACAGCAATCAGAGACTGGCTGAGGCTTAAAGCAGCCTACCTGCAGTA
TGGGTGCGAGTGGATCCAAGAAGCGTTCCAAGCCCTTGCAAGGACTACAAGAGAGACTCTTG
CAGGCGCGGGG

FIG. 22C

MKGSKNQLLIAIVLASAYLTHCKQFVTVFYGIPAWRNASIPLFCATKNRDTWGTVQCLPDND
DYQEIALNVTEAFDAWDNTVTEQAVEDVWNLFETSIKPCVKLTPLCVGAGHCNTSVIKESCD
KHYWDAMRFRYCAPPGFALLRCNDINYSGFAPNCSKVVAATCTRMMETQSSTWFGFNGTRTE
NRTYIYWHGKNNRTIISLNNFYNLTMHCKRPGNKGAGKPRQAWCWFKGEWKEAMQEVKETLA
KHPRYKGNRSRTENIKFKAPGRGSDPEAAYMWTNCRGEFLYCDMTWFLNWVDNRTGQKQRNY
APCHIRQIINTWHRVGKNVYLPPREGELTCNSTVTSIIANIDTGDQTDITFSAEVAELYRLE
LGDYKLVEITPIGFAPTSVKRYSSAHQRHTR

FIG. 22D

ATGAAGGGTAGTAAGAATCAACTGCTGATTGCTATTGTACTAGCTAGTGCTTACCTAACACA
TTGCAAGCAATTTGTGACTGTTTTCTATGGCATACCCGCGTGGAGGAATGCATCCATTCCCC
TGTTTTGTGCAACCAAAAATAGAGATACTTGGGGAACTGTACAGTGCTTGCCAGACAATGAT
GATTATCAGGAAATAGCTTTAAATGTAACAGAGGCTTTCGATGCATGGGATAATACAGTAAC
AGAACAAGCAGTGGAGGATGTCTGGAATCTATTTGAGACATCAATAAAACCATGTGTCAAAT
TAACACCCTTATGTGTAGGTGCCGGCCATTGCAATACATCAGTCATCAAAGAGTCATGTGAT
AAGCACTATTGGGATGCTATGAGGTTTAGATACTGTGCACCACCGGGTTTTGCCCTACTAAG
ATGCAATGATATTAATTATTCAGGCTTTGCACCTAATTGCTCTAAAGTAGTAGCTGCTACAT
GCACCAGAATGATGGAAACGCAATCTTCTACATGGTTTGGCTTTAATGGCACTAGAACAGAA
AATAGAACATATATCTATTGGCATGGTAAAAATAACAGAACTATTATCAGCTTAAATAACTT
TTATAATCTCACTATGCATTGTAAGAGGCCGGGAAATAAGGGTGCCGGCAAACCCAGGCAAG
CATGGTGTTGGTTCAAAGGCGAATGGAAGGAAGCCATGCAGGAGGTGAAGGAGACCCTTGCG
AAACATCCCAGATATAAAGGGAACAGGAGCCGCACAGAGAATATTAAATTTAAAGCACCAGG
AAGAGGCTCAGACCCAGAAGCAGCATACATGTGGACTAACTGCAGAGGGGAATTTCTCTACT
GCGACATGACTTGGTTCCTCAATTGGGTAGATAACAGGACGGGTCAGAAACAGCGCAATTAT
GCACCGTGCCATATAAGACAAATAATTAATACTTGGCACAGGGTAGGGAAAAACGTATATTT
GCCTCCCAGGGAAGGGGAGTTGACCTGCAACTCAACAGTGACCAGCATAATTGCCAACATTG
ATACGGGAGATCAAACAGATATTACCTTTAGTGCAGAGGTGGCAGAACTATACCGATTGGAA
TTGGGAGATTACAAATTAGTAGAAATCACACCAATTGGCTTCGCACCTACATCAGTAAAGAG
ATACTCCTCTGCTCACCAGAGACATACAAGA

FIG. 22E

GVFVLGFLGFLATAGSAMGAASVTLTAQSRTSLTGIVQQQQQLLDVVKKQQEMLRLTVWGTK
NLQARVTAIEKYLKDQAQLNSWGCAFRQVCHTSVPWVNDSLTPDWNNMTWQEWEQKVRYWEA
NISQSLEQAQIQQEKNLYELQKLNSWGVFTNWLDFTSWVRYIQYGVYVVVGIVALRIVIYIV
QMLSRLRKGYRPVFSSPPGYIQQIHIHKDQEQPAREETEEDVGSNGGDRSWL*PIAYIHFLI
RLLIRLLIGLYNICRDLLSRISPILQPIFQSLQRALTAIRDWLRLKAAYLQYGCEWIQEAFQ
ALARTTRETLAGAG

FIG. 22F

GGTGTGTTCGTGCTAGGGTTCTTGGGTTTTCTCGCAACGGCAGGTTCTGCAATGGGCGCGGC
GTCGGTGACGCTGACCGCTCAGTCCCGGACTTCATTGACTGGGATAGTGCAGCAACAGCAAC
AGCTGTTGGATGTGGTCAAGAAACAACAAGAAATGTTGCGACTGACCGTCTGGGGAACTAAA
AATCTCCAGGCAAGAGTCACTGCTATAGAGAAATACCTAAAGGACCAGGCGCAGCTAAATTC
ATGGGGATGTGCGTTTAGACAAGTCTGCCACACTTCTGTACCATGGGTAAATGATAGCTTGA
CACCTGATTGGAACAATATGACGTGGCAGGAATGGGAACAAAAAGTCCGCTACTGGGAGGCA
AATATCAGTCAAAGTCTAGAACAAGCACAAATTCAGCAAGAAAAGAATTTGTATGAGCTGCA
AAAATTAAATAGCTGGGGTGTTTTTACCAATTGGCTTGACTTCACCTCCTGGGTCAGGTATA
TTCAATATGGAGTTTACGTAGTAGTAGGAATAGTAGCTTTAAGAATAGTAATATATATAGTA
CAGATGTTAAGTAGACTTAGGAAGGGCTATAGGCCTGTTTTCTCCTCCCCCCCCGGTTATAT
CCAACAGATCCATATCCACAAGGACCAGGAACAGCCAGCCAGAGAAGAAACAGAAGAAGACG
TTGGAAGCAACGGTGGAGACAGATCTTGGCTTTAGCCGATAGCATATATTCATTTCCTGATC
CGCCTGCTGATTCGCCTCTTGATCGGGCTATACAACATCTGCAGAGACTTACTATCCAGGAT
CTCCCCGATCCTCCAACCAATCTTCCAGAGTCTCCAGAGAGCACTAACAGCAATCAGAGACT
GGCTGAGGCTTAAAGCAGCCTACCTGCAGTATGGGTGCGAGTGGATCCAAGAAGCGTTCCAA
GCCCTTGCAAGGACTACAAGAGAGACTCTTGCAGGCGCGGGG

FIG. 23A

MKGSKNQPLIAIVLASAYLTHCKQFVTVFYGIPAWRNASIPLFCATKNRDTWGTVQCLPDND
DYQEIALNVTEAFDAWDNTVTEQAVEDVWNLSETSIKPCVKLTPLCVGAGHCNTSVITESCD
KHYWDAMRFRYCAPPGFALLRCNDTNYSGFAPNCSKVVAATCTRMMETQSSTWFGFNGTRAE
NRTYIYWHGKNDRTIISLNNFYNLTMHCKRPGNKGAGKPRQAWCWFKGEWKEAMQEVKETLA
KHPRYKGNRSRTENIKFKAPGRGSDPEAAYMWTNCRGEFLYCDMTWFLNWVENRTGQKQRNY
APCHIRQIINTWHRVGKNVYLPPREGELTCNSTVTSIIANIDTGDQTDITFSAEVAELYRLE
LGDYKLVEITPIGFAPTSVKRYSSAHQRHTRGVFVLGFLGFLATAGSAMGAASVTLTAQSRT
SLTGVVQQQQQLLDVVKKQQEMLRLTVWGTKNLQARVTAIEKYLKDQAQLNSWGCAFRQVCH
TSVPWVNDSLTPDWNNMTWQEWEQKVRYWEANISQSLEQAQIQQEKNLYELQKLNSWGVFTN
WLDFTSWVRYIQYGVYVVVGIVALRIVIYIVQMLSRLRKGYRPVFSSPPGYIQQIHIHKDQE
QPAREETEEDVGSNGGDKSWL

FIG. 23B

ATGAAGGGTAGTAAGAATCAACCGCTGATTGCTATTGTACTAGCTAGTGCTTACCTAACACA
TTGCAAGCAATTTGTGACTGTTTTCTATGGCATACCCGCGTGGAGGAATGCATCCATTCCCC
TGTTTTGTGCAACCAAAAATAGAGATACTTGGGGAACCGTACAGTGCTTGCCAGACAATGAT
GATTATCAGGAAATAGCTTTAAATGTAACAGAGGCTTTCGATGCATGGGATAATACAGTAAC
AGAACAAGCAGTGGAGGATGTCTGGAATCTATCTGAGACATCAATAAAACCATGTGTCAAAT
TAACACCCTTATGTGTAGGTGCCGGCCATTGCAATACATCAGTCATCACAGAGTCATGTGAT
AAGCACTATTGGGATGCTATGAGGTTTAGATACTGTGCACCACCGGGTTTTGCCTTACTAAG
ATGCAATGATACTAATTATTCAGGCTTTGCACCTAATTGCTCTAAAGTAGTAGCTGCTACAT
GCACCAGAATGATGGAAACGCAATCTTCTACATGGTTTGGCTTTAATGGCACTAGAGCAGAA
AATAGAACATATATCTATTGGCATGGTAAAAATGACAGAACTATTATCAGCTTAAATAACTT
TTATAATCTCACTATGCATTGTAAGAGGCCGGGAAATAAGGGTGCCGGCAAACCCAGGCAAG
CATGGTGTTGGTTCAAAGGCGAATGGAAGGAAGCCATGCAGGAGGTGAAGGAGACCCTTGCG
AAACATCCTAGATATAAAGGGAACAGGAGCCGCACAGAGAATATTAAATTTAAAGCACCAGG
AAGAGGCTCAGACCCAGAAGCAGCATACATGTGGACTAACTGCAGAGGGGAATTTCTCTACT
GCGACATGACTTGGTTCCTCAATTGGGTAGAAAACAGGACGGGTCAGAAACAGCGTAATTAT
GCACCGTGCCATATAAGGCAAATAATTAATACTTGGCACAGGGTAGGGAAAAACGTATATTT
GCCTCCCAGGGAAGGGGAGTTAACCTGCAACTCAACAGTGACCAGCATAATTGCCAACATTG
ATACGGGAGATCAAACAGATATTACCTTTAGTGCAGAGGTGGCAGAACTATACCGGTTGGAA
TTGGGAGATTACAAATTAGTAGAAATCACACCAATTGGCTTCGCACCTACATCAGTAAAGAG
ATACTCCTCTGCTCACCAGAGACATACAAGAGGTGTGTTCGTGCTAGGGTTCTTGGGTTTTC
TCGCAACGGCAGGTTCTGCAATGGGCGCGGCGTCGGTGACGCTGACCGCTCAGTCCCGGACT
TCATTGACTGGGGTAGTGCAGCAACAGCAACAGCTGTTGGATGTGGTCAAGAAACAACAAGA
AATGTTGCGACTGACCGTCTGGGGAACTAAAAATCTCCAGGCAAGAGTCACTGCTATAGAGA
AATACCTAAAGGACCAGGCGCAGCTAAATTCATGGGGATGTGCGTTTAGACAAGTCTGCCAC
ACTTCTGTACCATGGGTAAATGATAGCTTGACACCTGATTGGAACAATATGACGTGGCAGGA
ATGGGAACAAAAAGTCCGCTACTGGGAGGCAAATATCAGTCAAAGTCTAGAACAAGCACAAA
TTCAGCAAGAAAAGAATTTGTATGAGCTGCAAAAATTAAATAGCTGGGGTGTTTTTACCAAT
TGGCTTGACTTCACCTCCTGGGTCAGGTATATTCAATATGGAGTTTATGTAGTAGTAGGAAT
AGTAGCTTTAAGAATAGTAATATATATAGTACAGATGTTGAGTAGACTTAGGAAGGGCTATA
GGCCTGTTTTCTCCTCCCCCCCCGGTTATATCCAACAGATCCATATCCACAAGGACCAGGAA
CAGCCAGCCAGAGAAGAAACAGAAGAAGACGTTGGAAGCAACGGTGGAGACAAATCTTGGCT
TTAG

FIG. 23C

MKGSKNQPLIAIVLASAYLTHCKQFVTVFYGIPAWRNASIPLFCATKNRDTWGTVQCLPDND
DYQEIALNVTEAFDAWDNTVTEQAVEDVWNLSETSIKPCVKLTPLCVGAGHCNTSVITESCD
KHYWDAMRFRYCAPPGFALLRCNDTNYSGFAPNCSKVVAATCTRMMETQSSTWFGFNGTRAE
NRTYIYWHGKNDRTIISLNNFYNLTMHCKRPGNKGAGKPRQAWCWFKGEWKEAMQEVKETLA
KHPRYKGNRSRTENIKFKAPGRGSDPEAAYMWTNCRGEFLYCDMTWFLNWVENRTGQKQRNY
APCHIRQIINTWHRVGKNVYLPPREGELTCNSTVTSIIANIDTGDQTDITFSAEVAELYRLE
LGDYKLVEITPIGFAPTSVKRYSSAHQRHTR

FIG. 23D

ATGAAGGGTAGTAAGAATCAACCGCTGATTGCTATTGTACTAGCTAGTGCTTACCTAACACA
TTGCAAGCAATTTGTGACTGTTTTCTATGGCATACCCGCGTGGAGGAATGCATCCATTCCCC
TGTTTTGTGCAACCAAAAATAGAGATACTTGGGGAACCGTACAGTGCTTGCCAGACAATGAT
GATTATCAGGAAATAGCTTTAAATGTAACAGAGGCTTTCGATGCATGGGATAATACAGTAAC
AGAACAAGCAGTGGAGGATGTCTGGAATCTATCTGAGACATCAATAAAACCATGTGTCAAAT
TAACACCCTTATGTGTAGGTGCCGGCCATTGCAATACATCAGTCATCACAGAGTCATGTGAT
AAGCACTATTGGGATGCTATGAGGTTTAGATACTGTGCACCACCGGGTTTTGCCTTACTAAG
ATGCAATGATACTAATTATTCAGGCTTTGCACCTAATTGCTCTAAAGTAGTAGCTGCTACAT
GCACCAGAATGATGGAAACGCAATCTTCTACATGGTTTGGCTTTAATGGCACTAGAGCAGAA
AATAGAACATATATCTATTGGCATGGTAAAAATGACAGAACTATTATCAGCTTAAATAACTT
TTATAATCTCACTATGCATTGTAAGAGGCCGGGAAATAAGGGTGCCGGCAAACCCAGGCAAG
CATGGTGTTGGTTCAAAGGCGAATGGAAGGAAGCCATGCAGGAGGTGAAGGAGACCCTTGCG
AAACATCCTAGATATAAAGGGAACAGGAGCCGCACAGAGAATATTAAATTTAAAGCACCAGG
AAGAGGCTCAGACCCAGAAGCAGCATACATGTGGACTAACTGCAGAGGGGAATTTCTCTACT
GCGACATGACTTGGTTCCTCAATTGGGTAGAAAACAGGACGGGTCAGAAACAGCGTAATTAT
GCACCGTGCCATATAAGGCAAATAATTAATACTTGGCACAGGGTAGGGAAAAACGTATATTT
GCCTCCCAGGGAAGGGGAGTTAACCTGCAACTCAACAGTGACCAGCATAATTGCCAACATTG
ATACGGGAGATCAAACAGATATTACCTTTAGTGCAGAGGTGGCAGAACTATACCGGTTGGAA
TTGGGAGATTACAAATTAGTAGAAATCACACCAATTGGCTTCGCACCTACATCAGTAAAGAG
ATACTCCTCTGCTCACCAGAGACATACAAGA

FIG. 23E

GVFVLGFLGFLATAGSAMGAASVTLTAQSRTSLTGVVQQQQQLLDVVKKQQEMLRLTVWGTK
NLQARVTAIEKYLKDQAQLNSWGCAFRQVCHTSVPWVNDSLTPDWNNMTWQEWEQKVRYWEA
NISQSLEQAQIQQEKNLYELQKLNSWGVFTNWLDFTSWVRYIQYGVYVVVGIVALRIVIYIV
QMLSRLRKGYRPVFSSPPGYIQQIHIHKDQEQPAREETEEDVGSNGGDKSWL

FIG. 23F

GGTGTGTTCGTGCTAGGGTTCTTGGGTTTTCTCGCAACGGCAGGTTCTGCAATGGGCGCGGC
GTCGGTGACGCTGACCGCTCAGTCCCGGACTTCATTGACTGGGGTAGTGCAGCAACAGCAAC
AGCTGTTGGATGTGGTCAAGAAACAACAAGAAATGTTGCGACTGACCGTCTGGGGAACTAAA
AATCTCCAGGCAAGAGTCACTGCTATAGAGAAATACCTAAAGGACCAGGCGCAGCTAAATTC
ATGGGGATGTGCGTTTAGACAAGTCTGCCACACTTCTGTACCATGGGTAAATGATAGCTTGA
CACCTGATTGGAACAATATGACGTGGCAGGAATGGGAACAAAAAGTCCGCTACTGGGAGGCA
AATATCAGTCAAAGTCTAGAACAAGCACAAATTCAGCAAGAAAAGAATTTGTATGAGCTGCA
AAAATTAAATAGCTGGGGTGTTTTTACCAATTGGCTTGACTTCACCTCCTGGGTCAGGTATA
TTCAATATGGAGTTTATGTAGTAGTAGGAATAGTAGCTTTAAGAATAGTAATATATATAGTA
CAGATGTTGAGTAGACTTAGGAAGGGCTATAGGCCTGTTTTCTCCTCCCCCCCCGGTTATAT
CCAACAGATCCATATCCACAAGGACCAGGAACAGCCAGCCAGAGAAGAAACAGAAGAAGACG
TTGGAAGCAACGGTGGAGACAAATCTTGGCTTTAG

FIG. 24A

MKGSKNQLLIAIILASAYLTHCKQFVTVFYGIPAWRNASIPLFCATKNRDTWGTIQCLPDND
DYQEIALNVTEAFDAWNNTVTEQAVEDVWNLFETSIKPCVKLTPLCVAMNCTRNMTTSTGTT
DTQNITIINDTSPCVRADNCTGLKEEEMVDCQFNMTGLERDKRKQYTGAWYSKDVICDNNTS
SRSKCYMNHCNTSVITESCDKHYWDAMRFRYCAPPGFALLRCNDTNYSGFAPNCSKVVAATC
TRMMETQSSTWFGFNGTRAENRTYIYWHGKNNRTIISLNNFYNLTMHCKRPGNKGAGKPRQA
WCWFKGEWKEAMQEVKETLAKHPRYKGNRSRTENIKFKAPGRGSDPEAAYMWTNCRGEFLYC
NMAWFLNWVDNRTGQKQRNYAPCHIRQIINTWHRVGKNIYLPPREGELTCNSTVTSIIANID
TGDQTDITFSAEVAELYRLELGDYKLVEITPIGFAPTSVKRYSSAHQRHTRGVFVLGFLGFL
ATAGSAMGAASVTLTAQSRTSLAGIVQQQQQLLDVVKKQQEMLRLTVWGTKNLQTRVTAIEK
YLKDQAQLNSWGCAFRQVCHTSVPWVNDSLTPDWNNMTWQEWEQKVRYWEANISQSLEQAQI
QQEKNLYELQKLNSWGVFTNWLDFTSWVRYIQYGVYVVVGIVTLRIVIYIVQMLSRLRKGYR
PVFSSPPGYIQQIHIHKDQEQPAREETEEDVGSNGGDRSWL

FIG. 24B

ATGAAGGGTAGTAAGAATCAACTGCTGATTGCTATTATACTAGCTAGTGCTTACCTAACACA
TTGCAAGCAATTTGTGACTGTTTTCTATGGCATACCCGCGTGGAGGAATGCATCCATTCCCC
TGTTTTGTGCAACCAAAAATAGAGATACTTGGGGAACCATACAGTGCTTGCCAGACAATGAT
GATTATCAGGAAATAGCTCTAAATGTAACAGAGGCTTTCGATGCATGGAATAATACAGTAAC
AGAACAAGCAGTGGAGGATGTCTGGAATCTATTTGAGACATCAATAAAACCATGTGTCAAAT
TAACACCCTTATGTGTAGCAATGAACTGTACAAGGAACATGACCACATCCACAGGGACCACA
GACACCCAAAATATCACAATTATAAATGACACTTCGCCATGCGTACGTGCAGACAACTGCAC
AGGATTAAAGGAGGAAGAAATGGTCGACTGTCAGTTTAATATGACAGGATTAGAGAGAGACA
AGAGAAAACAGTATACTGGAGCATGGTACTCAAAAGATGTGATTTGTGACAATAACACCTCA
AGTCGGAGCAAGTGTTACATGAACCATTGCAATACATCAGTCATCACAGAGTCATGTGATAA
GCACTATTGGGATGCTATGAGGTTTAGATACTGTGCACCACCGGGTTTTGCCCTACTAAGAT
GCAATGATACTAATTATTCAGGCTTTGCACCTAATTGCTCTAAAGTAGTAGCTGCTACATGC
ACCAGAATGATGGAAACGCAATCTTCTACATGGTTTGGATTTAATGGCACTAGAGCAGAAAA
TAGAACATATATCTATTGGCATGGTAAAAATAACAGAACTATTATCAGCTTAAATAACTTTT
ATAATCTCACTATGCATTGTAAGAGGCCGGGAAATAAGGGTGCCGGCAAACCCAGGCAAGCA
TGGTGTTGGTTCAAAGGCGAATGGAAGGAAGCCATGCAGGAGGTGAAGGAGACCCTTGCGAA
ACATCCCAGATATAAAGGGAACAGGAGCCGCACAGAGAATATTAAATTTAAAGCACCAGGAA
GAGGCTCAGACCCAGAAGCAGCATACATGTGGACTAACTGCAGAGGGGAATTTCTCTACTGC
AACATGGCTTGGTTCCTCAATTGGGTAGATAACAGGACGGGTCAGAAACAGCGCAATTATGC
ACCGTGCCATATAAGGCAAATAATTAATACTTGGCACAGGGTAGGGAAAAACATATATTTGC
CTCCCAGGGAAGGGGAGTTGACCTGCAACTCAACAGTGACCAGCATAATTGCCAACATTGAT
ACGGGAGATCAAACAGATATTACCTTTAGTGCAGAGGTGGCAGAACTATACCGATTGGAATT
GGGAGATTACAAATTAGTAGAAATCACACCAATTGGCTTCGCACCTACATCAGTAAAGAGAT
ACTCCTCTGCTCACCAGAGACATACAAGAGGTGTGTTCGTGCTAGGGTTCTTGGGTTTTCTC
GCAACGGCAGGTTCTGCAATGGGCGCGGCGTCGGTGACGCTGACCGCCCAGTCCCGGACTTC
ATTGGCTGGGATAGTGCAGCAACAGCAACAGCTGTTGGACGTGGTCAAGAAACAACAAGAAA
TGTTGCGACTGACCGTCTGGGGAACTAAAAATCTCCAGACAAGAGTCACTGCTATAGAGAAA
TACCTAAAGGACCAGGCGCAGTTAAATTCATGGGGATGTGCGTTTAGACAAGTCTGCCACAC
TTCTGTACCATGGGTAAATGATAGCTTGACACCTGATTGGAACAATATGACGTGGCAGGAAT
GGGAACAGAAAGTCCGCTACTGGGAGGCAAATATCAGTCAAAGTCTAGAACAAGCACAAATT
CAGCAAGAAAAGAATTTGTATGAGCTGCAAAAATTAAATAGCTGGGGTGTTTTTACCAATTG
GCTTGACTTCACCTCCTGGGTCAGGTATATTCAATATGGAGTTTATGTAGTAGTAGGAATAG
TAACTTTAAGAATAGTAATATATATAGTACAGATGTTAAGTAGACTTAGGAAGGGCTATAGG
CCTGTTTTCTCCTCCCCCCCCGGTTATATCCAACAGATCCATATCCACAAGGACCAGGAACA
GCCAGCCAGAGAAGAAACAGAAGAAGACGTTGGAAGCAACGGTGGAGACAGATCTTGGCTTT
AGCCGATAGCATATATTCATTTCCTGATCCGCCTGCTGATTCGCCTCTTGATCGGGCTATAC
AACATCTGCAGAGACTTACTATCCAGGATCTCCCCGATCCTCCAACCAATCTTCCAGAGTCT
CCAGAGAGCACTAACAGCAATCAGAGACTGGCTGAGGCTTAAAGCAGCCTACCTGCAGTATG
GGTGCGAGTGGATCCAAGAAGCGTTCCAAGCCCTTGCAAGGACTACAAGAGAGACTCTTGCA
GGCGCGGGG

FIG. 24C

MKGSKNQLLIAIILASAYLTHCKQFVTVFYGIPAWRNASIPLFCATKNRDTWGTIQCLPDND
DYQEIALNVTEAFDAWNNTVTEQAVEDVWNLFETSIKPCVKLTPLCVAMNCTRNMTTSTGTT
DTQNITIINDTSPCVRADNCTGLKEEEMVDCQFNMTGLERDKRKQYTGAWYSKDVICDNNTS
SRSKCYMNHCNTSVITESCDKHYWDAMRFRYCAPPGFALLRCNDTNYSGFAPNCSKVVAATC
TRMMETQSSTWFGFNGTRAENRTYIYWHGKNNRTIISLNNFYNLTMHCKRPGNKGAGKPRQA
WCWFKGEWKEAMQEVKETLAKHPRYKGNRSRTENIKFKAPGRGSDPEAAYMWTNCRGEFLYC
NMAWFLNWVDNRTGQKQRNYAPCHIRQIINTWHRVGKNIYLPPREGELTCNSTVTSIIANID
TGDQTDITFSAEVAELYRLELGDYKLVEITPIGFAPTSVKRYSSAHQRHTR

FIG. 24D

ATGAAGGGTAGTAAGAATCAACTGCTGATTGCTATTATACTAGCTAGTGCTTACCTAACACA
TTGCAAGCAATTTGTGACTGTTTTCTATGGCATACCCGCGTGGAGGAATGCATCCATTCCCC
TGTTTTGTGCAACCAAAAATAGAGATACTTGGGGAACCATACAGTGCTTGCCAGACAATGAT
GATTATCAGGAAATAGCTCTAAATGTAACAGAGGCTTTCGATGCATGGAATAATACAGTAAC
AGAACAAGCAGTGGAGGATGTCTGGAATCTATTTGAGACATCAATAAAACCATGTGTCAAAT
TAACACCCTTATGTGTAGCAATGAACTGTACAAGGAACATGACCACATCCACAGGGACCACA
GACACCCAAAATATCACAATTATAAATGACACTTCGCCATGCGTACGTGCAGACAACTGCAC
AGGATTAAAGGAGGAAGAAATGGTCGACTGTCAGTTTAATATGACAGGATTAGAGAGAGACA
AGAGAAAACAGTATACTGGAGCATGGTACTCAAAAGATGTGATTTGTGACAATAACACCTCA
AGTCGGAGCAAGTGTTACATGAACCATTGCAATACATCAGTCATCACAGAGTCATGTGATAA
GCACTATTGGGATGCTATGAGGTTTAGATACTGTGCACCACCGGGTTTTGCCCTACTAAGAT
GCAATGATACTAATTATTCAGGCTTTGCACCTAATTGCTCTAAAGTAGTAGCTGCTACATGC
ACCAGAATGATGGAAACGCAATCTTCTACATGGTTTGGATTTAATGGCACTAGAGCAGAAAA
TAGAACATATATCTATTGGCATGGTAAAAATAACAGAACTATTATCAGCTTAAATAACTTTT
ATAATCTCACTATGCATTGTAAGAGGCCGGGAAATAAGGGTGCCGGCAAACCCAGGCAAGCA
TGGTGTTGGTTCAAAGGCGAATGGAAGGAAGCCATGCAGGAGGTGAAGGAGACCCTTGCGAA
ACATCCCAGATATAAAGGGAACAGGAGCCGCACAGAGAATATTAAATTTAAAGCACCAGGAA
GAGGCTCAGACCCAGAAGCAGCATACATGTGGACTAACTGCAGAGGGGAATTTCTCTACTGC
AACATGGCTTGGTTCCTCAATTGGGTAGATAACAGGACGGGTCAGAAACAGCGCAATTATGC
ACCGTGCCATATAAGGCAAATAATTAATACTTGGCACAGGGTAGGGAAAAACATATATTTGC
CTCCCAGGGAAGGGGAGTTGACCTGCAACTCAACAGTGACCAGCATAATTGCCAACATTGAT
ACGGGAGATCAAACAGATATTACCTTTAGTGCAGAGGTGGCAGAACTATACCGATTGGAATT
GGGAGATTACAAATTAGTAGAAATCACACCAATTGGCTTCGCACCTACATCAGTAAAGAGAT
ACTCCTCTGCTCACCAGAGACATACAAGA

FIG. 24E

GVFVLGFLGFLATAGSAMGAASVTLTAQSRTSLAGIVQQQQLLDVVKKQQEMLRLTVWGTK
NLQTRVTAIEKYLKDQAQLNSWGCAFRQVCHTSVPWVNDSLTPDWNNMTWQEWEQKVRYWEA
NISQSLEQAQIQQEKNLYELQKLNSWGVFTNWLDFTSWVRYIQYGVYVVVGIVTLRIVIYIV
QMLSRLRKGYRPVFSSPPGYIQQIHIHKDQEQPAREETEEDVGSNGGDRSWL

FIG. 24F

GGTGTGTTCGTGCTAGGGTTCTTGGGTTTTCTCGCAACGGCAGGTTCTGCAATGGGCGCGGC
GTCGGTGACGCTGACCGCCCAGTCCCGGACTTCATTGGCTGGGATAGTGCAGCAACAGCAAC
AGCTGTTGGACGTGGTCAAGAAACAACAAGAAATGTTGCGACTGACCGTCTGGGGAACTAAA
AATCTCCAGACAAGAGTCACTGCTATAGAGAAATACCTAAAGGACCAGGCGCAGTTAAATTC
ATGGGGATGTGCGTTTAGACAAGTCTGCCACACTTCTGTACCATGGGTAAATGATAGCTTGA
CACCTGATTGGAACAATATGACGTGGCAGGAATGGGAACAGAAAGTCCGCTACTGGGAGGCA
AATATCAGTCAAAGTCTAGAACAAGCACAAATTCAGCAAGAAAAGAATTTGTATGAGCTGCA
AAAATTAAATAGCTGGGGTGTTTTTACCAATTGGCTTGACTTCACCTCCTGGGTCAGGTATA
TTCAATATGGAGTTTATGTAGTAGTAGGAATAGTAACTTTAAGAATAGTAATATATATAGTA
CAGATGTTAAGTAGACTTAGGAAGGGCTATAGGCCTGTTTTCTCCTCCCCCCCCGGTTATAT
CCAACAGATCCATATCCACAAGGACCAGGAACAGCCAGCCAGAGAAGAAACAGAAGAAGACG
TTGGAAGCAACGGTGGAGACAGATCTTGGCTTTAG

COMPOSITIONS, METHOD AND KITS RELATING TO DELETION MUTATIONS OF IMMUNODEFICIENCY VIRUS GP120 HYPERVARIABLE REGIONS

CROSS-REFERENCE TO RELATED APPLICATIONS

This application claims the benefit of priority under 35 U.S.C § 119(e) to U.S. Provisional Patent Application No. 60/443,364, filed Jan. 29, 2003, which is herein incorporated in its entirety by reference.

STATEMENT REGARDING FEDERALLY SUPPORTED RESEARCH AND DEVELOPMENT

This invention was supported in part by U.S. Government funds (National Institutes of Health grant AI45378-03), and the U.S. Government may therefore have certain rights in the invention.

BACKGROUND OF THE INVENTION

Human immunodeficiency virus (HIV) entry is known to require a complex interaction of the viral envelope glycoprotein (Env) with CD4 and cellular chemokine receptors. HIV Env protein is produced as a precursor (gp160) that is subsequently cleaved into two parts, gp120 which binds CD4 and chemokine receptors, and gp41 which is anchored in the viral membrane and mediates membrane fusion. Differential use of chemokine receptors by HIV and simian immunodeficiency virus (SIV) has largely explained differences in tropism among different isolates (Berger, 1997, AIDS 11:S3-S16; Hoffman and Doms, 1998, AIDS 12:S17-S26). While a number of chemokine receptors can be utilized by HIV or SIV (Deng et al., 1997, Nature 388:296-300; Choe et al., 1996, Cell 85, 1135-1148; Rucker et al., 1997, J. Virol. 71:8999-9007; Edinger et al., 1997, Proc. Natl. Acad. Sci. USA 94:14742-14747; Liao et al., 1997, J. Exp. Med. 185:2015-2023; Farzan et al., 1997, J. Exp. Med. 186:405-411), CCR5 and CXCR4 appear to be the principal coreceptors for HIV-1 (Zhang et al., 1998, J Virol. 72:9337-9344; Zhang et al., 1998, J. Virol. 72:9337-9344). Isolates of HIV that first establish infection target blood lymphocytes and macrophages using CCR5 (Alkhatib et al., 1996, Science 272:1955-1958; Deng et al., 1996, Nature 381:661-666; Dragic et al., 1996, Nature 381:667-673; Doranz et al., 1996, Cell 85:1149-1158), while viruses that are generally associated with progression to AIDS and can infect T cell lines in vitro use CXCR4 (Choe et al., 1996, Cell 85:1135-1148; Feng et al., 1996, Science 272: 872-876; Connor et al., 1997, J. Exp. Med. 185:621-628).

Binding of Env to CD4 initiates poorly understood conformational changes enabling gp120 to bind to a chemokine receptor and leading to fusion of the viral and cellular membranes (Jones et al., 1998, J. Biol Chem. 273:404-409; Moore et al., 1994, J. Virol. 68:469-484; Wyatt, 1992, J. Virol. 66:6997-7004; Wu et al., 1996, Nature 384:179-183). Thus, the Env glycoproteins gp120 and gp41 are important potential targets for neutralizing antibodies to HIV and SIV. As stated previously, Env is a protein structural component comprising the retroviral capsid, and is produced from a precursor molecule (gp160) that is cleaved in the Golgi, transported to the cell surface, and incorporated into virions as trimers of non-covalently associated gp120/gp41 subunits (Allan et al., 1985, Science 228:1091-1094; Chan et al., 1997, Cell 89:263-273; Earl et al., 1990, Proc. Nat. Acad. Sci. 87:648-652; Rizzuto et al., 2000, AIDS Res. Hum. Retroviruses 16:741-9; Pinter et al., 1989, J. Virol. 63:2674-2679; Robey et al., 1985, Science 228:593-595). Gp120 is extensively glycosylated and contains 5 conserved and 5 hypervariable regions. Four of the hypervariable regions, designated V1, V2, V3 and V4 are loops formed by intramolecular disulfide bonds and exposed on the protein surface (Modrow et al., 1987, J. Virol. 61:570-578; Starcich et al., 1986, Cell 45:637-648). In HIV-1, V1 extends from the V2 loop while in HIV-2 and SIV a more complex loop structure exists containing two additional disulfide bonds (Hoxie et al., 1991, AIDS Res Hum Retroviruses 7:495-9). The conserved regions on gp120 fold into a core structure containing a recessed cavity that forms a CD4 binding site (CD4bs) and a "bridging sheet" that connects an inner and outer domain and largely forms a coreceptor binding site for CCR5 and CXCR4 (Basmaciogullari et al., 2002, J. Virol. 76:10791-800; Kwong et al., 2000, Structure Fold Des. 8:1329-39; Kwong et al., 1998, Nature 393: 648-659; Rizzuto et al., 1998, Science 280:1949-1953; Wyatt et al., 1998, Nature 393:705-711). Conserved regions on the gp120 core also likely abut gp41 in the Env trimer and are exposed only if it dissociates from gp41 (Kwong et al., 2000, J. Virol. 74:1961-1972). Gp41 contains two heptad repeat regions, HR1 and HR2, and a hydrophobic amino-terminal fusion peptide required to initiate lipid mixing between viral and cell membranes (Martin et al., 1996, J. Virol. 70:298-304; Pereira et al., 1997, Biophys. J. 73:1977-86; Weng et al., 2000, J. Virol. 74:5368-5372; Wild et al.,1994, Proc. Natl. Acad. Sci. USA 91:9770-4).

Cell entry by HIV and SIV is initiated by an interaction of gp120 with CD4, leading to extensive conformational changes that, measured on monomeric gp120, are associated with a loss of entropic freedom (Myszka et al., 2000, Proc. Natl. Acad. Sci U.S.A. 97:9026-903 1), movement of hypervariable loops V1/V2 and V3 (Moore et al., 1993, J. Virol. 67:6136-6151; Sattentau et al., 1993, J. Virol. 67:7383-7393; Wyatt et al., 1995, J. Virol. 69:5723-5733; Wyatt et al., 1993, J. Virol. 67:4557-4565), and the exposure and/or formation of the bridging sheet (Myszka et al., 2000, Proc. Natl. Acad. Sci U.S.A. 97:9026-9031). V3 and particularly the β19 strand within the bridging sheet likely bind to the chemokine receptor and, at least for CCR5, create a high affinity interaction (Cormier et al., 2002, J. Virol. 76:8953-7; Dragic et al., 2001, J. Gen. Virol. 82:1807-14; Farzan et al., 1999, Cell 96:667-76; Trkola et al., 1996, Nature 384:184-7). V3 mediates specificity (i.e., determines whether CXCR4 or CCR5 are utilized) and likely interacts with extracellular loops of chemokine receptors, while the bridging sheet likely interacts with both receptors, and at least for CCR5 probably binds to the N-terminus (Basmaciogullari et al., 2002, J. Virol. 76:10791-800; Dragic et al., 2001, J. Gen. Virol. 82:1807-14; Farzan et al., 2002, J. Biol. Chem. 277:40397-402; Farzan et al., 2000, J. Biol. Chem. 275:33516-21; Rizzuto et al., 2000, AIDS Res. Hum. Retroviruses 16:741-9; Rizzuto et al., 1998, Science 280:1949-1953). Subsequent to or concurrent with chemokine receptor binding, the gp41 fusion peptide inserts into the membrane of the cell, and gp41 undergoes a conformational rearrangement in which HR1 and HR2, in the context of a trimer, associate in an antiparallel manner to form a highly stable six helix bundle, thereby bringing the viral and cell membranes into close proximity and inducing membrane fusion (Matthews et al., 1994, Immunol. Rev. 140:93-104; Melikyan et al., 2000, J. Cell Biol. 151:413-23). Thus, beginning with CD4 engagement, gp120 and gp41 undergo a highly coordinated sequence of events that involve extensive conformational changes and inter- and intra-molecular interactions as chemokine receptors are engaged and viral and cell membranes are brought together.

Given the complexity of viral entry and the numerous steps that could be blocked by antibody binding, it is remarkable that the humoral response in infected hosts fails to arrest this process. Initial antibody responses are directed against epitopes that are revealed only on dissociated gp120 monomers and exhibit limited or no reactivity with Env trimers (Parren et al., 1999, AIDS 13:S137-S162; Wyatt et al., 1998, Nature 393:705-711). Although neutralizing antibodies are produced within one month after infection, these are type-specific and directed primarily against variable loops V1/V2 and V3, which can tolerate extensive genetic changes, and viral escape mutants are rapidly generated (Richman et al., 2003, Proc. Nat. Acad. Sci. USA 100:4144-9). Broadly neutralizing antibodies are either not produced or are produced only late after infection and in low titer (Richman et al., 2003, Proc. Nat. Acad. Sci. USA 100:4144-9; Wyatt et al., 1998, Science 280:1884-1888). The basis for HIV's neutralization resistance likely arises from a number of structural attributes of Env, and in particular a lack of exposure, accessibility or immunogenicity of functionally important epitopes on the assembled Env trimer (Fouts et al., 1997, J. Virol. 71:2779-85; Kwong et al., 2000, Structure Fold Des 8:1329-39; Parren et al., 1999, AIDS 13:S137-S162; Sullivan et al., 1998, J. Virol. 72:6332-8). First, as noted above, substantial portions of surface exposed regions on gp120 contain N-linked carbohydrates, which are poorly immunogenic and capable of masking underlying domains, a property initially termed "carbohydrate cloaking" (Kwong et al., 2000, Structure Fold Des 8:1329-39) and more recently, the "glycan shield" (Wei et al., 2003, Nature 422:307-12). Second, gp120 undergoes extensive thermodynamic changes following CD4 binding with a large increase in enthalpy ($\Delta H$) and a decrease in entropy ($\Delta S$), reflecting increased molecular ordering and an extensive loss of conformational flexibility (Myszka et al., 2000, Proc. Natl. Acad. Sci U.S.A. 97:9026-903 1). It has been proposed that the intrinsic flexibility of gp120 prior to CD4 triggering could in itself mask epitopes for broadly neutralizing antibodies (Kwong, et al., 2002, Nature 420:678-82; Myszka et al., 2000, Proc. Natl. Acad. Sci U.S.A. 97:9026-903 1). Third, although crystallographic resolution of variable loops has not been achieved, two critical functional domains, the CD4bs and bridging sheet, are flanked by the V1/V2 and V3 loops, which are well positioned to restrict access to these conserved functional domains prior to CD4 triggering. Fourth, there are likely to be additional steric constraints on antibody binding to core domains in the context of an oligomeric Env trimer during its interaction with CD4 and chemokine receptors on target cell surface. Indeed, for some human monoclonal antibodies to CD4-induced epitopes that partially overlap the bridging sheet, their neutralizing activity is markedly enhanced as Fab and single chain (scFv) fragments compared to their intact immunoglobulins (Labrijn et al., 2003, J. Virol. 77: In Press; Moulard et al., 2002, Proc. Natl. Acad. Sci. USA 99:6913-8).

Despite these obstacles, anti-HIV-1 Env human monoclonal antibodies have been characterized that exhibit, to varying degrees, broadly neutralizing activity. These include b12, reactive with the CD4bs (Kessler, et al., 1997, AIDS Res. Hum. Retroviruses 13:575-582); 17b, 48d, X5, and others reactive with CD4-induced epitopes on the gp120 core (Moulard et al., 2002, Proc. Natl. Acad. Sci. USA 99:6913-8114; Xiang et al., 2002, AIDS Res Hum Retroviruses 18:1207-17); 2G12, reactive with an exposed conformational epitope on gp120 determined by high mannose carbohydrates (Calarese et al., 2003, Science 300:2065-71; Trkola et al., 1996, J. Virol. 70:1100-1108); and 2F5 and other monoclonal antibodies reactive with linear epitopes on the membrane proximal region of gp41 (Muster et al., 1993, J. Virol. 67:6642-6647; Parker et al., 2001, J. Virol. 75:10906-11; Zwick et al., 2001, J. Virol. 75:10892-905). As noted above, passive administration of combinations of these antibodies has protected animals from mucosal and parenteral challenges with pathogenic SHIVs (Baba et al., 2000, Nature Med. 6:200-206; Mascola et al., 1999, J. Virol. 73:4009-4018; Mascola et al., 2000, Nat. Med. 6:207-210; Ruprecht et al., 2003, Vaccine 21:3370-3). Recent studies have provided insights into remarkable structural attributes of some of these antibodies that contribute to their neutralizing activity including 1) extended CDR3 loops that can access recessed domains (Choe et al., 2003, Cell 114:161-70; Saphire et al., 2001, Acta. Crystal. D. Biol. Crystal. 57:168-71); 2) novel conformational rearrangements in heavy and light chain domains that increase the number of contact sites (Calarese et al., 2003, Science 300:2065-71); 3) variable domains that mimic CD4 (Saphire et al., 2001, Acta. Crystal. D. Biol. Crystal. 57:168-71); and 4) tyrosine sulfation at their antigen binding sites that likely mimics the sulfated N-terminus of CCR5 (Choe et al., 2003, Cell 114:161-70). Although the challenge of generating such antibodies with vaccine preparations may seem daunting, the monoclonal antibodies noted above were all derived from infected humans, and thus provide a strong indication that native immune responses to HIV exist that will produce broadly neutralizing antibodies when immunogens are designed that elicit them.

Given the failure of monomeric gp120 to elicit antibodies that neutralize or even react with native Env trimers of diverse isolates (Parren et al., 1999, AIDS 13:S137-S162), it is likely that Env-based immunogens will need to present relevant epitopes in the context of trimeric Env. Although attempts are underway to stabilize soluble Env trimers (Binley et al., 2000, J. Virol. 74:627-643; Yang et al., 2000, J. Virol. 74:5716-5725; Yang et al., 2002, J. Virol. 76:4634-42) or to present trimers on inactivated viral particles (Lifson et al., 2002, J. Med. Primatol. 31:205-16; Willey et al., 2003, J. Virol. 77:1163-74) or proteoliposomes (Grundner et al., 2002, J. Virol. 76:3511-21), little is known about modifications of Env that can enhance neutralizing antibody responses. Approaches have included gp120s that are deleted of variable loops (Barnett et al., 2001, J. Virol. 75:5526-40; Kim et al., 2003, Virology 305:124-37; Lu et al., 1998, AIDS Res. Hum. Retroviruses 14:151-5; Sanders et al., 2000, J. Virol. 74:5091-5100; Srivastava et al., 2003, J. Virol. 77:2310-20; Stamatatos et al., 1998, AIDS Res. Hum. Retrbviruses 14:1129-1139), deglycosylated (Bolmstedt et al., 2001, Vaccine 20:397-405; Reitter et al., 1998, Nature Med. 4:679-684), bound to CD4 (Dey et al., 2003, J. Virol. 77:2859-65; Fouts et al., 2002, Proc. Natl. Acad. Sci. USA 99:11842-7), or structurally modified to mimic a CD4-bound state (Xiang et al., 2002, J. Virol. 76:9888-99). Given the conserved nature of gp120 core domains between a neutralization-sensitive, lab-adapted isolate and a neutralization-resistant, primary isolate (Kwong et al., 2000, Structure Fold Des 8:1329-39), it is likely that differences in the overlying hypervariable loops play a central role in determining neutralization resistance, providing some rationale for deleting these structures from potential immunogens. Moreover, broadly neutralizing antibodies tend to recognize discontinuous epitopes on the gp120 core while type specific antibodies react with variable loops (Ho et al., 1991, J. Virol. 65:489-493; Posner et al., 1991, J. Immunol. 146:4325-4332; Thali et al., 1992, J. Virol. 66(9):5635; Trkola et al., 1996, Nature 384:184-7; Wu et al., 1996, Nature 384:179-183).

A drawback to genetic or biochemical modifications of gp120 is the potential to disrupt Env structure, ablating relevant epitopes that are exposed during entry. In this regard, Envs have been derived from HIV-1 (Wyatt et al., 1993, J. Virol. 67:4557-4565), SIV (Johnson et al., 2003, J. Virol. 77:375-81; Puffer et al., 2002, J. Virol. 76:2595-605) and SHIVs (Stamatatos et al., 1998, J. Virol. 72:7840-7845) with V1 and/or V2 deletions that remain replication competent, thereby preserving key functional domains. In one study soluble Env from a replication competent SHIV with a V2 deletion elicited a more broadly reactive and qualitatively different humoral immune response with increased reactivity to V3 and C5 domains (Barnett et al., 2001, J. Virol. 75:5526-40). However, this "minimalist" approach to Env modification has been limited by the extent to which Envs retain function and by inference biologically relevant domains after variable loops are deleted (Kim et al., 2003, Virology 305: 124-37; Wyatt et al., 1993, J. Virol. 67:4557-4565). Studies with soluble Envs containing more extensive variable loop deletions have been disappointing, likely due to perturbations in Env structure (Kim et al., 2003, Virology 305:124-37; Sanders et al., 2000, J. Virol. 74:5091-5100). Indeed, even partial deletions of the V3 loop (Wyatt et al., 1998, Nature 393:705-711) have resulted in fusion-defective Envs (Wyatt et al., 1995, J. Virol. 69:5723-5733; Wyatt et al., 1993, J. Virol. 67:4557-4565), consistent with its importance in coreceptor binding (Dragic et al., 2001, J. Gen. Virol. 82:1807-14).

HIV is particularly adept in evading humoral immune responses, a feature that likely contributes to the ability of this virus to establish a persistent infection. Although neutralizing antibodies are produced to viral envelope glycoproteins (Env), such antibodies are characteristically directed to hypervariable loops on gp120 (V1/V2 and V3), which can tolerate extensive genetic variation. These antibodies are in general "type specific" and easily circumvented by ongoing viral mutations.

The variable loops also serve to protect domains on the core of gp120, which include highly conserved binding sites for CD4 and chemokine receptors (CCR5 and CXCR4) that are required for entry into target cells. In order for broadly neutralizing antibodies to be produced against HIV, it is likely that these and/or other conserved domains will need to be targeted. A priority for HIV vaccine research efforts is to develop envelope-based immunogens that can elicit these antibodies.

For one simian immunodeficiency virus (SIV) and for HIV-1 Env proteins, it has been shown that V1/V2 can be deleted while preserving replication competence. These V1/V2-deleted viruses have exhibited novel biological properties including CD4-independence, increased neutralization sensitivity, and/or attenuated pathogenicity. In the SIV model, these proteins are under evaluation as vaccine candidates. However, to date, viruses with V3 deletions have not been generated, and it has been generally viewed that the V3 loop is indispensable for viral entry.

It has been an ongoing objective to identify determinants of HIV infectivity as well as determinants that enable it to evade the host immune response in order to gain an understanding of the means by which the virus establishes and maintains infection in the host. Despite the critical nature of the gp120 V1/V2 loops, it has been shown that deletion of the V1/V2 loops from HIV-1 (and SIV) does not abolish viral infectivity. Accordingly, there is a long-felt need to understand the minimal elements of the envelope glycoprotein that are essential for infection, as well as those that are required for immune evasion. Such an understanding is crucial to the development of immunogens capable of eliciting broadly neutralizing antibodies to HIV.

There is an urgent need to develop a vaccine that can prevent HIV infection. Evidence from infected humans and nonhuman primate models suggests both cellular and humoral immune responses can exert at least some control of virus infection in vivo (Amara et al., 2001, Science 292:69-74, Barouch et al., 2000, Science 290:486-92; Borrow et al., 1994, Journal of Virology 68:6103-6110; Egan et al., 2000, J. Virol. 74:7485-95; Gauduin et al., 1997, Nature Med. 3:1389-1393; Jin et al., 1999, J. Exp. Med. 189:991-998; Johnson et al., 2003, J. Virol. 77:375-81; Koup et al., 1994, J. Virol. 68:4650-4655; Kuroda et al., 1999, J. Immunol. 162:5127-5133; Mascola et al., 1999, J. Virol. 73:4009-4018; Mascola et al., 2000, Nat. Med. 6:207-210; Matano et al., 1998, J. Virol. 72:164-9; Parren et al., 2001, J. Virol. 75:8340-7; Schmitz et al., 1999, Science 283:857-860; Schmitz et al., 2003, J. Virol. 77:2165-73; Seth et al., 2000, J. Virol. 74:2502-9), and there is a growing consensus that both will be required to develop a vaccine that either blocks transmission or prevents disease onset (McMichael et al., 2003, Nature Med. 9:874-80). In addition, for protective immunity to be achieved, there is increasing evidence that broadly neutralizing antibodies will be required. Vaccines that elicit a primarily cellular immune response can delay or possibly prevent the onset of disease but in general fail to prevent infection (Barouch et al., 2000, Science 290:486-92; Robinson et al., 1999, Nature Med. 5:526-534; Shiver et al., 2002, Nature 415:331-5). However, in some animal models the level of neutralizing antibodies has correlated with protection from a viral challenge (Berman et al., 1992, J. Virol. 66:4464-9; Emini et al., 1992, Nature 355:728-730; Nishimura et al., 2002, J. Virol. 76:2123-30; Parren et al., 2001, J. Virol. 75:8340-7), and protection from parenteral and mucosal challenges has been achieved by passive administration of neutralizing monoclonal and polyclonal antibodies (Baba et al., 2000, Nature Med. 6:200-206; Mascola et al., 1999, J. Virol. 73:4009-4018; Mascola et al., 2000, Nat. Med. 6:207-210; Poignard et al., 1999, Immunity. 10:431-438; Ruprecht et al., 2003, Vaccine 21:3370-3; Shibata, et al., 1999, Nat. Med. 5:204-210). Unfortunately, while it has become clear that broadly neutralizing antibodies are highly desirable, to date no immunogen has been able to elicit them with any degree of efficiency (McMichael et al., 2003, Nat. Med. 9:874-80). It is therefore crucial for research to address why an infected host fails to produce these antibodies and how vaccines can be designed that will overcome this obstacle.

To date, the ability of HIV-1 to escape the immune system has hindered development of efficacious vaccines to this important human pathogen. Thus, there is a long-felt and unfilled need for the development of effective vaccines and therapeutic modalities for HIV-1 infection in humans. The present invention meets those needs.

BRIEF SUMMARY OF THE INVENTION

The invention includes an isolated nucleic acid encoding a mammalian immunodeficiency virus glycoprotein (gp) 120 polypeptide, or a mutant, derivative, or fragment thereof, wherein the gp120 polypeptide comprises a deletion of hypervariable loop 3 (V3), and further comprises a compensatory mutation. In one aspect, the mammalian immunodeficiency virus is selected from the group consisting of a simian immunodeficiency virus (SIV), a human immunodeficiency virus type 1 (HIV-1), and a human immunodeficiency virus type 2 (HIV-2). In a further aspect, the mammalian immunodeficiency virus is HIV-2.

In yet a further aspect, the deletion of V3 is selected from the group consisting of a deletion of from about amino acid residue number 303 to amino acid residue number 324 (ΔV3 (6,6)) relative to the amino acid sequence of HIV-2/vcp gp120 as provided in SEQ ID NO:5, and a deletion from about amino acid residue number 298 to amino acid residue number 331 (ΔV3(1,1)) relative to the amino acid sequence of HIV-2/vcp gp120 as provided in SEQ ID NO:5.

In another aspect, the deletion of V3 is a deletion from about nucleotide number 894 to nucleotide number 1032 (ΔV3(1,1)) encoding from about amino acid residue number 298 to amino acid residue number 331 relative to the amino acid sequence of HIV-2/vcp gp120 as provided in SEQ ID NO:5.

In yet another aspect, the gp120 further comprises a deletion of the V1/V2 region.

The invention also includes an isolated nucleic acid encoding a mammalian immunodeficiency virus glycoprotein (gp) 120 polypeptide, or a mutant, derivative, or fragment thereof, wherein the gp120 polypeptide comprises a deletion of hypervariable loop 3 (V3), and further comprises a compensatory mutation, wherein the compensatory mutation is at least one mutation selected from the group consisting of an amino acid substitution from isoleucine to valine at amino acid residue number 55, an amino acid substitution from asparagine to aspartic acid at amino acid residue number 79, an amino acid substitution from phenylalanine to serine at amino acid residue number 94, an amino acid substitution from aspartic acid to glycine at amino acid residue number 142, an amino acid substitution from threonine to isoleucine at amino acid residue number 160, an amino acid substitution from alanine to threonine at amino acid residue number 173, an amino acid substitution from threonine to lysine at amino acid residue number 202, an amino acid substitution from glutamic acid to lysine at amino acid residue number 203, an amino acid substitution from threonine to isoleucine at amino acid residue number 231, an amino acid substitution from alanine to threonine at amino acid residue number 267, an amino acid substitution from asparagine to aspartic acid at amino acid residue number 279, an amino acid substitution from asparagine to aspartic acid at amino acid residue number 280, an amino acid substitution from glutamic acid to lysine at amino acid residue number 334, an amino acid substitution from glutamic acid to lysine at amino acid residue number 340, an amino acid substitution from asparagine to aspartic acid at amino acid residue number 391, an amino acid substitution from threonine to alanine at amino acid residue number 393, an amino acid substitution from glutamine to arginine at amino acid residue number 399, an amino acid substitution from valine to isoleucine at amino acid residue number 405, an amino acid substitution from valine to isoleucine at amino acid residue number 429, an amino acid substitution from glutamic acid to valine at amino acid residue number 437, an amino acid substitution from threonine to alanine at amino acid residue number 439, and an amino acid substitution from glycine to alanine at amino acid residue number 666, wherein the amino acid residue number of the compensatory mutation is relative to the amino acid sequence of parental HIV-2/vcp gp120 as provided in SEQ ID NO:5.

In another aspect, the V3 deletion is ΔV3(6,6) and further wherein the compensatory mutation is at least one amino acid substitution selected from the group consisting of an amino acid substitution from isoleucine to valine at amino acid residue number 55, an amino acid substitution from asparagine to aspartic acid at amino acid residue number 79, an amino acid substitution from threonine to lysine at amino acid residue number 202, an amino acid substitution from threonine to isoleucine at amino acid residue number 231, an amino acid substitution from alanine to threonine at amino acid residue number 267, and an amino acid substitution from asparagine to aspartic acid at amino acid residue number 391, wherein the amino acid residue number of the compensatory mutation is relative to the amino acid sequence of parental HIV-2/vcp gp120 as provided in SEQ ID NO:5.

In yet another aspect, the V3 deletion is ΔV3(6,6) and further wherein the compensatory mutation is at least one amino acid substitution selected from the group consisting of an amino acid substitution from isoleucine to valine at amino acid residue number 55, an amino acid substitution from asparagine to aspartic acid at amino acid residue number 79, an amino acid substitution from phenylalanine to serine at amino acid residue number 94, an amino acid substitution from asparagine to aspartic acid at amino acid residue number 280, and an amino acid substitution from asparagine to aspartic acid at amino acid residue number 391, wherein the amino acid residue number of the compensatory mutation is relative to the amino acid sequence of parental HIV-2/vcp gp120 as provided in SEQ ID NO:5.

In yet a further aspect, the V3 deletion is ΔV3(6,6) and further wherein the compensatory mutation is at least one amino acid substitution selected from the group consisting of an amino acid substitution from threonine to alanine at amino acid residue number 393, and an amino acid substitution from valine to isoleucine at amino acid residue number 429, wherein the amino acid residue number of the compensatory mutation is relative to the amino acid sequence of parental HIV-2/vcp gp120 as provided in SEQ ID NO:5.

In another aspect, the V3 deletion is ΔV3(1,1) and further wherein the compensatory mutation is at least one of an amino acid substitution selected from the group consisting of an amino acid substitution from alanine to threonine at amino acid residue number 173, an amino acid substitution from glutamic acid to lysine at amino acid residue number 203, an amino acid substitution from threonine to alanine at amino acid residue number 393, an amino acid substitution from glutamine to arginine at amino acid residue number 405, an amino acid substitution from valine to isoleucine at amino acid residue number 429, an amino acid substitution from threonine to alanine at amino acid residue number 439, and an amino acid substitution from glycine to alanine at amino acid residue number 666, wherein the amino acid residue number of the compensatory mutation is relative to the amino acid sequence of parental HIV-2/vcp gp120 as provided in SEQ ID NO:5.

The invention includes an isolated nucleic acid encoding a mammalian immunodeficiency virus glycoprotein (gp) 120 polypeptide, or a mutant, derivative, or fragment thereof, wherein the gp120 polypeptide comprises a deletion of hypervariable loop 3 (V3), a deletion of hypervariable loops V1/V2, and further comprises a compensatory mutation wherein the nucleic acid sequence of the nucleic acid is selected from the group consisting of the sequence of SEQ ID NO:11, the sequence of SEQ ID NO:17, and the sequence of SEQ ID NO:29.

In one aspect, the deletion is selected from the group consisting of a deletion from about amino acid residue number 303 to amino acid residue number 324 (ΔV3(6,6)), and a deletion from about amino acid residue number 298 to amino acid residue number 331 (ΔV3(1,1)), relative to the amino acid sequence of HIV-2/vcp gp120 as provided in SEQ ID NO:5.

The invention includes an isolated nucleic acid encoding a mammalian immunodeficiency virus glycoprotein (gp) 120 polypeptide, or a mutant, derivative, or fragment thereof, wherein the gp120 polypeptide comprises a ΔV3(6,6) deletion, and further comprises a compensatory mutation wherein the nucleic acid sequence of the nucleic acid comprises the sequence of SEQ ID NO:23.

In one aspect, the isolated nucleic acid encoding a mammalian immunodeficiency virus glycoprotein (gp) 120 polypeptide, or a mutant, derivative, or fragment thereof, wherein the gp120 polypeptide comprises a deletion of hypervariable loop 3 (V3), and further comprises a compensatory mutation, the sequence of the nucleic acid is at least one sequence selected from the group consisting of SEQ ID NO:8, SEQ ID NO:14, SEQ ID NO:20, and SEQ ID NO:26.

In another aspect, the amino acid sequence of the gp120 polypeptide encoded by the nucleic acid is selected from the group consisting of the amino acid sequence of SEQ ID NO:11, the amino acid sequence of SEQ ID NO:17, the amino acid sequence of SEQ ID NO:23, and the amino acid sequence of SEQ ID NO:29.

The invention includes an isolated nucleic acid encoding a mammalian immunodeficiency virus gp41 polypeptide, wherein the gp41 polypeptide comprises a compensatory mutation.

In one aspect, the nucleic acid sequence of the isolated nucleic acid is selected from the group consisting of the nucleic acid sequence of SEQ ID NO:9, the sequence of SEQ ID NO:15, the sequence of SEQ ID NO:21, and the sequence of SEQ ID NO:27.

In another aspect, the amino acid sequence of the gp41 polypeptide encoded by the nucleic acid is selected from the group consisting of the amino acid sequence of SEQ ID NO:12, the amino acid sequence of SEQ ID NO:18, the amino acid sequence of SEQ ID NO:24, and the amino acid sequence of SEQ ID NO:30.

In yet a further aspect, the compensatory mutation is at least one mutation selected from the group consisting of an amino acid substitution from leucine to valine at amino acid residue number 518, an amino acid substitution from alanine to threonine at amino acid residue number 529, an amino acid substitution from isoleucine to valine at amino acid residue number 531, an amino acid substitution from alanine to threonine at amino acid residue number 561, and an amino acid substitution from alanine to threonine at amino acid residue number 673, wherein the amino acid residue number of the compensatory mutation is relative to the amino acid sequence of HIV-2/vcp gp41 (SEQ ID NO:6).

In yet another aspect, the compensatory mutation is a truncation of the cytoplasmic domain.

In another aspect, the truncation is selected from the group consisting of a truncation at amino acid residue number 733, a truncation at amino acid residue number 753, a truncation at amino acid residue number 764, wherein the amino acid residue number of the truncation is relative to the amino acid sequence of HIV-2/vcp gp41 (SEQ ID NO:6).

The invention includes an isolated mammalian immunodeficiency virus gp120 polypeptide, wherein the polypeptide comprises a substantial deletion of V3 and further comprises a compensatory mutation. In one aspect, the polypeptide is fusogenic.

In yet another aspect, the mammalian immunodeficiency virus is selected from the group consisting of a simian immunodeficiency virus (SIV), a human immunodeficiency virus type 1 (HIV-1), and a human immunodeficiency virus type 2 (HIV-2).

In a further aspect, the mammalian immunodeficiency virus is HIV-2.

In yet a further aspect, the deletion of V3 is selected from the group consisting of a deletion of from about amino acid residue number 303 to amino acid residue number 324 (ΔV3(6,6)) relative to the amino acid sequence of HIV-2/vcp gp120 as provided in SEQ ID NO:5, and a deletion from about amino acid residue number 298 to amino acid residue number 331 (ΔV3(1,1)) relative to the amino acid sequence of HIV-2/vcp gp120 as provided in SEQ ID NO:5.

In another aspect, the gp120 further comprises a deletion of the V1/V2 region.

In a further aspect, the compensatory mutation is at least one mutation selected from the group consisting of an amino acid substitution from isoleucine to valine at amino acid residue number 55, an amino acid substitution from asparagine to aspartic acid at amino acid residue number 79, an amino acid substitution from phenylalanine to serine at amino acid residue number 94, an amino acid substitution from aspartic acid to glycine at amino acid residue number 142, an amino acid substitution from threonine to isoleucine at amino acid residue number 160, an amino acid substitution from alanine to threonine at amino acid residue number 173, an amino acid substitution from threonine to lysine at amino acid residue number 202, an amino acid substitution from glutamic acid to lysine at amino acid residue number 203, an amino acid substitution from threonine to isoleucine at amino acid residue number 231, an amino acid substitution from alanine to threonine at amino acid residue number 267, an amino acid substitution from asparagine to aspartic acid at amino acid residue number 279, an amino acid substitution from asparagine to aspartic acid at amino acid residue number 280, an amino acid substitution from glutamic acid to lysine at amino acid residue number 334, an amino acid substitution from glutamic acid to lysine at amino acid residue number 340, an amino acid substitution from asparagine to aspartic acid at amino acid residue number 391, an amino acid substitution from threonine to alanine at amino acid residue number 393, an amino acid substitution from valine to isoleucine at amino acid residue number 399, an amino acid substitution from glutamine to arginine at amino acid residue number 405, an amino acid substitution from valine to isoleucine at amino acid residue number 429, an amino acid substitution from glutamic acid to valine at amino acid residue number 437, an amino acid substitution from threonine to alanine at amino acid residue number 439, and an amino acid substitution from glycine to alanine at amino acid residue number 666, wherein the amino acid residue number of the compensatory mutation is relative to the amino acid sequence of parental HIV-2/vcp gp120 as provided in SEQ ID NO:5.

In another aspect, the V3 deletion is ΔV3(6,6) and further wherein the compensatory mutation is at least one of an amino acid substitution selected from the group consisting of an amino acid substitution from isoleucine to valine at amino acid residue number 55, an amino acid substitution from asparagine to aspartic acid at amino acid residue number 79, an amino acid substitution from threonine to lysine at amino acid residue number 202, an amino acid substitution from threonine to isoleucine at amino acid residue number 231, an amino acid substitution from alanine to threonine at amino acid residue number 267, and an amino acid substitution from asparagine to aspartic acid at amino acid residue number 391, wherein the amino acid residue number of the compensatory mutation is relative to the amino acid sequence of parental HIV-2/vcp gp120 as provided in SEQ ID NO:5.

In yet another aspect, the V3 deletion is ΔV3(6,6) and further wherein the compensatory mutation is at least one of an amino acid substitution selected from the group consisting of an amino acid substitution from isoleucine to valine at amino acid residue number 55, an amino acid substitution from asparagine to aspartic acid at amino acid residue number 79, an amino acid substitution from phenylalanine to serine at amino acid residue number 94, an amino acid substitution from asparagine to aspartic acid at amino acid residue number 280, and an amino acid substitution from asparagine to aspartic acid at amino acid residue number 391, wherein the amino acid residue number of the compensatory mutation is relative to the amino acid sequence of parental HIV-2/vcp gp120 as provided in SEQ ID NO:5.

In a further aspect, the V3 deletion is ΔV3(6,6) and further wherein the compensatory mutation is at least one of an amino acid substitution selected from the group consisting of an amino acid substitution from threonine to alanine at amino acid residue number 393, and an amino acid substitution from valine to isoleucine at amino acid residue number 429, wherein the amino acid residue number of the compensatory mutation is relative to the amino acid sequence of parental HIV-2/vcp gp120 as provided in SEQ ID NO:5.

In yet a further aspect, the V3 deletion is ΔV3(1,1) and further the compensatory mutation is at least one of an amino acid substitution selected from the group consisting of an amino acid substitution from alanine to threonine at amino acid residue number 173, an amino acid substitution from glutamic acid to lysine at amino acid residue number 203, an amino acid substitution from threonine to alanine at amino acid residue number 393, an amino acid substitution from glutamine to arginine at amino acid residue number 405, an amino acid substitution from valine to isoleucine at amino acid residue number 429, an amino acid substitution from threonine to alanine at amino acid residue number 439, and an amino acid substitution from glycine to alanine at amino acid residue number 666, wherein the amino acid residue number of the compensatory mutation is relative to the amino acid sequence of parental HIV-2/vcp gp120 as provided in SEQ ID NO:5.

The invention includes an isolated gp120 polypeptide, or a mutant, derivative, or fragment thereof, wherein the gp120 polypeptide comprises a deletion of hypervariable loop 3 (V3), a deletion of hypervariable loops V1/V2, and further comprises a compensatory mutation wherein the amino acid sequence of the gp120 polypeptide is selected from the group consisting of the sequence of SEQ ID NO:11, the sequence of SEQ ID NO:17, and the sequence of SEQ ID NO:29.

The invention includes an isolated gp120 polypeptide, or a mutant, derivative, or fragment thereof, wherein the gp120 polypeptide comprises a deletion of hypervariable loop 3 (V3), and further comprises a compensatory mutation wherein the amino acid sequence of the gp120 polypeptide comprises the sequence of SEQ ID NO:23.

The invention includes an isolated mammalian immunodeficiency virus gp41 polypeptide, wherein the gp41 comprises a compensatory mutation.

In one aspect, the compensatory mutation is at least one mutation selected from the group consisting of an amino acid substitution from leucine to valine at amino acid residue number 518, an amino acid substitution from alanine to threonine at amino acid residue number 529, an amino acid substitution from isoleucine to valine at amino acid residue number 531, an amino acid substitution from alanine to threonine at amino acid residue number 561, and an amino acid substitution from alanine to threonine at amino acid residue number 673, wherein the amino acid residue number of the compensatory mutation is relative to the amino acid sequence of HIV-2/vcp gp41 (SEQ ID NO:6).

In another aspect, the compensatory mutation is a truncation of the cytoplasmic domain.

In yet another aspect, the truncation is selected from the group consisting of a truncation at amino acid 733, a truncation at amino acid 753, and a truncation at amino acid 764, wherein the amino acid residue number of the compensatory mutation is relative to the amino acid sequence of HIV-2/vcp gp41 (SEQ ID NO:6).

In another aspect, the amino acid sequence of the polypeptide is selected from the group consisting of the sequence of SEQ ID NO:12, the sequence of SEQ ID NO:18, the sequence of SEQ ID NO:24, and the sequence of SEQ ID NO:30.

The invention also includes a composition comprising a mammalian immunodeficiency virus gp120 polypeptide, wherein the gp120 polypeptide comprises a substantial deletion of V3, and a pharmaceutically acceptable carrier.

In one aspect, the composition further comprising a mammalian immunodeficiency virus gp41 polypeptide, wherein the gp41 comprises a compensatory mutation.

In yet another aspect, the gp120 further comprises a deletion of V1/V2.

In a further aspect, the amino acid sequence of the gp120 polypeptide comprises at least one sequence selected from the group consisting of the sequence of the sequence of SEQ ID NO:11, the sequence of SEQ ID NO:17, and the sequence of SEQ ID NO:29.

In yet a further aspect, the amino acid sequence of the gp41 polypeptide comprises at least one sequence selected from the group consisting of the sequence of the sequence of SEQ ID NO:12, the sequence of SEQ ID NO:18, and the sequence of SEQ ID NO:30.

In another aspect, the amino acid sequence of the gp120 polypeptide comprises at least one sequence selected from the group consisting of the sequence of the sequence of SEQ ID NO:11, the sequence of SEQ ID NO:17, the sequence of SEQ ID NO:23, and the sequence of SEQ ID NO:29.

In yet another aspect, the amino acid sequence of the gp41 polypeptide comprises at least one sequence selected from the group consisting of the sequence of the sequence of SEQ ID NO:12, the sequence of SEQ ID NO:18, the sequence of SEQ ID NO:24, and the sequence of SEQ ID NO:30.

The invention includes an isolated mammalian immunodeficiency virus, the virus comprising a gp120 polypeptide wherein the gp120 comprises a substantial deletion of V3.

In one aspect, the virus is fusion-competent.

In another aspect, the virus is replication-competent.

In yet another aspect, the virus further comprises a gp41 polypeptide wherein the gp41 comprises a compensatory mutation.

In a further aspect, the gp120 polypeptide comprises a compensatory mutation.

In another aspect, the amino acid sequence of the gp120 polypeptide comprises at least one sequence selected from the group consisting of the sequence of the sequence of SEQ ID NO:11, the sequence of SEQ ID NO:17, the sequence of SEQ ID NO:23, and the sequence of SEQ ID NO:29.

In yet a further aspect, the amino acid sequence of the gp41 polypeptide comprises at least one sequence selected from the group consisting of the sequence of the sequence of SEQ ID NO:12, the sequence of SEQ ID NO:18, the sequence of SEQ ID NO:24, and the sequence of SEQ ID NO:30.

The invention includes an isolated mammalian immunodeficiency virus Env, wherein the Env comprises a substantial deletion of V3 and further wherein the Env is fusogenic.

In one aspect, the amino acid sequence of the Env comprises at least one sequence selected from the group consisting of the sequence of SEQ ID NO:10, the sequence of SEQ ID NO:16, the sequence of SEQ ID NO:22, and the sequence of SEQ ID NO:28.

The invention includes a method of producing a neutralizing antibody in a mammal in need thereof, the method comprising administering to a mammal an immunogenic amount of an isolated gp120, wherein the gp120 comprises a substantial deletion of V3, and further comprises a deletion of V1/V2, thereby producing the neutralizing antibody in the mammal.

In one aspect, the invention includes an antibody produced by this method.

In a further aspect, the amino acid sequence of the isolated gp120 comprises at least one sequence selected from the group consisting of the sequence of SEQ ID NO:11, the sequence of SEQ ID NO:17, the sequence of SEQ ID NO:23, and the sequence of SEQ ID NO:29.

In another aspect, the gp120 further comprises a deletion of V4.

The invention includes a method of eliciting a neutralizing antibody in a mammal, the method comprising administering an immunogenic amount of a composition comprising a mammalian immunodeficiency virus gp120 polypeptide, wherein said gp120 polypeptide comprises a substantial deletion of V3, and a pharmaceutically acceptable carrier, and the composition further comprises a mammalian immunodeficiency virus gp41 polypeptide, wherein said gp41 comprises a compensatory mutation, and wherein the gp120 further comprises a deletion of V1/V2, thereby eliciting the neutralizing antibody in the mammal. The invention includes an antibody produced by this method.

In one aspect, the mammal is selected from the group consisting of an ape, and a human.

The invention includes a method of producing a replication-competent mammalian immunodeficiency virus comprising a deletion of at least one hypervariable loop domain. The method comprises:

a) producing a virus comprising gp120 wherein the gp120 comprises a deletion of V1/V2, the gp120 further comprising a substantial deletion of V3;

b) passaging the virus in cell culture and selecting for a virus that is capable of fusing with a cell;

c) introducing into the virus selected in (b) a gp41 comprising enhanced fusogenecity wherein the gp41 comprises at least one compensatory mutation; and d) passaging the virus of (c) in cell culture and selecting for a virus that is capable of fusing with a cell;

thereby producing the replication-competent virus.

In one aspect, the invention includes a replication-competent virus produced by this method.

The invention includes a method of identifying a determinant of a chemokine receptor that specifically binds with a gp120 polypeptide of a mammalian immunodeficiency virus. The method comprises contacting a high-affinity gp120 polypeptide of the virus with a panel of mutants of the chemokine receptor, assessing the binding of the gp120 polypeptide with each of the mutants, and comparing the binding of the gp120 with each of the mutants, thereby identifying the determinant of the chemokine receptor that specifically binds with the gp120.

The invention includes a method of identifying a compound that inhibits binding of a mammalian immunodeficiency virus gp120 polypeptide with a chemokine receptor. The method comprises assessing the level of binding of a gp120 polypeptide comprising a deletion of V1/V2, and a substantial deletion of V3, wherein the gp120 is fusogenic, with a chemokine receptor in the presence of a compound, and comparing the level of binding of the gp120 with the chemokine receptor in the presence of the compound with the binding of an otherwise identical gp120 with an otherwise identical chemokine receptor in the absence of the compound, wherein a lower level of binding of the gp120 with the chemokine receptor in the presence of the compound compared with the level of binding of the otherwise identical gp120 with the otherwise identical chemokine receptor in the absence of the compound is an indication that the compound inhibits binding of the gp120 with the chemokine receptor, thereby identifying a compound that inhibits binding of the gp120 with the chemokine receptor.

The invention includes a kit for producing an immunodeficiency virus-neutralizing antibody in a mammal. The kit comprises an immunogenic amount of a gp120 polypeptide of the mammalian immunodeficiency virus, wherein the gp120 comprises a deletion of V1/V2, and a substantial deletion of V3, the kit further comprising an applicator, and an instructional material for the use thereof.

In one aspect, the amino acid sequence of the gp120 polypeptide is at least one sequence selected from the group consisting of group consisting of the sequence of SEQ ID NO:11, the sequence of SEQ ID NO:17, the sequence of SEQ ID NO:23, and the sequence of SEQ ID NO:29.

The invention includes a kit for producing an immunodeficiency virus-neutralizing antibody in a mammal. The kit comprises an immunogenic amount of a mammalian immunodeficiency virus Env, wherein the Env comprises a deletion of V1/V2, and a substantial deletion of V3, and further wherein the Env comprises a compensatory mutation. The kit further comprises an applicator, and an instructional material for the use thereof.

In one aspect, the amino acid sequence of the Env comprises at least one sequence selected from the group consisting of the sequence of SEQ ID NO:10, the sequence of SEQ ID NO:16, the sequence of SEQ ID NO:22, and the sequence of SEQ ID NO:28.

The invention includes a kit for eliciting a neutralizing antibody in a mammal. The kit comprising an immunogenic amount of a composition comprising a mammalian immunodeficiency virus gp120 polypeptide, wherein said gp120 polypeptide comprises a substantial deletion of V3, and a pharmaceutically acceptable carrier, and the composition further comprises a mammalian immunodeficiency virus gp41 polypeptide, wherein said gp41 comprises a compensatory mutation, and wherein the gp120 further comprises a deletion of V1/V2. The kit further comprises an applicator, and an instructional material for the use thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 19A sets out the amino acid sequence of HIV-2/VCP Clone 8c.3 Env. (SEQ ID NO:28). The cleavage site used to produce gp120 and gp41 is underlined.

FIG. 19B sets out the nucleic acid sequence encoding HIV-2/VCP Clone 8c.3 Env. (SEQ ID NO:25).

FIG. 19C depicts the amino acid sequence of HIV-2/VCP Clone 8c.3 gp120 (SEQ ID NO:29).

FIG. 19D depicts the nucleic acid sequence encoding HIV-2/VCP Clone 8c.3 gp120 (SEQ ID NO:26).

FIG. 19E depicts the amino acid sequence of HIV-2/VCP Clone 8c.3 gp41 (SEQ ID NO:30).

FIG. 19F depicts the nucleic acid sequence encoding HIV-2/VCP Clone 8c.3 gp41 (SEQ ID NO:27).

FIG. 21A sets out the amino acid sequence of HIV-2/VCP Env (SEQ ID NO:4). The cleavage site used to produce gp120 and gp41 is underlined.

FIG. 21B sets out the complete nucleic acid sequence encoding HIV-2/VCP Env (SEQ ID NO:1).

FIG. 21C depicts the amino acid sequence of HIV-2/VCP gp120 (SEQ ID NO:5).

FIG. 21D depicts the nucleic acid sequence encoding HIV-2/VCP gp120 (SEQ ID NO:2).

FIG. 21E depicts the amino acid sequence of HIV-2/VCP gp41 (SEQ ID No. 6).

FIG. 21F depicts the nucleic acid sequence encoding HIV-2/VCP gp41 (SEQ ID NO:3).

FIG. 22A sets out the amino acid sequence of HIV-2/VCP Clone p16.5 Env. (SEQ ID NO:10). The cleavage site used to produce gp120 and gp41 is underlined.

FIG. 22B sets out the nucleic acid sequence encoding HIV-2/VCP Clone p16.5 Env (SEQ ID NO:7).

FIG. 22C depicts the amino acid sequence of HIV-2/VCP Clone p16.5 gp120 (SEQ ID NO:11).

FIG. 22D depicts the nucleic acid sequence encoding HIV-2/VCP Clone p16.5 gp120 (SEQ ID NO:8).

FIG. 22E depicts the amino acid sequence of HIV-2/VCP Clone p16.5 gp41 (SEQ ID NO:12).

FIG. 22F depicts the nucleic acid sequence encoding HIV-2/VCP Clone p16.5 gp41 (SEQ ID NO:9).

FIG. 23A sets out the amino acid sequence of HIV-2/VCP Clone p16.7 Env (SEQ ID NO:16). The cleavage site used to produce gp120 and gp41 is underlined.

FIG. 23B sets out the nucleic acid sequence encoding HIV-2/VCP Clone p16.7 Env (SEQ ID NO:13).

FIG. 23C depicts the amino acid sequence of HIV-2/VCP Clone p16.7 gp120 (SEQ ID NO:17).

FIG. 23D depicts the nucleic acid sequence encoding HIV-2/VCP Clone p16.7 gp120 (SEQ ID NO:14).

FIG. 23E depicts the amino acid sequence of HIV-2/VCP Clone p16.7 gp41 (SEQ ID NO:18).

FIG. 23F depicts the nucleic acid sequence encoding HIV-2/VCP Clone p16.7 gp41 (SEQ ID NO:15).

FIG. 24A sets out the complete amino acid sequence of HIV-2/VCP Clone p16.9 Env. (SEQ ID NO:22). The cleavage site used to produce gp120 and gp41 is underlined.

FIG. 24B sets out the complete nucleic acid sequence encoding HIV-2/VCP Clone p16.9 Env. (SEQ ID NO:19).

FIG. 24C depicts the amino acid sequence of HIV-2/VCP Clone p16.9 gp120 (SEQ ID NO:23).

FIG. 24D depicts the nucleic acid sequence encoding HIV-2/VCP Clone p16.9 gp120 (SEQ ID NO:20).

FIG. 24E depicts the amino acid sequence of HIV-2/VCP Clone p16.9 gp41 (SEQ ID NO:24).

FIG. 24F depicts the nucleic acid sequence encoding HIV-2/VCP Clone p16.9 gp41 (SEQ ID NO:21).

DETAILED DESCRIPTION OF THE INVENTION

Figure 1A:
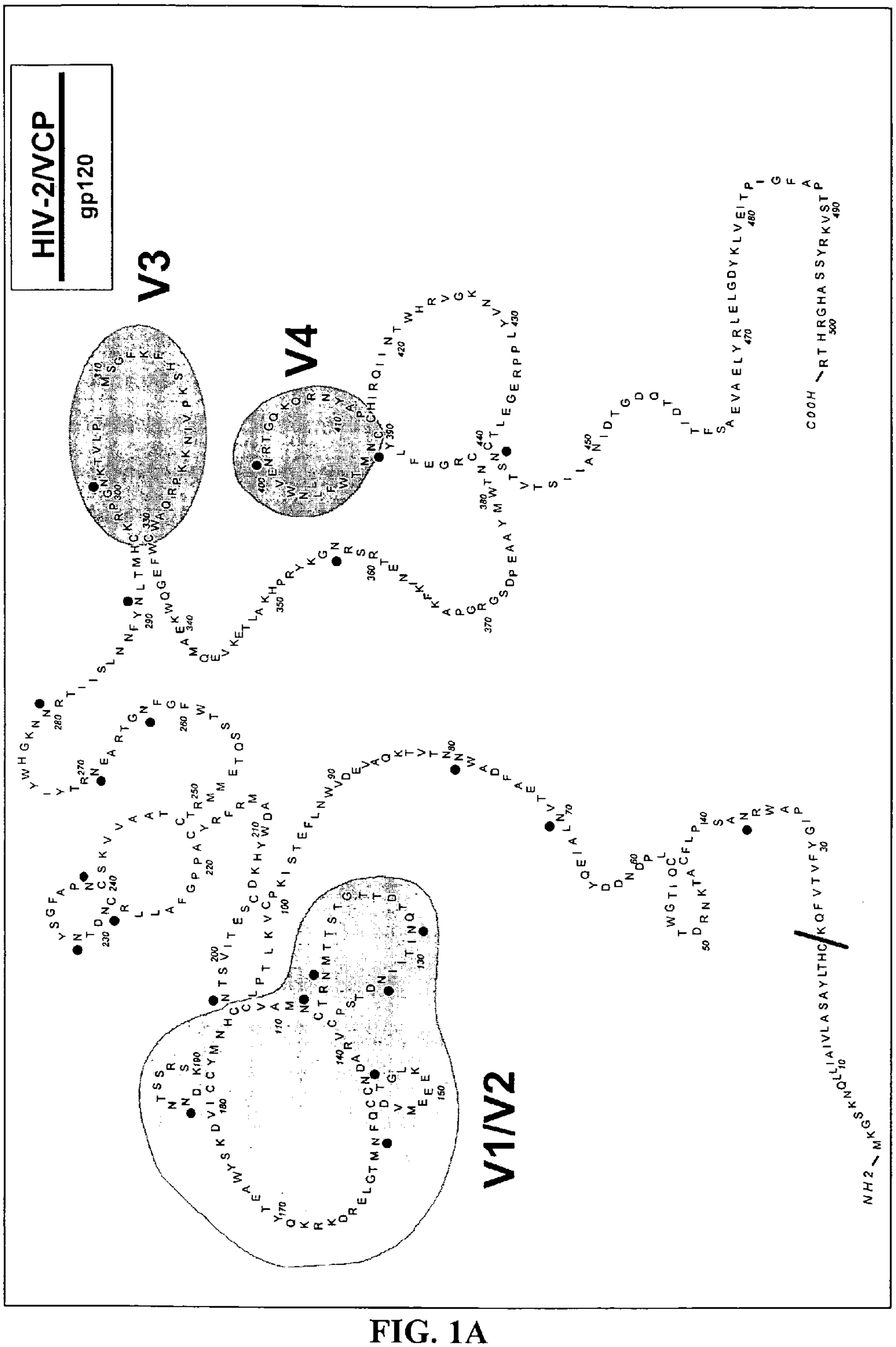
FIG. 1A is a diagram depicting the amino acid sequence, showing hypervariable loops formed by disulfide bonds at cysteines throughout the peptide, of parental HIV-2/VCP gp120.

The present invention relates to novel methods for producing novel mammalian immunodeficiency virus envelope proteins ("Envs") that conserve functional domains required for entry and/or replication while removing hypervariable loops and exposing core epitopes important for virus entry into cells and thereby providing useful constructs for development of therapeutic modalities relating to development of neutralizing antibodies.

The invention also relates to novel Env polypeptides (e.g., Env, gp120, gp41, and the like), and nucleic acids encoding the same, wherein V1 and V2 have been deleted therefrom, and further where the V3 region, or a substantial portion thereof, has also been removed from the polypeptide. Surprisingly, and despite contrary teachings thereto in the art, the data disclosed herein demonstrate, for the first time, that an Env lacking V1, V2, and at least a substantial portion of V3, or even the entire V3 region, can exhibit detectable function, including, but not limited to, binding with a ligand on a cell, fusion of the Env with the cell, and even replication competence, among other functions. These results are unprecedented and the data disclosed herein demonstrate that novel virus constructs, where hypervariable regions, including V3, have been removed, can be used as potential therapeutics to develop, among other things, useful virus neutralizing antibodies and compounds, such as small molecules, peptidomimetics and such, to inhibit virus infection. This is because the skilled artisan, armed with the teachings provided herein, would realize that the novel polypeptides, and nucleic acids encoding them, provide useful tools for elucidating the requisite interaction(s) between the virus Env and host cell surface ligands and further provide methods for developing and identifying molecules (such as, but not limited to, antibodies, small molecules, peptidomimetics, and others) that can inhibit these interactions thereby preventing infection or inhibiting further infection processes.

For example, and in no way limiting the invention to this, or any other, particular virus construct, it has been shown in the present invention, using an HIV-2 isolate known for its CD4-independent use of CXCR4 and CCR5 and its high affinity binding to CXCR4 as an exemplary system, that variants can be adapted for replication with truncated or even absent V3 loops. Prior to this finding, V3 has been considered and essential for viral entry as a result of its well-documented interactions with cellular chemokine receptors. The data disclosed herein demonstrate that adaptations enabling viruses to replicate in the absence of hypervariable loops entail novel compensatory mutations in gp120 and/or in gp41 that were selected during long term propagation in vitro. In one aspect of the invention, high efficiency replication has been achieved with Envs lacking V1/V2 and all but the first and last 6 amino acids of V3 flanking the disulfide bond forming the loop, termed ΔV3(6,6) and yielding a "gp12o" of only about 75 kD compared to full-length gp120 of about 120 kD in size. Therefore, critical protein function(s) have been remarkably conserved despite a reduction in the size of the polypeptide of almost 40%. Surprisingly, deletion of all but two amino acids flanking the disulfide bond, termed ΔV3(1,1), still maintained the fusogenicity of the construct while removing most, if not all, of V1/V2, and V3 regions. These remarkable accomplishments were achieved despite the widely held belief in the art that these mutants could not be produced because the V3 region was essential to Env function.

Thus, in one aspect, the present invention provides, for the first time, that HIVs can replicate without V3 (as well as V1/V2) while maintaining essential functional domains for cell binding, fusion and/or entry. Without wishing to be bound by any particular theory, the data disclosed herein support an evolutionary model suggesting that Envs of modern lentiviruses evolved from a primordial core protein, and that hypervariable loops were subsequently acquired not only to facilitate chemokine receptor utilization and to mediate specificity, but also to enable these viruses to replicate in the face of coevolving host immune responses. The data disclosed herein demonstrate for the first time, that functional "core" Env can be produced. This is an important breakthrough because such functional core particles, wherein potential neutralizing antibody-eliciting epitopes are exposed and presented in a useful context of a functional molecule, can be used to develop potentially therapeutic virus neutralizing antibodies to these important human pathogens. Given the current state of the art regarding the generation of broadly neutralizing antibodies, the minimized, functional Envs of the invention are useful for generating novel immune responses and provide a major achievement in the development of useful treatments for these devastating human pathogens.

In addition to vaccine potential, the V3-truncated or V3-deleted viruses of the present invention exhibit novel functional properties useful for development of various non-vaccine-based therapeutics. For example, although they can utilize CXCR4, mammalian immunodeficiency viruses of the invention show greater dependence on the CXCR4 N-terminus, in marked contrast to other X4 tropic strains, which utilize primarily the extracellular loops (ECL). Consistent with this, they become resistant to the CXCR4 inhibitor AMD3100, which is thought to interact with the extracellular loops of the receptor. This activity may reveal a mechanism by which HIV can acquire resistance to both CCR5 and CXCR4 inhibitors and thus provide an important system for design and development of therapeutics that prevent virus acquisition of such resistance. Moreover, replication competent, V3-truncated/deleted viruses of the invention can also utilize CCR5 to infect cells, and this property indicates that this dual-tropism in the absence of V3 is based on involvement of a conserved interaction between the bridging sheet domain on the Env core with a motif shared on the N-termini of CXCR4 and CCR5. These data demonstrate potential new drug targets for treatment of viral infection and provide useful tools for development of novel therapeutics relating to inhibiting these interactions now identified for the first time herein.

Definitions

The articles "a" and "an" are used herein to refer to one or to more than one (i.e. to at least one) of the grammatical object of the article. By way of example, "an element" means one element or more than one element.

As used herein, "amino acids" are represented by the full name thereof, by the three-letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |

-continued

| Full Name | Three-Letter Code | One-Letter Code |
|---|---|---|
| Phenylalanine | Phe | F |
| Tryptophan | Trp | W |

By the term "applicator," as the term is used herein, is meant any device including, but not limited to, a hypodermic syringe, a pipette, and the like, for administering the compounds and compositions of the invention.

"Instructional material," as that term is used herein, includes a publication, a recording, a diagram, or any other medium of expression which can be used to communicate the usefulness of the composition and/or compound of the invention in the kit for effecting alleviating or treating the various diseases or disorders recited herein. Optionally, or alternately, the instructional material may describe one or more methods of producing a mutant peptide of the invention, as disclosed elsewhere herein.

The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively.

By an "isolated nucleic acid," as used herein, is meant a nucleic acid sequence, or a fragment thereof, which has been separated from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector; into an autonomously replicating plasmid or virus; or into the genomic DNA of a prokaryote or eukaryote; or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequences.

By the terms "isolated peptide," "isolated polypeptide," or "isolated protein," as used herein, is meant a peptide or protein which has been substantially separated from the components, e.g., DNA, RNA, other proteins and peptides, carbohydrates and lipids, which naturally accompany the protein or peptide in the cell.

The terms isolated peptide and protein may be construed to include a peptide or protein which is expressed and/or secreted from a cell comprising an isolated nucleic acid.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T." Conventional notation is used herein to describe polynucleotide sequences: the left-hand end of a single-stranded polynucleotide sequence is the 5' end; the left-hand direction of a double-stranded polynucleotide sequence is referred to as the 5'-direction.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A "compensatory mutation" refers to one or more specific amino acids in a polypeptide sequence, where the identity of the amino acid(s) differs from that found at the same position(s) in the wild type polypeptide sequence, for the purpose or with the result of altering the properties and/or activity of the polypeptide in response to a second change affecting the properties and/or activity of the polypeptide. For example, in response to the deletion of a stabilizing domain from a polypeptide sequence, one or more amino acid mutations may be induced in the remaining polypeptide sequence in order to detectably increase the stability of the truncated polypeptide compared with the stability of the polypeptide under otherwise identical conditions but in the absence of the mutation. As disclosed herein, deletion of a hypervariable region can mediate a detectable loss or decrease in a virus function or activity. A compensatory mutation is any mutation in another region of the polypeptide, or in another polypeptide, that detectably increases the level of the function or activity affected by the deletion. In viruses containing the ΔV3(6,6) deletion, mutations that increased the replicative capacity of the virus include a loss of glycosylation sites in gp120 and novel changes in HR1 and fusion domains of gp41. Subsequent deletion of remaining portions of V3 to generate a ΔV3( I,1) Env were associated with adaptive changes that included the appearance of positively charged residues distal to the disulfide bond of the V3 remnant. The data disclosed herein suggest that these compensatory changes facilitate gp120 binding to chemokine receptors and the triggering mechanisms involved in the activation of gp41 to initiate cell fusion. Although these mutations are preferred, the invention is not limited to these particular mutations.

By the term "fusogenic," as used herein, is meant that the protein and/or Env can mediate detectable fusion between the virus, or a component thereof, and cell, or a component thereof. Fusogenicity can be assessed using any assay known in the art, including those disclosed herein, as well as any assay developed in the future.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. As used in the present invention, the term "polypeptide" can refer to a sequence of as little as two amino acids linked by a peptide bond, or an unlimited number of amino acids linked by peptide bonds.

The term "protein" typically refers to large polypeptides.

The term "peptide" typically refers to short polypeptides.

A "mutant" polypeptide as used in the present application is one which has the identity of at least one amino acid altered when compared with the amino acid sequence of the naturally-occurring protein. Further, a mutant polypeptide may have at least one amino acid residue added or deleted to the amino acid sequence of the naturally-occurring protein.

Conventional notation is used herein to portray polypeptide sequences: the left-hand end of a polypeptide sequence is the amino-terminus; the right-hand end of a polypeptide sequence is the carboxyl-terminus.

By the term "vector" as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of an immunodeficiency virus Env protein or nucleic acid encoding the protein, to a cell or tissue or a patient, or the vector may be a non-viral vector which is suitable for the same purpose.

Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example, at the publicly available world wide website of the National Center for Biotechnology Information (NCBI) at the National Library of Medicine (NLM) at the National Institutes of Health (NIH). BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (id.) and relationships between molecules which share a common pattern. When utilizing BLAST, Gapped BLAST, PSI-Blast, and PHI-Blast programs, the default parameters of the respective programs (e.g., XBLAST and NBLAST) can be used all of which are publicly available at the world wide web site of the NCBI at the NLM at the NIH.

Techniques for introducing changes in nucleotide sequences that are designed to alter the functional properties of the encoded proteins or polypeptides are well known in the art. Such modifications include the deletion, insertion, or substitution of bases, and thus, changes in the amino acid sequence. As is known to one of skill in the art, nucleic acid insertions and/or deletions may be designed into the gene for numerous reasons, including, but not limited to modification of nucleic acid stability, modification of nucleic acid expression levels, modification of expressed polypeptide stability or half-life, modification of expressed polypeptide activity, modification of expressed polypeptide properties and characteristics, and changes in glycosylation pattern. All such modifications to the nucleotide sequences encoding such proteins are encompassed by the present invention.

It is not intended that methods of the present invention be limited by the nature of the nucleic acid employed. The target nucleic acid encompassed by methods and compositions of the invention may be native or synthesized nucleic acid. The nucleic acid may be DNA or RNA and may exist in a double-stranded, single-stranded or partially double-stranded form. Furthermore, the nucleic acid may be found as part of a virus or other macromolecule. See, e.g., Fasbender et al., 1996, J. Biol. Chem. 272:6479-89.

Fragments of nucleic acids encoding smaller than fill-length protein are also included in the present invention, provided the protein expressed by the nucleic acid retains the biological activity of the full-length protein.

The nucleic acids useful in methods and compositions of the invention may be purified by any suitable means, as are well known in the art. For example, the nucleic acids can be purified by reverse phase or ion exchange HPLC, size exclusion chromatography or gel electrophoresis. Of course, the skilled artisan will recognize that the method of purification will depend in part on the size of the DNA to be purified.

Polypeptides of the present invention are not limited to those examples specifically set forth. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substantially pure protein isolated and obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, In: Guide to Protein Purification, Harcourt Brace Jovanovich, San Diego).

As used herein, to "alleviate" a virus infection means reducing the severity of the symptoms of the disease or disorder.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1988, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

By "biological activity," as the term is used herein, is meant that the protein has the ability to interact with its associated protein(s) and effectuate its normal function(s) within the cell and/or with respect to virus infection. In one embodiment, the gp120 retains its biological activity in that the protein does not require interaction with CD4 in order to bind to CXCR4 chemokine receptor protein, and to mediate fusion of the virus envelope with the host cell membrane. Further, biological activity, as it refers to any form or fragment of Env, means that the polypeptide has the ability to bind to a chemokine receptor protein without the requirement that it also bind to CD4. Given the evidence that viral entry involves a series of sequential and coordinated conformational changes in gp120 and gp41, and the view that these changes will involve the creation of new epitopes that will be better exposed in variable loop deleted viruses, biological activity also refers to any polypeptide that has the ability to block viral entry or virus Env-mediated fusion.

By "chemokine receptor binding site," as the term is used herein, is meant the portion(s) of the viral gp120 which specifically binds a human chemokine receptor protein such as, but not limited to, CXCR4, CCR5, or both. Thus, a CXCR4 chemokine receptor binding site means a portion of the HIV-1 gp120 molecule which specifically binds to CXCR4 chemokine receptor but which does not substantially bind to another chemokine receptor. Similarly, a CCR5 chemokine receptor binding site means a portion of the HIV-1 gp120 molecule which specifically binds to CCR5 but which does not significantly bind to any other molecule including another chemokine receptor.

By the term "CD4-independence," as the term is used herein, is meant that the virus strain is capable of infecting cells that do not express the CD4 protein and/or its gp120 can bind to a coreceptor in the absence of CD4-induced conformational change(s). However, the CD4-independent virus can infect cells that express CD4 and an appropriate chemokine receptor, although CD4 is not required. For purposes of the invention, an immunodeficiency virus strain variant is considered CD4-independent when it is able to infect at least about 5% of the susceptible cells in culture or the level of infection is about two to three-fold compared to background levels (i.e., fusion observed in the absence of chemokine receptors).

By the term "chimera," as used herein, is meant a nucleic acid encoding env comprising a portion of a nucleic acid encoding at least a portion of env covalently linked to at least one nucleic acid encoding a portion of an env from a different immunodeficiency virus, or strain thereof.

By the term "Env clone," as that term is used herein, is meant an env nucleic acid encoding an Env protein, gp160, comprising gp120 and gp41. A full-length Env clone encodes a complete Env protein, gp160, while a partial clone includes fragment(s) of a full-length clone that may be used to construct smaller portions of the Env that may comprise mutations that are specific for a particular virus or strain thereof.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

The use of the terms "nucleic acid encoding" or "nucleic acid coding" should be construed to include the RNA or DNA sequence which encodes the desired protein and any necessary 5' or 3' untranslated regions accompanying the actual coding sequence.

By the terms "encoding" and "coding," as these terms are used herein, is meant that the nucleotide sequence of a nucleic acid is capable of specifying a particular polypeptide of interest. That is, the nucleic acid may be transcribed and/or translated to produce the polypeptide. Thus, for example, a nucleic acid encoding HIV-1 Env is capable of being transcribed and/or translated to produce an HIV-1 envelope protein.

As used herein, the term "fragment" as applied to a polypeptide, may ordinarily be at least about seven contiguous amino acids, typically, at least about fifteen contiguous amino acids, more typically, at least about thirty contiguous amino acids, typically at least about forty contiguous amino acids, preferably at least about fifty amino acids, even more preferably at least about sixty amino acids and most preferably, the peptide fragment will be greater than about sixty contiguous amino acids in length.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'-ATTGCC-3' and 5'-TATGCG-3' share 50% homology. Further, algorithms may be used to calculate the percent homology between two nucleic acids or two proteins of interest and these are well-known in the art.

By the term "immunogenic dose," as the term is used herein, is meant an amount of a polypeptide of the invention, or portion thereof, whether administered to a mammal as protein or as nucleic acid encoding the protein, which generates a detectable humoral and/or cellular immune response to the protein compared to the immune response detected in an otherwise identical mammal to which the protein is not administered. In one aspect, the dose is administered as Env protein, a gp120 polypeptide, or a fragment thereof. In another aspect, the dose is administered as a nucleic acid encoding the polypeptide of the invention.

"Mutants," "derivatives," and "variants" of the peptides of the invention (or of the DNA encoding the same) are peptides which may be altered in one or more amino acids (or in one or more base pairs) such that the peptide (or DNA) is not identical to the sequences recited herein, but has the same property as the peptides disclosed herein, in that the peptide has the property of having a detectable function compared with the wild type polypeptide, even though the V1 and V2 regions have been deleted and the V3 region is completely of substantially deleted therefrom compared with the wild type protein.

As used herein, the term "fragment" as applied to a nucleic acid, may ordinarily be at least about 100 nucleotides in length, typically, at least about 200 nucleotides, more typically, from about 300 to about 600 nucleotides, typically at least about 700 to about 1000 nucleotides, preferably at least about 1000 to about 1400 nucleotides, even more preferably at least about 1600 nucleotides to about 2000 nucleotides, and most preferably, the nucleic acid fragment will be greater than about 2400 nucleotides in length.

As used herein, the term "pharmaceutically-acceptable carrier" means a chemical composition with which an appropriate Env protein, may be combined and which, following the combination, can be used to administer the protein to a patient.

By the term "specifically binds," as used herein, is meant a chemokine receptor binding site on a virus polypeptide, such as, but not limited to, Env polypeptide, a gp120, and a gp41, which recognizes and binds, for example, CXCR4 polypeptide, but does not substantially recognize or bind other molecules in a sample. Similarly, a chemokine receptor binding site "specifically binds CXCR4" if the binding site recognizes and binds CXCR4 in a sample but does not substantially recognize or bind to other molecules, e.g., CCR5, in a sample. Similarly, a chemokine receptor binding site may specifically bind CCR5 and, thus, would not bind other molecules such as CXCR4 or other molecules in a sample.

A "swarm" refers to an uncloned stock of immunodeficiency virus obtained from infected cells. Such stocks are known to contain many genetically distinct variants of a founder or a parental virus, hence the term "swarm."

The term "stably exposed chemokine receptor binding site," as used herein, means that the gp120 chemokine receptor binding site is available to bind to the chemokine receptor protein without the need for gp120 interaction with CD4, which interaction is typically a prerequisite to gp120 binding of the chemokine receptor protein. As demonstrated by the data disclosed herein, the chemokine receptor binding site of gp120 can exist in a stable, exposed configuration which is more sensitive to antibody neutralization than the otherwise identical CD4-dependent gp120 prior to binding of CD4. The stably exposed form of the chemokine binding site can exist in solution for a period of at least about three months and/or indefinitely.

By the term "gp120," as used herein, is meant a mammalian immunodeficiency virus glycoprotein that is typically about 120 kDa in size and corresponding to the 5' half of the viral Env protein, and containing binding sites for CD4 and chemokine receptors. However, the term also includes polypeptides that due to various modifications and/or deletions is detectably different in size, such as, but not limited to, a gp120 comprising a deletion of at least one hypervariable region, more preferably, two hypervariable regions, even more preferably, three hypervariable regions (e.g., V1, V2, and V3, or a substantial deletion of V3), where the size of the polypeptide is less than 120 kD, and encompasses a gp120 of about 75 kD as disclosed elsewhere herein.

Similarly, the term "gp41" refers to the region of the Env protein that contains an extracellular domain, a membrane spanning domain and a cytoplasmic tail. Given that some compensatory changes in viruses adapted to grow in the absence of hypervariable loops (particularly V3) occur in this protein, the invention also includes regions of gp41 and peptides corresponding to this region that mediate this activity.

As used herein, the term "substantially pure" describes a compound, e.g., a nucleic acid, protein or polypeptide, which has been separated from components which naturally accompany it. Typically, a compound is substantially pure when at least about 10%, preferably at least about 20%, more preferably at least about 50%, still more preferably at least about 75%, even more preferably at least about 90%, and most preferably at least about 99% of the total material (by volume, by wet or dry weight, or by mole percent or mole fraction) in a sample is the compound of interest. Purity can be measured by any appropriate method, e.g., by column chromatography, gel electrophoresis or HPLC analysis.

A compound, e.g., a nucleic acid, a protein or polypeptide is also "substantially purified" when it is essentially free of naturally associated components or when it is separated from the native contaminants which accompany it in its natural state. Thus, a "substantially pure" preparation of a nucleic acid, as used herein, refers to a nucleic acid sequence which has been purified from the sequences which flank it in a naturally occurring state, e.g., a DNA fragment which has been removed from the sequences which are normally adjacent to the fragment in a genome in which it naturally occurs.

Similarly, a "substantially pure" preparation of a protein or a polypeptide, as used herein, refers to a protein or polypeptide which has been purified from components with which it is normally associated in its naturally occurring state.

Figure 1B:
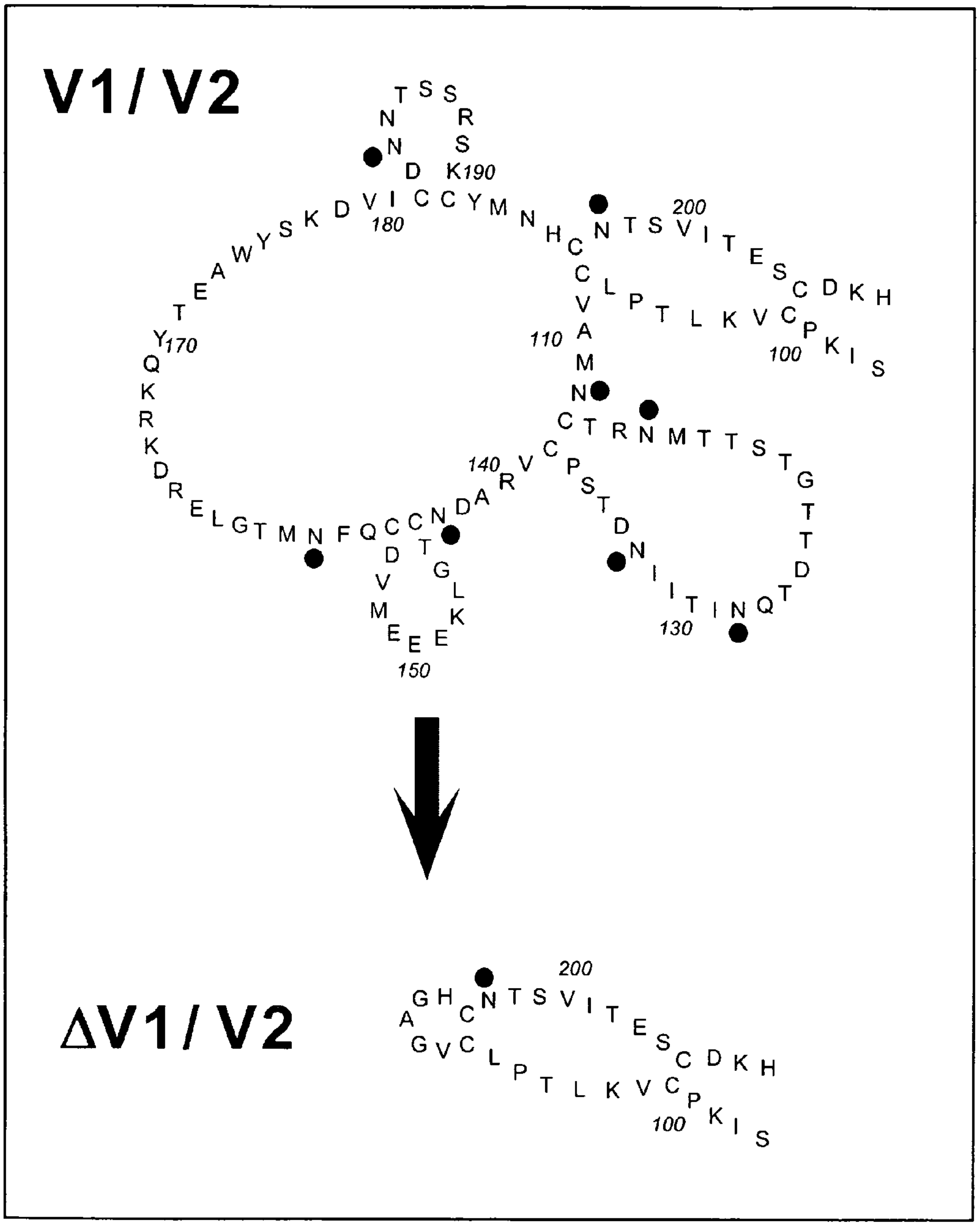
FIG. 1B is a diagram depicting a strategy for deleting the V1/V2 hypervariable loops from HIV-2/VCP gp120. The amino acid sequence of the HIV-2/VCP V1/V2 loop is shown with deletion mutations introduced by PCR, including insertion of a Gly-Ala-Gly (GAG) linker.
Figure 16:
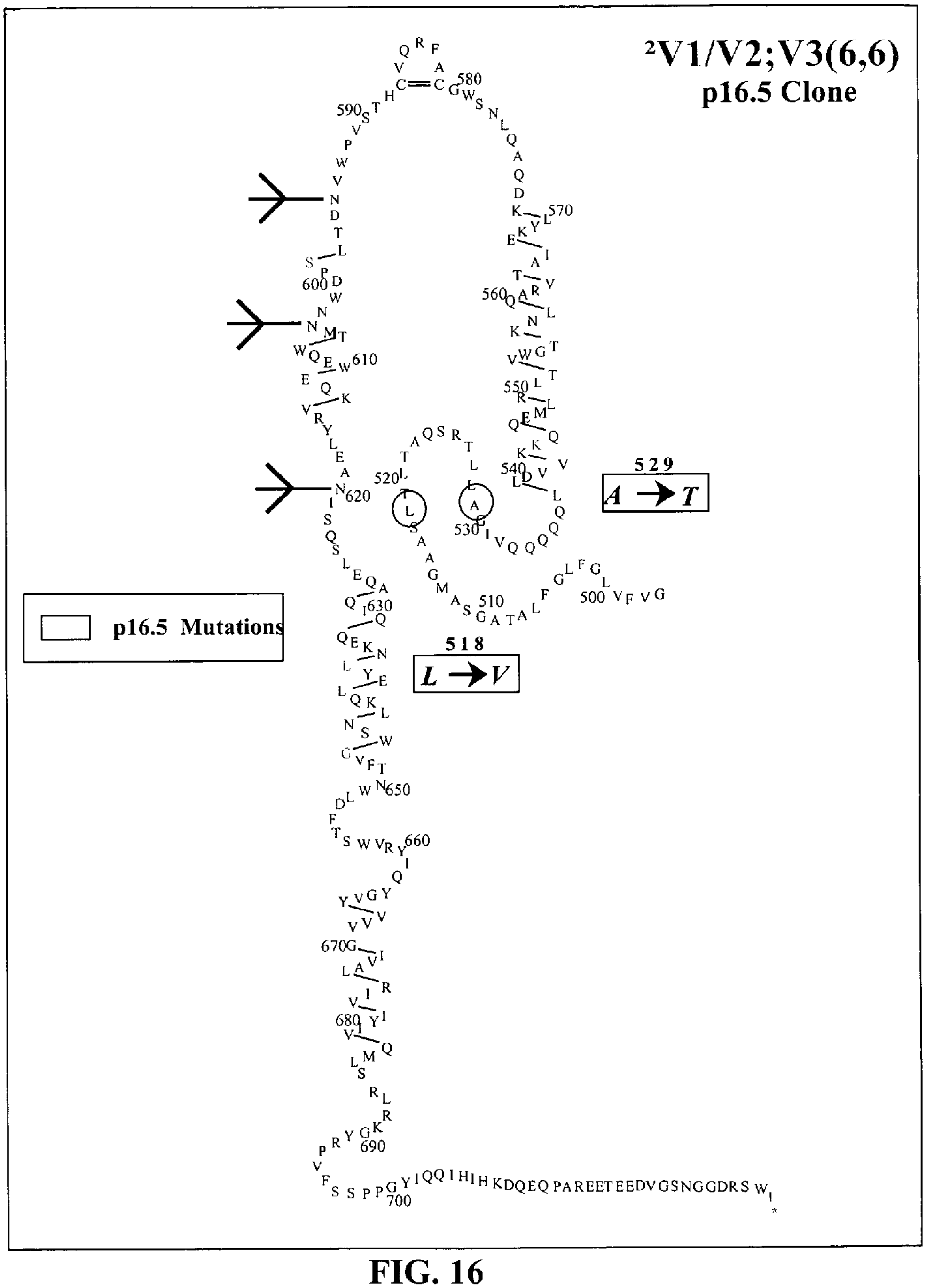
FIG. 16 is a diagram depicting the amino acid sequence and illustrating the conformation of HIV-2/VCP gp41 obtained from p16.5 clone. The diagram indicates the compensatory mutations as follows: an amino acid substitution from leucine to valine at amino acid residue number 518, and an amino acid substitution from alanine to threonine at amino acid residue 529.

A "substantial deletion" of gp120 V3, as used herein, means that at least about 303 amino acid residues of the V3 loop region (which spans from about amino acid residue number 297 to amino acid residue number 330 of the gp120 sequence) are deleted. More preferably, from about amino acid residue number 303 to residue number 324 are deleted (termed deletion "6,6" for HIV-2/VCP gp120 as shown in FIG. 1B, middle panel), and even more preferably, the amino acid residues from about number 297 to number 330 (termed deletion "1,1" for HIV-2/VCP gp120 and shown in FIG. 1B, bottom panel), are deleted from the amino acid sequence of gp120 (SEQ ID NO:5; the full-length amino acid sequence of HIV-2/VCP gp120 is depicted in FIG. 16). These deletions, while shown in HIV-2, are for illustrative purposes only and are not limited to HIV-2, but encompass similar V3 truncation mutations of gp120 of HIV-1 and SIV. Further, the skilled artisan would appreciate that deletion of an amino acid residue indicates a deletion of the nucleotide triplet codon that encodes it such that the particular deletion can be readily ascertained with regard to the nucleic acid sequence of the nucleic acid encoding gp120 as set forth in SEQ ID NO:2.

As used herein, to "treat" means reducing the frequency with which symptoms of the virus infection are experienced by a patient.

By "triggered," as the term is used herein, it is meant that the immunodeficiency virus Env protein does not require binding to CD4 before gp120 can bind to a chemokine receptor protein such as CXCR4 or CCR5. Preferably, a triggered Env comprises a gp120 that is in a conformation that can bind chemokine receptors in the absence of binding to CD4.

By the term "vaccine," as the term is used herein, is meant a compound which when administered to a human or veterinary patient, induces a detectable immune response, humoral and/or cellular, to a mammalian immunodeficiency virus, or a component(s) thereof.

Description

The invention includes a replication-competent derivative of a mammalian immunodeficiency virus that lacks in its entirety hypervariable loops V1/V2 and V3. As an example, although by no means limiting the invention in any way, ΔV1/V2; ΔV3(6,6), which has a 12 amino acid V3 remnant, and p16.9ΔV3(1,1) which contains no V3 loop, but still has V1/V2, were produced using a HIV-2/VCP backbone. The data shows that combinations of these viruses generate ΔV1/V2; ΔV3(1,1) (i.e., a "loopless" replication competent "core"). The findings set forth herein with HIV-2/vcp Env represent proof of concept that these variable loops can be deleted while preserving functional integrity of the viral Env and suggests that similar approaches are translatable to other HIV-1, HIV-2, and SIV strains because of the high degree of structural conservation of the core Env among these viruses. Thus, the skilled artisan would appreciated, based upon the disclosure provided herein, that the present invention includes replication-competent variants of mammalian immunodeficiency viruses, including, but not limited to, SIV, HIV-1 and HIV-2, and the present invention is in no way limited to any particular mammalian immunodeficiency virus. Thus, the present invention encompasses an Env protein (i.e., gp120 and gp41) where the V3 region is substantially deleted, and where the loop-deleted Env retains detectable biological activity and/or function when compared to full-length Env. That is, the variant Env retains detectable activity in that it binds with a chemokine receptor, mediates Env fusion with a cell, and when incorporated into a virus, permits a virus to establish and infection that spreads cell to cell, and/or there is detectable virus replication in a cell. The skilled artisan would appreciate, based upon the disclosure provided herein, that the invention encompasses adaptive changes in gp41, since mutations in gp41 also mediate the retention and/or restoration of protein function upon truncation of the V3 region of gp120.

The invention is based, in part, on the discovery of a variant of HIV-2, termed VCP, that can utilize both CXCR4 and CCR5 as primary receptors without a need for CD4 triggering, can further comprise a truncation of V3 and yet retain detectable biological activity. While CD4-independence is not a requisite feature of the novel viruses and polypeptides of the invention, the minimal gp120 components required for infectivity were demonstrated herein by making deletions of hypervariable loops V1/V2 and V3 on an infectious molecular clone of VCP. Remarkably, a virus containing deletion of approximately 65% deletion of the V3 loop (leaving only the first 6 and last 6 amino acids on either side of the disulfide bond and termed ΔV3(6,6)), was shown to be replication competent on SupT1 cells. This finding demonstrated for the first time that a full V3 is not required for infectivity and allowed the identification of determinants of gp120 required for virus infection of host cells involving cell receptor proteins.

Further, the present invention relates to a "combination deleted" virus, termed ΔV1/V2; ΔV3(6,6), that produced a gp120 of only about 70 kD. This combination deleted virus was also found to be replication competent. Thus, mammalian immunodeficiency viruses produced by deleting portions of the V3 hypervariable loop are useful for discovery of the gp120 and gp41-based determinants of fusogenicity and replication of such viruses.

The data disclosed herein suggest that changes in both gp120 and gp41 are required for virus ability to replicate in the absence of the V3 loop. This has been demonstrated for VCP and the data suggest that this can be readily applied to other viruses, including, HIV-1 and SIV. Thus, the invention involves mutations to both gp120 and gp41, preferably, about two mutations in gp120 and about two mutations in gp41 are required for the phenotype of being able to replicate without V3.

CD4-independence is important in that it is an indicator that the chemokine binding site of gp120 is stably exposed on the virus envelope and is capable of binding to the cellular chemokine receptor binding protein without prior binding of the gp120 to CD4. Typically, the chemokine receptor binding site on gp120 is hidden until such binding to CD4 causes a conformational change exposing the site and resulting in a "triggered" conformation capable of binding to the chemokine receptor protein on the host cell. CD4-independence (CD4i) is an apparent indicator for increased exposure of the chemokine coreceptor binding site for the host cell chemokine receptor, which is in some cases also associated with an increased affinity that appears to render binding of CD4 by the virus gp120 unnecessary for fusion. A virus gp120 that can bind a chemokine receptor with such affinity that the V3 region can be deleted and the gp120 can still mediate binding with the cell, fusion of the Env with the cell, and/or replication, even where CD4 binding is required, is encompassed in the present invention. The interaction of gp120 with chemokine receptors involves at least two steps: the binding of the V3 loop to extracellular loops of the chemokine receptor (principally the second extracellular loop), and the binding of the bridging sheet ("BS") of gp120 with the chemokine receptor amino terminus. The data disclosed herein suggest that that viruses with a sufficiently strong interaction of the BS with the chemokine receptor can better tolerate loss of the V3 loop. A "favorable" interaction of the BS with the chemokine amino terminus can be reflected in CD4-independence, dual tropism or (most notably) Envs that are resistant to inhibitors that act on the extracellular loops. Thus, HIV-2 VCP with deletions of V3 that could no longer interact with ECL2, became resistant to the CXCR4 inhibitor AMD3100. Thus, based upon the disclosure provided herein, a property that can be utilized in the screening of HIV envelope glycoproteins for the ability to tolerate a V3 deletion is relative resistance to AMD3100.

CD4-independent gp120 represents a stable intermediate configuration which may be used to, inter alia, identify the protein determinants involved in gp120 binding to a chemokine receptor protein, produce neutralizing antibodies capable of recognizing the gp120 chemokine receptor binding site, and to identify small-molecule inhibitors which can block gp120/chemokine receptor binding.

Moreover, production of gp120 hypervariable loop-deleted mutants has led to the discovery that a "core" domain of gp120, lacking some or all of the V1/V2 and V3 loop amino acids, is responsible for the fusogenicity and replication competence of the virus.

Accordingly, understanding which portions of the Env are involved in virus binding to cell proteins and thereby functionally mapping the protein determinant(s) that mediate immunodeficiency virus binding to host cell receptors is important in the development of effective antiviral vaccines to viral protein domains crucial for virus infection. Such domains are believed to be highly conserved but somehow "camouflaged" from the immune system such that a protective immune response is not mounted to such protein domains. Therefore, for example, identification of these protein domains and the ability to present them to the immune system such that an immune response is generated to HIV-1 is an important goal of vaccine development to this, and other important human pathogenic immunodeficiency viruses.

I. Isolated Nucleic Acids

The present invention includes an isolated nucleic acid encoding a mammalian immunodeficiency virus gp120 polypeptide, or a fragment thereof, wherein the nucleic acid encodes a variant of gp120 that comprises a deletion of hypervariable loop 1 (V1), a deletion of hypervariable loop 2 (V2) (hereinafter referred to as a "deletion of V1/V2"), and a substantial deletion of hypervariable loop 3 (V3). In an embodiment of the invention, a nucleic acid shares at least about 90% identity with at least one nucleic acid having the sequence of SEQ ID NO:8, SEQ ID NO:14, SEQ ID NO:20 and SEQ ID NO:26. Preferably, the nucleic acid is about 95% homologous, and most preferably, about 99% homologous to at least one sequence of SEQ ID NO:8, SEQ ID NO:14, SEQ ID NO:20 and SEQ ID NO:26, disclosed herein. Even more preferably, the nucleic acid is at least one sequence of SEQ ID NO:8, SEQ ID NO:14, SEQ ID NO:20 and SEQ ID NO:26.

Thus, the invention encompasses an isolated nucleic acid encoding a mammalian immunodeficiency virus glycoprotein (gp) 120 polypeptide, or a mutant, derivative, or fragment thereof, wherein the gp120 polypeptide comprises a deletion of hypervariable loop 3 (V3), and further comprises a compensatory mutation. This is because, as demonstrated by the data disclosed herein, the present invention provides deletion mutants of gp120 wherein the V3 region is deleted/truncated while retaining biological function of the gp120 peptide. Such biological activity includes, but is not limited to, detectable binding with a chemokine receptor, detectable fusogenic activity, and detectable virus replication competence using a variety of assays either well-known in the art, disclosed herein, as well as assays to be developed in the future. This is remarkable in that prior art dogma was that the V3 was essential for peptide function and that deletion of this region obliterated such biological activity so that V3-deletion mutant comprising detectable function could not be generated.

Therefore, the present invention demonstrates that despite prior art teachings to the contrary, functional V3-deletion mutants can be produced, as amply exemplified by the mutants disclosed herein. Further, the data disclosed herein demonstrate certain features and characteristics useful for identification of potential modifiable virus Env, gp120, and gp41 peptides that can be used, according to the methods disclosed elsewhere herein, to produce deletion mutants of the invention. These mutants are important potential therapeutics since such deletion mutants represent functional "core" components that can be used to examine virus interaction with host cell components, identify novel compounds that can inhibit such interactions, and for development of neutralizing antibodies as well as vaccines for the generation thereof.

Figure 20:
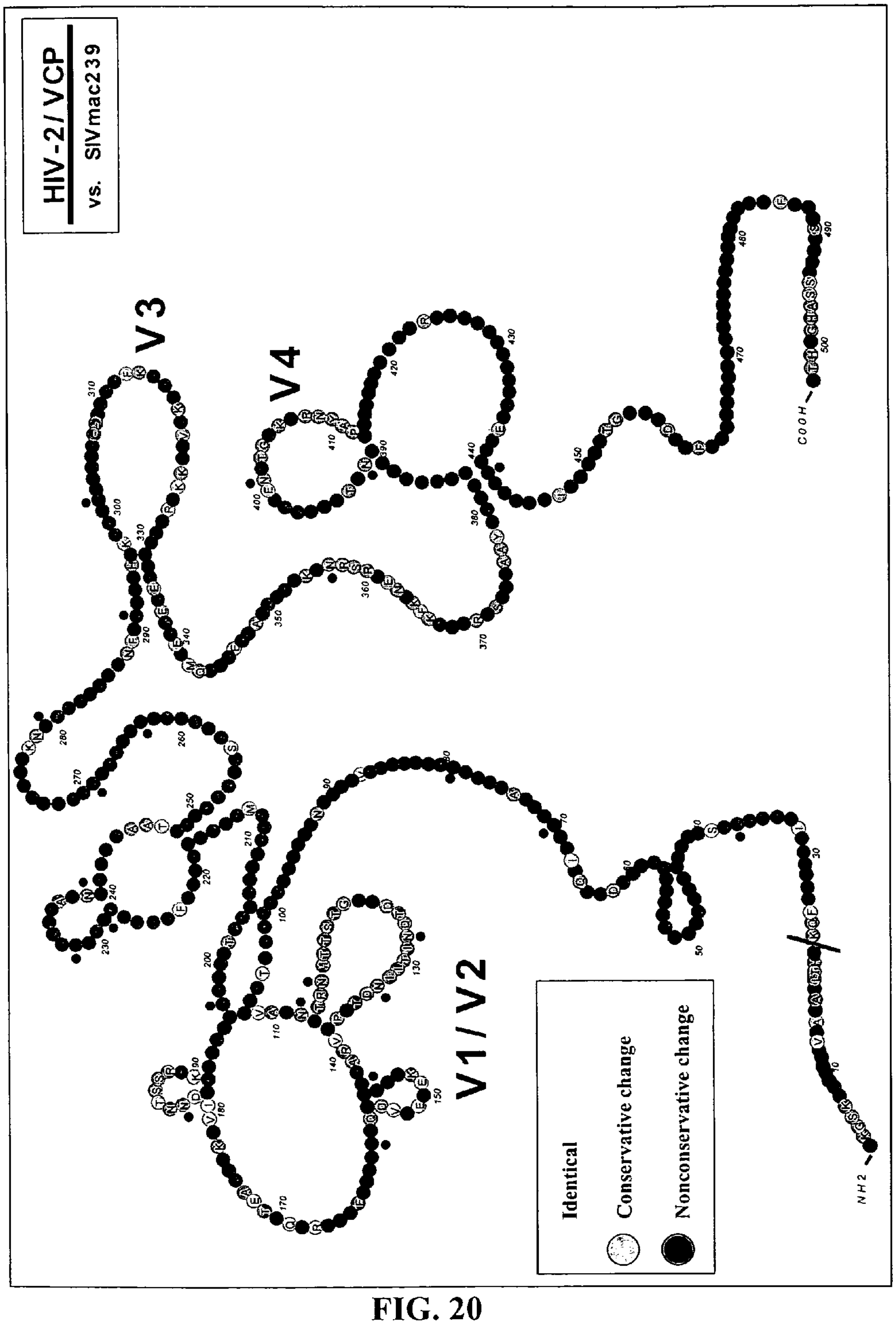
FIG. 20 is a diagram depicting the high degree of amino acid homology between HIV-2/VCP gp120 and SIVmac239 gp120. Identical amino acids shared between HIV-2/VCP and SIVmac239 are indicated by darker gray circles, whereas conservative amino acid changes are indicated by lighter gray circles and non-conservative changes are indicated by white circles.

While the present invention is exemplified herein by development of HIV-2 deletion mutants, the teachings provided herein can be readily adapted to development of similar mutants in other mammalian immunodeficiency viruses, including, but not limited to, HIV-1 and SIV. This is due, in part, to the high degree of amino acid homology in the Env proteins of these viruses, including high homology in the gp120 across these viruses as demonstrated diagrammatically in FIG. 20 comparing the amino acid sequences of HIV-2 and SIVmac239. Further, the teachings of the present invention have already been extended to HIV-1 as demonstrated by data establishing a functional V3-deletion mutant of HIV-1 "580". Therefore, one skilled in the art, based upon the disclosure provided herein, would appreciate that the present invention is not limited to any particular mammalian immunodeficiency virus, but encompasses various such viruses including, but not limited to, simian immunodeficiency virus (SIV), human immunodeficiency virus type 1 (HIV-1), and human immunodeficiency virus type 2 (HIV-2).

The invention relates to a nucleic acid encoding a V3-deleted/truncated gp120 where the deletion includes a deletion of V3 is selected from about amino acid residue number 303 to amino acid residue number 324 (ΔV3(6,6)) and a deletion from about amino acid residue number 298 to amino acid residue number 331 (ΔV3(1,1)). These deletions are mapped relative to the amino acid sequence of the parental HIV-2/vcp gp120 as provided in SEQ ID NO:5. Therefore, the invention encompasses deletions that remove all but a single amino acid adjacent to the cysteines that form the loop to deletions that leave no more than six amino acids adjacent to each of the cysteines.

One skilled in the art would appreciate, once provided with the nucleic and amino acid sequences of the various mutants of the invention, as well as with those sequences of the parental virus, that the deletions of the amino acids of interest correspond with a deletion of the nucleotides encoding the pertinent amino acid residues deleted. For instance, while in no way limiting the invention to this particular deletion, a deletion of V3 of HIV-2/VCP gp120 termed (ΔV3(1,1)), which deletes from about amino acid residue number 298 to amino acid residue number 331 relative to the amino acid sequence of HIV-2/vcp gp120 (SEQ ID NO:5) corresponds to a deletion from about nucleotide number 894 to nucleotide number 1032 relative to the nucleic acid encoding such gp120 (SEQ ID NO:2). Thus, each mutation specified according to a deletion of certain amino acids can be readily matched to the corresponding nucleotides encoding such amino acids to determine the corresponding deletion at the nucleic acid level of the nucleic acid encoding the gp120 peptide at issue.

The invention encompasses V-3 deletion mutants where the V1/V2 region of the gp120 is also deleted/truncated. Such double deletion mutants comprising deletion of both V1/V2 and V3 are exemplified by clone p16.5, clone p16.7, and clone 8c.3, but the invention is not limited to these or any particular mutants as would be appreciated by the artisan armed with the teachings provided herein.

The invention includes a compensatory mutation that mediates or is associated with prevention of loss of detectable virus function. While not limited to any particular compensatory mutation, such mutations in gp120 can include the following: an amino acid substitution from isoleucine to valine at amino acid residue number 55, an amino acid substitution from asparagine to aspartic acid at amino acid residue number 79, an amino acid substitution from phenylalanine to serine at amino acid residue number 94, an amino acid substitution from aspartic acid to glycine at amino acid residue number 142, an amino acid substitution from threonine to isoleucine at amino acid residue number 160, an amino acid substitution from alanine to threonine at amino acid residue number 173, an amino acid substitution from threonine to lysine at amino acid residue number 202, an amino acid substitution from glutamic acid to lysine at amino acid residue number 203, an amino acid substitution from threonine to isoleucine at amino acid residue number 231, an amino acid substitution from alanine to threonine at amino acid residue number 267, an amino acid substitution from asparagine to aspartic acid at amino acid residue number 279, an amino acid substitution from asparagine to aspartic acid at amino acid residue number 280, an amino acid substitution from glutamic acid to lysine at amino acid residue number 334, an amino acid substitution from glutamic acid to lysine at amino acid residue number 340, an amino acid substitution from asparagine to aspartic acid at amino acid residue number 391, an amino acid substitution from threonine to alanine at amino acid residue number 393, an amino acid substitution from glutamine to arginine at amino acid residue number 399, an amino acid substitution from valine to isoleucine at amino acid residue number 405, an amino acid substitution from valine to isoleucine at amino acid residue number 429, an amino acid substitution from glutamic acid to valine at amino acid residue number 437, an amino acid substitution from threonine to alanine at amino acid residue number 439, and an amino acid substitution from glycine to alanine at amino acid residue number 666. The amino acid residue position of these mutations is provided relative to the amino acid sequence of parental HIV-2/vcp gp120 (SEQ ID NO:5), which does not comprise a hypervariable region deletion.

This is because as more fully discussed elsewhere herein, certain mutations in gp120 and/or gp41 "compensate" for any loss of function resulting from truncation or deletion of a hypervariable region of gp120 such that the combination of at least one compensatory mutation, and more preferably, at least two compensatory mutations, in at least one of gp120 and gp41, can restore and/or preserve a biological function of gp120 once a substation, or all, of the V3 region is deleted from the protein.

Certain combinations of compensatory mutations are disclosed herein, and these include, but are not limited to, a gp120 comprising a ΔV3(6,6) deletion and further wherein the compensatory mutation is at least one amino acid substitution selected from the group consisting of an amino acid substitution from isoleucine to valine at amino acid residue number 55, an amino acid substitution from asparagine to aspartic acid at amino acid residue number 79, an amino acid substitution from threonine to lysine at amino acid residue number 202, an amino acid substitution from threonine to isoleucine at amino acid residue number 231, an amino acid substitution from alanine to threonine at amino acid residue number 267, and an amino acid substitution from asparagine to aspartic acid at amino acid residue number 391, where the amino acid residue number is relative to the amino acid sequence of parental HIV-2/vcp gp120 as provided in SEQ ID NO:5. This particular combination of V3-deletion and compensatory mutations is exemplified in the p16.5 clone, but the invention is not limited to these mutations, or to this particular combination thereof. While some combinations can be preferred, other combinations of these and additional mutations are encompassed in the invention where the methods of the invention provide useful assays for isolating and identifying additional compensatory mutations and combinations thereof, which preserve/restore biological function following deletion of a hypervariable region of gp120.

Additional preferred combinations of V-3 deletion mutations and compensatory mutations include, but are not limited to, ΔV3(6,6) deletion and compensatory mutations comprising an amino acid substitution from isoleucine to valine at amino acid residue number 55, an amino acid substitution from asparagine to aspartic acid at amino acid residue number 79, an amino acid substitution from phenylalanine to serine at amino acid residue number 94, an amino acid substitution from asparagine to aspartic acid at amino acid residue number 280, and an amino acid substitution from asparagine to aspartic acid at amino acid residue number 391, wherein the amino acid residue number of the compensatory mutation is relative to the amino acid sequence of parental HIV-2/vcp gp120 as provided in SEQ ID NO:5. This particular combination of V-3 deletion and compensatory mutations is exemplified by the gp120 p16.7 clone (SEQ ID NO:17), but the invention is not limited to this clone or to this particular combination of mutations.

Likewise, the invention encompasses a gp120 mutant comprising a ΔV3(6,6) deletion and further comprising an amino acid substitution from threonine to alanine at amino acid residue number 393, and an amino acid substitution from valine to isoleucine at amino acid residue number 429, wherein the amino acid residue number of the compensatory mutation is relative to the amino acid sequence of parental HIV-2/vcp gp120 as provided in SEQ ID NO:5. This particular combination is exemplified by the p16.9 clone, but as stated previously elsewhere herein, the present invention is not limited to this particular clone, these particular compensatory mutations, or the particular combination set forth herein. Rather, the invention includes additional compensatory mutations identified and produced according to the teachings provided herein, and any combination thereof.

Further, the invention encompasses a gp120 mutant comprising a ΔV3(1,1) deletion and further comprising a compensatory mutation such as an amino acid substitution from alanine to threonine at amino acid residue number 173, an amino acid substitution from glutamic acid to lysine at amino acid residue number 203, an amino acid substitution from threonine to alanine at amino acid residue number 393, an amino acid substitution from glutamine to arginine at amino acid residue number 405, an amino acid substitution from valine to isoleucine at amino acid residue number 429, an amino acid substitution from threonine to alanine at amino acid residue number 439, and an amino acid substitution from glycine to alanine at amino acid residue number 666, wherein the amino acid residue number of the compensatory mutation is relative to the amino acid sequence of parental HIV-2/vcp gp120 as provided in SEQ ID NO:5. The amino acid sequence of the 8c.3 clone is depicted in FIG. 19C (SEQ ID NO:29) and the nucleic acid sequence encoding this clone is depicted in FIG. 19D (SEQ ID NO:26). This particular combination of V-3 deletion and compensatory mutations is exemplified herein by HIV-2 clone 8c.3, but the invention is in no way limited to this clone.

The invention includes an isolated nucleic acid encoding a mammalian immunodeficiency virus glycoprotein (gp) 120 polypeptide, or a mutant, derivative, or fragment thereof, wherein the gp120 polypeptide comprises a deletion of hypervariable loop 3 (V3), a deletion of hypervariable loops V1/V2, and further comprises a compensatory mutation and where the nucleic acid sequence of the nucleic acid encoding the gp120 is selected from the group consisting of the sequence of SEQ ID NO:8, the sequence of SEQ ID NO:14, and the sequence of SEQ ID NO:26. Further, the V3 deletion encompasses a deletion from about amino acid residue number 303 to amino acid residue number 324 (ΔV3(6,6)), and a deletion from about amino acid residue number 298 to amino acid residue number 331 (ΔV3(1,1)), relative to the amino acid sequence of HIV-2/vcp gp120 as provided in SEQ ID NO:5. The invention also encompasses a nucleic acid that is, preferably, at least about 95% homologous, more preferably, 99% homologous, and even more preferably, is the sequence of at least one of SEQ ID NO:8, the sequence of SEQ ID NO:14, and the sequence of SEQ ID NO:26.

The invention encompasses an isolated nucleic acid encoding a mammalian immunodeficiency virus glycoprotein (gp) 120 polypeptide, or a mutant, derivative, or fragment thereof, wherein the gp120 polypeptide comprises a ΔV3(6,6) deletion, and further comprises a compensatory mutation wherein the nucleic acid sequence of the nucleic acid comprises the sequence of SEQ ID NO:20. That is because, as exemplified by HIV-2 clone p16.9 disclosed herein, a mutant of the invention can include a V-3 deletion mutant where V1/V2 region of gp120 is not deleted.

The invention further relates to an isolated nucleic acid encoding a gp120 V-3 deletion variant of the invention, wherein the sequence of the nucleic acid is at least one sequence selected from the group consisting of SEQ ID NO:8, SEQ ID NO:14, SEQ ID NO:20, and SEQ ID NO:26.

The invention encompasses an isolated nucleic acid encoding a gp120 V-3 deletion variant of the invention, wherein the amino acid sequence of the gp120 polypeptide encoded by the nucleic acid is selected from the group consisting of the amino acid sequence of SEQ ID NO:11, the amino acid sequence of SEQ ID NO:17, the amino acid sequence of SEQ ID NO:23, and the amino acid sequence of SEQ ID NO:29. Preferably, the amino acid sequence encoded by the nucleic acid is at least 95% homologous with, more preferably, at least about 99% homologous with, and even more preferably, the sequence is at least one of the amino acid sequence of SEQ ID NO:11, the amino acid sequence of SEQ ID NO:17, the amino acid sequence of SEQ ID NO:23, and the amino acid sequence of SEQ ID NO:29.

One skilled in the art would appreciate, based upon the disclosure provided herein, that similar gp120 variant homologs exist and/or may be created in mammalian immunodeficiency viruses and can be readily identified and isolated using the methods described herein using the sequence data disclosed herein regarding the. HIV-2 ΔV1/V2; ΔV3(6, 6), HIV-2 ΔV1/V2; ΔV3(1,1) HIV-2 ΔV3(6,6) and HIV-2 ΔV3(1,1) gp120 deletion mutants. Thus, the present invention encompasses additional gp120 variants that can be readily identified based upon the disclosure provided herein.

An isolated nucleic acid of the invention should be construed to include an RNA or a DNA sequence encoding a gp120 variant protein of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

The present invention should not be construed as being limited solely to the nucleic and amino acid sequences disclosed herein. Once armed with the present invention, it is readily apparent to one skilled in the art that other nucleic acids encoding gp120 variant proteins such as those present in other mammalian immunodeficiency viruses (e.g., HIV-1, SIV) can be obtained by using the sequence information disclosed herein for human HIV-2 gp120 variant nucleic acids encoding human HIV-2 gp120 variant polypeptides as disclosed herein as would be understood by one skilled in the art. Methods for isolating a nucleic acid based on a known sequence are well-known in the art (e.g., screening of genomic or cDNA libraries), and are not described herein.

Further, any number of procedures may be used for the generation of mutant, derivative or variant forms of a gp120 variant using recombinant DNA methodology well known in the art. A wide plethora of techniques is available to the skilled artisan to produce muteins of interest and to select those with desired properties.

Techniques to introduce random mutations into DNA sequences are well known in the art, and include PCR mutagenesis, saturation mutagenesis, and degenerate oligonucleotide approaches. See Sambrook and Russell (2001, Molecular Cloning, A Laboratory Approach, Cold Spring Harbor Press, Cold Spring Harbor, N.Y.) and Ausubel et al. (2002, Current Protocols in Molecular Biology, John Wiley & Sons, NY).

As described in detail elsewhere herein, the present invention also features a nucleic acid encoding a mutant, derivative or variant of a gp120 polypeptide, wherein the gp120 polypeptide comprises at least one compensatory mutation. By way of a non-limiting example, in response to the deletion of a stabilizing domain from a polypeptide sequence, one or more amino acid mutations may be induced in the remaining polypeptide sequence in order to stabilize the truncated polypeptide. Further, a compensatory mutation encompasses where a deletion in one region of a polypeptide would otherwise result in a loss of a biological activity or function, but a mutation in another region of the polypeptide can detectably preserve or restore the loss of biological activity of function.

A compensatory mutation useful in the present invention includes, but is not limited to, an amino acid mutation, insertion, or deletion in an Env protein, wherein an amino acid mutation, insertion, or deletion arises, is induced, or is designed such that the resulting gp120 has the property of being fusogenic, supporting replication competence of a mammalian immunodeficiency virus comprising such gp120, or both. As discussed in greater detail elsewhere herein, a compensatory mutation useful in the present invention may arise or be induced in a gp120.

Further, the skilled artisan, based upon the disclosure provided herein, would appreciate that any discussion relating to a compensatory mutation that preserves or restores function despite a truncation of gp120 includes a mutation in gp41. This is because binding of gp120 to chemokine receptors, typically though interactions of the bridging sheet ("BS") with the chemokine receptor amino terminus and the V3 loop with the ECLs, transmits a signal to gp41 that causes it to initiate the fusion reaction. Thus, one way to compensate for the loss of a V3 loop can be through changes in gp41 that facilitate transmission of this signal, i.e., a "hair triggered" Envelope protein), and such mutations are therefore encompassed in the invention.

Figure 1C:
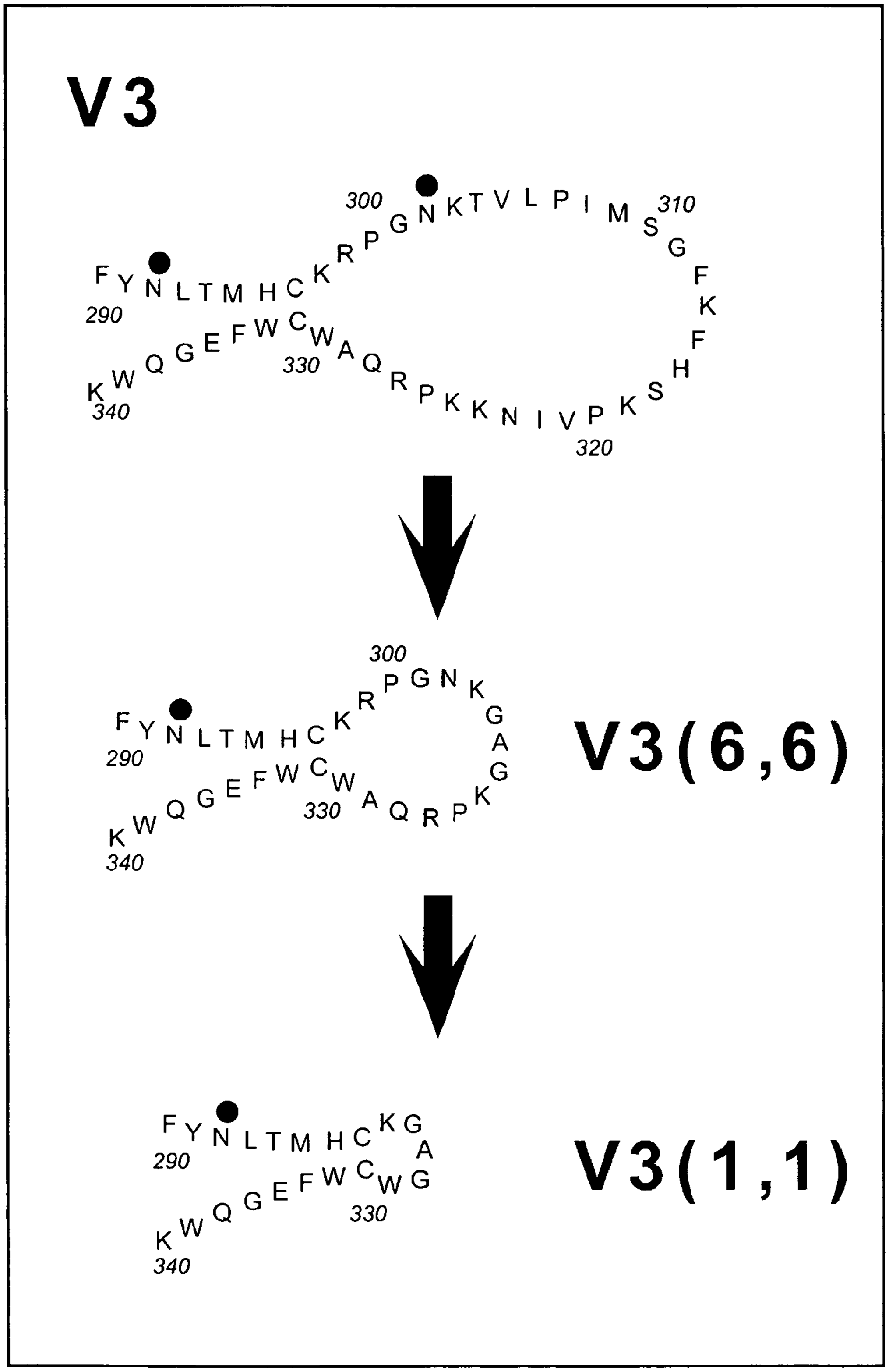
FIG. 1C is a diagram depicting a strategy for deleting the V3 hypervariable loop from HIV-2/VCP gp120. The sequence of the HIV-2/VCP V3 loop is shown with deletion mutations introduced by PCR, including insertion of a Gly-Ala-Gly linker. The top diagram depicts the intact V3 region, the middle diagram depicts deletion of all but six amino acids flanking the cysteine residues (i.e., from about amino acid residue number 303 to amino acid residue number 324 and termed "V3(6,6)"), and the bottom diagram depicts the deletion of all but a single amino acid residue on either side of the cysteine residues, i.e., from about amino acid residue number 298 to amino acid residue number 329 and termed "V3(1,1)."
Figure 1D:
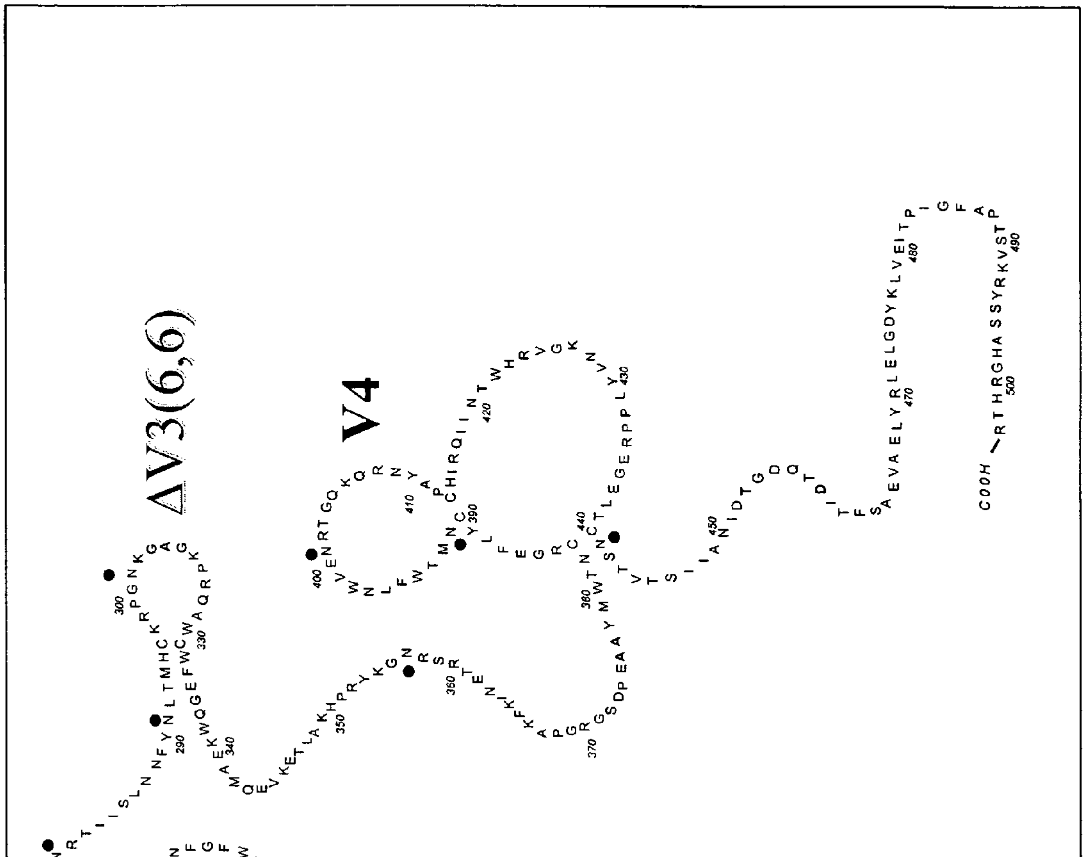
FIG. 1D is a diagram depicting the amino acid sequence and illustrating the loop structure of a HIV-2/VCP gp120 comprising a V1/V2 region and further comprising a V3(6,6) deletion.
Figure 1E:
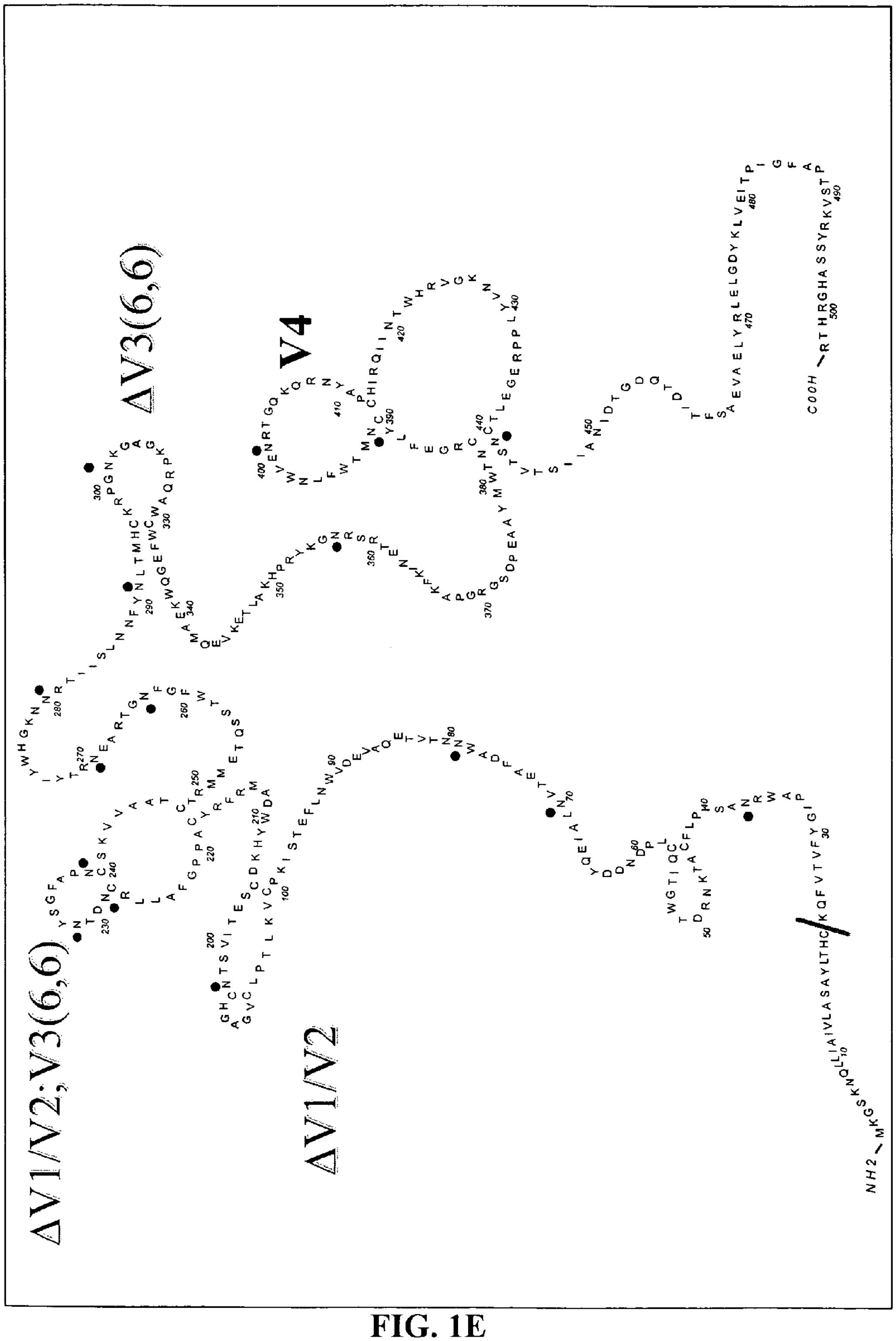
FIG. 1E is a diagram depicting the amino acid sequence and illustrating the loop structure of a HIV-2/VCP gp120 comprising a deletion of the V1/V2 region and further comprising a V3(6,6) deletion.
Figure 1F:
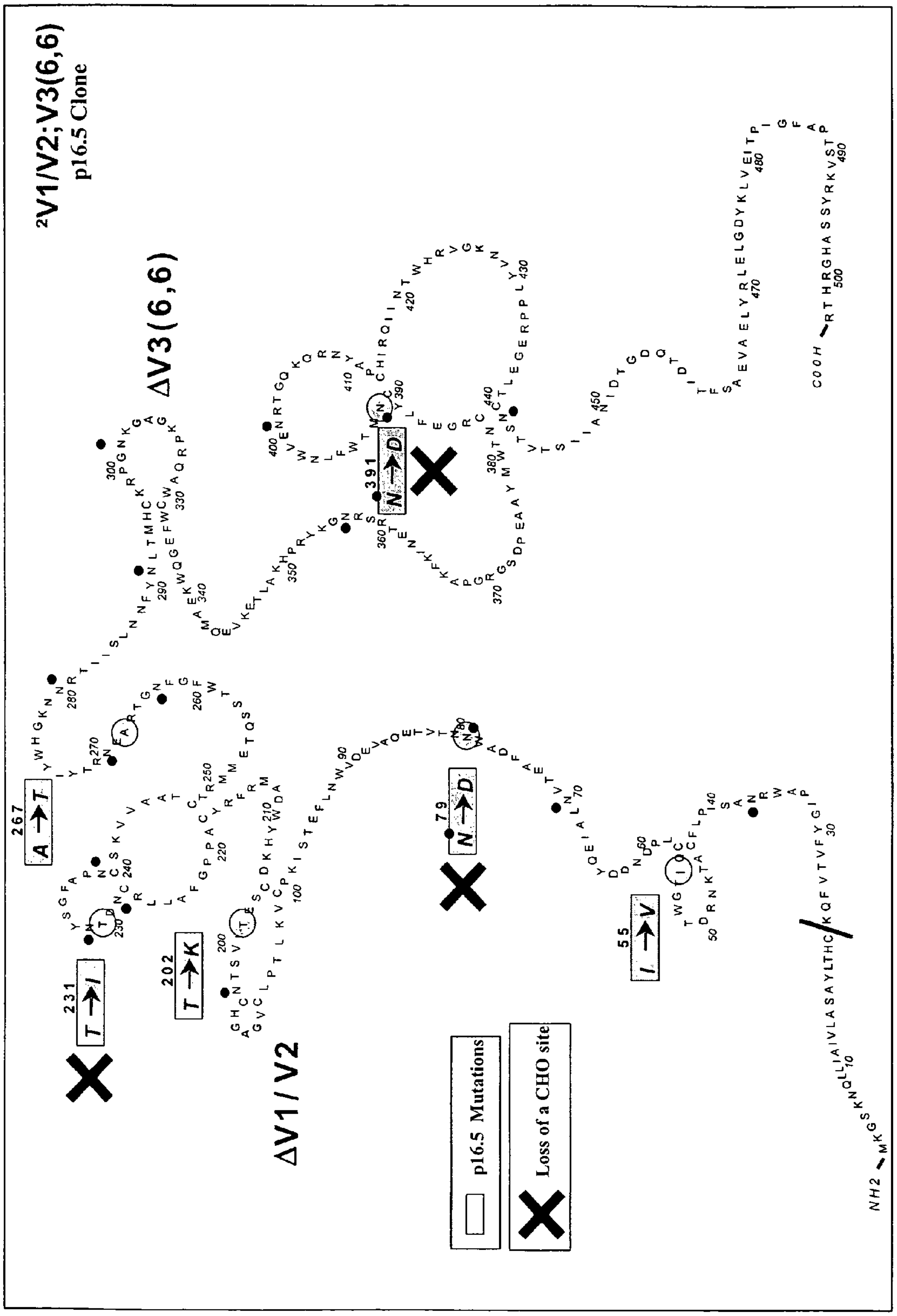
FIG. 1F is a diagram depicting the amino acid sequence and illustrating the loop structure of a HIV-2/VCP gp120 comprising a deletion of the V1/V2 region and further comprising a V3(6,6) deletion referred to as the "p16.5 clone". The amino acid sequence of the gp41 peptide corresponding to this clone is shown below at FIG. 16. The diagram further illustrates the position of various compensatory mutations of this gp120 as follows: an amino acid substitution from isoleucine to valine at amino acid residue number 55, an amino acid substitution from asparagine to aspartic acid at amino acid residue number 79, an amino acid substitution from threonine to lysine at amino acid residue number 202, an amino acid substitution from threonine to isoleucine at amino acid residue number 231, an amino acid substitution from alanine to threonine at amino acid residue number 267, and an amino acid substitution from asparagine to aspartic acid at amino acid residue number 391. Mutations resulting in loss of a glycosylation ("CHO") site are indicated by an "X".
Figure 1G:
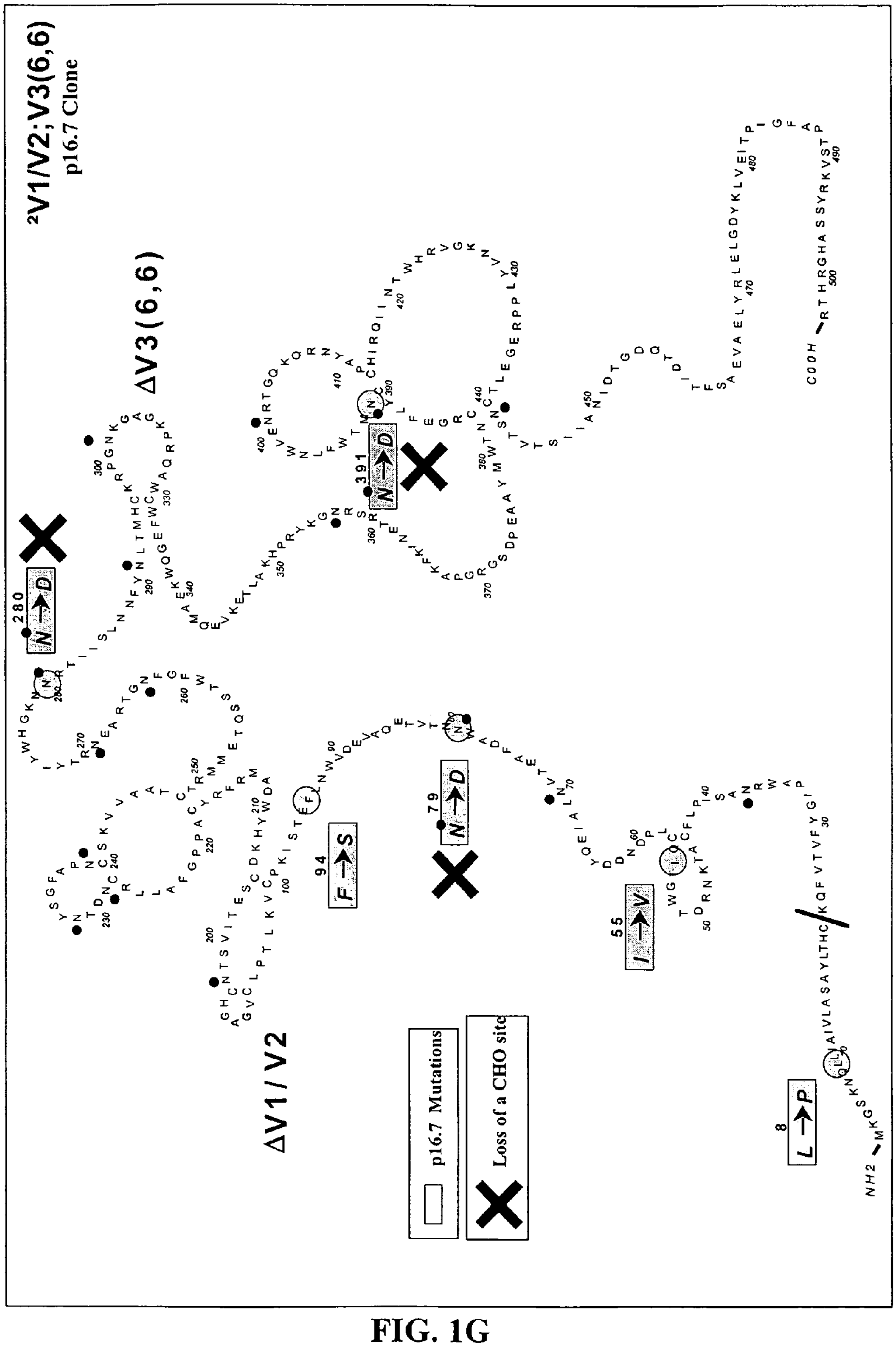
FIG. 1G is a diagram depicting the amino acid sequence and illustrating the loop structure of a HIV-2/VCP gp120 comprising a deletion of the V1/V2 region and further comprising a V3(6,6) deletion referred to as the "p16.7 clone". The amino acid sequence of the gp41 peptide corresponding to this clone is shown below at FIG. 17. The diagram further illustrates the position of various compensatory mutations of this gp120 as follows: an amino acid substitution from isoleucine to valine at amino acid residue number 55, an amino acid substitution from asparagine to aspartic acid at amino acid residue number 79, an amino acid substitution from phenylalanine to serine at amino acid residue number 94, an amino acid substitution from asparagine to aspartic acid at amino acid residue number 280, and an amino acid substitution from asparagine to aspartic acid at amino acid residue number 391 Mutations resulting in loss of a glycosylation ("CHO") site are indicated by an "X".
Figure 1H:
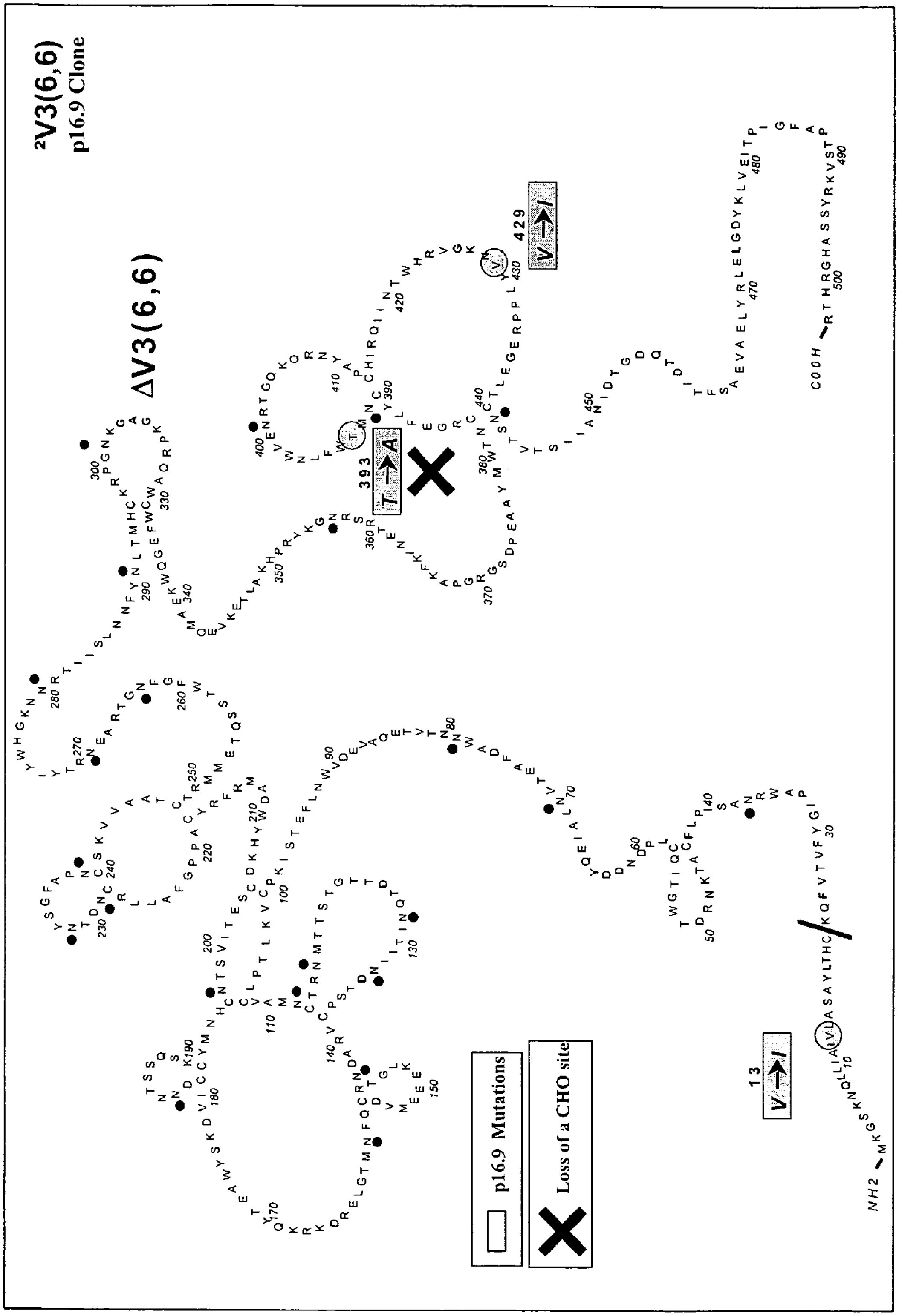
FIG. 1H is a diagram depicting the amino acid sequence and illustrating the loop structure of a HIV-2/VCP gp120 comprising a V3(6,6) deletion referred to as the "p16.9 clone". The amino acid sequence of the gp41 peptide corresponding to this clone is shown below at FIG. 18. The diagram further illustrates the position of various compensatory mutations of this gp120 as follows: an amino acid substitution from threonine to alanine at amino acid residue number 393, and an amino acid substitution from valine to isoleucine at amino acid residue 429. Mutations resulting in loss of a glycosylation ("CHO") site are indicated by an "X".

In the present invention, a "second change" that can induce or require the need for a compensatory mutation comprises a deletion of one or more hypervariable loops of a gp120. "Deletion of a hypervariable loop" of a gp120 comprises deletion of one or more amino acid residues in a hypervariable loop of the gp120, and is described in greater detail elsewhere herein. For example, "deletion of the V1/V2 loop" of a gp120 can range from the removal of a single nucleic acid triplet (codon) encoding the V1 loop region of a gp120 such that a single amino acid of the gp120 V1/V2 loop is not coded and is missing from the polypeptide where the reading frame for the rest of the sequence is maintained and the remaining amino acid residues following the deletion are produced. The deletion of the V1/V2 region can range to where all the nucleotides encoding amino acids on either sides of the disulfide bonds at amino acid residues number 110 to amino acid residue number 193 are deleted, resulting in a total deletion of the V1/V2 loop from a gp120. Such a deletion of V1/V2 is illustrated in FIGS. 1B and 1E using HIV-2/VCP for illustrative purposes only.

It would be understood by the skilled artisan, armed with the teachings provided herein, that reference to a "V1/V2" region encompasses the hypervariable loop V1 and V2 regions of a gp120 peptide since the loops of SIV and HIV-2 comprise more cysteines in this region such that it is well-known in the art that certain hypervariable region loops are not clearly divided into V1 and V2. The important feature of the invention is that truncation of V1/V2 at the base of the region can be readily applied to HIV-1, HIV-2 and SIV and it is not necessary to consider V1 and V2 regions separately for purposes of the present invention.

More specifically, one skilled in the art would appreciate, based upon the disclosure provided herein, that for HIV-2, the V1/V2 region includes from about amino acid residue number 110 to about amino acid residue number 194 relative to the amino acid sequence of SEQ ID NO:5 (full-length HIV-2/VCP gp120), corresponding to from about nucleotide number 330 to about nucleotide number 582 relative to the nucleic acid sequence of SEQ ID NO:2 (n.a. sequence of HIV-2/VCP gp120). Further, the V3 region comprises from about amino acid residue number 298 to about amino acid residue number 329 relative to the amino acid sequence of SEQ ID NO:5 (full-length HIV-2/VCP gp120), corresponding to from about nucleotide number 894 to about nucleotide number 1032 relative to the nucleic acid sequence of SEQ ID NO:2 (n.a. sequence of HIV-2/VCP gp120). Moreover, the HIV-2 V4 region comprises from about amino acid residue number 392 to about amino acid residue number 411 relative to the amino acid sequence of SEQ ID NO:5 (full-length HIV-2/VCP gp120), corresponding to from about nucleotide number 1176 to about nucleotide number 1233 relative to the nucleic acid sequence of SEQ ID NO:2 (n.a. sequence of HIV-2/VCP gp120).

For SIV, using SIVmac251 for illustrative purposes, the skilled artisan would understand, based upon the disclosure provided herein, that the V1/V2 region includes from about amino acid residue number 110 to about amino acid residue number 211 relative to the amino acid sequence of full-length SIVmac251 gp120 (FIG. 20), corresponding to from about nucleotide number 330 to about nucleotide number 633 relative to the nucleic acid sequence of the nucleic acid sequence of full-length SIVmac251 gp120 which is known in the art. Further, the V3 region comprises from about amino acid residue number 315 to about amino acid residue number 344 relative to the amino acid sequence of full-length SIVmac251 gp120, corresponding to from about nucleotide number 945 to about nucleotide number 1032 relative to the nucleic acid sequence of full-length SIVmac251 gp120. Moreover the SIV V4 region comprises from about amino acid residue number 406 to about amino acid residue number 432 relative to the amino acid sequence of full-length SIVmac251 gp120, corresponding to from about nucleotide number 1218 to about nucleotide number 1296 relative to the nucleic acid sequence of the nucleic acid sequence of full-length SIVmac251 gp120.

For HIV-1, using HIV-1/HXB c2 by way of non-limiting example, the skilled artisan would understand, based upon the disclosure provided herein, that the V1/V2 region includes from about amino acid residue number 128 to about amino acid residue number 194 relative to the amino acid sequence of full-length HIV-1/HXB c2 gp120, corresponding to from about nucleotide number 384 to about nucleotide number 582 relative to the nucleic acid sequence of the nucleic acid sequence of full-length HIV-1/HXB c2 gp120, which are both well-known in the art. Further, the V3 region comprises from about amino acid residue number 298 to about amino acid residue number 329 relative to the amino acid sequence of full-length HIV-1/HXB c2 gp120, corresponding to from about nucleotide number 894 to about nucleotide number 987 relative to the nucleic acid sequence of the nucleic acid sequence of full-length HIV-1/HXB c2 gp120. Moreover the HIV-1 V4 region comprises from about amino acid residue number 387 to about amino acid residue number 416 relative to the amino acid sequence of full-length HIV-1 gp120, corresponding to from about nucleotide number 1161 to about nucleotide number 1248 relative to the nucleic acid sequence of the nucleic acid sequence of full-length HIV-1/HXB c2 gp120.

Thus, the skilled artisan, based upon the disclosure provided herein, would readily understand which portion(s) of gp120 should be deleted to produce a deletion mutant of the invention. Once armed with the amino and nucleic acids which comprise the hypervariable region of interest, one skilled in the art could readily produce a desired mutation thereby deleting any amino acid, or acids, of interest, including the aforementioned amino acid residues and the corresponding nucleotides encoding them. The amino acids comprising the various hypervariable regions of a wide plethora of mammalian immunodeficiency virus gp120 are well known in the art, as are the nucleic acids encoding those amino acids, and these sequences are therefore not discussed further herein.

Likewise, the various amino and nucleic acid sequences, as well as the functional domains and structural regions of a wide plethora of pg41 peptides are well known in the art and are therefore not discussed further herein since the skilled artisan would readily understand, based upon the disclosure provided herein, which amino acids and/or nucleic acids to mutagenize and to produce the mutant peptides of the invention.

Deletion of an amino acid from a hypervariable loop of a gp120 protein can include deletion of one or more amino acids responsible for the structure, function, or both, of the hypervariable loop. Further, deletion of an amino acid from a hypervariable loop of a gp120 protein can include deletion of one or more amino acids responsible for interaction of the hypervariable loop with other hypervariable loops, with core regions of the gp120, or with other Env proteins. The structure and function of the hypervariable loops of gp120 of mammalian immunodeficiency viruses, including, but not limited to HIV-1, HIV-2, and SIV, are known in the art and will not be discussed herein. Similarly, methods of deleting nucleotides of interest to produce deletions of interest of certain amino acid residues of a polypeptide are well known in the art and are not discussed further herein. Techniques for selective mutagenesis to produce deletions of interest are well known in the art and are available to the routineer such that they need not be set forth. The invention is not limited in any way to any particular method for producing the relevant deletion mutants and encompasses such methods as are known in the art or which are developed in the future.

In one aspect of the invention, a deletion mutation is produced in a gp120 by a deletion of the nucleic acid sequence encoding at least one amino acid of hypervariable loop 1 ("the V1 loop"). In another aspect, a deletion mutation is induced in a gp120 by a deletion of the nucleic acid sequence encoding at least one amino acid of the V2 loop. In yet another aspect, a deletion mutation is induced in a gp120 by a deletion of the nucleic acid sequence encoding at least one amino acid of the V3 loop. In another aspect of the invention, a deletion mutation is induced in a gp120 by a deletion of the nucleic acid sequence encoding at least one amino acid of the V4 loop.

In yet another aspect of the invention, a deletion mutation is induced in a gp120 by a deletion of the nucleic acid sequence encoding an entire hypervariable loop of gp120. In one embodiment, the deletion of a nucleic acid sequence encoding an entire hypervariable loop of gp120 results in the deletion of the entire V1 loop. In another embodiment, the deletion of a nucleic acid sequence encoding an entire hypervariable loop of gp120 results in the deletion of the entire V2 loop. In another embodiment of the invention, the deletion of a nucleic acid sequence encoding an entire hypervariable loop of gp120 results in the deletion of the entire V3 loop. In yet another embodiment, the deletion of a nucleic acid sequence encoding an entire hypervariable loop of gp120 results in the deletion of the entire V4 loop.

The present invention also features a nucleic acid encoding a gp120, wherein a mutation is induced by deletion of more than one hypervariable loop of a gp120. By way of a non-limiting example, a compensatory mutation may be induced in a gp120 comprising a deletion of the entire V1 loop, the entire V2 loop, and a substantial portion of the V3 loop of the gp120. By way of another example, a compensatory mutation may be introduced into a gp120 by deletion of the V1/V2 loops. By way of a further non-limiting example, a compensatory mutation may be induced in a gp120 by deletion of only the V3 hypervariable loop.

The skilled artisan would appreciate, once armed with the teachings provided herein, that an Env containing a V3 deletion was inserted into a replication competent clone of HIV-2/VCP and electroporated into SupT1 cells. Virus produced by these cells was then serially passaged on SupT1 and, following several rounds of infection, viruses were isolated that demonstrated increased infectivity. However, the invention is not limited to these methods for producing a replication-competent clone, as other methods would be understood to be included in the invention by one skilled in the art provided with the disclosure provided herein.

Envs were cloned from these viruses, sequenced, and were evaluated in cell to cell fusion assays. Differences that were identified in the adapted Env have been interpreted as being "compensatory mutations" (i.e., they impart increased infectivity to a parental loop-deleted Env). The following shows compensatory mutations that were observed in the serial passaging of HIV-2/VCP containing V3(6,6) deletion. This adapted Env was further mutated to V3(1,1) and when introduced into a virus and the process repeated, different mutations were observed as follows:

TABLE 1

| | Compensatory mutation | |
|---|---|---|
| Deletion mutation | Gp120 | Gp41 |
| ΔV3(6,6) | 55 I/V | 518 L/V |
| | 79 N/D | 529 A/T |
| | 202 T/K | 561 A/T |
| | 231 T/I | |
| | 267 A/T | |
| | 280 N/D | |
| | 391 N/D | |
| | 393 T/A | |
| | 429 V/I | |
| ΔV3(1,1) | 142 D/G | |
| | 160 T/I | |
| | 203 E/K | |
| | 279 N/D | |
| | 334 E/K | |
| | 340 E/K | |
| | 399 V/I | |
| | 437 E/V | |

When armed with the disclosure provided herein, the skilled artisan will understand that multiple variations of hypervariable loop deletions can be used in any combination with an additional compensatory mutation in a nucleic acid encoding a gp120 polypeptide. Further, the present disclosure provides ample guidance for the skilled artisan to select either a portion or the entirety of a hypervariable loop for deletion, and for the skilled artisan to select multiple hypervariable loops for deletion, as well as for the production and selection of at least one compensatory deletion that detectably preserves or restores a gp120-mediated function or activity.

The present invention also includes a nucleic acid encoding a gp120 variant wherein the nucleic acid encoding a tag polypeptide is covalently linked thereto. That is, the invention encompasses a chimeric nucleic acid wherein the nucleic acid sequences encoding a tag polypeptide is covalently linked to the nucleic acid encoding at least one of HIV-2 ΔV1/V2; ΔV3(6,6), HIV-2 ΔV1/V2; ΔV3(1,1), HIV-2 ΔV3(6,6) and HIV-2 ΔV3(1,1). Such tag polypeptides are well known in the art and include, for instance, green fluorescent protein (GFP), myc, myc-pyruvate kinase (myc-PK), His6, maltose biding protein (MBP), an influenza virus hemagglutinin tag polypeptide, a flag tag polypeptide (FLAG), and a glutathione-S-transferase (GST) tag polypeptide. However, the invention should in no way be construed to be limited to the nucleic acids encoding the above-listed tag polypeptides. Rather, any nucleic acid sequence encoding a polypeptide which may function in a manner substantially similar to these tag polypeptides should be construed to be included in the present invention.

The nucleic acid comprising a nucleic acid encoding a tag polypeptide can be used to localize a gp120 variant within a cell, a tissue, and/or a whole organism (e.g., a mammalian embryo), and to study the role(s) of a gp120 variant in a cell or animal. Further, addition of a tag polypeptide facilitates isolation and purification of the "tagged" protein such that the proteins of the invention can be produced and purified readily.

As described in detail above with respect to compensatory mutations in nucleic acids encoding gp120 polypeptides, the present invention also provides for a compensatory mutation that can be induced in a nucleic acid encoding a gp41 polypeptide. A compensatory mutation of the invention in a gp41 can be selected for that detectably preserves or restores a virus activity or function despite the presence of a hypervariable loop deletion of gp120, as discussed in greater detail elsewhere herein.

A gp41 compensatory mutation useful in the present invention includes, but is not limited to, an amino acid mutation, insertion, or deletion in a gp41 protein, wherein an amino acid mutation, insertion, or deletion arises, is induced, or is designed such that the resulting gp41 has the property of being fusogenic, supporting replication competence of a mammalian immunodeficiency virus comprising such gp41, or both, where the gp120 of the virus comprises deletion of at least one hypervariable region, more preferably, where the gp120 deletion is a V3 deletion, and even more preferably, where the gp120 deletion is a deletion of V1, V2, and a substantial portion of V3, and most preferably, where the gp120 deletion is deletion of V1, V2, and V3.

The present invention includes an isolated nucleic acid encoding a mammalian immunodeficiency virus gp41 polypeptide, or a fragment thereof, wherein the nucleic acid encodes a variant of gp41 that comprises a compensatory mutation where the compensatory mutation comprises deletion comprising a truncation of the cytoplasmic domain. In an embodiment of the invention, a nucleic acid shares at least about 90% identity with at least one nucleic acid having the sequence of gp41 Δ733, gp41 Δ753 and gp41 Δ764. Preferably, the nucleic acid is about 95% homologous, and most preferably, about 99% homologous to at least one of a nucleic acid encoding a truncated gp41 comprising the amino acid sequence disclosed herein where the truncation is set forth relative to the full-length sequence of parental HIV-2/VCP g41 (SEQ ID NO:6).

The invention relates to an isolated nucleic acid encoding a mammalian immunodeficiency virus gp41 polypeptide, wherein the gp41 polypeptide comprises a compensatory mutation. This is because, as more fully-discussed elsewhere herein, such compensatory mutation can surprisingly preserve and/or restore detectable biological function following deletion/truncation of a V3 region of gp120.

The invention includes an isolated nucleic acid comprising a nucleic acid sequence of SEQ ID NO:9, SEQ ID NO:15, SEQ ID NO:21, and SEQ ID NO:27. However, the invention is no way limited to these, or any other, particular nucleic acid sequences as other mutants comprising these and other compensatory mutations can be readily produced, identified and isolated following the novel teachings provided herein.

The amino acid sequence of the gp41 polypeptide encoded by the nucleic acid of the invention includes, but is not limited to, the amino acid sequence of SEQ ID NO:12, the amino acid sequence of SEQ ID NO:18, the amino acid sequence of SEQ ID NO:24, and the amino acid sequence of SEQ ID NO:30. While not limited to these particular amino acid sequences, the skilled artisan would appreciate that changes in the nucleotide sequence of the nucleic acid encoding the gp41 peptide of the invention which do not alter the amino acid sequence of the gp41 due to the degeneracy of the genetic code, are clearly encompassed by the present invention.

The invention encompasses a nucleic acid encoding a gp41 polypeptide of the invention, where the compensatory mutation in gp41 is a truncation of the cytoplasmic domain. The truncation can include, but is not limited to, truncation at amino acid residue number 733, truncation at amino acid residue number 753, and truncation at amino acid residue number 764, wherein the amino acid residue number of the truncation is provided in reference to the amino acid sequence of HIV-2/vcp gp41 (SEQ ID NO:6).

Further, the invention encompasses a nucleic acid encoding a gp41 of the invention where the compensatory mutation is at least one mutation selected from the group consisting of an amino acid substitution from leucine to valine at amino acid residue number 518, an amino acid substitution from alanine to threonine at amino acid residue number 529, an amino acid substitution from isoleucine to valine at amino acid residue number 531, an amino acid substitution from alanine to threonine at amino acid residue number 561, and an amino acid substitution from alanine to threonine at amino acid residue number 673, wherein the amino acid residue number of the compensatory mutation is relative to the amino acid sequence of HIV-2/vcp gp41 (SEQ ID NO:6). While these mutations are preferred, the invention is not limited in any way to these, or any other, particular compensatory mutations in gp41, or combinations thereof.

The present invention includes an isolated nucleic acid encoding mammalian immunodeficiency virus gp41 polypeptide, or a fragment thereof, wherein the nucleic acid comprises at least one compensatory mutation selected from the group consisting of a mutation that encodes a substitution of leucine to valine at amino acid residue number 518, and a mutation that encodes a substitution of an alanine to a threonine at amino acid residue number 529, relative to the amino acid sequence of SEQ ID NO:6 (HIV-2/VCP gp41). This particular mutant is exemplified by gp41 obtained from HIV-2 clone p16.5 and the sequence is depicted in FIG. 16 (SEQ ID NO:12).

Figure 17:
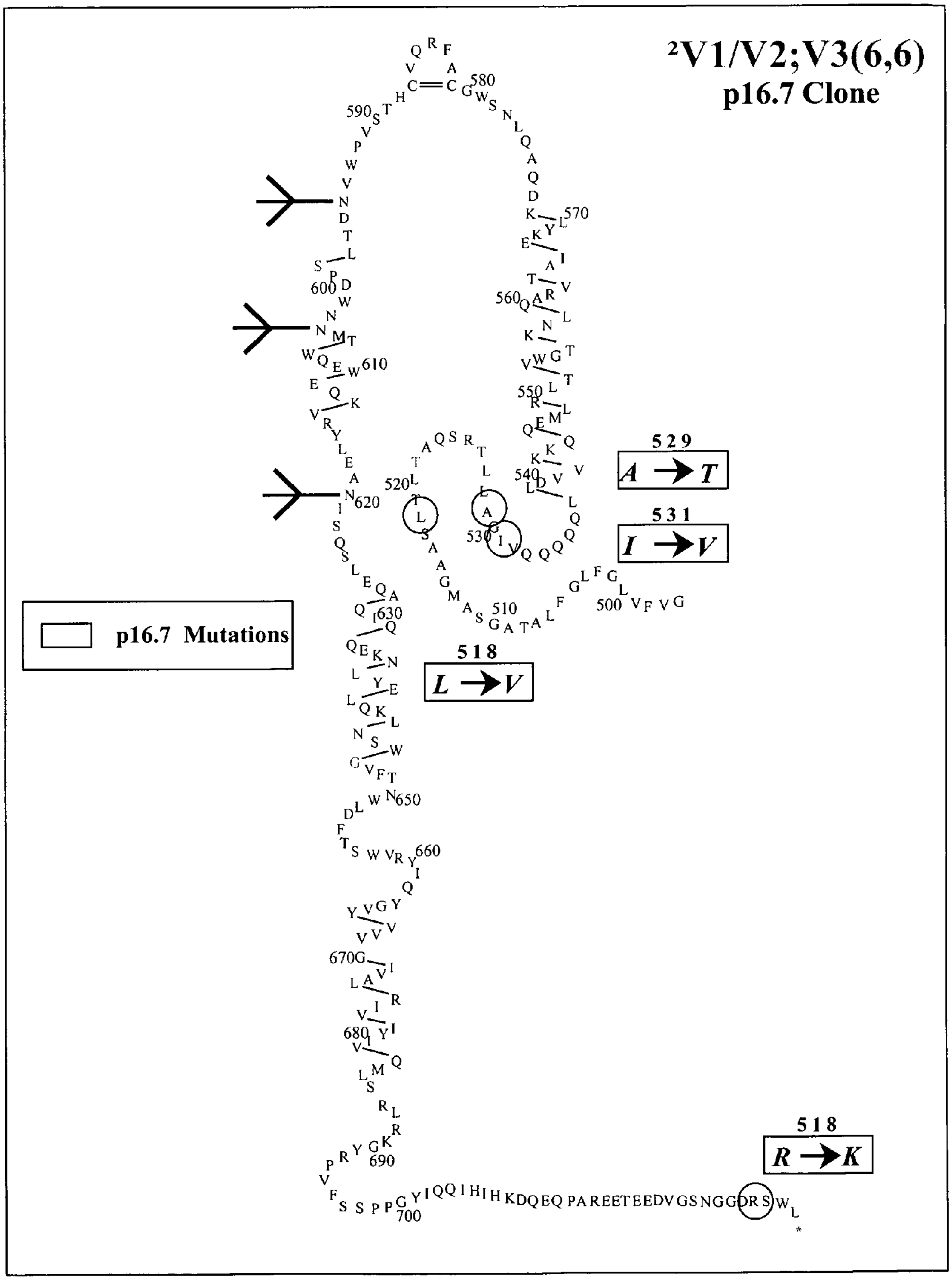
FIG. 17 is a diagram depicting the amino acid sequence and illustrating the conformation of HIV-2/VCP gp41 obtained from p16.7 clone. The diagram indicates the compensatory mutations as follows: an amino acid substitution from leucine to valine at amino acid residue number 518, an amino acid substitution from alanine to threonine at amino acid residue 529, and an amino acid substitution from isoleucine to valine at amino acid residue 531. The amino acid substitution of a arginine to lysine near the carboxy-terminus of the peptide is likely not a compensatory mutation.

The present invention includes an isolated nucleic acid encoding mammalian immunodeficiency virus gp41 polypeptide, or a fragment thereof, wherein the nucleic acid comprises at least one compensatory mutation selected from the group consisting of a mutation that encodes a substitution of leucine to valine at amino acid residue number 518, a mutation that encodes a substitution of an alanine to a threonine at amino acid residue number 529, and an amino acid substitution from isoleucine to valine at amino acid residue number 531, relative to the amino acid sequence of SEQ ID NO:6 (HIV-2/VCP gp41). This particular mutant is exemplified by gp41 obtained from HIV-2 clone p16.7 and the sequence is depicted in FIG. 17 (SEQ ID NO:18).

Figure 18:
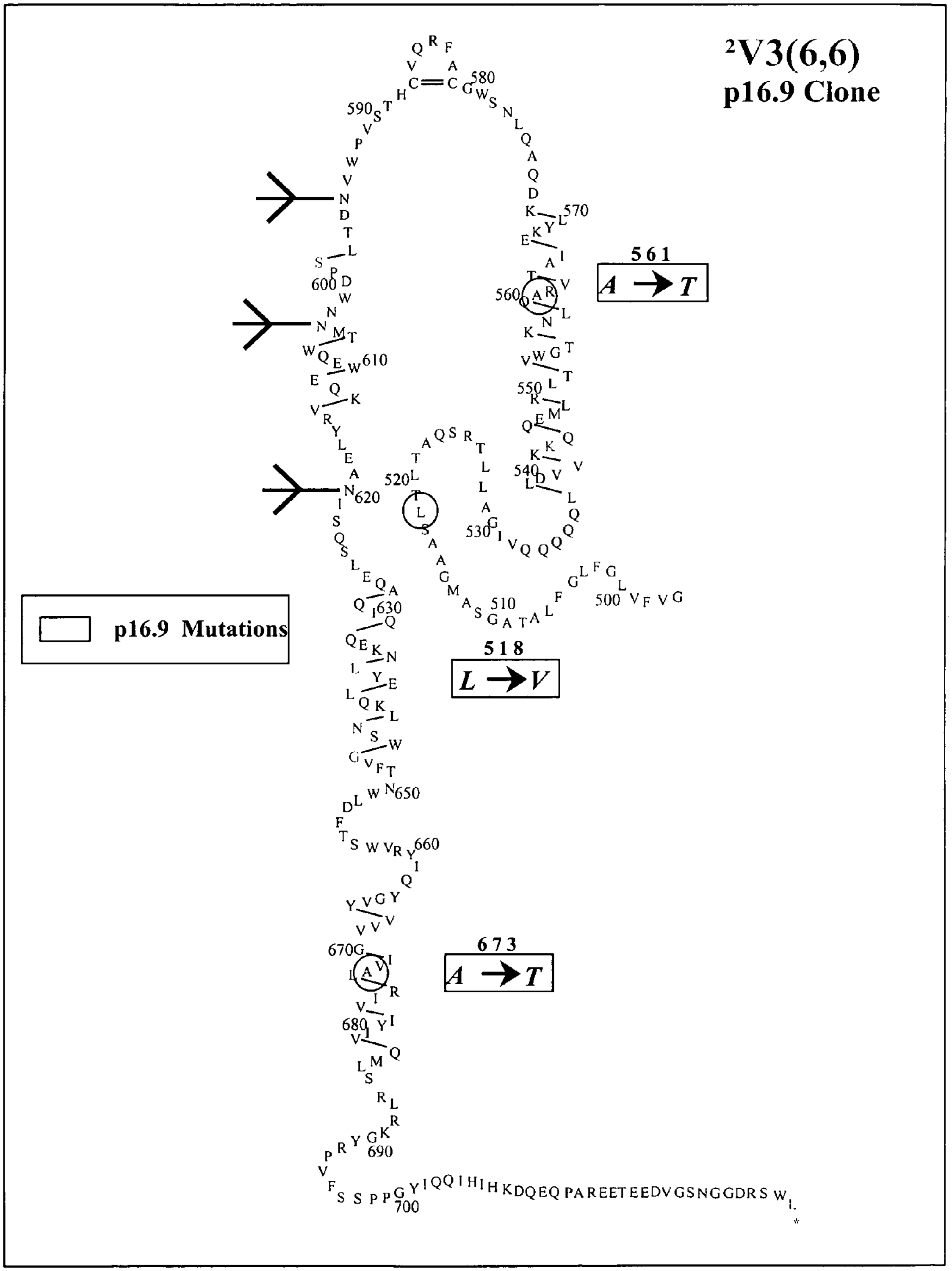
FIG. 18 is a diagram depicting the amino acid sequence and illustrating the conformation of HIV-2/VCP gp41 obtained from p16.9 clone. The diagram indicates the compensatory mutations as follows: an amino acid substitution from leucine to valine at amino acid residue number 518, an amino acid substitution from alanine to threonine at amino acid residue 561, and an amino acid substitution from alanine to threonine at amino acid residue 673.

The present invention includes an isolated nucleic acid encoding mammalian immunodeficiency virus gp41 polypeptide, or a fragment thereof, wherein the nucleic acid comprises at least one compensatory mutation selected from the group consisting of a mutation that encodes a substitution of leucine to valine at amino acid residue number 518, and an amino acid substitution from alanine to threonine at amino acid residue number 561, relative to the amino acid sequence of SEQ ID NO:6 (HIV-2/VCP gp41). This particular mutant is exemplified by gp41 obtained from HIV-2 clone p16.9 and the amino acid sequence is depicted in FIG. 18 (SEQ ID NO:24).

The present invention includes an isolated nucleic acid encoding mammalian immunodeficiency virus gp41 polypeptide, or a fragment thereof, wherein the nucleic acid comprises at least one compensatory mutation as depicted in the amino acid sequence set out in FIG. 19E (SEQ ID NO:30), which shows the amino acid sequence of gp41 obtained from clone 8c.3. The nucleic acid encoding this clone comprises the nucleic acid sequence depicted in FIG. 19F (SEQ ID NO:27).

As noted previously with respect to various mutants of gp120, the present invention is not limited in any way to these, or any other, gp41 mutants comprising compensatory mutations, or combinations thereof. Rather, the gp41 mutants described herein serve illustrative purposes and demonstrate that using the methods disclosed herein these and additional mutants of the invention can be readily produced and isolated by the skilled artisan once armed with the disclosure provided herein.

The present invention includes an isolated nucleic acid encoding mammalian immunodeficiency virus gp41 polypeptide, or a fragment thereof, wherein the nucleic acid shares greater than about 90% homology with at least one of SEQ ID NO:9, SEQ ID NO:15, SEQ ID NO:21, and SEQ ID NO:27. Preferably, the nucleic acid is about 95% homologous, and most preferably, about 99% homologous to at least one of SEQ ID NO:9, SEQ ID NO:15, SEQ ID NO:21, and SEQ ID NO:27. Even more preferably, the nucleic acid is at least one of SEQ ID NO:9, SEQ ID NO:15, SEQ ID NO:21, and SEQ ID NO:27.

One skilled in the art would appreciate, based upon the disclosure provided herein, that similar gp41 variant homologs exist and/or may be created in mammalian immunodeficiency viruses and can be readily identified and isolated using the methods described herein using the sequence data and the selection strategy and assays disclosed herein regarding the Δ733, Δ753, Δ764 gp41 deletion mutants. Thus, the present invention encompasses additional gp41 variants that can be readily identified based upon the disclosure provided herein.

An isolated nucleic acid of the invention should be construed to include an RNA or a DNA sequence encoding a gp41 variant protein of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

The present invention should not be construed as being limited solely to the nucleic and amino acid sequences disclosed herein. Once armed with the present invention, it is readily apparent to one skilled in the art that other nucleic acids encoding gp41 variant proteins such as those present in other mammalian immunodeficiency viruses (e.g., HIV-1, SIV) can be obtained by using the sequence information disclosed herein for human HIV-2 gp41 variant nucleic acids encoding human HIV-2 gp41 variant polypeptides as disclosed herein as would be understood by one skilled in the art. Methods for isolating a nucleic acid based on a known sequence are well-known in the art (e.g., screening of genomic or cDNA libraries), and are not described herein.

Further, any number of procedures may be used for the generation of mutant, derivative or variant forms of a gp41 variant using recombinant DNA methodology well known in the art. A wide plethora of techniques is available to the skilled artisan to produce muteins of interest and to select those with desired properties.

The present invention also includes a nucleic acid encoding a gp41 variant wherein the nucleic acid encoding a tag polypeptide is covalently linked thereto. That is, the invention encompasses a chimeric nucleic acid wherein the nucleic acid sequences encoding a tag polypeptide is covalently linked to the nucleic acid encoding at least one of HIV-2 Δ733 gp41, HIV-2 Δ753 gp41, HIV-2 Δ764 gp41, gp41 encoded by a nucleic acid comprising at least one sequence of SEQ ID NO:9, SEQ ID NO:15, SEQ ID NO:21, and SEQ ID NO:27. Such tag polypeptides are well known in the art and include, for instance, green fluorescent protein (GFP), myc, myc-pyruvate kinase (myc-PK), His6, maltose biding protein (MBP), an influenza virus hemagglutinin tag polypeptide, a flag tag polypeptide (FLAG), and a glutathione-S-transferase (GST) tag polypeptide. However, the invention should in no way be construed to be limited to the nucleic acids encoding the above-listed tag polypeptides. Rather, any nucleic acid sequence encoding a polypeptide which may function in a manner substantially similar to these tag polypeptides should be construed to be included in the present invention.

II. Isolated Polypeptides

The invention also includes an isolated mammalian immunodeficiency virus gp120 polypeptide. Preferably, the isolated polypeptide is about 95% homologous, more preferably, about 99% homologous, to at least one amino acid sequence of SEQ ID NO:11, SEQ ID NO:17, SEQ ID NO:23 and SEQ ID NO:29. More preferably, the isolated polypeptide is at least one of an amino acid sequence of SEQ ID NO:11, SEQ ID NO:17, SEQ ID NO:23 and SEQ ID NO:29.

The skilled artisan would appreciate, based upon the disclosure provided herein, that the mammalian immunodeficiency virus includes, but is not limited to, human and simian virus, such as, but not limited to, SIV, HIV-1 and HIV-2.

The invention includes a mammalian immunodeficiency virus gp120 polypeptide comprising a deletion of V1 and V2, and further comprising a deletion of V3. The skilled artisan would understand, once armed with the teachings provided herein, that the deletion is one that deletes all but the first and last amino acid of the V1/V2 loop. The deletion of V3 can range from one that deletes all but the first and last 6 amino acids of the V3 loop, to one that contains only the first and the last amino acid. (i.e., in the HIV-2/VCP sequence a deletion of a single amino acid residue from the residues from about amino acid residue number 110 to amino acid residue number 194 of gp120), to a deletion of the entire V3 region (i.e., a deletion of from about amino acid residue number 298 to amino acid residue number 331).

The invention includes an isolated gp120 polypeptide, where the deletion of V3 can be a deletion of from about amino acid residue number 303 to amino acid residue number 324 (ΔV3(6,6)) relative to the amino acid sequence of HIV-2/vcp gp120 as provided in SEQ ID NO:5, and a deletion from about amino acid residue number 298 to amino acid residue number 331 (ΔV3(1,1)) relative to the amino acid sequence of HIV-2/vcp gp120 as provided in SEQ ID NO:5. And the gp120 polypeptide can further comprise a deletion of the V1/V2 region. This is because, as more fully disclosed elsewhere, such V-loop deletion peptides are useful for elucidating the structure and function of otherwise obscured or inaccessible domains of gp120 and also provide important potential immunogens for generation of neutralizing antibodies and for the development of novel therapeutics for immunodeficiency virus related diseases.

As disclosed previously elsewhere herein, the invention includes a gp120 mutant comprising at least one compensatory mutation. Such compensatory mutations include, but are not limited to, an amino acid substitution from isoleucine to valine at amino acid residue number 55, an amino acid substitution from asparagine to aspartic acid at amino acid residue number 79, an amino acid substitution from phenylalanine to serine at amino acid residue number 94, an amino acid substitution from aspartic acid to glycine at amino acid residue number 142, an amino acid substitution from threonine to isoleucine at amino acid residue number 160, an amino acid substitution from alanine to threonine at amino acid residue number 173, an amino acid substitution from threonine to lysine at amino acid residue number 202, an amino acid substitution from glutamic acid to lysine at amino acid residue number 203, an amino acid substitution from threonine to isoleucine at amino acid residue number 231, an amino acid substitution from alanine to threonine at amino acid residue number 267, an amino acid substitution from asparagine to aspartic acid at amino acid residue number 279, an amino acid substitution from asparagine to aspartic acid at amino acid residue number 280, an amino acid substitution from glutamic acid to lysine at amino acid residue number 334, an amino acid substitution from glutamic acid to lysine at amino acid residue number 340, an amino acid substitution from asparagine to aspartic acid at amino acid residue number 391, an amino acid substitution from threonine to alanine at amino acid residue number 393, an amino acid substitution from valine to isoleucine at amino acid residue number 399, an amino acid substitution from glutamine to arginine at amino acid residue number 405, an amino acid substitution from valine to isoleucine at amino acid residue number 429, an amino acid substitution from glutamic acid to valine at amino acid residue number 437, an amino acid substitution from threonine to alanine at amino acid residue number 439, and an amino acid substitution from glycine to alanine at amino acid residue number 666, wherein the amino acid residue number of the compensatory mutation is relative to the amino acid sequence of parental HIV-2/vcp gp120 as provided in SEQ ID NO:5.

The data disclosed herein demonstrate that these mutations are associated with and can potentially mediate the preservation and/or restoration of detectable biological acitivity to gp120 following deletion/truncation of the V3 region of the protein.

Additionally, the invention encompasses a gp120 where the V3 deletion is ΔV3(6,6) and further wherein the compensatory mutation is at least one of an amino acid substitution selected from the group consisting of an amino acid substitution from isoleucine to valine at amino acid residue number 55, an amino acid substitution from asparagine to aspartic acid at amino acid residue number 79, an amino acid substitution from threonine to lysine at amino acid residue number 202, an amino acid substitution from threonine to isoleucine at amino acid residue number 231, an amino acid substitution from alanine to threonine at amino acid residue number 267, and an amino acid substitution from asparagine to aspartic acid at amino acid residue number 391, wherein the amino acid residue number of the compensatory mutation is relative to the amino acid sequence of parental HIV-2/vcp gp120 as provided in SEQ ID NO:5. Such combination of V3 deletion and compensatory mutations is exemplified by the HIV-2 p16.5 clone gp120. The amino acid sequence of this clone is depicted in FIG. 22C (SEQ ID NO:11).

Likewise, the invention encompasses a gp120 polypeptide where the V3 deletion is ΔV3(6,6) and where the compensatory mutation is at least one of an amino acid substitution selected from the group consisting of an amino acid substitution from isoleucine to valine at amino acid residue number 55, an amino acid substitution from asparagine to aspartic acid at amino acid residue number 79, an amino acid substitution from phenylalanine to serine at amino acid residue number 94, an amino acid substitution from asparagine to aspartic acid at amino acid residue number 280, and an amino acid substitution from asparagine to aspartic acid at amino acid residue number 391, wherein the amino acid residue number of the compensatory mutation is relative to the amino acid sequence of parental HIV-2/vcp gp120 as provided in SEQ ID NO:5. Such combination of V3 deletion and compensatory mutations is exemplified by the HIV-2 p16.7 clone gp120. The amino acid sequence of this clone is depicted in FIG. 23C (SEQ ID NO:17).

The invention encompasses an isolated gp120 polypeptide where the V3 deletion is ΔV3(6,6) and further where the compensatory mutation is at least one of an amino acid substitution selected from the group consisting of an amino acid substitution from threonine to alanine at amino acid residue number 393, and an amino acid substitution from valine to isoleucine at amino acid residue number 429, wherein the amino acid residue number of the compensatory mutation is relative to the amino acid sequence of parental HIV-2/vcp gp120 as provided in SEQ ID NO:5. Such combination of V3 deletion and compensatory mutations is exemplified by the HIV-2 p16.9 clone gp120. The amino acid sequence of this clone is depicted in FIG. 24C (SEQ ID NO:23).

The invention also includes an isolated gp120 polypeptide where the V3 deletion is ΔV3(1,1) and further where the compensatory mutation is at least one of an amino acid substitution selected from the group consisting of an amino acid substitution from alanine to threonine at amino acid residue number 173, an amino acid substitution from glutamic acid to lysine at amino acid residue number 203, an amino acid substitution from threonine to alanine at amino acid residue number 393, an amino acid substitution from glutamine to arginine at amino acid residue number 405, an amino acid substitution from valine to isoleucine at amino acid residue number 429, an amino acid substitution from threonine to alanine at amino acid residue number 439, and an amino acid substitution from glycine to alanine at amino acid residue number 666, wherein the amino acid residue number of the compensatory mutation is relative to the amino acid sequence of parental HIV-2/vcp gp120 as provided in SEQ ID NO:5. Such combination of V3 deletion and compensatory mutations is exemplified by the HIV-2 8c.3 clone gp120. The amino acid sequence of this clone is depicted in FIG. 19C (SEQ ID NO:29).

As more fully discussed elsewhere herein, these various clones of HIV-2 are set forth herein for illustrative purposes only. The present invention is not limited in any way to these, or any other, particular combinations of V3 deletions and compensatory mutations.

The invention encompasses a n isolated gp120 polypeptide, or a mutant, derivative, or fragment thereof, comprising a deletion of hypervariable loop 3 (V3), a deletion of hypervariable loops V1/V2, and further comprising a compensatory mutation wherein the amino acid sequence of the gp120 polypeptide is selected from the group consisting of the sequence of SEQ ID NO:11, the sequence of SEQ ID NO:17, and the sequence of SEQ ID NO:29. Also, the invention includes an isolated gp120 polypeptide, or a mutant, derivative, or fragment thereof, wherein the gp120 polypeptide comprises a deletion of hypervariable loop 3 (V3), and further comprises a compensatory mutation wherein the amino acid sequence of the gp120 polypeptide comprises the sequence of SEQ ID NO:23, as exemplified, for illustrative purposes only, but HIV-2 gp120 p16.9 clone.

The present invention also provides for analogs of proteins or peptides which comprise a mammalian immunodeficiency virus gp120 polypeptide as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "mutants," "derivatives," and "variants" of the peptides of the invention (or of the DNA encoding the same) which mutants, derivatives and variants are mammalian immunodeficiency virus gp120 peptides which are altered in one or more amino acids (or, when referring to the nucleotide sequence encoding the same, are altered in one or more base pairs) such that the resulting peptide (or DNA) is not identical to the sequences recited herein, but has the same biological property as the gp120 variant peptides disclosed herein, in that the peptide has biological/biochemical properties of a mammalian immunodeficiency virus gp120 polypeptide of the present invention (e.g., despite deletion of all or a substantial portion of the V3 region, the polypeptide specifically binds with its ligand chemokine coreceptor, it can mediate detectable fusion with the host cell, and/or the polypeptide can mediate detectable replication competence of the virus).

The skilled artisan would understand, based upon the disclosure provided herein, that gp120 biological activity encompasses, but is not limited to, the ability of a molecule to specifically interact with a cellular chemokine coreceptor, to mediate detectable fusogenicity, and/or to mediate detectable virus replication in a cell.

Further, the invention should be construed to include naturally occurring variants or recombinantly derived mutants of gp120 variant sequences, which variants or mutants render the protein encoded thereby either more, less, or just as biologically active as the sequences of the invention.

The nucleic acids disclosed herein, and peptides encoded thereby, are useful tools for elucidating the function(s) of a gp120 molecule in a cell. Further, nucleic and amino acids comprising a mammalian gp120 polypeptide of the invention are useful diagnostics which can be used, for example, to identify a compound that affects gp120 function or expression, which compound is a potential drug candidate for a disease, disorder or condition associated with, or mediated by, mammalian immunodeficiency virus infection. The nucleic acids, the proteins encoded thereby, or both, can be administered to a cell, tissue, or mammal to increase or decrease expression or function of gp120 as disclosed herein, in the cell, tissue or mammal to which it is administered. This can be beneficial for the cell, tissue, and/or mammal in situations where the presence of gp120, or variant thereof, on the surface of a mammalian immunodeficiency virus in the cell, tissue or mammal mediates a disease or condition associated with gp120 interaction with one or more cellular cytokine receptors.

That is, the data disclosed herein demonstrate for the first time that core regions of the gp120 protein are responsible, at least in part, for immunodeficiency virus entry into a cell. Thus, these gp120 molecules are important targets for the production of potential therapeutics. Further, the data suggest that specific segments and amino acid residues of gp120 are non-essential for immunodeficiency virus entry into a cell. Production of the gp120 polypeptides of the invention in a cell provide sufficient quantities of the polypeptide to be used, for instance, in an assay to assess the role of various determinants in chemokine coreceptor binding and also to identify a compound that affects such binding, which is a potential useful therapeutic to inhibit the binding and thereby prevent and/or treat virus invention, but the invention is not limited to these, or any other particular use of such polypeptides.

The invention also includes an isolated mammalian immunodeficiency virus gp41 polypeptide comprising a compensatory mutation. Preferably, the isolated mammalian immunodeficiency virus gp41 polypeptide is shares greater than about 90% identity with a polypeptide having the amino acid sequence of at least one of SEQ ID NO:12, SEQ ID NO:18, SEQ ID NO:24, and SEQ ID NO:30. Preferably, the isolated polypeptide is about 95% homologous, and most preferably, about 99% homologous to at least one of SEQ ID NO:12, SEQ ID NO:18, SEQ ID NO:24, and SEQ ID NO:30. Most preferably, the amino acid sequence of the gp41 polypeptide is at least one of the sequence of SEQ ID NO:12, SEQ ID NO:18, SEQ ID NO:24, and SEQ ID NO:30.

The invention also encompasses an isolated mammalian immunodeficiency virus gp41 polypeptide comprising a truncation of the cytoplasmic domain where the gp41 polypeptide is at least one of HIV-2 gp41 Δ733, HIV-2 gp41 Δ753 and HIV-2 gp41 Δ764, where the truncation is located at the indicated amino acid residue number relative to the amino acid sequence of full-length parental HIV-2/VCP gp41 (SEQ ID NO:6).

The invention encompasses a gp41 polypeptide comprising at least one compensatory mutation selected from the following: an amino acid substitution from leucine to valine at amino acid residue number 518, an amino acid substitution from alanine to threonine at amino acid residue number 529, an amino acid substitution from isoleucine to valine at amino acid residue number 531, an amino acid substitution from alanine to threonine at amino acid residue number 561, and an amino acid substitution from alanine to threonine at amino acid residue number 673, wherein the amino acid residue number of the compensatory mutation is relative to the amino acid sequence of HIV-2/vcp gp41 (SEQ ID NO:6).

The invention further includes an isolated mammalian immunodeficiency virus gp41 polypeptide comprising a compensatory mutation where, preferably, the gp41 polypeptide is shares greater than about 90% identity with a polypeptide having the amino acid sequence of at least one of SEQ ID NO:12 (gp41 of p16.5 clone, shown in FIG. 22E), SEQ ID NO:18 (gp41 p16.7 clone shown on FIG. 23E), SEQ ID NO:24 (gp41 p16.9 clone depicted in FIG. 24E), and SEQ ID NO:30 (clone 8c.3 gp41 depicted in FIG. 19E). Preferably, the isolated polypeptide is about 90% homologous, more preferably, about 95% homologous, and most preferably, about 99% homologous to at least one of SEQ ID NO:12, SEQ ID NO:18, SEQ ID NO:24, and SEQ ID NO:30. More preferably, the isolated polypeptide comprising a mammalian immunodeficiency virus gp41 variant is at least one of HIV-2 gp41 p16.5, HIV-2 gp41 p16.7, HIV-2 gp41 p16.9, and HIV-2 gp41 p16.7. Most preferably, the isolated polypeptide comprising a mammalian gp41 variant is at least one of SEQ ID NO:12, SEQ ID NO:18, SEQ ID NO:24, and SEQ ID NO:30.

The invention also includes an isolated human immunodeficiency virus gp41 polypeptide comprising at least one compensatory mutation selected from the group consisting of an amino acid substitution from leucine to valine at amino acid residue number 518, an amino acid substitution from alanine to threonine at amino acid residue number 529, and an amino acid substitution from alanine to threonine at amino acid residue number 561. This is the combination of mutations as depicted in FIG. 16, setting forth the amino acid sequence of HIV-2/VCP gp41 obtained from p16.5 clone. The invention also includes a gp41 comprising at least one compensatory mutation as follows: an amino acid substitution from leucine to valine at amino acid residue number 518, an amino acid substitution from alanine to threonine at amino acid residue 529, and an amino acid substitution from isoleucine to valine at amino acid residue 531. This combination of mutations is depicting in FIG. 17, setting forth the amino acid sequence of HIV-2/VCP gp41 obtained from p16.7 clone. Additionally, the invention includes a gp41 comprising at least one compensatory mutation as follows: an amino acid substitution from leucine to valine at amino acid residue number 518, an amino acid substitution from alanine to threonine at amino acid residue 561, and an amino acid substitution from alanine to threonine at amino acid residue 673. This combination of mutations is depicted in FIG. 18, showing amino acid sequence and illustrating the conformation of HIV-2/VCP gp41 obtained from p16.9 clone. Clone 8c.3 comprises a gp41 (SEQ ID NO:30) comprising certain compensatory mutations when compared with parental HIV-2/VCP gp41 (SEQ ID NO:6).

As noted previously elsewhere herein, the present invention is in no way limited to these, or any other, particular compensatory mutations, or combinations thereof. Thus, one skilled in the art would appreciate, based upon the disclosure provided herein, that the present invention is not limited to these particular gp41 compensatory mutations, nor to compensatory mutations limited solely to truncation of the cytoplasmic domain of gp41. Nor is the present invention limited to these particular truncation mutations in the cytoplasmic domain of gp41. This is because the skilled artisan, armed with the teachings provided herein, could readily identify and isolate additional compensatory mutations of gp41 that detectably preserve and/or restore gp120 function and/or activity upon deletion of all, or part, of gp120 V3 by following the teachings set forth herein.

The present invention should also be construed to encompass "mutants," "derivatives," and "variants" of the peptides of the invention (or of the DNA encoding the same) which mutants, derivatives and variants are mammalian immunodeficiency virus gp41 peptides which are altered in one or more amino acids (or, when referring to the nucleotide sequence encoding the same, are altered in one or more base pairs) such that the resulting peptide (or DNA) is not identical to the sequences recited herein, but has the same biological property as the gp41 variant peptides disclosed herein, in that the peptide has biological/biochemical properties of a mammalian immunodeficiency virus gp120 polypeptide of the present invention (e.g., the gp120 can specifically bind a chemokine coreceptor, mediates detectable fusogenicity, and/or can mediate detectable virus replication in a cell).

The present invention should not be construed as being limited solely to the polypeptides disclosed herein. Once armed with the present invention, it is readily apparent to one skilled in the art that other gp120 and gp41 variant proteins such as those present in other mammalian immunodeficiency viruses (e.g., HIV-1, SIV) can be obtained by using the sequence information and the extensive teachings disclosed herein for human HIV-2 gp120 and HIV-2 gp41 variant polypeptides, respectively, as disclosed herein and as would be understood by one skilled in the art. Methods for isolating a polypeptide based on a known sequence are well-known in the art (e.g., affinity chromatography), and are not described herein. Further, as will be understood by the skilled artisan in light of the disclosure provided herein, gp120 and gp41 variant proteins such as those present in other mammalian immunodeficiency viruses (e.g., HIV-1, SIV) would be useful in the present invention due to similarities in sequence, structure, and function of such proteins to the polypeptides of the present invention. Therefore, using the methods and techniques disclosed herein, additional gp120 and/or gp41 mutants can be readily produced, characterized and isolated which possess the requisite characteristics disclosed herein in that they can, among other things, comprise a complete or substantial deletion of V3 and can nevertheless demonstrate detectable binding with a chemokine coreceptor, fuse with a cell, and/or demonstrate detectable replication in a cell.

III. Vectors

In other related aspects, the invention includes an isolated nucleic acid encoding a mammalian immunodeficiency virus gp120 as disclosed previously elsewhere herein operably linked to a nucleic acid specifying a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

That is, the invention encompasses an isolated nucleic acid encoding a mammalian immunodeficiency virus glycoprotein gp120 polypeptide, wherein the gp120 comprises a deletion of V1, a deletion of V2, and further comprises a substantial deletion of V3, where the nucleic acid is operably linked to a nucleic acid specifying a promoter/regulatory sequence.

Similarly, the invention encompasses an isolated nucleic acid encoding a mammalian immunodeficiency virus glycoprotein gp41 polypeptide, wherein the gp41 comprises a compensatory mutation, including, but not limited to a truncation of the cytoplasmic domain of the gp41, where the nucleic acid is operably linked to a nucleic acid specifying a promoter/regulatory sequence.

Expression of the afore-mentioned gp120 and/or gp41, either alone or fused to a detectable tag polypeptide, in cells which either do not normally express the polypeptide, or which do not express the polypeptide fused with a tag polypeptide, can be accomplished by generating a plasmid, viral, or other type of vector comprising the desired nucleic acid operably linked to a promoter/regulatory sequence which serves to drive expression of the protein, with or without tag, in cells in which the vector is introduced. Many promoter/regulatory sequences useful for driving constitutive expression of a nucleic acid of interest are available in the art and include, but are not limited to, for example, the cytomegalovirus immediate early promoter enhancer sequence, the SV40 early promoter, as well as the Rous sarcoma virus promoter, and the like.

Moreover, inducible and tissue specific expression of the nucleic acid encoding the gp120 and/or gp41 of the present invention can be accomplished by placing the nucleic acid encoding WNK, with or without a tag, under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein operably linked thereto.

The invention includes methods of inhibiting expression, translation, and/or activity in a cell of gp120 and/or gp41 of the invention, as well as methods relating to increasing expression, protein level, and/or activity of the gp120 and/or gp41 of the invention since both decreasing and increasing gp120 and/or gp41 expression and/or activity can be useful in providing effective therapeutics and/or diagnostic reagents.

Selection of any particular plasmid vector or other DNA vector is not a limiting factor in this invention and a wide variety of vectors is well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook et al. (1989, Molecular Cloning: A Laboratory Manual, Cold Spring Harbor Laboratory, N.Y.), and in Ausubel et al. (1997, Current Protocols in Molecular Biology, John Wiley & Sons, New York).

The invention thus includes a vector comprising an isolated nucleic acid encoding a mammalian immunodeficiency virus gp120 and/or gp41 of the invention as disclosed elsewhere herein. The incorporation of a desired nucleic acid into a vector and the choice of vectors is well-known in the art as described in, for example, Sambrook et al. (1989, Molecular Cloning: A Laboratory Manual, Cold Spring Harbor Laboratory, N.Y.), and in Ausubel et al. (1997, Current Protocols in Molecular Biology, John Wiley & Sons, New York).

The invention also includes cells, viruses, proviruses, and the like, containing such vectors. Methods for producing cells comprising vectors and/or exogenous nucleic acids are well-known in the art, and is detailed in, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

The nucleic acids encoding a gp120 and/or gp41 of the invention can be cloned into various plasmid vectors. However, the present invention should not be construed to be limited to plasmids, or to any particular vector. Instead, the present invention encompasses a wide plethora of vectors which are readily available and/or well-known in the art, or as will be developed in the future. One skilled in the art would understand, once provided with the nucleic and amino acid sequences of the present invention, as well as the various teachings provided herein, that a wide plethora of molecular biology techniques can be applied to producing various recombinant constructs which can be used in a variety of techniques as are well-known in the art.

IV. Recombinant Cells

The invention includes a recombinant cell comprising, inter alia, an isolated nucleic acid encoding a mammalian immunodeficiency virus gp120 polypeptide, wherein the polypeptide comprises a deletion of a V1, deletion of V2, and further comprises a substantial deletion of V3, or a complete deletion thereof. The invention also encompasses an antisense nucleic acid complementary thereto, a nucleic acid encoding an antibody that specifically binds a gp120 polypeptide encoded by that nucleic acid, and the like. In one aspect, the recombinant cell can be transiently transfected with a plasmid encoding a portion of the nucleic acid encoding the gp120 V3 deletion polypeptide. The nucleic acid need not be integrated into the cell genome nor does it need to be expressed in the cell. Moreover, the cell may be a prokaryotic or a eukaryotic cell and the invention should not be construed to be limited to any particular cell line or cell type. Such cells include, but are not limited to, bacterial cells, yeast, insect cells, mammalian cells, and the like.

The invention should be construed to include any cell type into which a nucleic acid encoding a mammalian immunodeficiency virus gp120 polypeptide (a transgene) is introduced, including, without limitation, a prokaryotic cell and a eukaryotic cell comprising an isolated nucleic acid encoding the mammalian gp120 polypeptide of the invention.

The invention also encompasses a recombinant cell where an endogenous target nucleic acid gp120 variant is activated by introduction of an exogenous activating nucleic acid into the cell such that the endogenous target nucleic acid is expressed and/or the gp120 polypeptide is produced. Such techniques of gene activation are well-known in the art and are described, for example, in U.S. Pat. No. 6,270,989, among many others.

When the cell is a eukaryotic cell, the cell may be any eukaryotic cell which, when the transgene of the invention is introduced therein, and the protein encoded by the desired gene is no longer expressed therefrom, a benefit is obtained. Such a benefit may include the fact that there has been provided a system in which lack of expression of the desired gene can be studied in vitro in the laboratory or in a mammal in which the cell resides, a system wherein cells comprising the introduced gene deletion can be used as research, diagnostic and therapeutic tools, and a system wherein animal models are generated which are useful for the development of new diagnostic and therapeutic tools for selected disease states in a mammal including, for example, Acquired Immune Deficiency Syndrome, or any other disease, disorder or condition mediated by gp120 interaction with a cellular chemokine receptor, and the like.

Alternatively, the invention includes a eukaryotic cell which, when the transgene of the invention is introduced therein, and the protein encoded by the desired gene is expressed therefrom where it was not previously present or expressed in the cell or where it is now expressed at a level or under circumstances different than that before the transgene was introduced, a benefit is obtained. Such a benefit may include the fact that there has been provided a system in the expression of the desired gene can be studied in vitro in the laboratory or in a mammal in which the cell resides, a system wherein cells comprising the introduced gene can be used as research, diagnostic and therapeutic tools, and a system wherein animal models are generated which are useful for the development of new diagnostic and therapeutic tools for selected disease states in a mammal.

Further, expression in a cell of an immunodeficiency virus gp120, comprising a deletion of the V3 region of the protein can provide a target for an immune response against that cell now bearing the gp120 of the invention. That is, by expressing a gp120 of the invention in which the lack of at least one hypervariable region can expose certain epitopes that are otherwise "camouflaged" by various hypervariable regions in an unmodified virus, the cell can be targeted for an immune response such that expression of the polypeptides of the invention can provide a therapeutic method whereby infected cells can be targeted by the immune system.

Additionally, a cell expressing an isolated nucleic acid encoding a gp120 polypeptide of the invention can be used to provide the gp120 polypeptide to a cell, tissue, or whole animal where a higher level of gp120 variant can be useful to treat or alleviate a disease, disorder or condition wherein soluble gp120 can alleviate such a disease, disorder or condition. Therefore, the invention includes a cell expressing a gp120 polypeptide comprising a substantial, or complete, deletion of the V3 such as, but not limited to, HIV-2 ΔV1/V2; ΔV3(6,6) gp120; HIV-2 ΔV1/V2; ΔV3(1,1) gp120; HIV-2 ΔV3(6,6) gp120; and HIV-2 ΔV3(1,1) gp120, to increase or induce gp120 variant activity, where increasing gp120 variant protein level and/or activity can be useful to treat or alleviate a disease, disorder or condition, since increasing soluble gp120 V3 deletion polypeptide can, for instance, inhibit the binding of virus-bound gp120 to a cellular chemokine receptor and inhibit viral entry into the cell.

Methods and compositions useful for maintaining mammalian cells in culture are well known in the art, wherein the mammalian cells are obtained from a mammal including, but not limited to, a rat and a human.

The recombinant cell of the invention can be used to study the effect of qualitative and quantitative alterations in the level of gp120 polypeptide comprising a substantial deletion of V3 on a cell, including the effect of decreased viral entry into the cell. This is because the fact that HIV-2 virus gp120, and variants thereof comprising core gp120 structures and sequences, have now been demonstrated to mediate CD4-independent entry into a cell, wherein viral entry is correlated with, among other things, Acquired Immune Deficiency Syndrome. Further, the recombinant cell can be used to produce a gp120 polypeptide of the invention for use for therapeutic and/or diagnostic purposes. That is, a recombinant cell expressing a gp120 V3 deletion polypeptide of the invention can be used to, among other things, produce large amounts of purified and isolated gp120 polypeptide that can in turn be administered to treat or alleviate a disease, disorder or condition associated with or caused by an increased or inappropriate level of viral-associated gp120 polypeptide.

Alternatively, recombinant cells expressing a gp120 V3 deletion polypeptide of the invention can be administered in ex vivo and in vivo therapies where administering the recombinant cells thereby administers the protein to a cell, a tissue, and/or an animal. Additionally, the recombinant cells are useful for the discovery of processes affected and/or mediated by gp120 polypeptide core components and/or gp120 determinants that are exposed after CD4 binding. Thus, the recombinant cell of the invention may be used to study the effects of elevated or decreased gp120 where the polypeptide comprises a deletion of the V3 region, and further comprises deletions of V1 and V2 regions as well.

The invention further includes a recombinant cell comprising an isolated nucleic acid encoding a mammalian immunodeficiency virus gp41 polypeptide, wherein the polypeptide comprises a compensatory mutation. The invention encompasses a nucleic acid encoding such a gp41 polypeptide, where the compensatory mutation is truncation of the cytoplasmic domain (CD) of the peptide. The invention also encompasses an antisense nucleic acid complementary thereto, a nucleic acid encoding an antibody that specifically binds a gp41 polypeptide encoded by that nucleic acid, and the like.

In one aspect, the recombinant cell can be transiently transfected with a plasmid encoding a portion of the nucleic acid encoding the gp41 compensatory mutation polypeptide. The nucleic acid need not be integrated into the cell genome nor does it need to be expressed in the cell. Moreover, the cell may be a prokaryotic or a eukaryotic cell and the invention should not be construed to be limited to any particular cell line or cell type. Such cells include, but are not limited to, bacterial cells, yeast, insect cells, mammalian cells, and the like.

The invention should be construed to include any cell type into which a nucleic acid encoding a mammalian immunodeficiency virus gp41 polypeptide (a transgene) is introduced, including, without limitation, a prokaryotic cell and a eukaryotic cell comprising an isolated nucleic acid encoding the mammalian gp41 polypeptide of the invention.

The invention also encompasses a recombinant cell where an endogenous target nucleic acid gp41 comprising a compensatory mutation is activated by introduction of an exogenous activating nucleic acid into the cell such that the endogenous target nucleic acid is expressed and/or the gp41 polypeptide is produced. Such techniques of gene activation are well-known in the art and are described, for example, in U.S. Pat. No. 6,270,989, among many others.

When the cell is a eukaryotic cell, the cell may be any eukaryotic cell which, when the transgene of the invention is introduced therein, and the protein encoded by the desired gene is no longer expressed therefrom, a benefit is obtained. Such a benefit may include the fact that there has been provided a system in which lack of expression of the desired gene can be studied in vitro in the laboratory or in a mammal in which the cell resides, a system wherein cells comprising the introduced gene deletion can be used as research, diagnostic and therapeutic tools, and a system wherein animal models are generated which are useful for the development of new diagnostic and therapeutic tools for selected disease states in a mammal including, for example, Acquired Immune Deficiency Syndrome, or any other disease, disorder or condition mediated by gp41, including fusion with a cell membrane, and the like.

Additionally, a cell expressing an isolated nucleic acid encoding a gp41 polypeptide of the invention can be used to provide the gp41 polypeptide to a cell, tissue, or whole animal where a higher level of gp41 variant can be useful to treat or alleviate a disease, disorder or condition wherein gp41 can alleviate such a disease, disorder or condition. Therefore, the invention includes a cell expressing a gp41 polypeptide comprising a compensatory mutation such as, but not limited to, truncation of the CD. Such mutations include, but are not limited to, gp41 Δ733 (SEQ ID NO:22), gp41 Δ753 (SEQ ID NO:23), and gp41 Δ764 (SEQ ID NO:25), where truncation of CD of the gp41 polypeptide increased fusogenicity of the virus.

V. Antibodies

The invention also includes an antibody that specifically binds a mammalian immunodeficiency virus gp120, wherein the polypeptide comprises a substantial deletion of V3. The invention further includes an antibody that binds the gp120 wherein the polypeptide further comprises deletion of V1 and V2 as well.

One skilled in the art would understand, based upon the disclosure provided herein, that an antibody that specifically binds a gp120 polypeptide of the invention binds a polypeptide such as, but not limited to, HIV-2 ΔV1/V2; ΔV3(6,6) gp120, HIV-2 ΔV1/V2; ΔV3(1,1) gp120, HIV-2 ΔV3(6,6) gp120 or HIV-2 ΔV3(1,1) gp120, or an immunogenic portion thereof. In one embodiment, the antibody is directed to: HIV-2 ΔV1/V2; ΔV3(6,6) gp120, comprising the amino acid sequence of SEQ ID NO:2, HIV-2 ΔV1/V2; ΔV3(1,1) gp120, comprising the amino acid sequence of SEQ ID NO:4, HIV-2 ΔV3(6,6) gp120, comprising the amino acid sequence of SEQ ID NO:2a, and HIV-2 ΔV3(1,1) gp120, comprising the amino acid sequence of SEQ ID NO:4a.

The invention encompasses a wide plethora of antibodies, including, but not limited to, polyclonal and monoclonal antibodies, among many others. Polyclonal antibodies are generated by immunizing rabbits according to standard immunological techniques well-known in the art (see, e.g., Harlow et al., 1988, In: Antibodies, A Laboratory Manual, Cold Spring Harbor, N.Y.; and Wilson et al., 2001, Science 293: 1107-1112). Such techniques include immunizing an animal with a chimeric protein comprising a portion of another protein such as a maltose binding protein or glutathione (GSH) tag polypeptide portion, and/or a moiety such that the gp120 variant portion is rendered immunogenic (e.g., gp120 variant conjugated with keyhole limpet hemocyanin, KLH) and a portion comprising the respective gp120 variant amino acid residues. The chimeric proteins are produced by cloning the appropriate nucleic acids encoding a gp120 variant (e.g., SEQ ID NO:8, SEQ ID NO:14, SEQ ID NO:20, and SEQ ID NO:26) or a gp41 variant (e.g., SEQ ID NO:3, SEQ ID NO:9, SEQ ID NO:15 and SEQ ID NO:27) or a variant Env (e.g., SEQ ID NO:7, SEQ ID NO:13, SEQ ID NO:19 and SEQ ID NO:25) into a plasmid vector suitable for this purpose, such as but not limited to, pMAL-2 or pCMX.

However, the invention should not be construed as being limited solely to these antibodies or to these portions of the protein antigens. Rather, the invention should be construed to include other antibodies, as that term is defined elsewhere herein, to a gp120 variant of the invention, or portions thereof. Further, the present invention should be construed to encompass antibodies, inter alia, that bind to a gp120 variant and they are able to bind a gp120 variant present on Western blots, in immunohistochemical staining of tissues thereby localizing a gp120 variant in the tissues, and in immunofluorescence microscopy of a cell transiently transfected with a nucleic acid encoding at least a portion of a gp120 variant.

Moreover, the invention encompasses an antibody that specifically binds with a gp41 polypeptide comprising a compensatory mutation, and, more preferably, where the compensatory mutation comprises truncation of the CD of the polypeptide. Further, the present invention should be construed to encompass antibodies, inter alia, that bind to a gp41 of the invention and they are able to bind the gp41 of the invention when present on Western blots, in immunohistochemical staining of tissues thereby localizing a gp41 of the invention in a cell, a tissue, and any sample, and in immunofluorescence microscopy of a cell transiently transfected with a nucleic acid encoding at least a portion of the relevant gp41.

One skilled in the art would appreciate, based upon the disclosure provided herein, that the antibody can specifically bind with any portion of the protein and the full-length protein can be used to generate antibodies specific therefor. However, the present invention is not limited to using the full-length protein as an immunogen. Rather, the present invention includes using an immunogenic portion of the protein to produce an antibody that specifically binds with a mammalian immunodeficiency virus gp41 variant. That is, the invention includes immunizing an animal using an immunogenic portion, or antigenic determinant, of the gp120 variant protein.

The antibodies can be produced by immunizing an animal such as, but not limited to, a rabbit or a mouse, with a protein of the invention, or a portion thereof, or by immunizing an animal using a protein comprising at least a portion of a gp120 polypeptide of the invention, or a fusion protein including a tag polypeptide portion comprising, for example, a maltose binding protein tag polypeptide portion, covalently linked with a portion comprising the appropriate gp120 variant amino acid residues. One skilled in the art would appreciate, based upon the disclosure provided herein, that smaller fragments of these proteins can also be used to produce antibodies that specifically bind an gp120 variant.

One skilled in the art would appreciate, based upon the disclosure provided herein, that various portions of an isolated bp120 variant polypeptide can be used to generate antibodies to either conserved regions of a gp120 variant or to non-conserved regions of the polypeptide. As disclosed elsewhere herein, gp120 comprises various conserved domains, including core domains that have been shown herein to be responsible for gp120-containing virus into a cell.

Once armed with the sequence of gp120 of the invention, and the detailed analysis localizing the various conserved and non-conserved domains of the protein and their potential function(s), the skilled artisan would understand, based upon the disclosure provided herein, how to obtain antibodies specific for the various portions of a gp120 variant polypeptide using methods well-known in the art or to be developed in the future.

Further, the skilled artisan, based upon the disclosure provided herein, would appreciate that the non-conserved regions of a protein of interest can be more immunogenic than the highly conserved regions which are conserved among various organisms. Further, immunization using a non-conserved immunogenic portion can produce antibodies specific for the non-conserved region thereby producing antibodies that do not cross-react with other proteins which can share one or more conserved portions. Thus, one skilled in the art would appreciate, based upon the disclosure provided herein, that the non-conserved regions of each gp120 molecule can be used to produce antibodies that are specific only for that gp120 variant and do not cross-react non-specifically with other gp120 variants or with other proteins. More specifically, the skilled artisan, once armed with the teachings provided herein, would readily appreciate that antibodies can be produced that react with HIV-2 ΔV1/V2; ΔV(6,6) gp120, but not with HIV-2 ΔV1/V2; ΔV(1,1) gp120, and vice-a-versa.

Alternatively, the skilled artisan would also understand, based upon the disclosure provided herein, that antibodies developed using a region that is conserved among one or more gp120 molecules can be used to produce antibodies that react specifically with one or more gp120 molecule(s). That is, once armed with the sequences disclosed herein, one skilled in the art could readily prepare, using methods well-known in the art, antibodies that specifically bind with HIV-2 ΔV1/V2; ΔV(6,6) gp120 and with HIV-2 ΔV1/V2; ΔV(1,1) gp120. Methods for producing antibodies that specifically bind with a conserved protein domain which may otherwise be less immunogenic than other portions of the protein are well-known in the art and have been discussed previously, and include, but are not limited to, conjugating the protein fragment of interest to a molecule (e.g., keyhole limpet hemocyanin, and the like), thereby rendering the protein domain immunogenic, or by the use of adjuvants (e.g., Freund's complete and/or incomplete adjuvant, and the like), or both. Thus, the invention encompasses antibodies that recognize at least one gp120 variant and antibodies that specifically bind with more than one gp120 variant, including antibodies that specifically bind with all gp120 variants of the invention.

The teachings provided herein can be applied with equal force to development of antibodies of interest that specifically bind with the gp41 and Env polypeptides of the invention.

One skilled in the art would appreciate, based upon the disclosure provided herein, which portions of a gp120 variant are less homologous with other proteins sharing conserved domains. However, the present invention is not limited to any particular domain; instead, the skilled artisan would understand that other non-conserved regions of the gp120 variant proteins of the invention can be used to produce the antibodies of the invention as disclosed herein.

Therefore, the skilled artisan would appreciate, based upon the disclosure provided herein, that the present invention encompasses antibodies that neutralize and/or inhibit gp120 variant activity (e.g., by inhibiting necessary gp120 variant/cytokine receptor protein/protein interactions) which antibodies can recognize one or more gp120 variants, including, but not limited to, HIV-2 ΔV1/V2; ΔV(6,6) gp120 and with HIV-2 ΔV1/V2; ΔV(1,1) gp120.

One skilled in the art would also understand, based upon the disclosure provided herein, that it may be advantageous to inhibit the activity of one type of gp120 variant molecule without affecting the activity of other gp120 variants or other gp120 molecules. For example, it may be beneficial to inhibit HIV-2 ΔV1/V2; ΔV(6,6) gp120 activity, while not inhibiting the activity of HIV-2 ΔV1/V2; ΔV(1,1) gp120, or wildtype parental gp120. Thus, whether inhibition of gp120 activity is achieved using antibodies or other techniques, one skilled in the art would appreciate, based upon the disclosure provided herein, that the present invention encompasses selectively affecting one or more gp120 molecules and, in certain cases, the invention encompasses inhibiting the activity of all gp120 molecules. Whether one or more gp120 molecule should be affected can be readily determined by the skilled artisan based on which disease, disorder or condition is being treated, and the specific cell and/or tissue being targeted.

The invention should not be construed as being limited solely to the antibodies disclosed herein or to any particular immunogenic portion of the proteins of the invention. Rather, the invention should be construed to include other antibodies, as that term is defined elsewhere herein, to gp120 polypeptide comprising a substantial deletion of V3, or portions thereof, or to proteins sharing greater than 90% homology with a polypeptide having the amino acid sequence of at least one of SEQ ID NO:11, SEQ ID NO:17, SEQ ID NO:23, and SEQ ID NO:29. Preferably, the polypeptide is about 95% homologous, and more preferably, about 99% homologous to at least one of SEQ ID NO:11, SEQ ID NO:17, SEQ ID NO:23, and SEQ ID NO:29. More preferably, the polypeptide that specifically binds with an antibody specific for mammalian gp120 variant is at least one of SEQ ID NO:11, SEQ ID NO:17, SEQ ID NO:23, and SEQ ID NO:29.

The invention should not be construed as being limited solely to the antibodies disclosed herein or to any particular immunogenic portion of the proteins of the invention. Rather, the invention should be construed to include other antibodies, as that term is defined elsewhere herein, to gp41 polypeptide comprising at least one compensatory mutation, or portions thereof, or to proteins sharing greater than 90% homology with a polypeptide having the amino acid sequence of at least one of SEQ ID NO:12, SEQ ID NO:18, SEQ ID NO:24, and SEQ ID NO:30. Preferably, the polypeptide is about 95% homologous, and more preferably, about 99% homologous to at least one of SEQ ID NO:12, SEQ ID NO:18, SEQ ID NO:24, and SEQ ID NO:30. More preferably, the polypeptide that specifically binds with an antibody specific for mammalian gp120 variant is at least one of SEQ ID NO:12, SEQ ID NO:18, SEQ ID NO:24, and SEQ ID NO:30.

The invention should not be construed as being limited solely to the antibodies disclosed herein or to any particular immunogenic portion of the proteins of the invention. Rather, the invention should be construed to include other antibodies, as that term is defined elsewhere herein, to Env polypeptide comprising a substantial deletion of V3, or portions thereof, and further comprising at least one compensatory mutation, or to proteins sharing greater than 90% homology with a polypeptide having the amino acid sequence of at least one of SEQ ID NO:10, SEQ ID NO:16, SEQ ID NO:22, and SEQ ID NO:28. Preferably, the polypeptide is about 95% homologous, and more preferably, about 99% homologous to at least one of SEQ ID NO:10, SEQ ID NO:16, SEQ ID NO:22, and SEQ ID NO:28. More preferably, the polypeptide that specifically binds with an antibody specific for mammalian gp120 variant is at least one of SEQ ID NO:10, SEQ ID NO:16, SEQ ID NO:22, and SEQ ID NO:28.

The invention encompasses polyclonal, monoclonal, synthetic antibodies, and the like. One skilled in the art would understand, based upon the disclosure provided herein, that the crucial feature of the antibody of the invention is that the antibody bind specifically with a gp120 variant. That is, the antibody of the invention recognizes a gp120 variant, or a fragment thereof (e.g., an immunogenic portion or antigenic determinant thereof), on Western blots, in immunostaining of cells, and immunoprecipitates a gp120 variant using standard methods well-known in the art.

One skilled in the art would appreciate, based upon the disclosure provided herein, that the antibodies can be used to localize the relevant protein in a cell and to study the role(s) of the antigen recognized thereby in cell processes. Moreover, the antibodies can be used to detect and or measure the amount of protein present in a biological sample using well-known methods such as, but not limited to, Western blotting and enzyme-linked immunosorbent assay (ELISA). Moreover, the antibodies can be used to immunoprecipitate and/or immuno-affinity purify their cognate antigen using methods well-known in the art. In addition, the antibody can be used to decrease the level of a gp120 variant in a cell thereby inhibiting the effect(s) of gp120 variant in a cell. Thus, by administering the antibody to a cell or to the tissues of an animal or to the animal itself, the required gp120 variant/cytokine receptor protein/protein interactions are therefore inhibited such that the effects of gp120 variant-mediated activity are also inhibited. One skilled in the art would understand, based upon the disclosure provided herein, that detectable effects upon inhibiting gp120 variant/cytokine receptor protein/protein interaction and/or activity using an anti-gp120 variant antibody can include, but are not limited to, decreased interaction of virus-bound gp120 with a cytokine receptor (such as CCR5 and CXCR4), decreased entry into a cell of a virus having gp120 as part of the Env, decreased fusogenicity of a virus having gp120 as part of the Env, decreased apparent replication competence of a virus having gp120 as part of the Env, and the like.

One skilled in the art would appreciate, based upon the disclosure provided herein, that the invention encompasses administering an antibody that specifically binds with a gp120 variant orally, parenterally, or both, to inhibit gp120 variant function in enabling entry into a cell of a virus having gp120 as part of the Env.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein.

Further, the antibody of the invention may be “humanized” using the technology described in, for example, Wright et al. (1992, Critical Rev. Immunol. 12:125-168), and in the references cited therein, and in Gu et al. (1997, Thrombosis and Hematocyst 77:755-759), and other methods of humanizing antibodies well-known in the art or to be developed.

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al., (1989, Molecular Cloning: A Laboratory Manual, Cold Spring Harbor Laboratory, New York).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al. (1992, Critical Rev. Immunol. 12:125-168).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222: 581-597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

Further, the invention encompasses production of an antibody that specifically binds with a mammalian immunodeficiency virus gp41 polypeptide, wherein the polypeptide comprises a compensatory mutation, more specifically, the compensatory mutation is a truncation of the CD of the protein. As discussed previously with regard to gp120, similar methods can be applied to the gp41 polypeptide of the invention. Because certain important epitopes of the gp41 are exposed due to truncation of the cytoplasmic domain, as evidenced by the increased fusogenicity of the gp41 polypeptide of the invention compared with wild type gp41, development of an antibody directed against such a polypeptide can provide a method for producing antibodies that specifically bind with important functional epitopes of gp41 and can provide important diagnostic and therapeutic tools relating to gp41-mediated entry of the virus into a cell.

VI. Methods and Compositions Relating to Mammalian Immunodeficiency Viruses Containing Hypervariable Loop Mutations The present invention features compositions and methods related to mammalian immunodeficiency viruses comprising one or more amino acid mutations in at least one of hypervariable loops V1, V2, V3 and V4, whereby such mutation does not result in loss of fusogenicity and/or replication competence. Deletion mutation of the hypervariable loops of gp120 and mutations relating to compensatory mutation of gp41, including truncation of the cytoplasmic domain of the polypeptide, are set forth more fully previously elsewhere herein and are therefore referred to herein without further discussion.

The present invention encompasses a composition comprising a mammalian immunodeficiency virus gp120 polypeptide, wherein the polypeptide comprises a substantial, or complete, deletion of the V3 region. Methods of making the desired deletion, as well as assays for selecting the deletion mutants of interest, that is, those mutants having the desired quality (e.g., where detectable chemokine receptor binding, fusogenicity and/or replication competence are maintained despite deletion of all, or part, of the V3 region), are described in great detail elsewhere herein.

The composition further comprises a deletion of V1 and a deletion of V2, such that most of the hypervariable regions of the gp120 are absent from the polypeptide. Surprisingly, the data disclosed herein demonstrate that even though the gp120 comprises these deletions, the polypeptide retains the ability to mediate detectable binding with a chemokine receptor, fuse with a cell, and/or virus replication competence is preserved. As more fully disclosed elsewhere herein, such compositions are useful in that they provide a "core" polypeptide, with little or no hypervariable regions to camouflage various domains of the polypeptide that are important for function. Thus, the skilled artisan would appreciate, based upon the disclosure provided herein, that the compositions of the invention can be used for, among many other things, identifying and studying the functional domains of gp120, as well for the development of useful therapeutics based on inhibiting such functions and for the development of useful immune-based methods, including vaccine development, for inhibiting and/or preventing virus infection. This is because, as more fully discussed elsewhere, exposure of the core functional domains of gp120 can provide a useful immunogen for development of a neutralizing antibody that can inhibit requisite virus function mediated by such core domain(s) of gp120.

The invention also encompasses a composition comprising a gp120 as discussed previously, and further comprising a gp41 polypeptide. Further, the gp41 polypeptide can comprise a compensatory mutation, such as, but not limited to, truncation of the cytoplasmic domain of the gp41 polypeptide. Such compositions are useful as noted previously, for the study and identification of virus domains and mechanisms required for virus infection. Further, the compositions are useful for the development of useful therapeutics based on inhibition of core functions and the development of a virus neutralizing antibody that specifically binds with the polypeptides of the compositions of the invention.

The invention encompasses an isolated mammalian immunodeficiency virus wherein the virus comprises a gp120 comprising a substantial deletion of V3 where the virus retains detectable function, such as, but not limited to, chemokine receptor binding, fusogenicity and replication competence, compared with an otherwise identical virus not comprising the mutation deletion of V3. One skilled in the art would appreciate, once armed with the teachings provided herein, that the virus can further comprise a deletion of V1 and a deletion of V2. Such viruses are useful for the study of function of the various protein domains that remain after deletions of the hypervariable region(s). Moreover, as more fully discussed elsewhere herein, the virus can be used to produce a useful neutralizing antibody, as well as to identify a useful compound that can inhibit virus function required for infection. The skilled artisan would understand that the mammalian human immunodeficiency virus includes, but is not limited to, SIV, HIV-1 and HIV-2, among others.

The invention further includes the an isolated mammalian immunodeficiency virus comprising a gp120 wherein the gp120 comprises a substantial deletion of V3, wherein the virus further comprises a gp41. Additionally, the invention comprises a virus where the gp41 further comprises a compensatory mutation. This virus is useful not only for the study and identification of gp120 domains that mediate virus function needed for infection, but also for the development of useful therapeutics such as, but not limited to, a neutralizing antibody and a compound that can inhibit the function of gp120 thereby preventing or inhibiting virus infection.

As described elsewhere herein, a compensatory mutation enables a mammalian immunodeficiency virus to remain fusogenic, to remain replication competent, or to become highly cytopathic, despite at least one other mutation in a virus polypeptide that would otherwise reduce the level of that function/characteristic of the virus. Thus, compensatory mutation enables a virus containing a deletion of one or more hypervariable loops to remain replication competent and highly infectious. That is, a compensatory mutation "compensates" for the effect of the other mutation.

As discussed in detail elsewhere herein a deletion of the gp120 V1 loop may comprise the deletion of at least one amino acid naturally present in the loop. In another embodiment, a deletion of the gp120 V1 loop may comprise deletion of the entire V1 loop. As discussed elsewhere herein, any gp120 hypervariable loop (i.e., V1, V2, V3 or V4) may be deleted for the purposes of the present invention. Further, any combination of hypervariable loop deletion may be used in the present invention for the purpose of producing an isolated mammalian immunodeficiency virus comprising a mutation in a gp120 protein where at least a substantial portion of V3 is deleted, where the virus can further comprise a gp41 protein, where gp41 comprises a compensatory mutation. For example, an isolated mammalian immunodeficiency virus of the invention can be produced by deletion of the gp120 V1/V2 loops in their entirety, in addition to substantial deletion of the gp120 V3 loop, wherein despite such loop deletions, the gp120 retains detectable function (e.g., binding of a chemokine receptor, fusogenicity, and replication competence). As described elsewhere herein, isolated virus containing compensatory mutations may be obtained by serially passaging virus onto $CD4^+$ cell lines, among other methods.

Another embodiment of the invention provides an isolated mammalian immunodeficiency virus, wherein deletion of the gp120 V1/V2 loops in their entirety, in addition to partial deletion of the gp120 V3 loop, and where the virus further comprises at least one compensatory mutation in the gp41 protein of the virus. Yet another embodiment of the invention provides an isolated mammalian immunodeficiency virus, wherein deletion of the gp120 V1/V2 loops in their entirety, in addition to partial deletion of the gp120 V3 loop, is used to produce a gp41 comprising at least one compensatory mutation.

The invention includes a method of producing a replication-competent mammalian immunodeficiency virus comprising deletion of at least one hypervariable V3 loop of gp120. The invention further includes a method where the virus further comprises a compensatory mutation. As discussed in detail elsewhere herein, a compensatory mutation in the virus comprising a loop-deleted gp120 polypeptide provides a mammalian immunodeficiency virus with increased or enhanced fusogenic property, replication competence, or both, compared with an otherwise identical virus not comprising the compensatory mutation.

In one aspect of the invention, a compensatory mutation is induced in a gp120 polypeptide by deletion of the entirety of hypervariable loops V1 and V2, along with a partial deletion of hypervariable loop V3, such that only the first six and the last six amino acids of the V3 loop remain. This mutation resulted in gp120 and/or gp41 that retained detectable function, and where the polypeptides comprised mutations including, in gp120: 55 I/V, 79 N/D, 202 T/K, 231 T/I, 280 N/D, 391 N/D, 429 V/I, and in gp41: 518 L/V, 529 A/T, 561 A/T.

In another aspect of the invention, a mutation is induced in a gp120 polypeptide by deletion of the entirety of hypervariable loops V1 and V2, along with a partial deletion of hypervariable loop V3, such that only the first and the last amino acids of the V3 loop remain. This mutation resulted in gp120 and/or gp41 that retained detectable function, and where the polypeptides comprised mutations including a mutation in gp120 such as, but not limited to, 142 D/G, 160 T/I, 203 E/K, 279 N/D, 334 E/K, 340 E/K, 399 V/I, 437 E/V.

In order to produce a compensatory mutation, an infectious molecular clone of HIV-2/VCP was used to create a gp120 polypeptide by deletion of the entirety of hypervariable loops V1 and V2, along with a partial deletion of hypervariable loop V3, as discussed in greater detail in the Experimental Examples.

It will be appreciated by one skilled in the art, based upon the disclosure provided herein, that, for example, an isolate of an HIV-2 strain containing compensatory mutations in gp120, gp41, or both gp120 and gp41 may be obtained by serially passaging a clone of HIV-2/VCP comprising deletions in V1/V2 and V3 hypervariable loops in $CD4^+$ cells and screening for highly cytopathic variants. Methods of serially passaging and screening cells are well known in the art. For example, as disclosed in U.S. patent application No. 2003/0091594A1, incorporated herein by reference in its entirety, HIV-1/IIIBx was obtained by passaging virus in $CD4^+$ SupT1 cells followed by passaging virus on the otherwise identical but $CD4^-$ BC7 cells. However, the present invention should not be construed to be limited to these particular cell types. Instead, the invention encompasses a variety of $CD4^+$ and $CD4^-$ cells including, but not limited to, 293, Cf2TH, $CCC^+L^-$, and QT6 cells as well as stably transfected cells (U87, HeLa, HOS), or any other cell either known in the art or to be developed in the future. One skilled in the art, armed with the teachings set forth herein, could readily determine what cell could be used in the methods of the invention.

The invention also includes a method of identifying an amino acid residue of an gp120 protein which is a compensatory mutation. The method comprises producing gp120 proteins comprising a total deletion of the V1/V2 hypervariable loops and a partial deletion of the V3 hypervariable loop, wherein the remaining V3 loop contains only about the first six and the last six amino acid residues of the native HIV-2 V3 loop. The resulting gp120 loop deletion mutant is then examined to determine the ability of the loop-deleted protein to generate functional virus using various assays, including, but not limited to, cell fusion assays and to generate replication-competent virus by various assays as disclosed elsewhere herein.

As discussed elsewhere herein, a preferred embodiment is disclosed wherein portions of the gp120 protein acquire mutations such that highly cytopathic viral variants emerge. Also as noted elsewhere herein, the present invention is not limited to these particular combinations or to these particular strains. Rather, one skilled in the art would appreciate, based on the disclosure provided herein, that any combination of gp120 loop-deleted variants may be examined to produce and identify useful compensatory mutations in gp120, gp41, or both, and to identify viruses comprising such compensatory mutations, where the virus is functional in cell fusion assays and that is replication-competent. Further, the effect of compensatory mutations that arise using methods of the present invention may be examined using a variety of assays using a wide plethora of mammalian cell lines as described elsewhere herein.

VII. Compositions, Methods and Kits Relating to Antibodies and/or Inhibiting Chemokine Receptor Binding of gp120 and Identification of Useful Compounds Therefor The invention encompasses a method of producing a neutralizing antibody. The method comprises administering an immunogenic amount of a polypeptide gp120 of the invention to a mammal. As disclosed previously elsewhere, the gp120 polypeptide comprises a substantial deletion of a V3 region, and more preferably, contains a deletion of V1 and a deletion of V2. As set forth elsewhere herein, such deletions expose core domains, epitopes, and/or amino acid residues of the gp120 to the immune system of a mammal such that a neutralizing antibody to such domains, epitopes, and/or amino acids are generated in the mammal. That is, a detectable immune response can be elicited in the mammal such that a neutralizing antibody is produced that can detectably inhibit a virus function that is associated with, or mediates, virus infection. This is because, as would be appreciated by the skilled artisan based on the disclosure provided herein, deletion of the hypervariable regions, while preserving certain virus function(s), provides for the presentation of certain important functional domains of the gp120 to the immune system in the context of a functional molecule. This novel composition provides a useful immunogenic gp120 that can elicit a neutralizing antibody recognizing at least one functional core domain of the virus polypeptide, thereby producing a neutralizing antibody that specifically binds with a polypeptide domain required for virus function and/or infection.

The invention encompasses a method of eliciting a mammalian immunodeficiency virus-neutralizing antibody in a mammal. The method comprises administering to a mammal an immunogenic amount of a composition comprising a mammalian immunodeficiency virus gp120 polypeptide where the gp120 comprises a substantial deletion of V3. More preferably, the gp120 also comprises a deletion of V1 and a deletion of V2. This is because, as demonstrated by the data disclosed herein, deletion of the hypervariable regions exposes protein domains and/or amino acid residues that are involved in, or necessary for, virus function relating to infection. Surprisingly, the data disclosed herein demonstrate that such gp120 hypervariable regions can be deleted while still maintaining detectable virus protein function. Therefore, for the first time, the invention provides a method of presenting important virus core domains that are important in virus infection in the context of a functional gp120 polypeptide. One skilled in the art would readily appreciate, armed with the teachings provided herein, that presenting such domains in the context of a functional polypeptide provides a method of eliciting a neutralizing antibody that by specifically binding to such domains, can inhibit virus function and/or infection.

The invention encompasses a method of producing a immunodeficiency virus-neutralizing antibody in a mammal where the method comprises administering to the mammal an immunogenic amount of a replication-competent mammalian immunodeficiency virus where the virus comprises a gp120 polypeptide comprising a substantial deletion of V3. More preferably, the virus further comprises a deletion of V1 and a deletion of V2. Even more preferably, the virus comprises a gp41 polypeptide, where the gp41 comprises a compensatory mutation. Even more preferably, the gp41 compensatory mutation is a truncation of the cytoplasmic domain of gp41. As discussed previously elsewhere herein, deletion of V3 and/or deletion of V1 and V2 can expose a functional virus domain which is not otherwise immunogenic in the mammal, to the mammalian immune system such that a neutralizing antibody is elicited and/or produced in the mammal that would not otherwise be produced where at least one hypervariable region of gp120 is not substantially deleted. Accordingly, the routineer would understand, based upon the disclosure provided herein, that the invention encompasses production of a neutralizing antibody in a mammal by administration of an immunogenic amount of a replication competent immunodeficiency virus where the virus comprises the gp120 polypeptide of the invention. Further, the routineer would also appreciate, once provided with the teachings provided herein, that the virus can comprise a gp41 comprising a compensatory mutation. This is because the data disclosed herein demonstrate that a compensatory mutation, such as, but not limited to, truncation of the gp41 CD, can restore and/or preserve virus function (e.g., binding with a chemokine receptor, fusogenicity, replication competence, and the like) where the virus comprises a substantial, or complete, deletion of V3.

The skilled artisan would understand, based upon the disclosure provided herein, that a neutralizing antibody of the invention can be produced in a mammal in order to treat, alleviate, or prevent virus infection in that mammal, where the mammal is in need thereof. Further, the neutralizing antibody can be produced in one mammal and can be administered to another mammal in need thereof (i.e., passive immunization) to inhibit or prevent virus infection in the mammal that receives the antibody. Methods for preventing and/or inhibiting virus infection in a mammal using a neutralizing antibody are known in the art and are not further described herein.

The invention includes a method of eliciting an immune response to an immunodeficiency virus chemokine receptor binding site. In one aspect, the method comprises administering an immunogenic dose of a mammalian immunodeficiency virus gp120 variant protein to a mammal wherein the protein comprises a stably exposed chemokine receptor binding site. More preferably, an immunogenic amount of a gp120 polypeptide of the invention, comprising a substantial deletion of V3, is administered to the mammal, thereby providing an immunogen wherein a chemokine binding site of the gp120, is presented to the immune system in the context of a functional gp120 polypeptide such that an immune response is elicited to such site. This is because, as more fully discussed elsewhere herein, the present invention provides a gp120 comprising a substantial deletion of at least one hypervariable region such that domains of the polypeptide, such as the chemokine binding site, are exposed and/or presented to the immune system in the context of a functional protein, thus providing an important novel method for producing an antibody that specifically binds with such domain.

The use of purified nucleic acid to generate an immune response, where the nucleic acid is provided using a vector (e.g., a plasmid or a virus), or where the nucleic acid comprises naked nucleic acid not associated with any other nucleic acid, is well-known in the art. For example, methods for construction of nucleic acid vaccines are described in Burger et al. (1991, J. Gen. Virol. 72:359-367), and are well-known in the art. See also Sambrook et al., 1989, In: Molecular Cloning: A Laboratory Manual, Cold Spring Harbor Laboratory Press, New York; Ausubel et al., 1997, In: Current Protocols in Molecular Biology, Green & Wiley, New York.

Therefore, such methods are encompassed herein as would be well-understood by one skilled in the art based upon the disclosure provided herein.

Further, a cell expressing the gp120 protein of the invention can be used to generate an immune response to an immunodeficiency virus chemokine receptor binding site. This is because the polypeptide can be expressed by the cell and the cell can be administered to a mammal, thereby producing an immune response in the mammal to which the cell is administered.

The immune response to the gp120 immunogen can be detected and/or assessed using standard immunological techniques such as ELISA, Western blotting and other such techniques well-known in the art or to be developed in the future. A variety of immunoassay formats may be used to select antibodies specifically immunoreactive with a particular protein. See, e.g., Harlow and Lane (1988, Antibodies, A Laboratory Manual, Cold Spring Harbor Publications, New York) for a description of immunoassay formats and conditions that can be used to determine specific immunoreactivity.

The mammalian immunodeficiency virus gp120 protein of the invention, or any other composition of the invention, may be formulated in a pharmaceutical composition which is suitable for administration of the protein to a human or veterinary patient. It will be appreciated that the precise formulation and dosage amounts will vary depending upon any number of factors, including, but not limited to, the type and severity of the disease to be treated, the route of administration, the age and overall health of the individual, the nature of the Env protein, etc. However, the preparation of a pharmaceutically acceptable composition having an appropriate pH, isotonicity, stability and other characteristics is within the skill of the art. Pharmaceutical compositions are described in the art, for example, in Remington's Pharmaceutical Sciences (1985, Genaro, ed., Mack Publishing Co., Easton, Pa.).

The amount of the gp120 variant administered, whether it is administered as protein, as nucleic acid, as a virus comprising the gp120, or as a cell expressing the gp120 polypeptide, is sufficient to elicit an immune response to a mammalian immunodeficiency virus chemokine receptor binding site. The pharmaceutical compositions useful for practicing the invention may be administered to deliver a dose of between about 1 ng/kg and about 100 mg/kg of patient body weight. Suitable amounts of the gp120 variant protein for administration include doses which are high enough to have the desired effect without concomitant adverse effects. When the gp120 variant is a protein or peptide, a preferred dosage range is from about 10 to about 1000 μg of protein or peptide per kg of patient body weight. When the gp120 variant is administered in the form of DNA encoding the same contained within a recombinant virus vector, a dosage of between about $10^2$ and about $10^{11}$ plaque forming units of virus per kg of patient body weight may be used. When naked DNA encoding the gp120 variant is to be administered as the pharmaceutical composition, a dosage of between about 10 μg to about several mg of DNA per kg of patient body weight may be used.

In the practice of the methods of the invention, a composition containing a mammalian immunodeficiency virus gp120 variant protein is administered to a patient in a sufficient amount to treat, prevent, or alleviate an immunodeficiency virus infection in the individual.

One skilled in the art would appreciate, based on the disclosure provided herein, that the gp120 variant protein/nucleic acid encoding the gp120 variant protein may be administered to a patient to prevent immunodeficiency virus infection by interfering with virus binding to the appropriate chemokine receptor using the virus chemokine receptor binding site and, thereby preventing infection. Further, the gp120 variant protein/nucleic acid encoding the gp120 variant protein may also treat or alleviate the condition in a previously infected individual by augmenting the immune response in the person that could, in turn, be beneficial as an adjunct to antiretroviral pharmacologic therapy. That is, the immunogen may boost the immune response to the virus chemokine receptor binding site thereby generating antibodies which block the requisite interactions between the virus chemokine receptor binding site and the target cell chemokine receptor.

The frequency of administration of a gp120 variant protein to a mammal will also vary depending on several factors including, but not limited to, the type and severity of the viral infection to be treated, the route of administration, the age and overall health of the mammal, the nature of the gp120 variant, etc. It is contemplated that the frequency of administration of the gp120 variant protein to the mammal may vary from about once every few months to about once a month, to about once a week, to about once per day, to about several times daily.

Pharmaceutical compositions that are useful in the methods of the invention may be administered systemically in parenteral, oral solid and liquid formulations, ophthalmic, suppository, aerosol, topical or other similar formulations. In addition to the appropriate Env polypeptide of the invention, a gp120 variant protein of the invention, a gp41 of the invention, or a combination thereof, and/or nucleic acid encoding same, these pharmaceutical compositions may contain pharmaceutically-acceptable carriers and other ingredients known to enhance and facilitate drug administration. Thus such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to administer the appropriate protein or nucleic acid encoding it to a patient according to the methods of the invention.

Preferably, the composition of the invention is administered to the human by a parenteral or intravenous route.

A gp120 variant protein/nucleic acid encoding the gp120 variant protein, may be administered in conjunction with other compounds which are used to treat immunodeficiency virus infection. Such compounds include, but are not limited to, protease inhibitors, reverse transcriptases inhibitors (nucleoside and non-nucleoside analogs), AZT, interferons, interleukin-2, other cytokines, and the like. The choice of which additional compound to administer will vary depending upon any number of the same types of factors that govern the selection of dosage and administration frequency of the gp120 variant protein or nucleic acid encoding same. Selection of these types of compounds for use in conjunction with a gp120 variant protein for practice of the method of the invention is well within the skill of those in the art.

The invention also includes a composition comprising an immunogenic dose of a mammalian immunodeficiency virus gp120 variant protein. As discussed previously elsewhere herein, generation of an immune response to the virus chemokine receptor binding site can block interaction of this virus site with the host chemokine receptor ligand thereby interfering with and/or inhibiting the requisite virus/host cell interaction needed for immunodeficiency virus infection.

In addition, the invention includes a method of identifying a compound which affects exposure of a gp120 protein chemokine receptor binding site. The method comprises contacting a cell with the compound and comparing the amount of labeled gp120 specifically bound to the cell with the amount of labeled chemokine bound to an otherwise identical cell not contacted with the compound. In one embodiment, the gp120 of interest was $^{125}$I-labeled and bound to cells expressing various chemokine receptors in the presence or absence of soluble CD4. However, the present invention should not be construed to be limited to radioiodination or to any particular gp120 or to expression of only these chemokine receptors. Rather, the invention should be construed to encompass a variety of protein labels such that binding of the gp120 of interest may be quantitated. Such methods are well-known in the art and include, but are not limited to, biotinylation, and $^{35}$S-cys and $^{35}$S-met.

The invention also includes a method of identifying a compound that inhibits binding of a chemokine receptor by an immunodeficiency virus gp120 using its chemokine receptor binding site. The method comprises contacting a cell with a compound prior to or contemporaneous with contacting the cell with labeled gp120 with or without preincubation of the gp120 with soluble CD4. Then, the amount of label bound to the cell is measured thereby detecting the amount of labeled gp120 bound to the cell. The amount of bound gp120 bound to a cell contacted with the compound is compared to the amount of gp120 bound to a cell not contacted with the compound. If a lower amount of gp120 is bound to the cell contacted with the compound compared with the amount of gp120 bound to the cell which was not contacted with the compound, this is an indication that contacting the cell with the compound inhibits binding of immunodeficiency virus gp120 to a chemokine receptor using its chemokine receptor binding site, thereby identifying a compound that inhibits such binding. Because binding of the virus gp120 with a host cell chemokine receptor is typically required for virus infection, the compound identified using the methods of the invention is an important potential therapeutic for treatment or prevention of such infection.

The invention encompasses a method of identifying a compound that inhibits binding of a mammalian immunodeficiency virus gp120 polypeptide with a chemokine receptor. The method comprises contacting a gp120 of the invention, that is, one comprising a substantial, or complete, deletion of V3, and, more preferably, a gp120 further comprising a deletion of V1 and a deletion of V2, with a compound prior to or contemporaneous with contacting the gp120 with a chemokine receptor. The binding of the gp120 with the receptor in the presence of the compound is compared with the binding of an otherwise identical gp120 with an otherwise identical receptor in the absence of the compound. Where the binding of the gp120 with the receptor in the presence of the compound is detectably less than the binding of the otherwise identical gp120 with the otherwise identical receptor in the absence of the compound, this is an indication that the compound inhibits binding of a gp120 with a chemokine receptor, thereby identifying such a useful compound. The skilled artisan would appreciate that the novel gp120 polypeptide of the invention is useful for such methods of screening for a useful compound because the gp120 of the invention comprises deletion of at least one hypervariable region such that important functional core domains of the polypeptide are exposed and the minimal portions of the polypeptide that remain following the deletions disclosed herein represent those portions of the gp120 molecule likely involved in function required for virus infection, including, but not limited to, binding with a chemokine receptor. Thus, the gp120 of the invention provide a important novel screening tool for the identification of useful compounds that affect the virus functions that remain after removal of the hypervariable domain, and can be used in a wide plethora of assays to identify such compounds as would be appreciated by one skilled in the art based upon the disclosure provided herein.

One skilled in the art would appreciate, based on the disclosure provided herein, that such compound, including small-molecules, are useful therapeutics inhibiting HIV-1 infection of cells in that such small-molecules would inhibit the requisite HIV-1 gp120/ chemokine receptor interactions necessary for virus infection of the target cell. Further, the prior art teaches that antibodies and chemokines which specifically bind to chemokine receptors and which block gp120 binding to the chemokine receptor often also block HIV infection (Lee et al., 1999, J. Biol. Chem., in press; Olson et al., 1999, J. Virol., in press; Wu et al., 1997, J. Exp. Med.). Thus, the small-molecule inhibitors of gp120 binding to the chemokine receptor identified using the methods of the invention are useful inhibitors of HIV infection.

Further, one skilled in the art, based upon the disclosure provided herein, would appreciate that a compound that inhibits gp120 binding using its chemokine receptor binding site to a chemokine receptor which compound is identified using the methods of the invention, is a useful inhibitor of a chemokine binding to and activation of its receptor. That is, the compound can be useful for inhibiting the natural function of chemokine receptors unrelated to the role of the chemokine receptors in immunodeficiency virus infection. Thus, a compound identified herein is a useful therapeutic having potential uses for, among other things, immune system treatments, inflammation, and development in any non-immunodeficiency virus infected human.

The invention includes a method of inhibiting HIV-1 gp120 binding, using its chemokine receptor binding site, to a chemokine receptor. The method comprises contacting the gp120 with a compound which inhibits binding of gp120 to a chemokine receptor where such binding is mediated by the chemokine receptor binding site of the virus gp120 protein. The compound is identified as disclosed previously elsewhere herein. Contacting the gp120 with the compound inhibits binding of the gp120 with the cell chemokine receptor. The compound can therefore be used to treat or prevent virus infection.

The invention also includes a method of inhibiting HIV-1 infection of a cell. The method comprises contacting a cell with a compound identified as described previously elsewhere herein. The compound so identified inhibits the binding an HIV-1 gp120 to a cell chemokine receptor mediated by the virus gp120's chemokine receptor binding site. The compound, by interfering with the requisite gp120/chemokine receptor interaction(s), thereby inhibits HIV-1 infection of the cell. Indeed, it has been demonstrated previously (Lee et al., 1999, J. Biol. Chem., in press; Olson et al., 1999, J. Virol., in press; Wu et al., 1997, J. Exp. Med.), that antibodies and chemokines that block gp120 binding to the chemokine receptor often also block HIV infection. Thus, the invention includes a method of inhibiting HIV-1 infection by interfering with the receptor/ligand interactions required for HIV-1 infection of a target cell using a compound that inhibits gp120 binding to the cell chemokine receptor using the gp120 chemokine receptor binding site.

The invention also includes method of using a composition comprising a mammalian immunodeficiency virus gp120 variant and at least one compound used to treat HIV infection in a pharmaceutically suitable carrier. As described elsewhere herein, the HIV-1 Env may be a HIV-1 Env polypeptide, a nucleic acid encoding HIV-1 Env, and/or a cell expressing HIV-1 env. Further, as disclosed previously elsewhere herein, the invention should be construed to encompass compounds used to treat HIV infection such as, for example but not limited to, protease inhibitors, reverse transcriptase inhibitor, reverse transcriptase inhibitors (including both nucleoside and non-nucleoside analogs), interferons, AZT, interleukin-2, and cytokines.

The invention includes a method of treating HIV-1 infection in a human. The method comprises administering an immunogenic dose of a mammalian immunodeficiency virus gp120 variant to an HIV-1 infected human. Administration of such mammalian immunodeficiency virus gp120 variant induces the production of antibodies to the stably exposed chemokine receptor binding site of gp120. Thus, administration of the mammalian immunodeficiency virus gp120 variant causes the production of potentially neutralizing antibodies which block the gp120/ chemokine receptor interaction(s) required for HIV-1 infection of the host cell. This is suggested by the fact, disclosed elsewhere herein, that the CD4-independent gp120 is more sensitive to neutralizing antibodies than otherwise identical CD4-dependent gp120 which does not comprise a stably exposed chemokine receptor binding site. Further, antibodies that block Env-chemokine receptor interactions can neutralize HIV-1 (Wu et al., 1996, Nature 384:179-183; Trkola et al., 1996, Nature 384:184-187). Thus, increased exposure of the chemokine receptor binding site will enhance the production of antibodies to this conserved region which antibodies inhibit the requisite gp120-chemokine receptor interactions. Therefore, immunizing a human with CD4-independent Env causes the production of antibodies to the stably exposed chemokine receptor binding site which antibodies block requisite Env-chemokine receptor interactions needed for infection, thereby treating HIV-1 infection in the human.

One skilled in the art would appreciate, based upon the disclosure provided herein, that the immunogenic dose of a mammalian immunodeficiency virus gp120 variant may be a useful therapeutic to treat and/or alleviate the HIV-1 infection in a human both before and after exposure to the HIV-1 virus. That is, the immunogenic dose may be administered prior to, during, or after infection of a human by HIV-1. Irrespective of when it is administered, the immunogen elicits a response in the human to, inter alia, the stably exposed chemokine receptor binding site of gp120 thereby inducing a response which inhibits the binding of the virus gp120 to the chemokine receptor. This inhibition is generated in both previously infected individuals as well as uninfected persons. In the individual already infected with HIV-1, the immunogen generates an immune response in addition to any immune response already present in the individual and thus mediates a reduction in the virus load in that individual. Thus, the mammalian immunodeficiency virus gp120 variant is useful as a therapeutic vaccine in a human already infected by HIV-1 virus.

Armed with the disclosure of the present invention, the skilled artisan will appreciate that the methods and compositions set forth herein for use in the investigation and treatment of HIV-1 infection are equally applicable and useful for the investigation and treatment of infection with other mammalian immunodeficiency viruses. Such immunodeficiency viruses include, but are not limited to, HIV-2 and SIV. The disclosure set forth above and the Experimental Examples set forth below provide the skilled artisan with abundant guidance in the use of HIV-2 and SIV, as well as HIV-1, in the preparation and use of methods and compositions of the present invention.

VIII. Compositions

As disclosed previously elsewhere herein, one skilled in the art would appreciate, based on the disclosure provided herein, that an immunogenic dose of a gp120 variant may be administered as a protein, a nucleic acid (comprising a vector or as naked DNA), and/or a cell expressing a nucleic acid encoding a gp120 variant.

The present invention therefore features a method of treating HIV-1 infection in a human that comprises further administering a compound used to treat HIV infection. As disclosed previously elsewhere herein, such compounds include, but are not limited to, a protease inhibitors, a reverse transcriptase inhibitor (including both nucleoside and non-nucleoside analogs), an interferon, AZT, interleukin-2, and a cytokine. The compound may be administered before, during, or after the administration of the immunogenic dose of a Gp120 variant.

One skilled in the art would appreciate, based upon the disclosure provided herein, that the timing of the compound relative to the immunogenic dose of a gp120 variant would depend upon the immunization regimen regarding the gp120 variant and the particular compound(s) administered with the gp120 immunogen, as well as the health and age of the patient and the severity and stage of the disease process.

The gp120 variant immunogen(s) and/or compounds which are identified using any of the methods described herein may be formulated and administered to a mammal for treatment and/or prevention of HIV infection as now described.

The invention encompasses the preparation and use of pharmaceutical compositions comprising a compound useful for treatment of HIV infection as an active ingredient. Such a pharmaceutical composition may consist of the active ingredient alone, as a combination of at least one active ingredient (e.g., an immunogenic dose of a gp120 variant and a compound used to treat HIV infection such as interleukin-2) in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs, birds including commercially relevant birds such as chickens, ducks, geese, and turkeys, fish including farm-raised fish and aquarium fish, and crustaceans such as farm-raised shellfish.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers and AZT, protease inhibitors, reverse transcriptase inhibitors, interleukin-2, interferons, cytokines, and the like.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropyl methylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

Typically dosages of the compound of the invention which may be administered to an animal, preferably a human, range in amount from 1 μg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

The compound used to treat immunodeficiency virus infection may be co-administered with the immunogenic dose of a mammalian immunodeficiency virus gp120 variant. Alternatively, the compound(s) may be administered an hour, a day, a week, a month, or even more, in advance of the immunogenic dose(s) of gp120 variant, or any permutation thereof. Further, the compound(s) may be administered an hour, a day, a week, or even more, after the immunogenic dose(s) of gp120 variant, or any permutation thereof. The frequency and administration regimen will be readily apparent to the skilled artisan and will depend upon any number of factors such as, but not limited to, the type and severity of the disease being treated, the age and health status of the animal, the identity of the compound or compounds being administered, the route of administration of the various compounds and gp120 variant, and the like.

IX. Kits

The invention further encompasses kits for the practice of the methods disclosed herein. That is, the invention includes various kits which comprise a composition, such as an immunogenic amount of a gp120 polypeptide of a mammalian immunodeficiency virus, for the purpose of producing an immunodeficiency virus-neutralizing antibody in a mammal.

In an embodiment of the invention, a kit includes a gp120 polypeptide of the invention, wherein the gp120 polypeptide comprises a deletion of V1, a deletion of V2, and a substantial deletion of V3, an applicator, and instructional materials which describe use of the composition to perform the methods of the invention. The kits relate to the novel discovery that an HIV-2 comprising a gp120 polypeptide lacking the V1/V2 loops and lacking a substantial portion of the V3 loop remains fusogenic and replication competent.

In another embodiment of the invention, a kit includes a gp120 polypeptide of the invention, wherein the gp120 polypeptide comprises a substantial deletion of V3, an applicator, and instructional materials which describe use of the composition to perform the methods of the invention. The kits relate to the novel discovery that an HIV-2 comprising a gp120 polypeptide lacking a substantial portion of the V3 loop remains fusogenic.

In yet another embodiment of the invention, a kit includes a gp120 polypeptide of the invention, wherein the gp120 polypeptide comprises a deletion of V1, a deletion of V2, and a substantial deletion of V3, and further wherein the gp120 protein comprises at least one compensatory mutation. The kit further comprises an applicator, and instructional materials which describe use of the composition to perform the methods of the invention. The kits relate to the novel discovery that an HIV-2 comprising a gp120 polypeptide lacking the V1/V2 loops and lacking a substantial portion of the V3 loop gains at least one compensatory mutation in the gp120 protein, and thereby remains fusogenic and replication competent.

In an embodiment of the invention, a kit includes a gp120 polypeptide of the invention, wherein the gp120 polypeptide comprises a deletion of V1, a deletion of V2, and a substantial deletion of V3, and further wherein the gp41 protein comprises a compensatory mutation. The kit further comprises an applicator, and instructional materials which describe use of the composition to perform the methods of the invention. The kits relate to the novel discovery that an HIV-2 comprising a gp120 polypeptide lacking the V1/V2 loops and lacking a substantial portion of the V3 loop gains at least one compensatory mutation in the gp41 protein, and thereby remains fusogenic and replication competent.

In yet another embodiment of the invention, a kit includes a gp120 polypeptide of the invention, wherein the gp120 polypeptide comprises a deletion of V1, a deletion of V2, and a substantial deletion of V3, and further wherein each of the gp120 protein and the gp41 comprises at least one compensatory mutation. The kit further comprises an applicator, and instructional materials which describe use of the composition to perform the methods of the invention. The kits relate to the novel discovery that an HIV-2 comprising a gp120 polypeptide lacking the V1/V2 loops and lacking a substantial portion of the V3 loop gains at least one compensatory mutation in each of the gp120 protein and the gp41 protein, and thereby remains fusogenic and replication competent.

In another aspect, the kit comprises a gp41 comprising a compensatory mutation. This is because the data disclosed herein demonstrate that certain mutations, termed "compensatory," can restore and/or preserve the biological function of a gp120 comprising a deletion/truncation of the V3 region, even where the gp120 further comprises a deletion of V1/V2 as well. Thus, by providing the gp120 and gp41, a neutralizing antibody can be produced due to presentation to the immune system of core epitopes otherwise not immunogenic when presented in the context of a gp120 comprising the intact V3 region, and/or when presented in the context of a V3-deleted but non-functional gp120 peptide. Thus, as would be appreciated by the skilled artisan once armed with the disclosure provided herein, the present invention provides novel methods and kits for producing a virus neutralizing antibody.

The invention also includes a kit for producing a neutralizing antibody where the kit comprises an immunogenic amount of an Env where the Env comprises a deletion/truncation of V3 and at least one compensatory mutation. The kit further comprises a pharmaceutically acceptable carrier, as well as an applicator and instructional material setting forth the use of the kit pursuant to the teachings of the invention. The compensatory mutation comprised by Env can be in the gp120 domain of the Env, in the gp41 portion of the Env, or both. This kit is useful in that it has been amply demonstrated herein that mutant Env where the V3 region had been deleted or substantially truncated can expose core domains of gp120 thereby allowing production of neutralizing antibodies to such domain, which are presented in the context of a functional virus polypeptide. Unlike unsuccessful prior art methods where the epitopes were either not exposed to the immune system or were presented in the context of a non-functional virus peptide, the present invention provides novel functional deletion mutants that represent a crucial breakthrough for the development of important therapeutics.

The skilled artisan would readily appreciate, based upon the disclosure provided herein, that the present invention includes a wide variety of kits for practicing the various methods of the invention.

In an aspect of the invention, a kit of the present invention includes a pharmaceutically-acceptable carrier. The composition is provided in an appropriate amount as set forth elsewhere herein. Further, the route of administration and the frequency of administration are as previously set forth elsewhere herein.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The invention is now described with reference to the following examples. These examples are provided for the purpose of illustration only and the invention should in no way be construed as being limited to these examples but rather should be construed to encompass any and all variations which become evident as a result of the teaching provided herein.

EXAMPLES

Disclosed herein is a novel strategy for producing replication competent variants of mammalian immunodeficiency viruses (e.g. SIV, HIV-1, HIV-2, and the like) that lack the V1/V2 and V3 hypervariable loops, novel polypeptides produced thereby, as well as nucleic acids encoding them. The production of replication-competent variants of mammalian immunodeficiency viruses (e.g., simian and human) lacking hypervariable loops resulted from 1) the initial selection of a virus that exhibited a high affinity binding to a chemokine receptor, and 2) the discovery of compensatory mutations that permitted these loop-deleted variants to replicate with high efficiency, but the present invention is not limited to these strategies. The unique viruses and novel variants of their envelope glycoproteins disclosed herein are useful in eliciting novel and potentially therapeutic immune responses and provide important vaccine candidates. Additionally, replication-competent "core" HIV and SIV particles lacking hypervariable regions while preserving virus functions, are useful in the design and development of drugs therapies for preventing and treating virus infection, including modalities relating to inhibiting the virus entry process.

Example 1

Production of Replication-Competent HIV-2 Lacking V1/V2 and V3 Loops

A variant of HIV-2, termed VCP, can utilize both CXCR4 and CCR5 as primary receptors without a need for CD4 triggering (Endres, et al. Cell 1996; Lin, G. et al., J. Virol 2001; Lin, G., et al., J. Virol. 2001). In contrast to HIV-1, the gp120 Env of HIV-2/VCP exhibited a remarkably high affinity for CXCR4, a feature that enabled binding sites on CXCR4 to be mapped (Lin, G., et al., J. Virol. 2003). In an attempt to determine the minimal gp120 components required for infectivity, deletions of hypervariable loops V1/V2 and V3 were performed on an infectious molecular clone of VCP. Similar to what has been observed for other viruses, a VCP Env lacking the entire V1/V2 loop remained infectious and replicated to near wild type levels. Remarkably, a virus containing a 65% deletion of the V3 loop (leaving only the first 6 and last 6 amino acids), termed ΔV3(6,6), continued to be replication competent on SupT1 cells. This remained the case even when this deletion was introduced on a gp120 that also lacked V1/V2. This later "combination deleted" virus, termed ΔV/V2; ΔV3(6,6), produced a gp120 of only 70 kD. Of note, ΔV3(6,6) and ΔV1/V2;ΔA3(6,6) though replication competent were attenuated in vitro, replicating with slower kinetics and with reduced cytopathicity. Although HIV-2/vcp Envs that contained a complete deletion of the V3 loop, designated ΔV3(1,1), with or without the V1/V2 deletion were functional in cell-cell fusion assays, they failed to allow generation of a functional virus, indicating that in this context some portion of V3 was required.

In an effort to improve the infectivity of the loop-deleted viruses, both ΔV3(6,6) and ΔV1/V; ΔV3(6,6) were serially passaged onto $CD4^+$ T cell lines. Remarkably, after 16 passages, highly cytopathic variants emerged. Further evaluation of cloned Envs demonstrated that novel compensatory changes in both gp120 and gp41 had occurred, which apparently compensated for the variable loop deletions. These changes included the loss of conserved glycosylation sites in gp120, the acquisition of positively charged mutations in regions involved with chemokine receptor binding, and mutations in regions of gp41 that likely interact with gp120 and/or enhance the fusion reaction. These changes likely function to increase the exposure and/or affinity of gp120 for a chemokine receptor and to improve the efficiency of gp120 to gp41 triggering that is essential for fusion to occur.

Using one cloned Env from a ΔV3(6,6) variant containing the compensatory changes noted above, the entire Y3 loop has been deleted, yielding a virus termed HIV-2/VCP-p16.9ΔV3 (1,1). Presumably, changes acquired during the adaptation of the original ΔV3(6,6) virus were sufficient to enable the virus to tolerate the elimination of the remaining portion of V3. Further passaging of this p16.9.ΔV3(1,1) virus is then conducted to produce a V3-deleted virus that will tolerate a subsequent elimination of V1/V2. A ΔV1/V2;ΔV3 virus is considered the first replication competent "core" HIV, and as such, represents a truly novel reagent for vaccine and drug design.

Example 2

CD4 Independent Isolates of HIV-2

As described in detail elsewhere herein, a variant of HIV-2/nihz, termed VCP, utilizes CXCR4 for entry in the absence of CD4. This virus was the first HIV strain shown to infect cells efficiently in the absence of CD4, and exhibited an expanded host range that included many $CD4^-$/$CXCR4^+$ hematopoietic and non-hematopoietic cells including B cell lines, epithelial lines, and even primary human endothelial cells. HIV-2/VCP Env clones recapitulated this phenotype in both cell/cell fusion assays and when introduced into an infectious HIV-2 molecular clone. VCP can also utilize rhesus CCR5 in the absence of CD4 but required CD4 for human CCR5. The basis for this difference was shown to be an acidic residue (Asp) at amino acid (aa) 13 in the rhesus CCR5 amino terminus, which is an Asn in the human sequence. Additionally, structure-function studies demonstrated the critical importance of a positively charged residue (Lys) at aa. 427 in the VCP C4 domain, which is analogous to the β2 strand of the HIV-1 bridging sheet. These results were consistent with reports demonstrating an electrostatic interaction between the C4 domain of HIV-1 and the CCR5 N-terminus. The present invention showed that for VCP, when binding between the CCR5 N-terminus and the C4 domain is sufficiently strong, CD4 is not required for fusion. These results provided new insights into the role of CD4 in stabilizing the Env/CCR5 interaction, identified a pathway by which HIV can evolve CD4-independence, and showed how some genetic variation in a highly conserved region of Env can be tolerated.

HIV-2/VCP of the present invention was also highly useful in identifying CXCR4 determinants for gp120 binding. HIV-1 gp120s evaluated in this manner have exhibited a low CXCR4 binding affinity (e.g. 200-500 nM), which has precluded an analysis of gp120/X4 interactions in standard equilibrium binding assays. In contrast, VCP gp120 of the invention showed a relatively high X4 binding affinity that could be measured easily in western blot assays on cells transfected with CXCR4. Binding to CXCR4-expressing cells was highly specific and inhibitable by SDF-1, AMD3100 and monoclonal antibodies to CXCR4. Using this assay and a panel of CXCR4 mutants, it was shown that charged and aromatic amino acids in the CXCR4 N-terminus (E14, E15, D20, Y21, and D22), ECL2 (D187, R188, F189, Y190, and D193) and ECL3 (D262, E268, E277, and E282) were critical for gp120 binding. The residues corresponded to those previously shown to be required for HIV fusion. Interestingly, the CXCR4 residues identified also included those shown to be important for SDF-1 binding, indicating that gp120 binding mimics that of the natural ligand.

In summary, the HIV-2/VCP Env is remarkable for its CD4-independent use of both CXCR4 and rhesus CCR5 and its high affinity binding to CXCR4. Presumably, in the absence of CD4 its Env presents a conformation that is both open and highly avid for chemokine receptors, thus circumventing a need for CD4. When mutations were introduced into gp120 that reduced CCR5 or CXCR4 binding, a K427E mutation for CCR5 and a K314A mutation (in V3) for CXCR4, fusion became strictly CD4 dependent. However, aside from the apparent role of CD4 in stabilizing Env/chemokine receptor binding, CD4 clearly induces major conformation changes in gp120, and it is also possible that CD4i Envs have acquired other changes required for coreceptor engagement and gp41 triggering. As noted and described extensively elsewhere herein, some or all of these properties enabled further adaptation of VCP for replication without variable loops V1/V2 and V3, opening a new area for structure/function and vaccine studies, and demonstrating that similar approaches can be used to produce similar HIV-1 and SIV.

Example 3

CD4-Independent Isolates of HIV-1

A CD4i variant created from the lab-adapted X4 virus HIV-1/IIIB was termed 8x. Like VCP, the 8x Env could mediate fusion with cells expressing only CXCR4, and it remained fusion competent even when engineered to contain a mutation known to ablate the CD4 binding site. However, unlike VCP, 8x was strictly X4 tropic, and using an optical biosensor its gp120 exhibited low affinity for CXCR4 (~500 nM) characteristic of CD4-dependent HIV-1 Envs, suggesting that 8x exhibits an “open” conformation, though not one with a change in CXCR4 affinity.

Direct demonstration of conformational changes in 8x gp120: Using surface plasmon resonance analysis (Biacore, Uppsala, Sweden), it was shown that monoclonal antibodies to CD4-induced epitopes that partially overlie the bridging sheet domain could bind to 8x gp120 in the absence of CD4 whereas for the CD4-dependent HXBc2 Env, preincubation with soluble CD4 was required. These findings provided direct evidence that a CD4-induced epitope on a CD4i virus was exposed and that this phenotype appeared to involve a more open conformation that permitted engagement of coreceptors in the absence of CD4 triggering. As noted elsewhere herein, CD4 binding produces a marked decrease in entropy, thereby reducing the extensive conformational flexibility of gp120 in the absence of CD4. This flexibility has been proposed to play a role in immune evasion.

Mapping determinants for CD4-independence: By constructing chimeric Envs between 8x and the isogenic CD4-dependent HXBc2 Env along with a panel of site-directed mutants, it was shown that the key mutations on gp120 required for CD4-independent use of CXCR4 were R298K, I320V (within V3), I423V (in the C4 domain), and N386K (ablating a conserved CHO site at the base of V4 loop). Surprisingly, R298K, N386K and I423V could be mapped to positions that immediately flanked the bridging sheet and overlapped CD4-induced epitopes for monoclonal antibodies 17b and 48d. Coupled with the surface plasmon resonance studies described above, these findings illustrate that these mutations exposed this epitope resulting in CD4-independent use of a chemokine receptor.

Dissociation of determinants for tropism from those for CD4-independence: Given that 3 of 4 residues required for CD4 independent use of CXCR4 were located on or near the gp120 core and that determinants for coreceptor specificity reside largely within the V3 loop, the dissociability of CD4-independence and coreceptor specificity was determined. It was found that an 8x Env containing a V3 loop from the R5-tropic Env became tropic for CCR5 but remained CD4-independent, suggesting that a conserved region on the gp120 core was exposed and in the absence of CD4 could govern use of CXCR4 or CCR5. Therefore, while the V3 loop plays a role in choosing a chemokine receptor, the core domain plays a key role in using the receptor for fusion.

Increased neutralization sensitivity of CD4-independnet Envs: It has previously been demonstrated that 8x has increased neutralization sensitivity to anti-gp120 sera and monoclonal antibodies than when compared to its CD4-dependent counterpart. Utilizing an extensive series of chimeric Envs and site-directed mutants we demonstrated that all CD4-independent Envs were significantly more neutralization sensitive to sera from HIV-infected humans than CD4-dependent Envs. This finding strongly suggested that there are likely to be strong selection pressures against the emergence of CD4i viruses in vivo. Thus, viruses that are CD4-independent or that are less dependent on CD4 may evolve in immune-privileged sites such as the CNS or later in the course of the disease in the face of immune system collapse.

Role of the gp41 cytoplasmic tail in CD4-independence and neutralization sensitivity: Surprisingly, although the changes in gp120 noted above were necessary for CD4-independence and neutralization sensitivity, their effects were markedly enhanced by a frameshift mutation at a.a.706 in the gp41 cytoplasmic domain, resulting in a prematurely truncated tail of only 27 amino acids. Also, the frameshift mutation alone could induce exposure of CD4i epitopes and confer increased neutralization sensitivity to heterologous R5 and X4 isolates. It has also been found that such truncations also lead to greatly increased levels of Env incorporation on virus particles.

In summary, the above findings led to several new findings on the genetic determinants of the CD4i phenotype, the underlying mechanism, and its immunological consequences, including new insights into ways in which Env structure and function can be manipulated.

Example 4

CD4-Independent Isolates of SIV

Several neuropathogenic isolates of SIV exhibit CD4-independent fusion on CCR5, suggesting a relationship between CD4-independence and neurovirulence, and in particular suggesting the potential for SIVs to adapt in vivo to cells with low levels of or absent CD4. Reduced dependence on CD4 has been suggested in other SIV models of brain or macrophage infection and for primary brain-derived isolates of HIV-1. It has been shown that the Env from SIVmac316, a macrophage tropic variant of the T-cell tropic SIVmac239, was capable of CD4-independent fusion on CCR5. This finding was consistent with evidence that rhesus alveolar macrophages (from which SIVmac316 was derived) have undetectable levels of CD4. Similar to CD4i HIV-1 Envs, it was found that CD4i SIV Envs, including SIVmac316, are neutralization sensitive to sera from SIV-infected animals. This indicates that SIVmac316 and other CD4i SIV strains are much less pathogenic in vivo. Given that pathogenic SIVmac239 is entirely CD4-dependent and highly neutralization resistant, these findings demonstrate a correlation between increased pathogenicity, CD4-dependence, and neutralization resistance. Interestingly, replication competent variants of SIVmac239 with deletions of glycosylation sites in V1/V2 or with a full deletion of V1/V2 were both neutralization sensitive and CD4-independent on CCR5.

These results have extended to an in vivo model evidence that CD4i viruses are selected against and that they may have reduced virulence. They also demonstrated the remarkable ability of the SIV Env to tolerate a deletion of over 100 amino acids of the V1/V2 loop, which was associated with CD4 independence, likely a more open gp120 conformation, and increased neutralization sensitivity. As with HIV-2, adapted variants with increasingly minimized hypervariable loops provide a new useful immunogen for vaccine studies.

Example 5

Generation of HIV-2/VCP Variants With Deletions of V1/V2 and V3 Loops

The results disclosed herein illustrate that the HIV-2/VCP Env interacts with multiple chemokine receptors and binds to CXCR4 with high affinity. Through an iterative selection process that incorporated targeted mutagenesis, in vitro adaptation, env cloning, and further mutagenesis, VCP Envs were derived that mediate fusion in the absence of V1/V2, V3, or V1/V2 and V3 together. This work is significant in that it 1) provides new tools to address questions of Env structure/function; 2) illustrates that these findings can be extended to SIV and HIV-1 models; and 3) demonstrates that replication competent HIV core Envs, devoid of protective hypervariable loops, will be able to elicit novel antibody responses focused on core domains critical for fusion.

Figure 2:
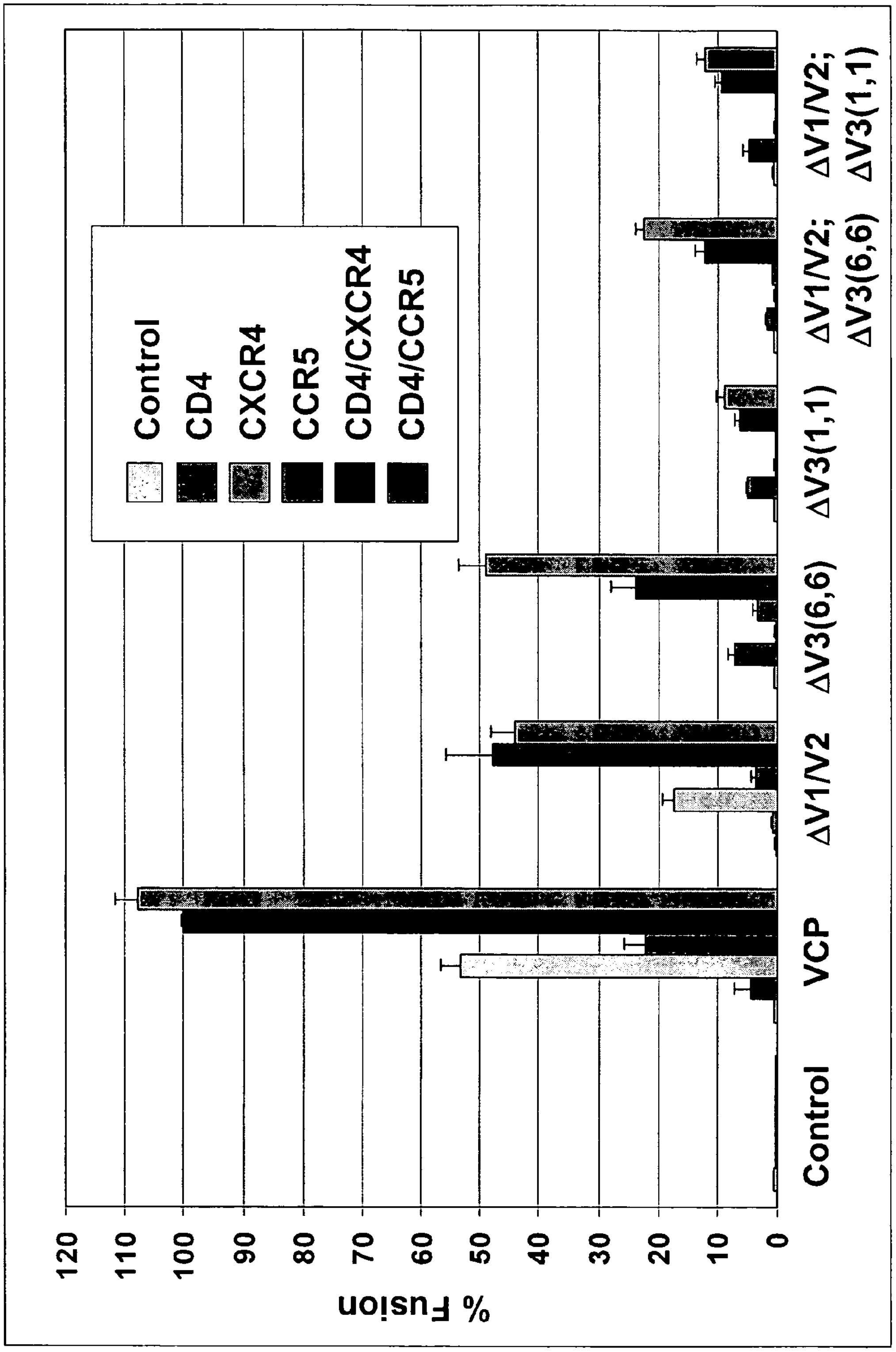
FIG. 2 is a graph depicting the fusogenicity of envelope ("Env") proteins containing ΔV1/V2 and/or ΔV3 deletions, which were produced using methods as depicted in FIGS. 1A and 1B. Fusogenicity of gp120 proteins containing ΔV1/V2 and/or ΔV3 deletions depicted in FIGS. 1A through 1N was assessed using QT6 cells expressing indicated chemokine receptors ±CD4. Results are shown for rhesus CXCR4 and CCR5, and the results are plotted on the bar chart as percent cell fusion for each receptor. These data demonstrate that double deletion mutants comprising a deletion of both V1/V2 and V3, e.g., both ΔΔV1/V2; ΔV3(6,6) and ΔΔV1/V2; ΔV3 (1,1), were detectably fusogenic.
Figures 1, 2, 9A:
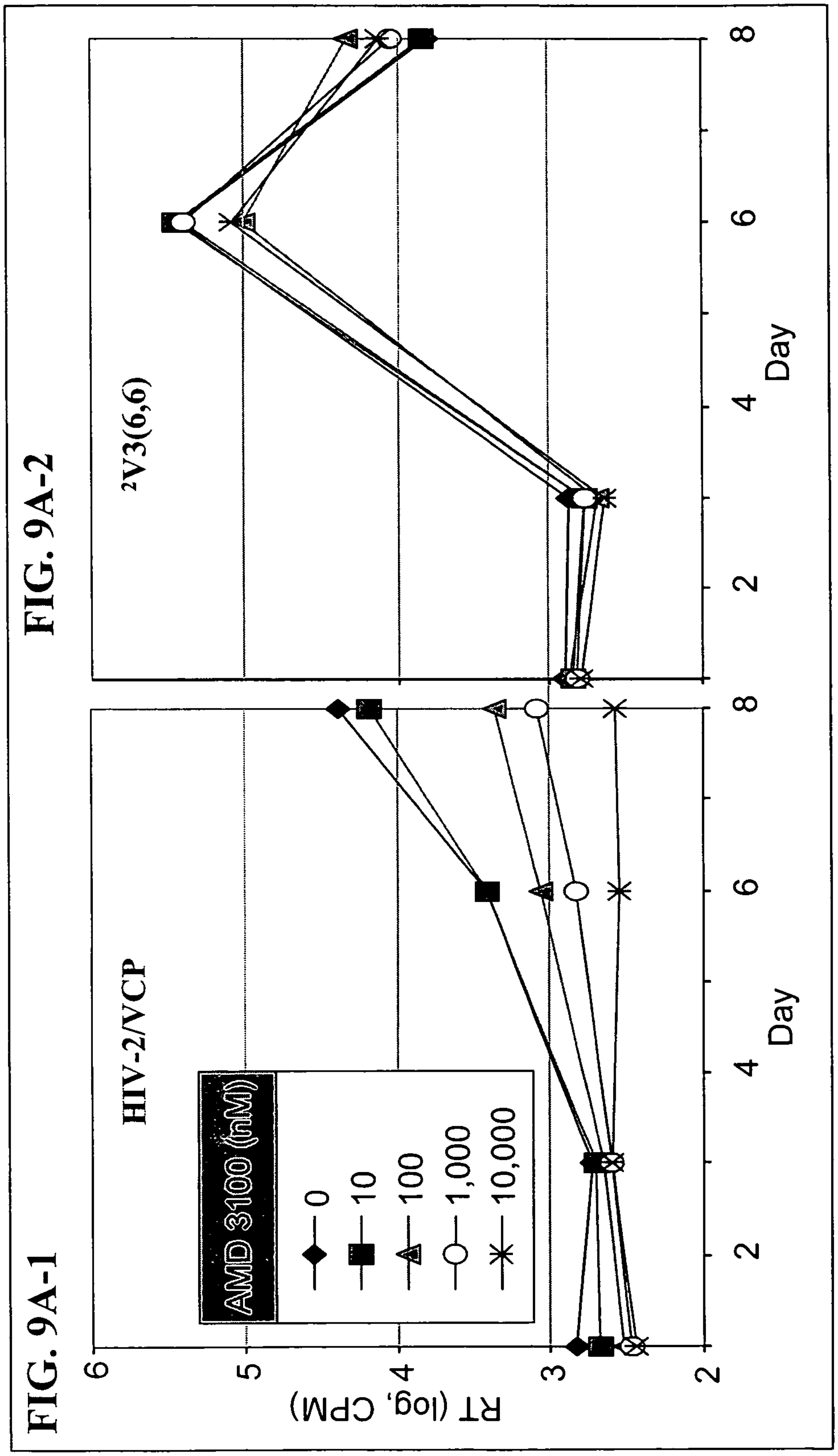
FIG. 9A, comprising panels A-1 and A-2, is a graph comparing the AMD3100 resistance of HIV-2/VCP virus (FIG. 9A-1) with the resistance of an adapted ("p16") virus containing a ΔV3(6,6) Env mutation (designated "V3(6,6)"). Each virus was innoculated onto SupT1 cells in the presence of varying concentrations of AMD3100 (0, 10, 100, 1,000, and 10,000 nm as indicated). The reverse transcriptase activity was monitored and plotted as log counts per minute as a function of days post innoculation. ΔV3(6,6) virus was completely resistant to AMD3100 up to 10,000 nm AMD3100 concentration. HIV-2/VCP virus, the parental strain, was sensitive to AMD3100 concentration.

The strategy for deleting hypervariable loops from the HIV/VCP Env was adapted from the approach taken by Wyatt to delete variable loops from HIV-1 gp120 (FIG. 1). For the ΔV1/V2 deletion, the first and last amino acids past the distal disulfide bond of the V1/V2 stem were retained and connected via a Gly-Ala-Gly (GAG) linker. For ΔV3 deletions, one construct retained the first and last 6 amino acids of V3, also connected by the GAG linker, designated ΔV3(6,6), while the other retained only the first and last amino acid, designated ΔV3(1,1). Deletion mutations were made individually and in combination and evaluated in a cell/cell fusion assays on QT6 cells expressing human or rhesus (rh)-CXCR4 and -CCR5 (FIG. 2) in the presence or absence of CD4. In these assays, VCP Env exhibited its characteristic CD4 independent fusion on CXCR4 and rhCCR5. ΔV1/V2 showed a slightly reduced but qualitatively similar level of fusion. ΔV3 (6,6) constructs, including one that also contained a ΔV1/V2 deletion, retained some fusion activity on CXCR4 and CCR5, although fusion for these constructs was completely CD4-dependent (FIG. 2). Low levels of fusion with the ΔV3(1,1) mutation were also observed, although these were not convincingly different from the CD4-only control. Thus, in the context of these Env clones, VCP retained fusion activity following ΔV1/V2 or ΔV3(6,6) deletions of its hypervariable loops.

Figure 3A:
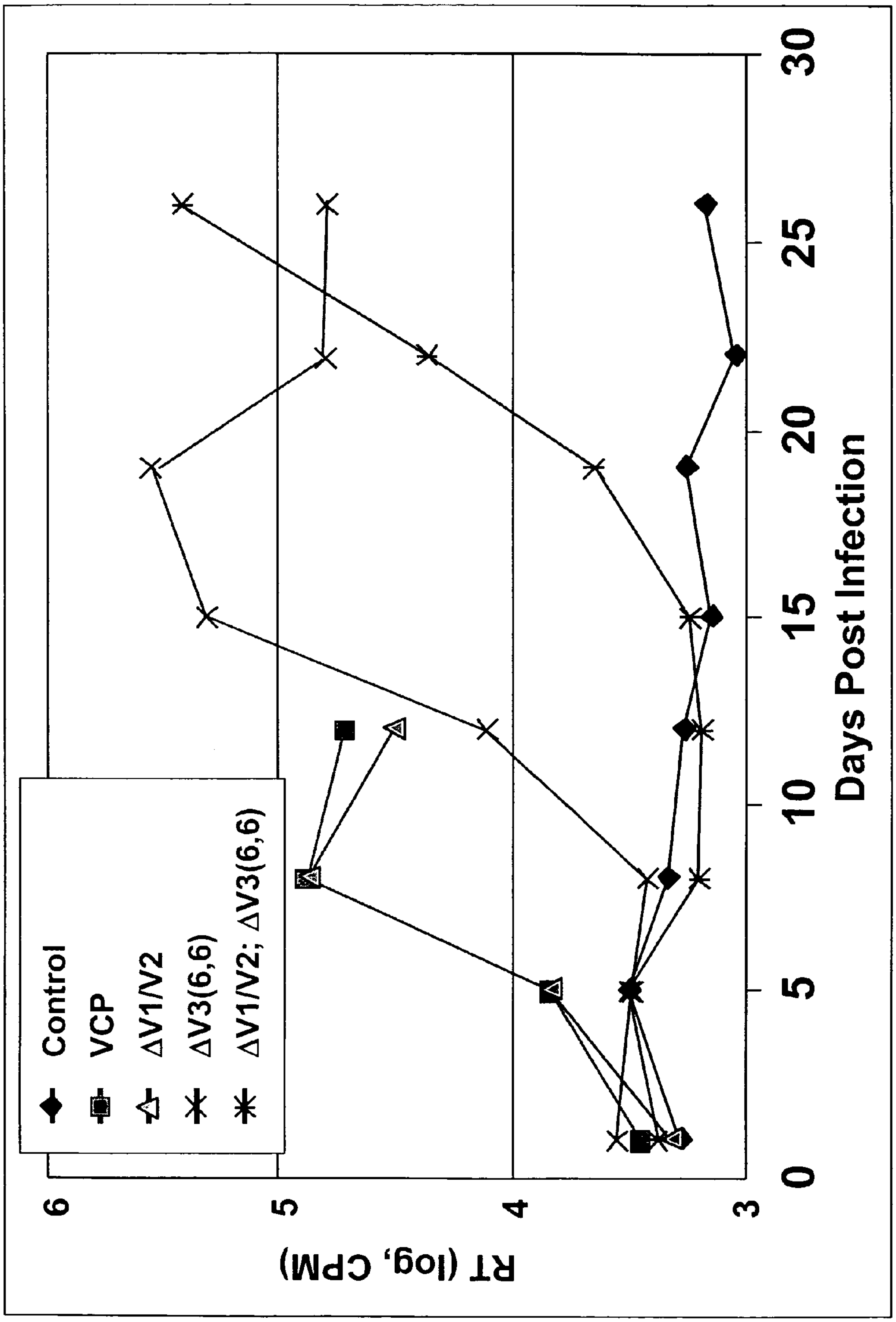
FIG. 3A is a graph depicting reverse transcriptase activity of viruses containing the Env proteins set forth in FIG. 2. Viruses were innoculated onto SupT1 cells and reverse transcriptase activity was plotted as log counts per minute as a function of days post infection.
Figure 3B:
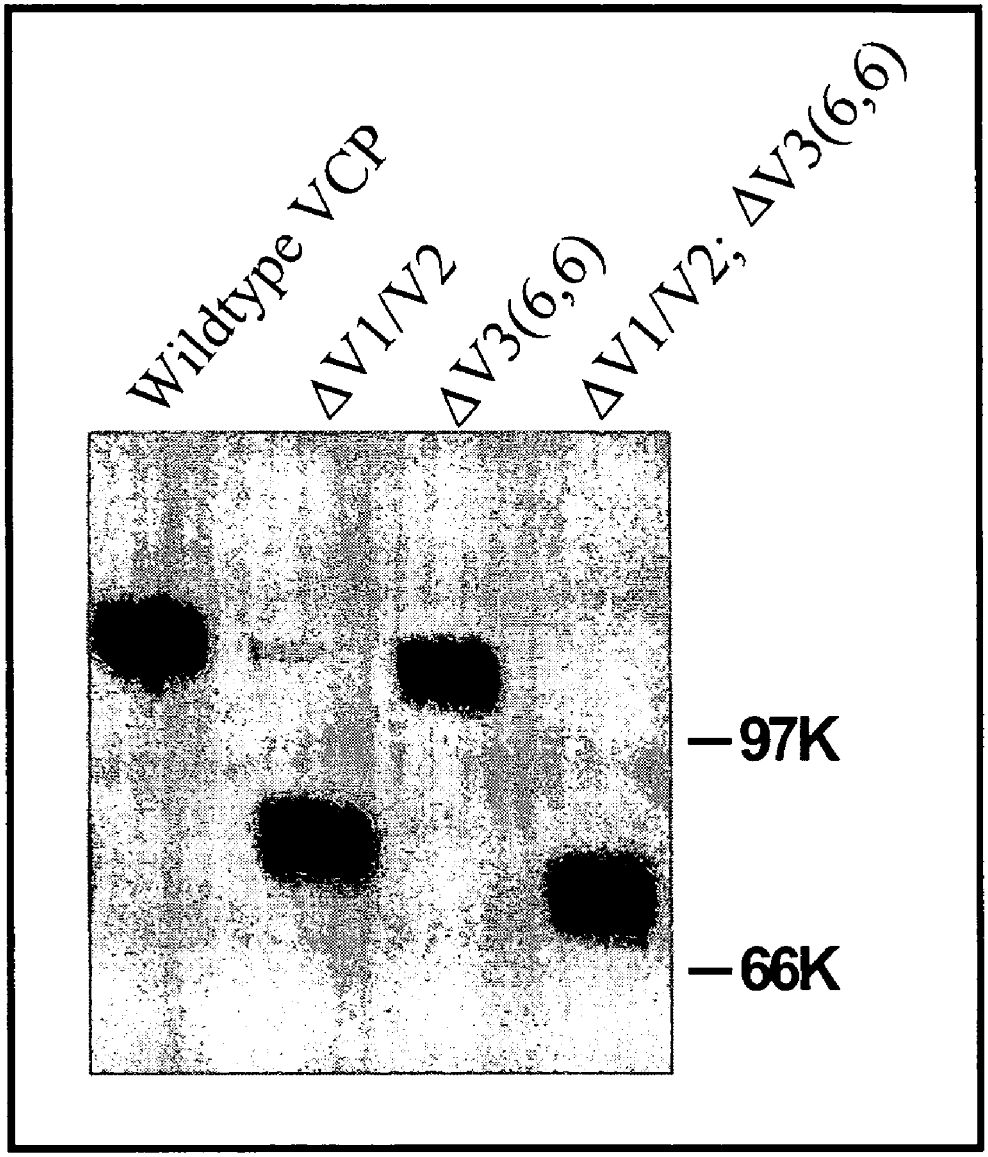
FIG. 3B is an image depicting Western blot analysis of Env proteins from pelleted virions. Monoclonal antibody DA6 was used to probe Env proteins in the blot in order to show that sizes of the Env proteins were consistent with the deletions introduced into each individual Env protein. The deletions in the gp120 peptide are indicated along the top of the figure, e.g., wildtype VCP, ΔV1/V2, ΔV3(6,6), and ΔV1/V2; ΔV3 (6,6).

To determine if this activity could be demonstrated in a replication competent virus, Envs shown in FIG. 2 were inserted into a full length infectious molecular clone of HIV-2/ROD, virus produced in 293T cells and inoculated onto SupT1 cells. The ΔV1/V2-only and ΔV3(6,6) viruses (±the ΔV1/V2 mutation) established a spreading infection as shown by IFA ($p27^{gag+}$ cells), syncytia formation, and RT activity (FIG. 3, Left). All viruses with the ΔV3(6,6) mutation exhibited delayed kinetics relative to wildtype VCP and reduced cytopathicity. No replication occurred for any virus with a ΔV3(1,1) mutation . "Gp120s" of viruses pelleted from these cultures showed the expected reduced size compared to parental VCP with ΔV1/V2;ΔV3(6,6) having the smallest MW of approximately 75 kD (FIG. 3, Right). The identity of these viruses was also confirmed by PCR and sequencing of genomic DNA.

Figure 4:
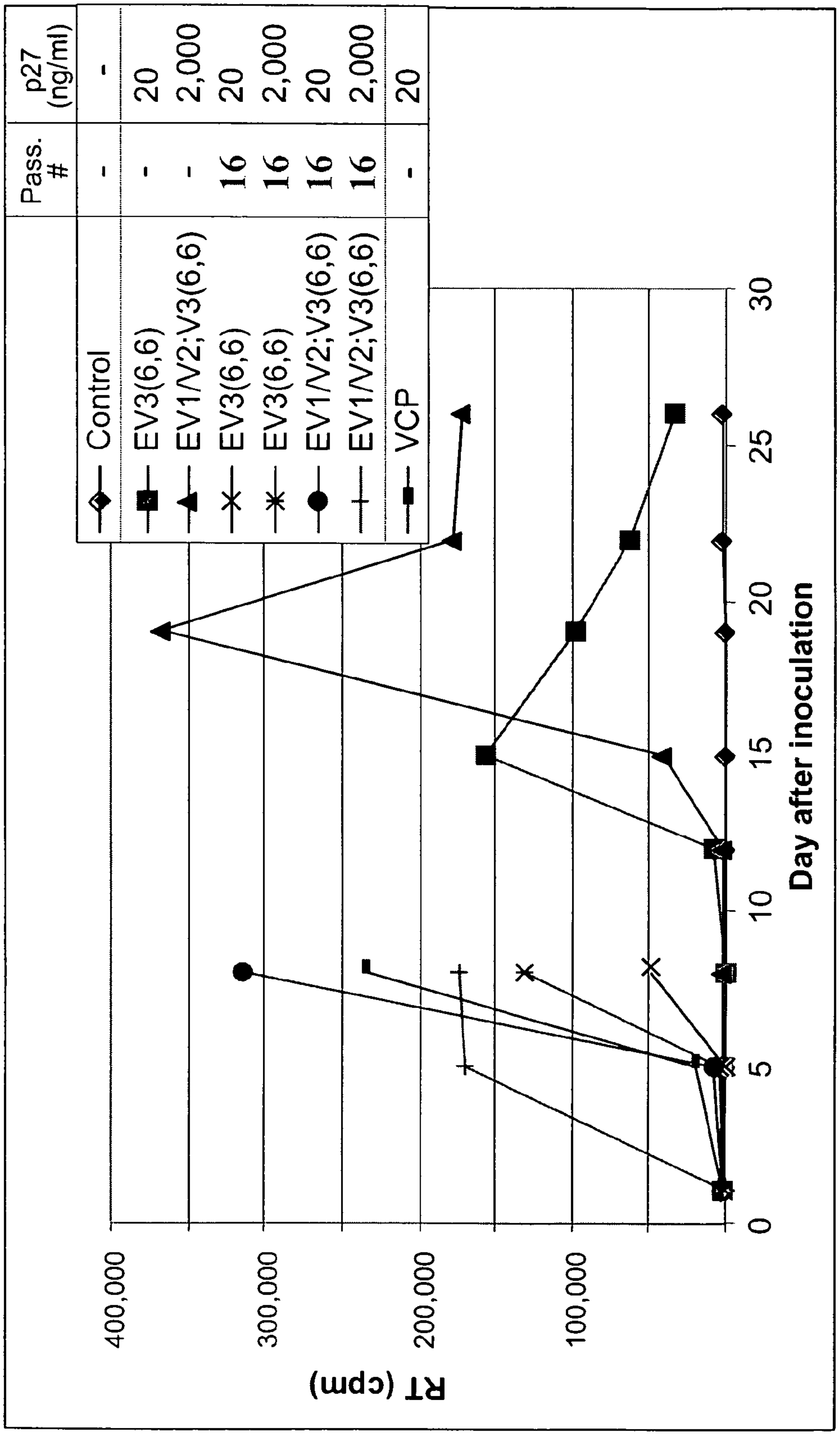
FIG. 4 is a graph depicting the replication of variable loop-deleted viruses adapted for in vitro growth. The viruses depicted in FIGS. 3A and 3B were serially passaged on SupT1 cells 16 times and growth kinetics were compared to viruses not serially passaged. Reverse transcripase activity was plotted as a function of days post inoculation. The inset to the graph shows input amount of each virus added measured in levels of p27 gag protein (ng/ml). All passaged viruses exhibited accelerated replication as a result of novel changes in the viral envelope described below.
Figure 5A:
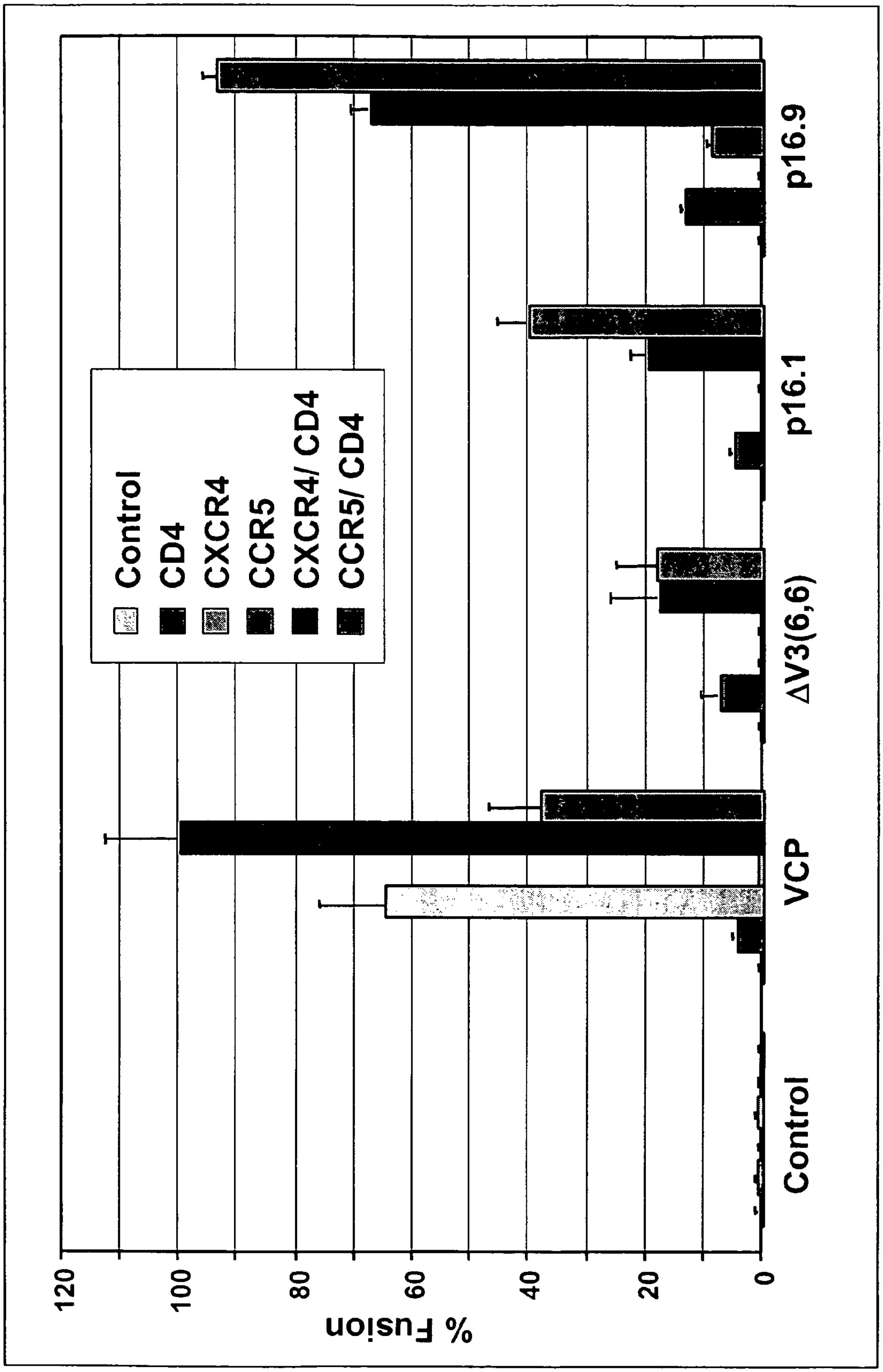
FIG. 5A is a graph depicting the enhanced fusogenicity of Env clones from adapted viruses with variable loop deletions. The ΔV3(6,6) Env protein was cloned from the corresponding virus as depicted in FIG. 4 and was compared with parental loop-deleted Env proteins in a cell/cell fusion assay on QT6 cells expressing human chemokine receptors. Percent cell fusion for the p16.1 and p16.9 ΔV3(6,6) Env clones was plotted as a function of receptor type, and showed that enhanced, CD4-dependent fusion was observed for all p16 clones on both CCR5 and CXCR4.
Figure 5B:
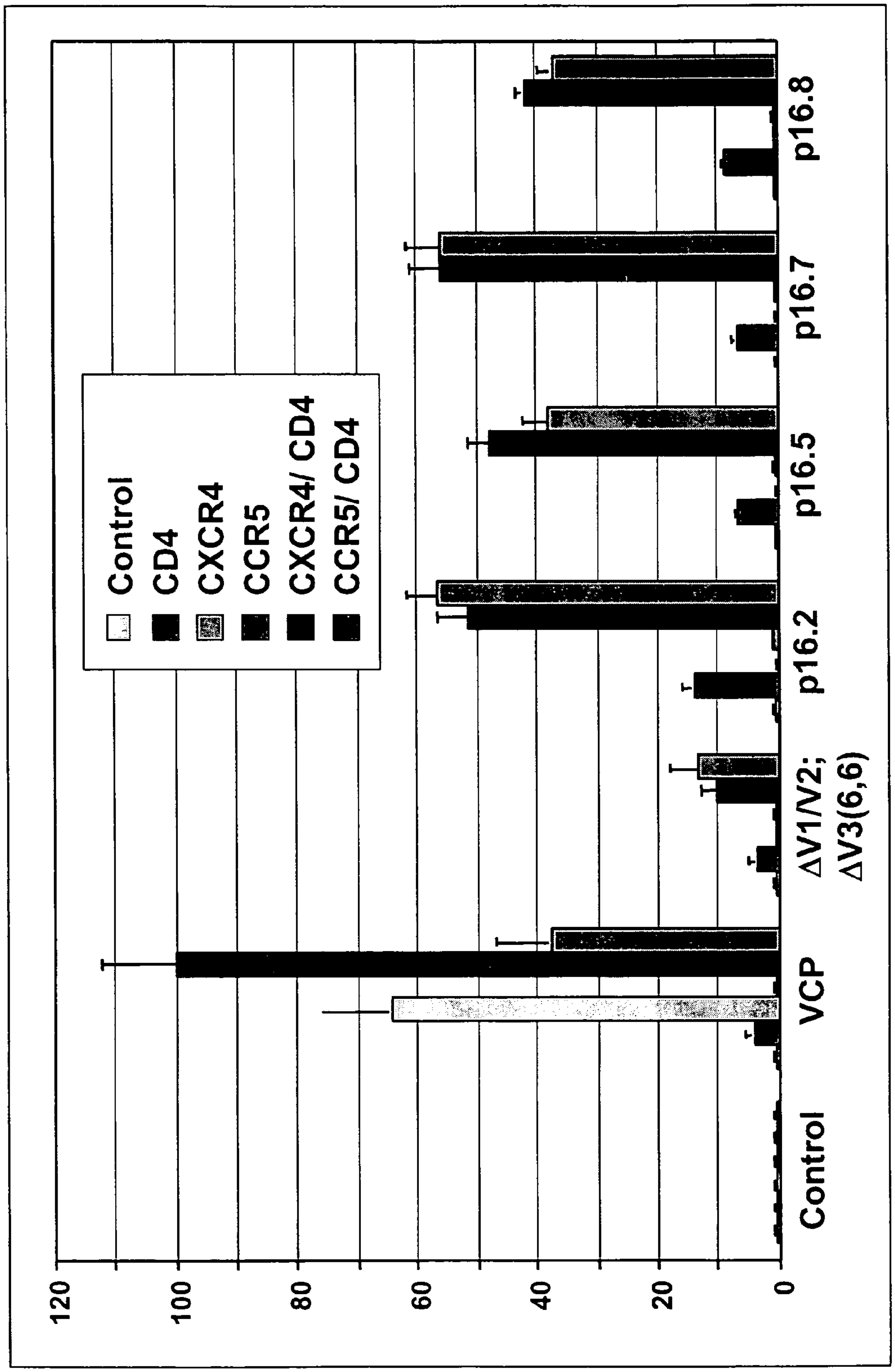
FIG. 5B is a graph depicting the enhanced fusogenicity of Env clones from adapted viruses with variable loop deletions. The ΔV1/V2; ΔΔV3(6,6) Env protein was cloned from the corresponding virus as depicted in FIG. 4 and was compared to parental loop-deleted Env proteins in a cell/cell fusion assay on QT6 cells expressing human chemokine receptors. Percent cell fusion for the p16.2, p16.5, p16.7 and p16.8 ΔV1/V2; ΔV3(6,6) Env clones was plotted function of receptor type, and showed that enhanced, CD4-dependent fusion is observed for all p16 clones on both CCR5 and CXCR4.

Since VCP variants with a ΔV3(6,6) truncation grew with slower kinetics, they were serially passaged in SupT1 cells to derive viruses better adapted for replication with a shortened V3 loop. After 16 passages, both ΔV3(6,6) and ΔV1/V2;ΔV3 (6,6) exhibited growth kinetics similar to wildtype VCP (FIG. 4). These viruses also induced increased syncytia formation and induced cell killing. All passaged viruses remained strictly CD4-dependent and were unable to replicate in BC7, a CD4-negative subclone of SupT1. Env clones derived by PCR from these cultures demonstrated increased fusion efficiency in cell/cell fusion assays compared to the parental ΔV3(6,6) and ΔV1/V2;ΔV3(6,6) Envs (FIG. 5). These clones also recapitulated the "adapted" phenotype of more rapid growth kinetics when introduced into the infectious HIV-2/ROD molecular clone.

Figure 6:
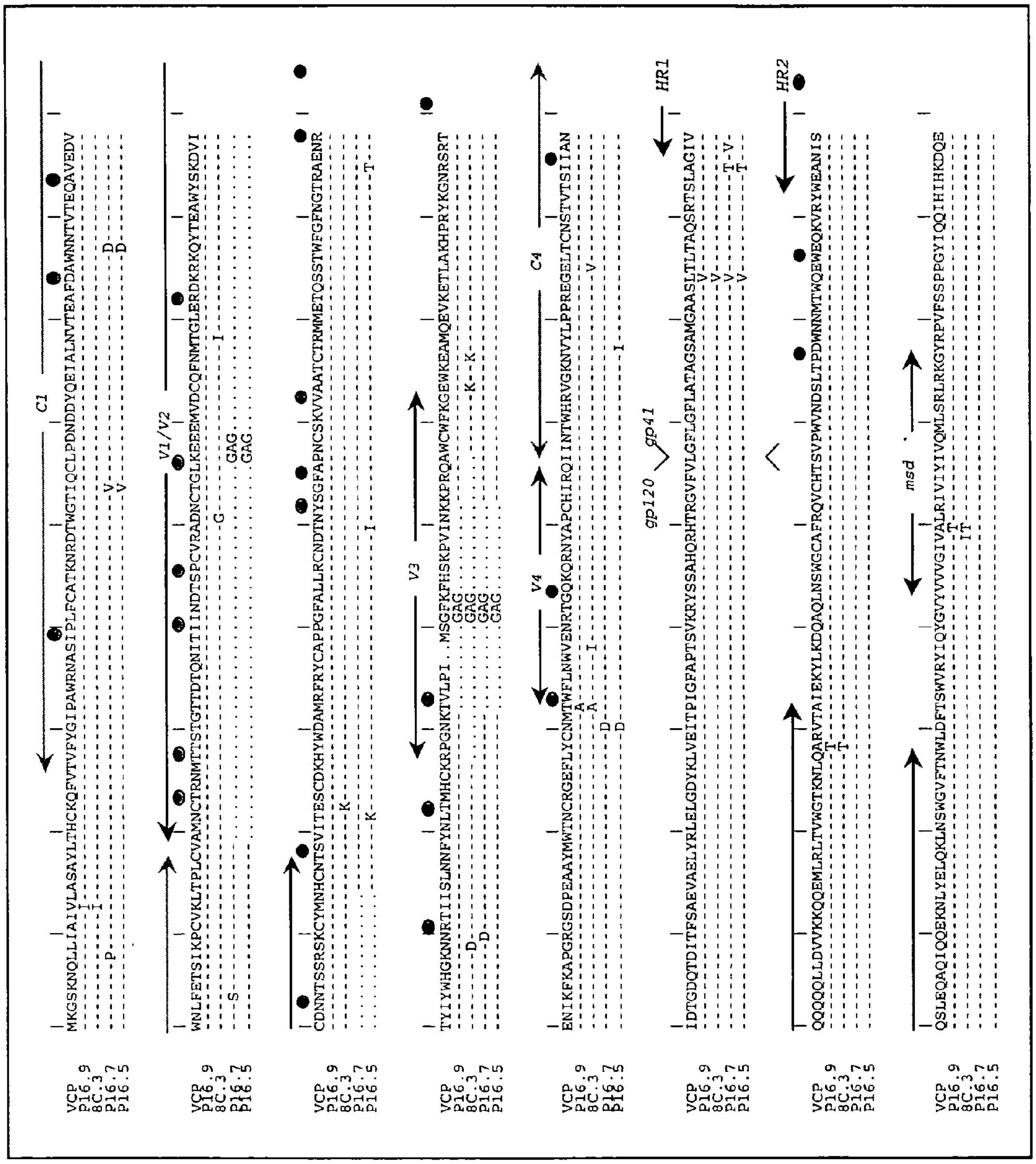
FIG. 6 sets forth amino acid sequences of Env from adapted clones (p16.5, p16.7, p16.9, and 8c.3) obtained from the viruses obtained in cell passage 16 as depicted in FIGS. 5A and 5B and compared with the amino acid sequence of parental HIV-2/VCP Env. Amino acid sequences of variable loop-deleted Env clones as shown in FIGS. 5A and 5B are shown compared to the amino acid sequence of HIV-2/VCP. Env p16.9 contains only the ΔV3(6,6) mutation, while p16.5 and p16.7 contain ΔV3(6,6) and a ΔV1/V2 deletion, and 8c.3 contains ΔV3(1,1) and a ΔV1/V2 deletions. Acquired mutations and the GAG linker are shown within each deleted region. Conserved (C) and variable (V) regions are indicated as are sites for N-linked glycosylation and heptad repeat (HR) regions in gp41.

Sequences of three "adapted" Env clones from passage 16 are shown in FIG. 6, one ΔV3(6,6) clone (p16.9) and two ΔV1/V2;ΔV3(6,6) clones (p16.5 and p16.7). While there were no changes in the remnant of the V3 loop in any virus, significant and at times convergent changes were evident in other regions. All clones lost a conserved glycosylation (CHO) site at the base of V4, and CHO sites were also lost from individual clones in C1 and C2 regions. A Lys was acquired in the V1/V2 stem in one clone, which flanks the bridging sheet on the analogous position in HIV-1. Changes in gp41 included an L/V mutation distal to the fusion peptide, and A/T mutations in HR1. Similar mutations were seen in these and in other clones demonstrate that mutations in gp120 (particularly the loss of CHO sites) and in gp41 compensate for the truncated V3 loop. No similar mutations were acquired when parental VCP or a virus with only the ΔV1/V2 mutation were serially passaged in SupT1. The loss of CHO sites may increase exposure of the core chemokine receptor binding site, while the changes in the gp41 ectodomain may facilitate signaling from 120 to gp41 during fusion (i.e., a "hair-triggered" Env).

Figure 7:
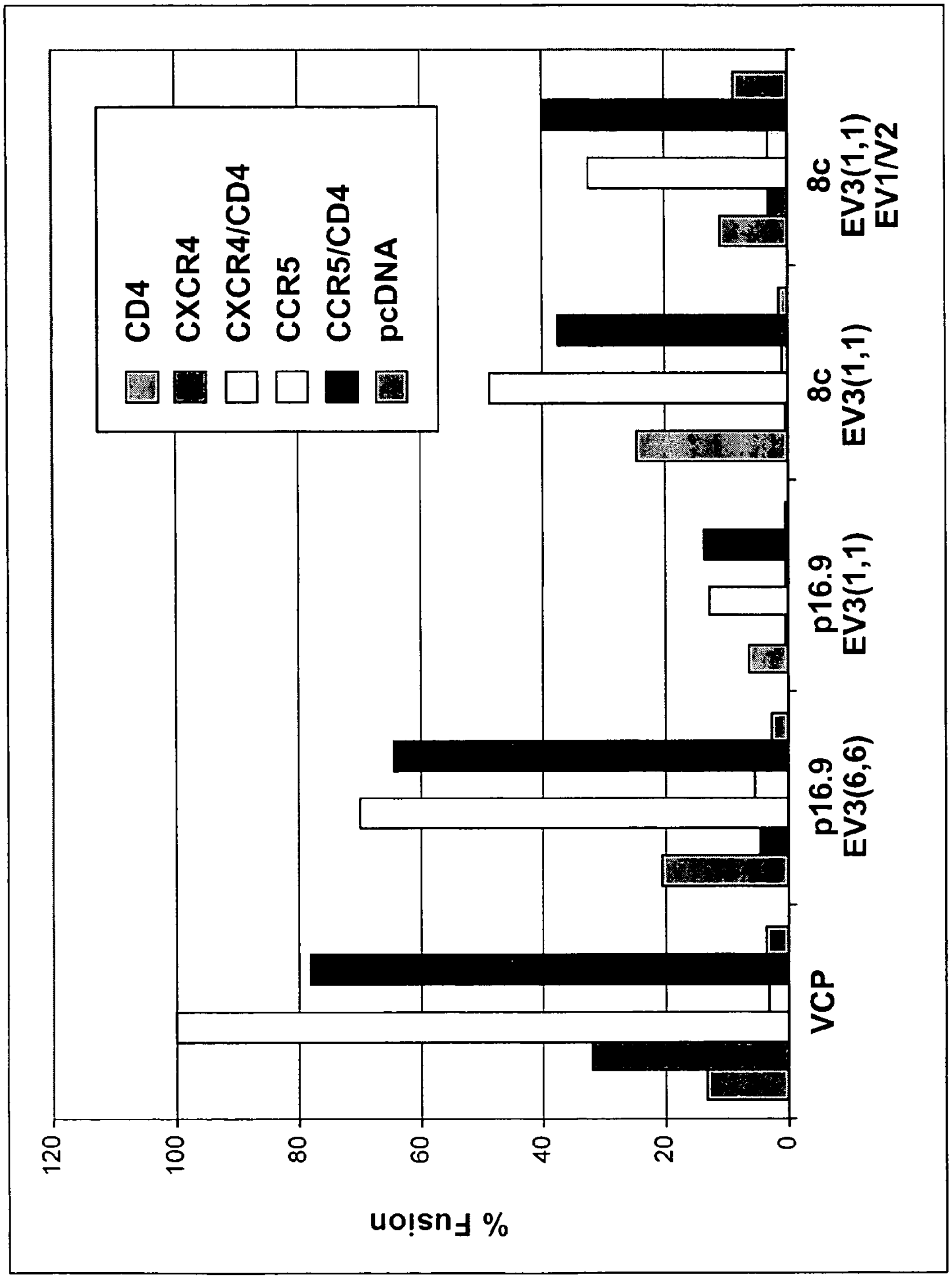
FIG. 7 is a graph depicting the effect of a full deletion of the V3 loop from Env using a cell/cell fusion assay. The p16.9 Env, which contains a ΔV3(6,6) deletion, was further mutagenized to a ΔV3(1,1) Env and evaluated in a cell/cell fusion assay. This clone showed reduced but detectable fusion on CXCR4 and CCR5. When the gp120 lacking all of the V3 loop was introduced into a virus and serially passaged, an Env, "8c," was derived exhibiting enhanced fusogenicity. The sequence of the 8c clone, which is shown in FIG. 6, exhibits novel changes that include the appearance of positively charged lysine (Lys) residues just adjacent to the V3 remnant. Fusion activity persisted even when a ΔV1/V2 mutation was inserted to generate a gp120 lacking V1/V2 and V3 in their entirety. Cell fusion was plotted as a function of receptor type.

To generate viruses that could replicate without V1/V2 and V3, further deletions of V3 were made using the growth-adapted p16.9 clone of ΔV3(6,6) (FIGS. 5 and 6). When a ΔV3(1,1) mutation (FIG. 1C) was introduced, the resulting Env, designated p16.9 ΔV3(1,1), exhibited low but significant fusion activity (FIG. 7). Moreover, when this Env was inserted into an HIV-2 provirus, the virus could replicate in SupT1. As this virus was passaged, it also acquired new changes that included positive charges in the V1/V2 stem and in the proximal region of C3 just past the base of the V3 loop. One Env cloned from this culture, designated "8cΔV3 (1,1)" exhibited increased fusion efficiency, and when a ΔV1/V2 mutation was introduced, fusion activity persisted on both CXCR4 and CCR5 (FIG. 7). This Env, now with a fully deleted V1/V2 and V3, will likely enable generation of V1/V2/V3-deleted virus given its already impressive level of membrane fusion activity. Thus, by combining a stepwise process of mutagenesis, biological adaptation, and further mutagenesis, Envs have been obtained which represent the most "minimized" functional HIV Envs to date.

Structure/function studies of some of the loop-deleted HIV-2 Envs suggest a novel mechanism for their function. X4-tropic Envs including VCP are dependent on extracellular loops (ECL) of their chemokine coreceptors, particularly ECL2, for entry. However, the N-terminus also contributes to fusion and binding. Because the V3 crown has been proposed to interact with chemokine receptor ECLs while the base of V3 and, in particular the bridging sheet core domain, interacts with the N-terminus, in the absence of V3, HIVs would exhibit increased dependence on the N-terminus. Indeed, while neither VCP nor an Env containing a ΔV(6,6) deletion could utilize CXCR2, the ΔV3(6,6,) Env, p16.9 clone, but not the parental VCP Env could utilize a CXCR2 chimera containing the CXCR4 N-terminus (4222 in FIG. 8). These "gain of function" findings indicate that in absence of V3, a core domain of VCP evolved to optimize use of the CXCR4 N-terminus. Given that ΔV3 viruses remain tropic for CCR5, it is possible that this interaction is based on determinants shared between the CCR5 and CXCR4 N-termini. In addition, V3-deleted Envs could also fuse using 2444 chimeras, indicating that Env core domains could also interact with ECLs. These data suggest that ΔV3 variants exhibit increased dependence on tyrosine sulfation in the N-termini of both CCR5 and CXCR4. Tyrosine sulfation is the most likely shared motif in this region of these two coreceptors. Certainly the acquisition of positive charges in the V1/V2 stem and in C3, seen in several of the adapted Env clones of the invention, is consistent with this indication.

Figure 9B:
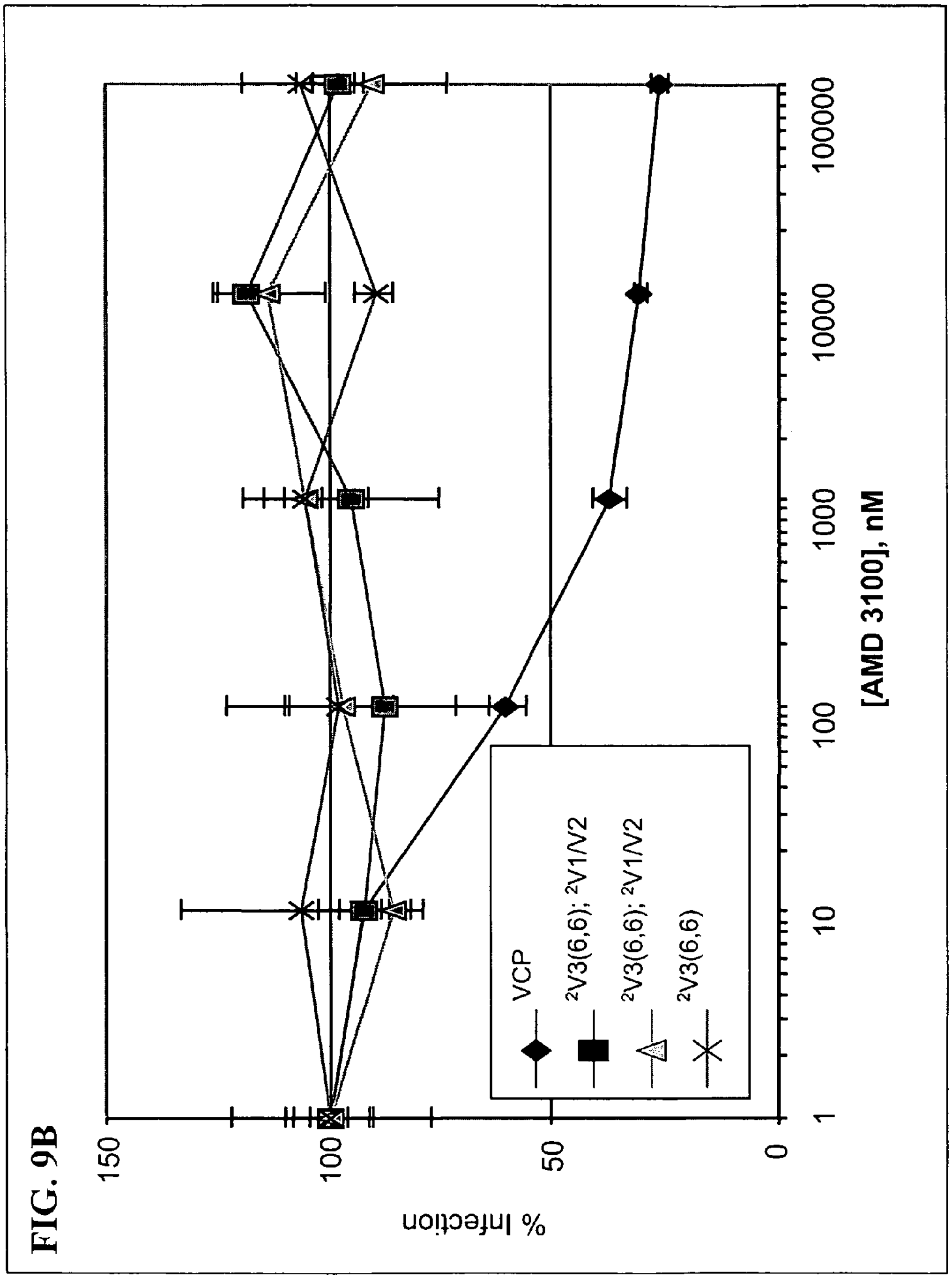
FIG. 9B is a diagram depicting AMD3100 sensitivity for viral pseudotypes containing the indicated Envs as indicated, i.e., VCP, V3(6,6); V1/V2, and V3(6,6). Sensitivity to AMD3100 was assessed using U87/CD4/CXCR4 target cells. Two different Env clones comprising deletion of V3(6, 6) in combination with deletion of V1/V2 are depicted. The data demonstrate the sensitivity of VCP to AMD3100 while the deletion mutants demonstrate complete resistance to AMD3100.

Additional data demonstrating novel features of ΔV3-deleted or -truncated viruses has come from studies of the CXCR4 inhibitor AMD3100. This bicyclam specifically blocks CXCR4 function and its ability to serve as a receptor for X4 Envs by binding to two Asp residues at the base of the CXCR4 second and fourth extracellular loops. Surprisingly, although infection of SupT1 cells by wildtype VCP was inhibitable by AMD3100 ($IC_{50}$~50 nM), neither the ΔV3(6,6) nor ΔV1/V2; ΔV3(6,6) viruses could be blocked by AMD3100 at concentrations of about greater than 10,000 nM (FIG. 9). These viruses are inhibitable by combinations of anti-CXCR4 monoclonal antibodies, indicating that CXCR4 is still being utilized.

Example 6

Generation of Replication Competent SIVs With Deletions of V3

Figure 10:
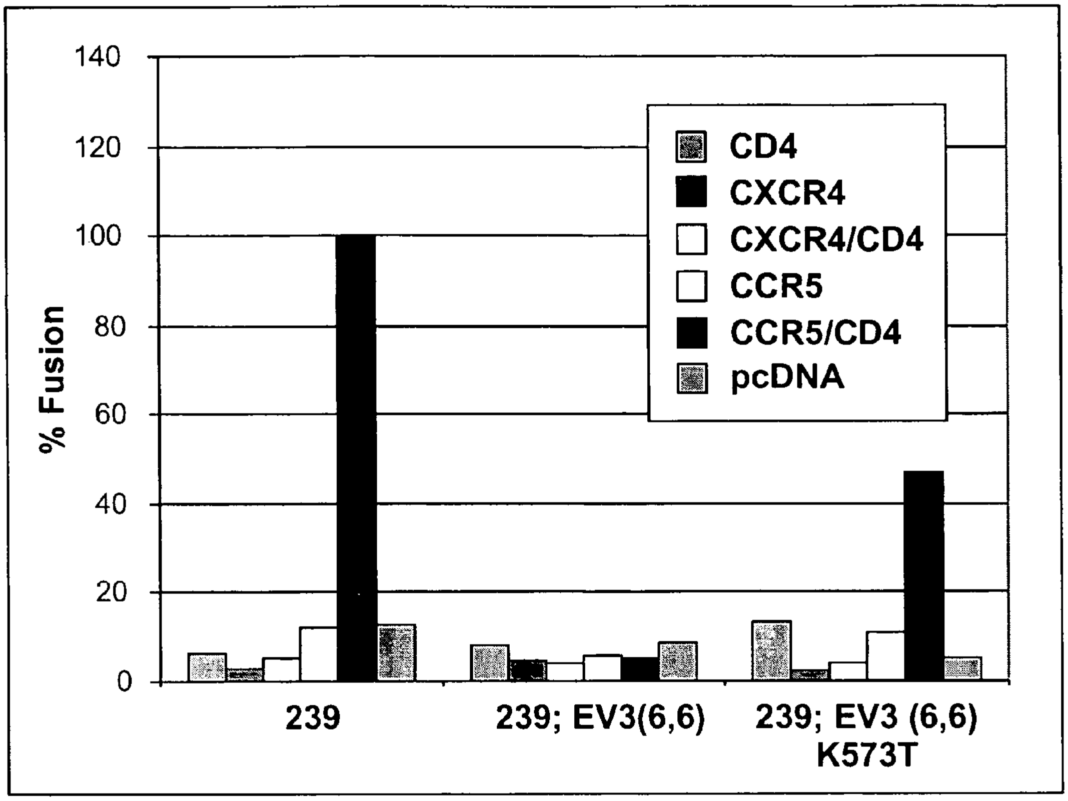
FIG. 10 is a graph depicting the fusogenicity of SIV Env containing a ΔV3(6,6) mutation. Cell/cell fusion on CD4, CXCR4, CXCR4/CD4, CCR5, and CCR5/CD4 receptors is shown for Env proteins derived from SIVmac239. gp120 proteins are parental mac239, as well as clones having ΔV3 (6,6) alone, ΔV3(6,6) plus K573T in HR1, and ΔV1/V2 plus K573T. Cell fusion was measured and plotted as percent cell fusion as a function of receptor. The results demonstrate that K573T confers fusogenicity to SIVmac239 comprising a ΔV3(6,6) deletion mutation.

Given the close genetic relationship between HIV-2 and SIVmac, SIVmac239 may tolerate deletions of V3. Desrosiers demonstrated that SIVmac239 can replicate despite a ΔV1/V2 deletion. It has been shown herein that this virus becomes CD4-independent on CCR5 and is highly neutralization sensitive. Surprisingly, mutations in gp41 were required to adapt this ΔV1/V2 mutant for efficient replication in vitro. It was determined that for the related SIVmac316 Env, which is macrophage-tropic and CD4-independent on CCR5, a K573T mutation in HR1 of gp41 is required for this phenotype. An analogous ΔV3(6,6) mutation (FIG. 1) was introduced onto the SIVmac239 Env with and without K573T. While 239;ΔV3(6,6) was not functional, this clone with the K573T mutation was functional on rhesus $CD4^+$/$CCR5^+$ cells (FIG. 10). Also shown is a 239ΔV1/V2 clone with K573T that used CCR5 independently of CD4. The ΔV3(6,6)/K573T Env shown in FIG. 8 was inserted into a 3' hemigenome of SIVmac239 following cotransfection into 293T cells with a 5' half. The resulting virus was used to infect GHOST/$CD4^+$/$CCR5^+$ reporter cells. This virus generated a spreading infection with GFP fluorescent cells observed along with $p27^{gag}$ in culture supernatants. Passage this virus in R221 cells, a rhesus cell line that is $CD4^+$/$CCR5^+$ and highly sensitive to SIVmac infection, can be used to generate variants that will tolerate further deletions of V3 with or without the ΔV1/V2 deletion.

The above findings illustrate that the present studies demonstrating how viruses can become CD4-independent and remain replication competent despite genetic deletion of a critical domain such as the V3-loop are useful to provide insights that can be used to generate novel, replication competent viruses.

Example 8

Modifications in the HIV-1 Env That Enhance Fusion

Figure 11:
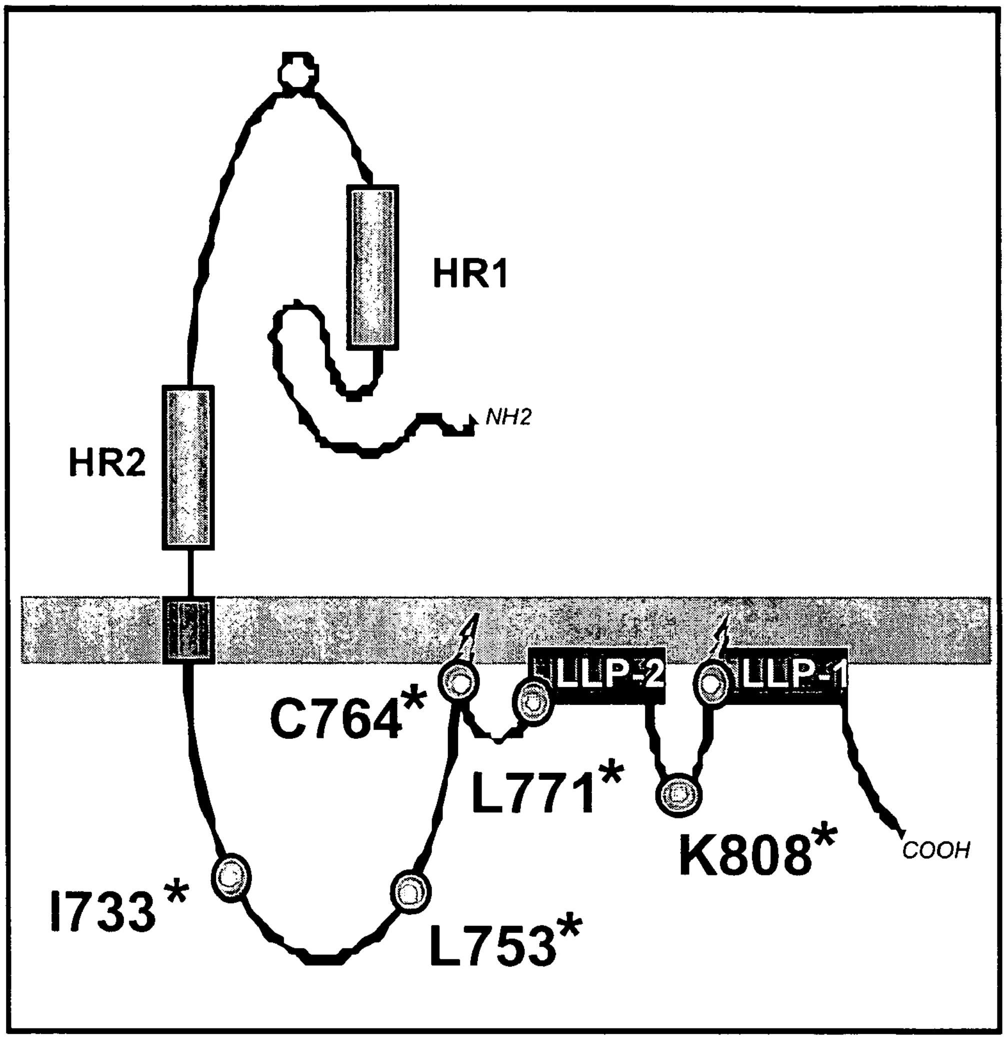
FIG. 11 is a diagram depicting the mutagenesis of the HIV-1 gp41 cytoplasmic domain. HXBc2 gp41 is shown, illustrating the positions of the stop codons introduced into the sequence. Palmitoylated cysteines at positions 764 and 837 are shown, along with LLP1 and LLP2 domains.
Figure 12A:
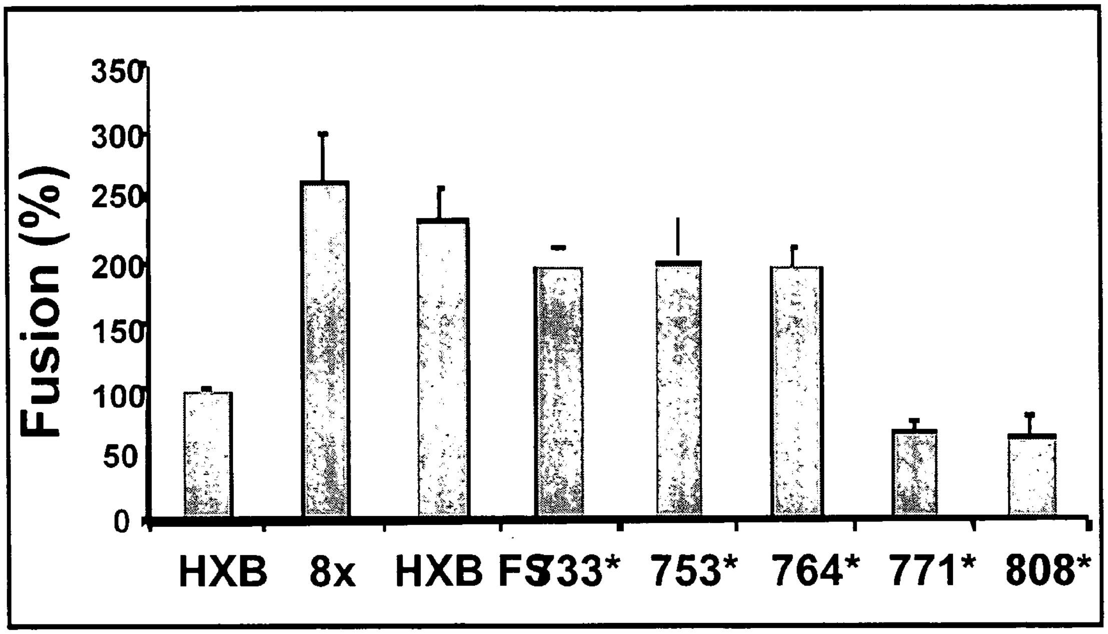
FIG. 12A is a graph depicting the enhanced fusogenicity of HIV-1 Env comprising truncation of the gp41 cytoplasmic domain ("CD"). Cell-cell fusion on $CD4^+$/$CXCR4^+$ cells was illustrated as a function of gp41 mutant as shown in FIG. 11. Controls include parental HXBc2, CD4-independent 8x, and HXBc2 further comprising the 8x gp41 frameshift mutation.
Figure 12B:
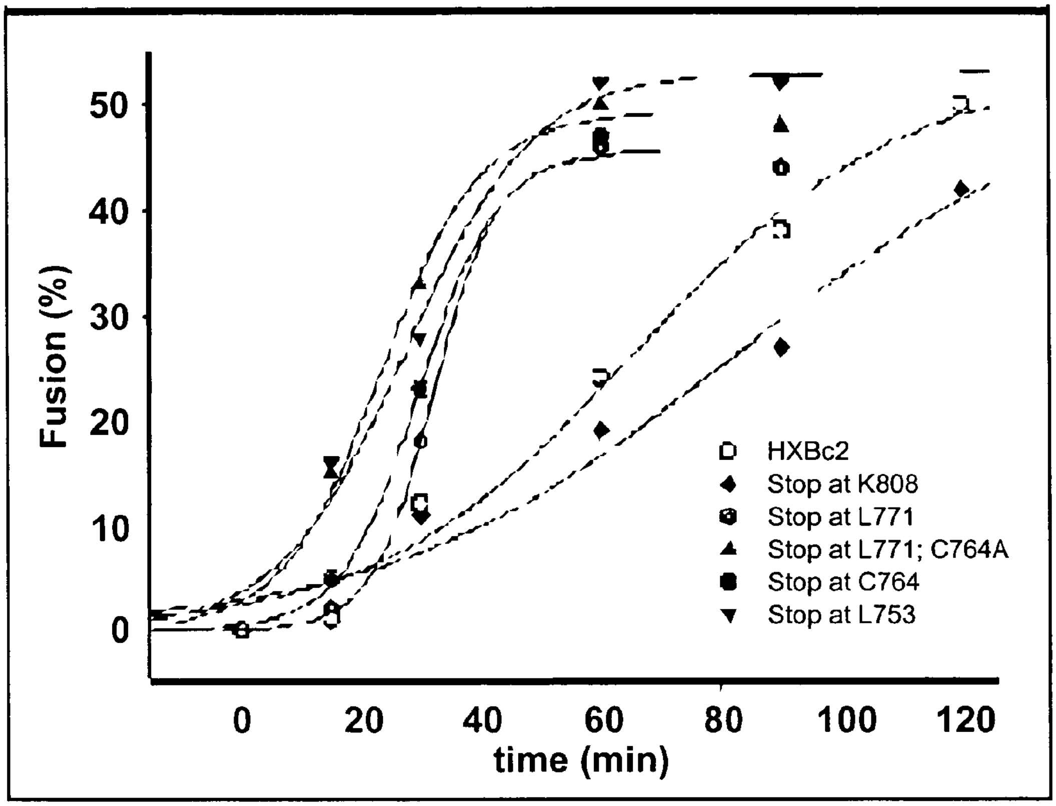
FIG. 12B is a graph depicting the enhanced fusogenicity of HIV-1 Env having truncations in the gp41 cytoplasmic domain. Fusion kinetics were assessed as percent fusion using a dye transfer assay, and are set forth as a function of gp41 mutant as shown in FIG. 11. The results show that a distal membrane interaction of the gp41 CD between about amino acid residue number 764 and 771down-modulates Env fusogenicity.

A frame shift mutation in the 8x gp41 cytoplasmic domain (CD) of HIV-1 that results in truncation of this domain, while not sufficient for CD4-independence, increased fusogenicity and the exposure of CD4-induced epitopes on heterologous R5 and X4 Envs (Edwards et al., 2001, J. Virol. 75:5230-9, Edwards et al., 2002, J. Virol. 76:2683-91). It was determined that the premature truncation resulting from this mutation accounts for the increased fusogenicity. The gp41 CD contains 2 palmitoylated cysteines (Rousso et al., 2000, Proc. Natl. Acad. Sci. USA 97:13523-5) and amphipathic alpha-helical regions termed LLP-1 and LLP-2 that are proposed to interact with the plasma membrane (FIG. 11) (Andreassen et al., 1990, J. Acquir. Immune Defic. Syndr. 3:615-22, Eisenberg et al., 1990, Biopolymers 29:171-7, Kalia et al., 2003, J. Virol. 77:3634-46, Kliger et al., 1997, Biochemistry 36:5157-69, Miller et al., 1993, Virology 196:89-100) and, for LLP1, to bind to calmodulin (Miller et al., 1993, AIDS Research and Human Retroviruses 9:1057-1066). Stop codons were introduced at various positions in the HXBc2 gp41 cytoplasmic tail (FIG. 11) and fusogenicity evaluated (FIG. 12) (Gallo et al., 2001, Biochemistry 40:12231-6). Fusion efficiency was clearly enhanced by the FS mutation and by stop codons at 733, 753 and 764, but not at 771 and 808. In addition, fusion kinetics for Envs with prematurely truncated tails up to and including 771 were more rapid than for the 808 truncation or the full length tail. Despite slight differences between these assays, the findings presented herein illustrate that an interaction of a distal region in the CD with the plasma membrane, beginning with LLP2, reduced fusion efficiency and kinetics. These findings are reminiscent of ecotropic murine leukemia virus where cleavage of an alpha helical R peptide in the distal cytoplasmic tail is required for a fusion active conformation of Env (Aguilar et al., 2003, J. Virol. 77:1281-91, Melikyan et al., 2000, J. Virol. 74:447-55, Olsen et al., 1999, J. Virol. 73:8975-81, Yang et al., 1997, J. Virol. 71:8490-6). Although the HIV or SIV gp41s are not cleaved, the present results reveal influences and in particular, constraints on Env fusogenicity by the gp41 cytoplasmic tail. It was also shown that, at least for SIV, truncation of the CD greatly increases Env incorporation into virus particles by as much as 10-fold (Chertova et al., 2002, J. Virol. 76:5315-25, Zhou et al., 2002, J. Biol. Chem. 277:17476-85).

Example 7

Figure 13:
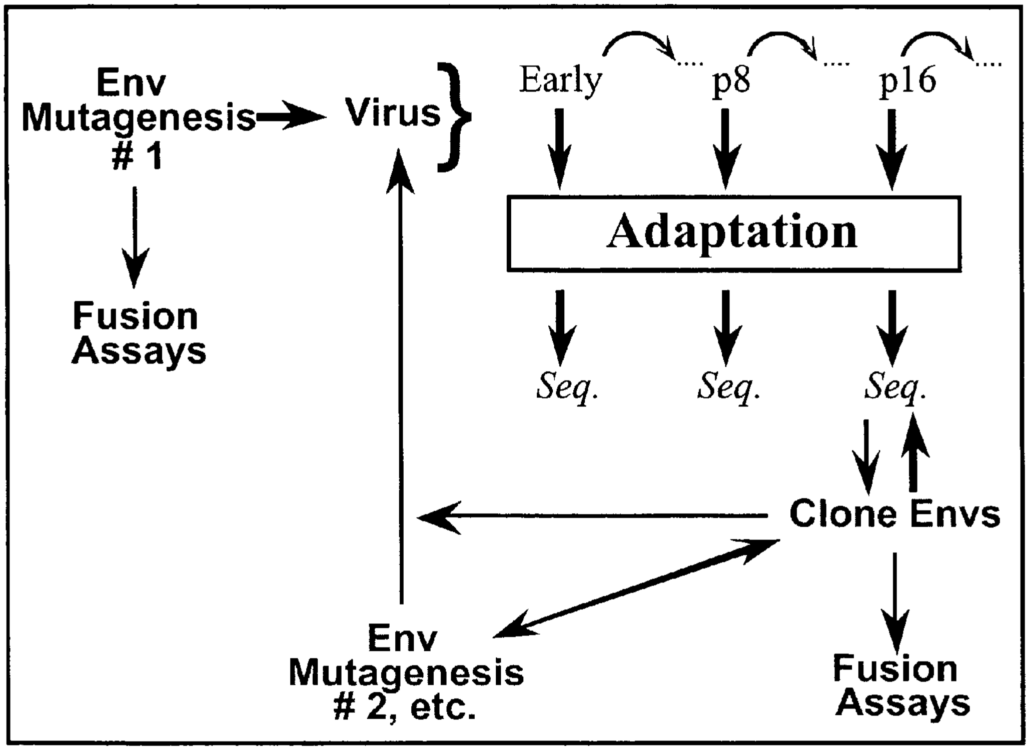
FIG. 13 is a diagram illustrating, without wishing to be bound by any particular theory, a mutagenesis and adaptation protocol for selecting Env having hypervariable loop deletions. Env proteins that retain function after an initial deletion mutation [e.g., ΔV3(6,6)] are introduced into viruses and serially passaged, selecting for more rapid growth and monitored for molecular evolution. Env proteins from "adapted" viruses are cloned, further mutagenized, screened for fusion, and introduced into viruses for additional rounds of adaptation.

Derivation of Replication Competent Variants of HIV-2 Lacking Hypervariable Loops As, described elsewhere herein, isolates of HIV-2/VCP containing extensive deletions of hypervariable loops V1/V2 and V3 were derived, including viruses with a) ΔV1/V2 in combination with ΔV3(6,6); b) ΔV3(6,6) alone, and c) ΔV3 (1,1) alone (FIG. 1). Rounds of targeted mutagenesis with in vitro passaging that enables compensatory mutations to accumulate over time were used to produce to produce a replication competent virus that lacks all of V1/V2 and V3 (i.e., a ΔV1/V2;ΔV3(1,1) virus. The general strategy used is shown in FIG. 13. Briefly, loop deletions [e.g., ΔV1/V2 or ΔV3(6,6)] were initially introduced individually on selected Envs and evaluated for function in cell/cell fusion assays. By assessing fusion on cells that overexpress Env and receptors, the assay provided an excellent screen for Envs with residual functional competence. Envs were then introduced into an infectious provirus and electroporated into either SupT1 cells ($CD4^+$/$CXCR4^+$) or SupT1 engineered to express CCR5. Viral growth was monitored by $p27^{gag}$ antigen in supernatant, and $p27^{gag+}$ cells by IFA. Virus was then serially passaged onto uninfected cells and cultures monitored for cytopathic effects (CPE) (syncytia formation, cell killing) and the % of $p27^{gag+}$ cells. Viruses with V3 deletions initially replicate slowly and show little syncytia formation, but adapt to replicate more rapidly and with increasing CPE. Cultures were also monitored molecularly by "bulk sequencing" of uncloned DNA every 8-10 passages to determine whether new and/or adaptive mutations were emerging. When both biological and molecular screens indicated that changes are occurring, Envs were cloned by PCR from genomic DNA and fusion activity was compared to non-passaged, parental Envs. Functional Envs were sequenced and introduced into the infectious molecular clone to determine whether the phenotype of more rapid and/or cytopathic replication was recapitulated. Adapted Env clones were then further deleted (i.e. with a more extensive deletion of the same loop or deletion of a different loop) and the adaptation/cloning process repeated. This strategy allowed progress from parental VCP to ΔV3(6,6) to ΔV3(1,1) and finally to ΔV3(1,1) plus a ΔV1/V2. Although the later Env, which was fully deleted of V1/V2 and V3, was not introduced into an infectious virus, its competence in fusion assays (FIG. 7) demonstrates that it is possible to create an infectious virus with this Env.

Additional strategies. In the event that a particular ΔV1/V2;ΔV3(1,1) Env does not support virus replication well enough to allow a spreading infection and adaptation, even though it exhibits good activity in cell-cell fusion assay, several options are available. First, SupT1 cells are co-cultured with B-THP-DC-SIGN cells. DC-SIGN efficiently binds HIV, and when expressed on B-THP cells transmits virus to adjoining T-cells or T-cell lines. This greatly enhances infection efficiency. Second, the V3 loop is progressively shortened, adapting virus at each step. If going from ΔV3(6,6) to ΔV3(1,1) is not tolerated, a ΔV3(4,4) virus is produced, then a ΔV3(3,3) virus is produced, and so on. Third, the structure-function studies described herein suggest mutations that can be introduced into loop-deleted Envs that will enhance their fusogenicity. As described elsewhere herein, this strategy has been used successfully to obtain a replication competent SIVmac ΔV3(6,6) strain.

Example 8

HIV-2/VCP with Deletions of V4

The two cysteines at the base of the V4 loop of HIV are immediately adjacent to those forming the base of V3 loop indicating that V4, like V3, is well positioned to alter exposure of core domains involved in chemokine receptor binding and to affect, directly or indirectly, entry events and neutralization sensitivity. Indeed, V4 has been implicated to interact with V3 and can develop mutations over time that correlate with pathogenesis and/or neutralization resistance. Therefore, the approach to delete V4 from HIV-2/vcp is similar to that taken to delete V3. ΔV4 Envs are created that contain the first and last 6 amino acids or the first and last amino acid (each with a GAG linker) producing ΔV4(6,6) and ΔV4(1,1) Envs, respectively. Mutations are introduced onto the parental VCP Env and onto the "adapted" ΔV1/V2 and ΔV3 clones described in detail elsewhere herein and are fusion evaluated in cell/cell fusion assays. Competent clones are then inserted into infectious viruses (FIG. 13) to derive replication competent cores of HIV-2 (i.e. fully deleted of V1/V2, V3 and V4).

The HIV-2/vcp variants and cloned Envs derived provide a rich panel of reagents for structural, functional and immunologic studies. The variants and clones allow an assessment of the direct contribution made by the conserved domains in the gp120 core to Env function. "Gp120s" from these Envs provide tools to address biophysical and structural questions that bear on the interaction of the gp120 core domains to the chemokine receptor. Studies on the role of mutations in compensating for the loss of variable loops will identify intramolecular interactions involved in fusion, particularly those between gp120 and gp41. Further, "minimized" but functional HIV-2 Envs are useful for devising strategies to generate similar variants in other viruses, including SIV and HIV-1, and in determining the impact of structural alterations on immunogenicity and the potential to generate broadly neutralizing antibodies.

Example 9

Biological, Biochemical, Morphologic and Immunologic Characterization of Variable Loop-Deleted HIV-2 Envs Standard Fusion Assays to Ascertain Receptor Dependence and Fusion Levels.

The cell/cell fusion assay described herein was used to ascertain receptor dependence, the overall level of fusogenicity, and processing efficiency for each Env. Envs were expressed in "effector" cells off of the T7 promoter by T7 polymerase, while various combinations of CD4 and all known viral coreceptors (CCR5, CXCR4, CCR8, CCR3, etc.) were expressed in target cells along with luciferase under control of the T7 promoter. Effector and target cells were mixed, and the amount of luciferase activity (which results from cytoplasmic mixing after fusion) was determined at different times. This rapid, high-throughput assay made it possible to test large numbers of Env constructs for the ability to mediate membrane fusion with different receptor combinations. In addition to monitoring receptor dependence, overall fusion levels was also monitored. With continued cell passage, some Envs lacking variable loops became more 'fusogenic', thus mediating virus entry more efficiently, as described above in reference to VCP adapted viruses of the invention.

Figure 8:
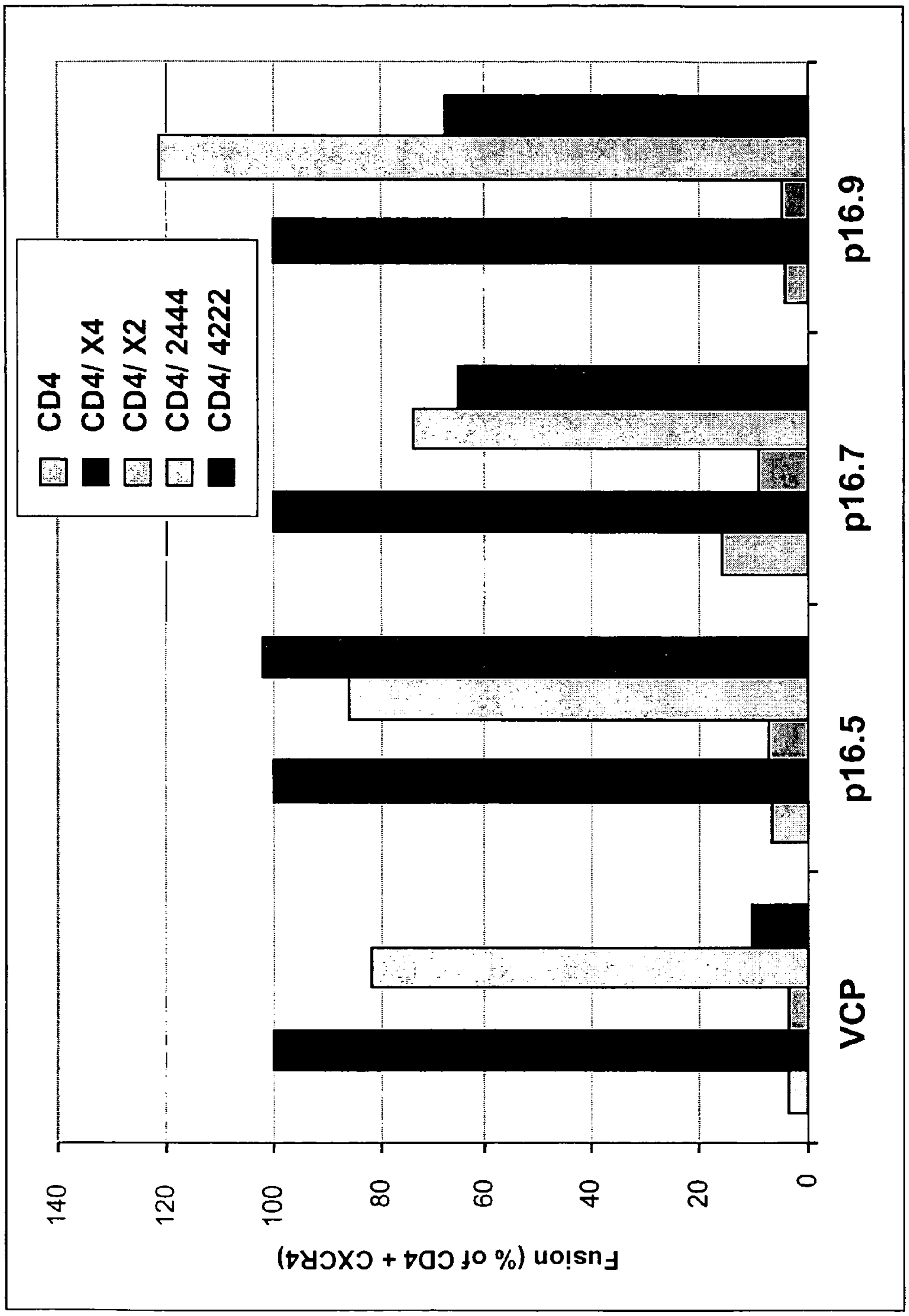
FIG. 8 is a graph depicting the increased dependence on the CXCR4 N-terminus by Env proteins containing a ΔV3(6,6) mutation. Adapted Env proteins p16.5, p16.7 and p16.9, as depicted in FIGS. 5A, 5B and 6, were evaluated in cell/cell fusion assays on cells expressing CD4 with CXCR4, CXCR2, or chimeric receptors in which N-terminal extracellular (EC) domains were swapped. Results for each Env are shown as a % of its fusion on CXCR4. Neither VCP nor any Env could utilize CXCR2. However, mutant Env—but not wildtype VCP—fused well with 4222, indicating improved use of the X4 N-terminus. All clones utilized 2444, indicating that extracellular loops (ECL) 1, 2 and 3 are still utilized.

Finally, as shown in FIG. 8, coreceptor mutants are used to demonstrate how adaptations in Env affect how it interacts with chemokine receptors.

Dependence upon receptor expression levels. Coreceptor expression levels affect both the efficiency and kinetics of membrane fusion as well as sensitivity to entry inhibitors. Deletion of variable loops reduced Env affinity for coreceptor, making fusion at low levels of coreceptor less efficient. However, continued passage of viruses with deleted Envs led to the acquisition of mutations that either restored coreceptor affinity, or made Envs more easily triggered upon coreceptor binding. To measure the effects of coreceptor and CD4 density on membrane fusion, the fusion assay described above was used, but with a panel of T-REX target cells in which CCR5 or CXCR4 were under the control of an inducible promoter. These target cells afford the means to rapidly vary coreceptor expression levels.

Fusion kinetics. The β-lactamase fusion assay described by Michael Miller and colleagues to monitor rates of membrane fusion. This assay enabled measurement of fusion rates in real-time in a fluorimeter. Cells did not have to be lysed to measure fusion activity. Using this assay, it was found that coreceptor density affects membrane fusion rates. Accordingly, some loop-deleted Envs are more easily triggered as a result of compensatory mutations, resulting in more rapid fusion kinetics. Thus, Envs were tested for fusion kinetics using target cells that express low, intermediate and high levels of coreceptor. Because differences in fusogenicity may be masked when Env is expressed at high levels, Env expression plasmids are serially diluted so that assays are performed when Env levels are limiting for membrane fusion.

Virus entry assays. Fusion assays were routinely cross-checked by producing pseudotype reporter viruses, which were then used to measure virus entry. Briefly, 293T cells were transfected with plasmids bearing the Env of interest as well as an HIV-1 core construct that has luciferase in place of Env. SIV and MLV core constructs were also used, as some Envs pseudotype more efficiently on one of these cores compared to the other. Virus particles bearing the desired Env and the genetically modified viral genome provided a single-cycle infection assay that is rapid and quantitative. Virus stocks were normalized by p24 or p27 assays and stored at −85°. To monitor infection of primary cells, the lactamase assay described by Warner Greene and colleagues was used. In this assay, lactamase fused to HIV-1 Vpr was overexpressed, resulting in its incorporation into the virus core. The resulting virus stocks were normalized and used to infect human PBMCs that were loaded with CCF2 dye. Usually by 6 hours, infected cells changed from green to blue, making it possible to measure virus entry and infection of primary cells.

Example 10

Receptor Binding Assays

It was found that HIV-2/VCP binds to CXCR4 with unusually high affinity in the absence of CD4. Variable loop deletions reduced the affinity of gp120 for coreceptor, and mutations acquired during viral passage can enhance affinity. Therefore, monitoring gp120 affinity for this coreceptor is useful to elucidate mechanisms that enable virus strains to replicate efficiently despite lacking functionally important domains such as the V3 loop. In addition, although VCP utilizes CCR5 for fusion, its interaction with this coreceptor is below the level of detection by western blot. Therefore, to assess binding to each of these coreceptors, several assays were developed to monitor gp120-coreceptor interactions with varying degrees of precision, as described below.

Western blot binding assay. HIV-2/VCP gp120 binding to CXCR4 occurs with sufficient affinity so that binding can be detected by western blot. In this assay, the gp120 of interest is added to cells expressing the desired coreceptor either in the absence or presence of sCD4. After binding for 30 min, the cells are washed, lysed, and bound gp120 detected by western blot. Under these conditions, endocytosis of gp120 does not occur at appreciable levels, and a rough measure of binding affinity can be obtained.

Competition assays. When a more sensitive measure of receptor binding is needed, a competition assay using an iodinated chemokine ligand (RANTES for CCR5 and SDF-1 for CXCR4) is used. In this assay, the gp120 is incubated with receptor positive cells (+/−sCD4) at different concentrations prior to the addition of trace amounts of the iodinated chemokine. Whether the gp120 competes with the high affinity ligand for binding is determined. This technique is useful to measure relatively weak affinities, on the order of 100-200 nM. However, mutations in gp120 may affect the manner in which it engages its coreceptor without actually altering its affinity. Therefore, in addition to the iodinated chemokine, the parental gp120 protein can also be iodinated and used as a probe to assess the affinity of mutants Envs.

Optical biosensor assay. The real-time nature of the optical biosensor assay described above provides the most detailed information about binding constants. In this assay, MLV virus particles are produced in cells over-expressing CXCR4 or CCR5. These particles are then attached to the biosensor surface, thus presenting the chemokine receptor in native conformation. The desired gp120 is applied to the flow cells, and by varying protein concentration and using needed controls, binding constants can be derived. This assay is described fully in Hoffman et al.

Example 11

Entry Inhibitor Assays

Alterations in how a viral Env protein engages its receptor can influence its sensitivity to entry inhibitors. Therefore, where a genetically modified or passage-adapted Env exhibits alterations in sensitivity to an entry inhibitor, the Env can in some way interacts with its receptors differently, at least in the case of coreceptor antagonists. For the fusion inhibitor T20, changes in drug sensitivity may be due to alterations in receptor affinity, fusion kinetics, and changes at or near the T20 binding sites. Therefore, all Envs are routinely screened for their sensitivity to SCH-C (a CCR5 inhibitor under clinical development), AMD-3100 (a CXCR4 inhibitor) and T-20 (a fusion inhibitor). The standard cell-cell fusion assay set forth herein is adequate for these assays. Typically, $IC_{50}$ values are higher in the fusion assay compared to infection assays, but overall patterns of sensitivity are not affected.

Example 12

Immunologic Assays

The invention as described herein is useful for the development of more effective Env immunogens. Therefore, the present invention is also useful to determine whether the modified Envs described herein exhibit enhanced sensitivity to neutralization by sera from infected patients and animals (in the case of SIV) and by monoclonal antibodies to well defined epitopes. Neutralization assays are performed with luciferase reporter viruses and U87 cell lines expressing the appropriate combinations of CD4 and coreceptor.

Example 13

Structural and Thermodynamic Assays

The novel Envs of the present invention and disclosed herein can provide useful information about the thermodynamics of the conformational changes that result from receptor binding, and the extent to which the ability to function in the absence of variable loops may correlate with reduced conformational flexibility. By analyzing the entropic changes associated with antibody and CD4 binding, it was shown that a novel mechanism of immune evasion, termed entropic masking, may play a role in allowing primary HIV-1 isolates to resist neutralization.

Additional Reagents

Large quantities of well-characterized, broadly cross reactive neutralizing antibodies have been produced, including 2F5, IgG1b12, 2G12, 4E10 and r447D.

Example 14

Structure/Function Analyses of Loop-Deleted Envs

The present invention also provides for the identification of the molecular determinants that enable Envs to function in the face of extensive loop deletions disclosed herein. Accordingly, the invention provides information on how chemokine receptors are utilized by Env and what interactions between gp120 and gp41 occur following receptor engagement. For example, some mutations arising during adaptation of loop-deleted viruses for enhanced replication will alter poorly understood gp120-gp41 triggering reactions that occur after coreceptor binding. Also, the present invention is useful to identify common structural themes that enable loop-deleted viruses to replicate efficiently. For example, if loss of glycosylation sites in the C3 region of gp120 commonly occurs upon adaptation of V3-deleted viruses, introduction of these mutations into HIV-1 and SIV Envs can be used to enable these viruses to tolerate a similar deletion.

Example 15

Selection of Envs for Structure/Function Studies

Figure 14:
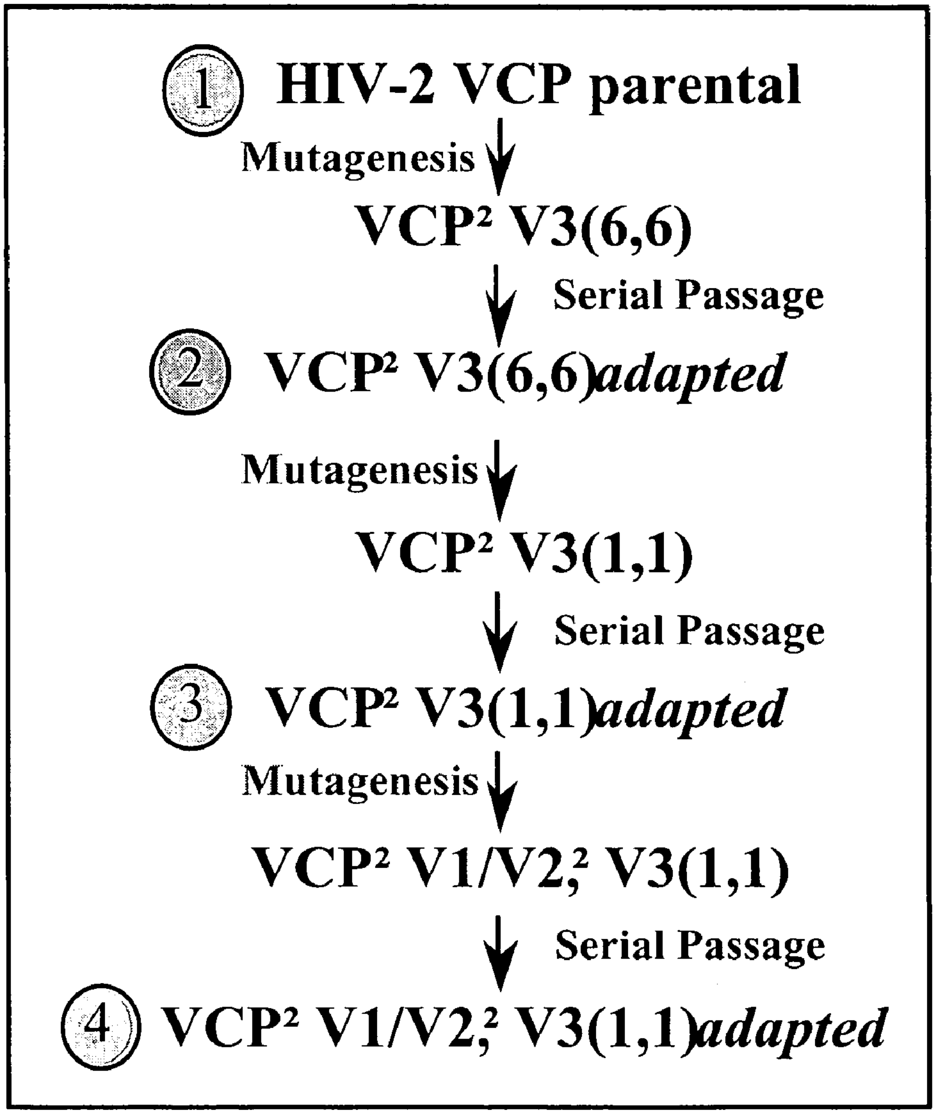
FIG. 14 is a diagram illustrating, without wishing to be bound by any particular theory, a strategy for selection of functional HIV-2 Env proteins comprising deletions of variable loops. The diagram shows how the selection/adaptation protocol shown in FIG. 13 was used to derive functional HIV-2/VCP Envs with deletions of V1/V2 and V3.

An example of a selection series of the present invention is shown in FIG. 14. In this example, HIV-2/VCP is the parental Env (Env #1). A portion of the V3 loop was removed (i.e., the ΔV3(6,6) mutation) and Env function assessed in fusion assays and a replication competent virus constructed. This virus was then adapted for efficient replication by serial passaging and an Env cloned, characterized, and selected (Env #2). A deletion of the remainder of the V3 loop [i.e., the ΔV3(1,1) mutation] was then introduced and a virus was constructed and adapted, ultimately enabling a third deletion (i.e. ΔV1/V2) to be introduced, generating an Env that lacked V1/V2 and V3. The resulting virus will be adapted enabling it to be used for large scale production for structural and immunogenicity studies.

Example 16

Selection of Assays

Identification of residues that are responsible for enhanced viral replication in the face of extensive loop deletions is accomplished by placing Env chimeras and mutants described herein into a replication competent virus and measuring the growth of each. The replication is measured at early times after infection, lest new mutations arise. Alternatively, other assays disclosed herein to analyze each Env are used to reveal functional and immunological differences that can be readily detected. Choice of assays depends upon the outcome of experiments disclosed herein, with several assays optionally being used, in order to successfully recapitulate all of the properties that enable a virus to replicate efficiently in the absence of variable loops. For example, the cell/cell fusion assay makes it possible to quickly measure absolute fusion levels, fusion kinetics, and dependence on coreceptor expression levels. Alternatively, where changes in affinity prove important, then gp120 binding assays are be used. Antibody binding assays can also be used, to examine Envs that lack variable loops but retain important neutralizing epitopes.

Example 17

Production of Env Chimeras and Site-Directed Mutagenesis

The present invention also includes the comparison of two closely related Envs that differ phenotypically, and production of chimeras in which their respective gp120 and gp41 domains are exchanged. The Envs are tested in the assays described elsewhere herein. It is known that Env expression levels, cleavage efficiency, and gp120 shedding are all factors that can impact function, and these features are controlled for in the present invention. Where exchanging gp120 and gp41 domains demonstrates that one domain is responsible for differences in phenotype, then site-directed mutagenesis is used to identify the responsible residues. Where changes in both gp41 and gp120 are important as was observed for a ΔV1/V2 deleted variant of SIVmac239, this can be revealed herein by introducing mutations in various combinations. The findings regarding growth-adapted variants of HIV-2/VCP with loop deletions disclosed herein demonstrated that a manageable number of mutations arise over time, which enable the virus to grow more efficiently.

It is apparent from the HIV-2/VCP findings disclosed herein that in the case of HIV-2/VCP Envs that became adapted for replication with a ΔV3(6,6) deletion±ΔV1/V2, multiple clones lost a glycosylation site (CHO) in gp120 at position 392 near the base of the V4 loop (FIG. 7). The fact that this site was lost in different ways (i.e., changes in the N or the T position of the "N×T" motif for N-linked glycosylation) indicates the strong selection pressure for loss of a CHO site. The loss of this site increases exposure of the coreceptor binding domain. Additionally, it is noted that multiple clones from different ΔV3(6,6)-adapted viruses also developed mutations in gp41, including L518V distal to the fusion peptide, and A529T or A561T in HR1. Therefore, the data disclosed herein demonstrate that certain "features" can be readily applied to development of similar V3 deletion mutants of similar viruses, e.g., SIV and HIV-1, and such mutants are thus encompassed in the present invention as would be understood by the skilled artisan upon being provided the teachings disclosed herein. For instance, exposure of the bridging sheet domain ("BS") as is suggested by the deletion of the N-linked glycosylation site that would otherwise prevent exposure of the BS can be readily accomplished using site-directed mutagenesis to alter and obliterate the glycosylation site. This is because the data disclosed herein demonstrate that loss of the carbohydrate site, thereby mediating loss of the glycan structure believed to cover the bridging sheet domain in the wild type gp120 peptide, mediates a compensatory mutation such that deletion the V3 region does not cause loss of function. Therefore, other mutations that remove a glycosylation site such that a core functional domain is exposed that would not otherwise be exposed in the absence of a V3 interaction, are also encompassed in the invention since such useful mutations would be understood by one skilled in the art to be included in the invention based upon the disclosure provided herein.

Surprisingly, different mutations were observed when a ΔV3(6,6) clone was mutated to ΔV3(1,1) and adapted for in vitro growth. For these Envs, positively charged residues were observed in the C3 region past V3 leading to the conclusion that an increase in the net positive charge on the gp120 core enables the virus to interact more efficiently with coreceptors in the absence of V3. Importantly, mutations acquired during adaptation of ΔV3(6,6) were essential, since a ΔV3(1,1) mutation engineered onto a VCP background was nonfunctional when introduced into a virus.

Example 18

Derivation of Replication Competent SIV and HIV-1 Envs with Deletions of Variable Loops Replication competent SIV and HIV-1 Envs with deletions of variable loops are produced according to the methods and compositions set forth for the production of replication competent HIV-2 as described in detail elsewhere herein. Prior to the disclosure of the present invention herein, no isolates have been described with truncated or absent V3 loops.

Example 19

Variable Loop Deletions in SIVmac239

It was demonstrated that a principal determinant for the CD4-independence of the SIVmac316 was a K573T mutation in the gp41 HR1 domain (Doms, unpublished). This mutation indirectly affects exposure of CD4-induced epitopes and/or chemokine receptor binding domains, and possibly even the kinetics or threshold for gp120-to-gp41 triggering, obviating a need for CD4. Surprisingly, when K573T was introduced onto SIVmac239 (a strictly CD4-dependent Env) the resulting Env could then tolerate introduction of a ΔV3(6,6) mutation (FIG. 10). Not only was an Env with this mutation competent in cell/cell fusion assays, but a virus bearing this Env was able to initiate a spreading infection on a luciferase reporter cell line (GHOST/CCR5$^+$ cells).

SIVmac239-based viruses with ΔV3(6,6) and K573T mutations can be derived by transfecting constructs into 293T cells, transfer virus to target cells, and once infection is established, serially passaged and adapted (FIG. 13). Given that rhesus CD4 and CCR5 are used more efficiently by SIV Envs, rhesus R221 cells are useful for adaptation, since they express high levels of rhesus CD4 and CCR5 and are exquisitely sensitive to SIV infection. Based on the replication competence of the SIV ΔV3(6,6); K573T virus of the present invention, it is suitable for the serial adaptation/mutagenesis protocol used for HIV-2/VCP, enabling viruses to be derived with progressively shorter V1/V2, V3 and possibly V4 variable loops.

Example 20

Variable Loop Deletions in HIV-1

Loop-deleted mutants of HIV-1 are produced using the protocols set forth herein for HIV-2 and SIV. HIV-1 Envs useful for the production of loop-deleted mutants of the present invention include Envs with high coreceptor affinity, CD4 independence, and/or dual tropism, all of which could be associated with more exposed core domains that might be adapted to function without variable loops. Further examples include a) well described dual tropic Clade B Envs (89.6, DH12); and b) isolates obtained from studies that exhibit either enhanced fusogenicity or promiscuous use of other chemokine receptors. The latter Envs include HIV-1/TYBE, a brain-derived isolate that utilizes CXCR4 on macrophages (Yi et al., 2003, J. Neurovirol. 9:432-41), and a highly fusogenic Env, termed 580, that utilizes both CXCR4, CCR5 and CCR8 in fusion assays (provided by Lishan Su, Univ. North Carolina). In addition, because Envs having a higher intrinsic affinity for CXCR4 may be more permissive for loop deletions, and in this context, a number of Envs identified from clinical isolates that are less sensitive to AMD3100 (including the TYBE Env) are useful in these studies.

HIV-1 Envs selected for loop deletions initially have ΔV3(6,6) and ΔV1/V2 mutations introduced individually, and fusion competence is assessed on CCR5- and CXCR4-expressing cells. Those Envs with good fusion activity are cloned into a full length NL43-based provirus and following transfection into 293T cells, inoculated onto SupT1 or SupT1/CCR5 cells and monitored for infection by IFA ($p24^{gag+}$ cells) and $p24^{gag}$ antigen. This later line is highly permissive to most HIV-1 primary isolates and is a useful host cell line to serially passage and adapt these loop-deleted viruses of the present invention (Chertova et al., 2002, J. Virol. 76:5315-25; Chertova et al., 2003, Curr. Mol. Med. 3:265-72). As described elsewhere herein for HIV-2/VCP, several rounds of mutagenesis and adaptation are required to derive loop-deleted HIV-1 isolates, and may be accomplished by a combination of functional assays, mutagenesis, and adaptation protocols as described elsewhere herein. Targeted mutations that impact functional attributes of the HIV-1 core domain may also be introduced at this point, based on findings related to compensatory mutations in loop-deleted HIV-2s and SIVs as described herein, such as the role of mutations in the gp41 HR1 domain or the loss of particular CHO sites. For example, the CHO site at HIV-2/VCP aa. 392 is highly conserved in among SIVmac, HIV-2 and HIV-1 isolates and was relevant to the CD4-independent phenotype of HIV-1/8x (LaBranche et al., 1999, J. Virol. 73:10310-9). Thus, this mutation may be introduced into Envs to improve their ability to tolerate an initial ΔV3(6,6) truncation, "jump starting" the adaptation process. Because it has been shown herein identified a key role for the HIV-1 cytoplasmic tail in modulating fusion (i.e., truncations that enhanced fusion efficiency, kinetics, and CD4-independence) (Edwards et al., 2001, J. Virol. 75:5230-9; Edwards et al., 2002, J. Virol. 76:2683-91), tail mutations could be introduced into loop-deleted Env clones to assess the extent to which they may permit variable loop deletions to be tolerated, although their effects on overall replication will need to be carefully assessed.

Example 21

Modifications in the HIV-1 Env that Enhance Fusion

Generation of variable loop-deleted, replication competent variants of HIV-1 can be developed using the teachings disclosed herein for production of similar mutants of HIV-2/VCP. Although it is not clear what properties of VCP permitted these mutations to be tolerated, features that may have contributed include its 1) CD4-independent and more open Env conformation (Endres et al., 1996, Cell: 745-756, Lin et al., 2001, J. Virol. 75:10766-78); 2) dual tropism for CXCR4 and CCR5 (Lin et al., 2001, J. Virol. 75:10766-78); 3) high affinity interaction with chemokine receptors (Lin et al., 2003, J. Virol. 77:931-42); and/or 4) high fusogenicity. Simply starting with a CD4i HIV-1 Env was not sufficient, since a ΔV3(6,6) deletion in the HIV-1/8x Env was nonfunctional, possibly because 8x has a low affinity for CXCR4 (Hoffman et al., 2000, Proc. Natl. Acad. Sci. USA 97:11215-20, Lin et al., 2003, J. Virol. 77:931-4288).

Figure 15:
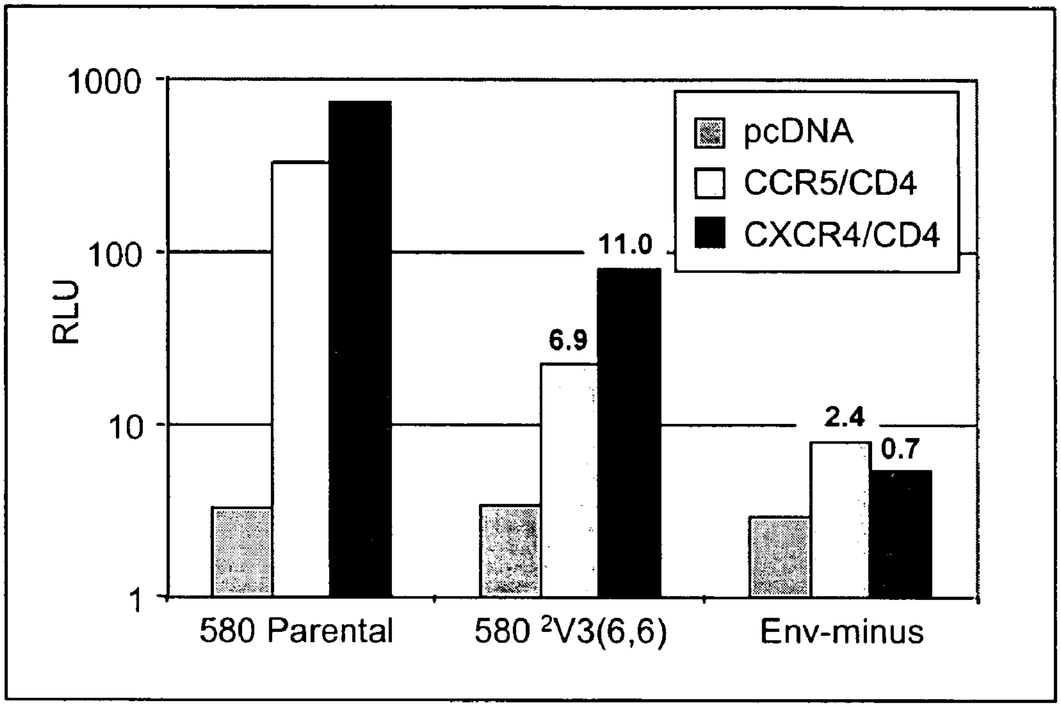
FIG. 15 is a diagram demonstrating that V3 deletion results in a functional HIV-1 Env. A truncation analogous to the ΔV3(6,6) mutation used in HIV-2 (FIG. 1) was introduced in the dual tropic HIV-1 Env clone 580. Fusion efficiency is shown on QT6 cells expressing the indicated receptors. The percent fusion of the parental Env containing V3 is indicated. A control with no Env is shown. Fusion activity of this ΔV3 Env was demonstrated in 3 independent experiments. RLU refers to "relative light units" of luciferase activity.

Several dual-tropic primary HIV-1 isolates are now available from ViroLogic, Inc. Envs have been cloned and evaluated for the ability to tolerate a ΔV3(6,6) mutation as an indication of their suitability for the stepwise mutagenesis/adaptation protocol used to derive ΔV3 variants of HIV-2/VCP. Remarkably, one primary HIV-1 Env, activity in cell/cell fusion assays after introduction of a ΔV3(6,6) mutation (FIG. 15). This is among the first HIV-1 Envs that can be used to produce infectious viruses comprising deletion of V3. These data demonstrate the general applicability of the techniques discussed previously elsewhere herein for HIV-2 for production of functional V3 deletion mutants of HIV-1 and SIV.

Example 22

Immunogenic Consequences of Replication Competent Viruses with Variable Loop Deletions Preparation of immunogens. Mild oxidizing agents such as Aldrithiol-2 (AT-2), are useful to covalently modify key internal proteins required for viral replication in HIV and SIV virions through preferential attack on the free sulffhydryl moieties of cysteines. This is accomplished without affecting cysteines involved in disulfide linkages, such as those in the viral envelope glycoproteins. AT-2 treatment inactivates treated viruses while preserving native, conformationally and functionally intact Env trimer spikes on the virion surface. These preparations are non-infectious, in vitro and in vivo, and are highly immunogenic and capable of eliciting high titer antibody responses to Env in small animals and in non-human primates. Envs of the present invention are derived from replication competent viruses, and these loop-deleted viruses selected for immunization are produced in quantity for this protocol.

Typically, 4-5 liters from either chronically or acutely infected cells are harvested and clarified by tangential flow filtration. For inactivation, 1x clarified culture supernatant is treated with AT-2 (1 mM, 4° C., 18 hours, with mixing). The inactivated virions are purified and concentrated, and residual AT-2 quantitatively removed by centrifugation on sucrose gradients in a continuous flow ultracentrifuge. Purified virions from peak gradient fractions are then pelleted by ultracentrifugation and resuspended to the desired concentration, aliquotted, and stored in vapor phase liquid nitrogen until use. AT-2 inactivated virion preparations are tested for residual infectivity and characterized biochemically, including quantitation of gag ($p24^{gag}$ or $p27^{gag}$), estimation of relative virion gp120 and gp41 content and Gag:Env ratio using a combination of SDS-PAGE (Coomassie and silver staining), calibrated immunoblots, and HPLC analysis, supplemented by quantitative amino acid analysis and mass spectrometry, as needed. Monoclonal antibodies developed according to methods of the present invention and directed to conserved gp120 core epitopes are especially useful for this work, including DA6, which detects a linear epitope in the HIV-2/SIVmac C1 domain and J3, which detects a linear epitope in the HIV-1 C2 domain. It has also been found that Env trimers can be directly visualized on AT-2-inactivated particles by EM, and all particles produced will be analyzed by EM to directly observe Env content and determine if the trimeric structure, morphology, and number of spikes per virion are altered by the Env modification or the purification protocol.

Immunization protocol. Extensive studies by the NCI AIDS Vaccine Program have optimized dosing, immunization schedule, and the selection of adjuvants to generate high titer anti-Env immune responses to inactivated SIV particles. Guinea pigs are used to pilot these immunogenicity studies given the relatively clean background activity of this model for neutralization assays and experience at the AVP in using guinea pigs in other immunogenicity studies of AT-2 inactivated viral particles. Protocols for the use of animals are described elsewhere herein.

Neutralization assays. For each immunization set, animals receive a) parental virus particles that contain variable loops and b) particles from mutagenized/adapted viruses with deletions of V1/V2 and V3 in combination. Viruses with V4 deletions may also be included. For each parental virus selected for this protocol, approximately 2-3 loop-deleted Envs are generated using the stepwise selection scheme noted above (FIG. 13), thus providing a powerful tool to assess the impact of partial and more extensive deletions. Sera from inoculated guinea pigs is obtained for evaluation in various quantitative neutralization assays including a) inhibition of cell free viruses, b) inhibition of viral pseudotypes, and c) inhibition of cell/cell fusion. The large number of Envs and viruses are available for comparative studies is useful for determination of whether loop-deleted particles of the present invention can generate responses that cross-neutralize parental viruses (containing variable loops) used to generate the immunogens as well as heterologous isolates. To ensure that any observed neutralization activity is generated against viral and not cellular determinants, following routine heat inactivation, sera is extensively adsorbed with uninfected cells from the line used to generate the virus stocks.

Immunological evaluations of antisera includes ELISA, western blot and immunoprecipitation protocols to compare reactivity to parental and loop-deleted Env proteins (as described elsewhere herein) and virions. On parental virions, antibodies are directed predominantly to variable loops whereas for loop-deleted virions, reactivity is primarily against core domains. Assays that measure antibody binding to free gp120s are used along with assays on virions and infected cells to identify reactivity with native trimeric Envs. The techniques set forth herein are useful to assess the potential for the ΔV1/V2, ΔV3 HIV-2/VCP virions of the present invention to elicit immune responses that cross react with SIVmac core domains. Without V1/V2 and V3, HIV-2 and SIVmac239 gp120s are 82% identical (86% identical when conserved amino acid differences are included). Moreover, when regions comprising the analogous HIV-1 bridging are compared (i.e., residues from the V1/V2 stem, the distal region of C3 and the C4 domain) VCP and SIVmac239 are 98% identical. Thus, immune responses to the fully-deleted ΔV1/V2, ΔV3 HIV-2/VCP Env can cross react with SIVmac gp120 core domains and even neutralize these isolates to a greater extent than sera to virions with variable loops.

Example 23

Prioritization of Envs for Evaluation

The invention provides Envs selected for immunogenicity studies having a ΔV1/V2 and ΔV3(1,1) in combination. For each immunization set, immune responses of a ΔV1/V2 and ΔV3 virus to the parental wildtype virus are compared. As noted elsewhere herein, V4 deletions can be incorporated into this strategy where deletion mutants remain replication competent. As described in detail elsewhere herein, monoclonal antibodies to core domains have structural attributes that permit access to these sites and confer neutralization function (i.e., sulfated tyrosines and extended CDR3 loops).

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated nucleic acid encoding a mammalian immunodeficiency virus glycoprotein (gp) 120 polypeptide, wherein said gp120 polypeptide comprises a deletion of hypervariable loop 3 (V3), and further comprises a compensatory mutation, wherein said compensatory mutation is an amino acid substitution from threonine to alanine at amino acid residue number 391, wherein the amino acid residue number of said compensatory mutation is relative to the amino acid sequence of parental HIV-2/vcp gp120 as provided in SEQ ID NO:5.

2. The isolated nucleic acid of claim 1, wherein said mammalian immunodeficiency virus is human immunodeficiency virus type 2 (HIV-2).

3. The isolated nucleic acid of claim 2, wherein said deletion of V3 is a deletion of from about amino acid residue number 303 to amino acid residue number 324 (ΔV3(6,6)) relative to the amino acid sequence of HIV-2/vcp gp120 as provided in SEQ ID NO:5.

4. The isolated nucleic acid of claim 3, wherein said V3 deletion is ΔV3(6,6).

5. The isolated nucleic acid of claim 1, wherein the amino acid sequence of said gp120 polypeptide encoded by said nucleic acid is the amino acid sequence of SEQ ID NO:11.

6. An isolated nucleic acid encoding a mammalian immunodeficiency virus glycoprotein (gp) 120 polypeptide wherein said gp120 polypeptide comprises a deletion of hypervariable loop 3 (V3) and further comprises a compensatory mutation wherein the nucleic acid sequence of said nucleic acid is the sequence of SEQ ID NO:8.

7. The isolated nucleic acid of claim 6, wherein said deletion is from about amino acid residue number 303 to amino acid residue number 324 (ΔV3(6,6)), relative to the amino acid sequence of HIV-2/vcp gp120 as provided in SEQ ID NO:5.

* * * * *

SEQUENCE LISTING

```
<160> NUMBER OF SEQ ID NOS: 30

<210> SEQ ID NO 1
<211> LENGTH: 2475
<212> TYPE: DNA
<213> ORGANISM: HIV-2/VCP (env)

<400> SEQUENCE: 1

atgaagggta gtaagaatca actgctgatt gctattgtac tagctagtgc ttacctaaca      60

cattgcaagc aatttgtgac tgttttctat ggcatacccg cgtggaggaa tgcatccatt     120

cccctgtttt gtgcaaccaa aaatagagat acttggggaa ccatacagtg cttgccagac     180

aatgatgatt atcaggaaat agctctaaat gtaacagagg ctttcgatgc atggaataat     240

acagtaacag aacaagcagt ggaggatgtc tggaatctat ttgagacatc aataaaacca     300

tgtgtcaaat taacaccctt atgtgtagca atgaactgta caaggaacat gaccacatcc     360

acagggacca cagacaccca aaatatcaca attataaatg acacttcgcc atgcgtacgt     420

gcagacaact gcacaggatt aaaggaggaa gaaatggtcg actgtcagtt taatatgaca     480

ggattagaga gagacaagag aaaacagtat actgaagcat ggtactcaaa agatgtgatt     540

tgtgacaata acacctcaag tcggagcaag tgttacatga accattgcaa tacatcagtc     600

atcacagagt catgtgataa gcactattgg gatgctatga ggtttagata ctgtgcacca     660

ccgggttttg ccctactaag atgcaatgat actaattatt caggctttgc acctaattgc     720

tctaaagtag tagctgctac atgcaccaga atgatggaaa cgcaatcttc tacatggttt     780

ggctttaatg gcactagagc agaaaataga acatatatct attggcatgg taaaaataac     840

agaactatta tcagcttaaa taacttttat aatctcacta tgcattgtaa gaggccggga     900

aataagacag tgttaccaat aatgtcaggg tttaagtttc actccaagcc ggtcatcaat     960

aaaaaaccca ggcaagcatg gtgttggttc aaaggcgaat ggaaggaagc catgcaggag    1020

gtgaaggaga cccttgcgaa acatcccaga tataaaggga acaggagccg cacagagaat    1080

attaaattta aagcaccagg aagaggctca gacccagaag cagcatacat gtggactaac    1140

tgcagagggg aatttctcta ctgcaacatg acttggttcc tcaattgggt agataacagg    1200

acgggtcaga aacagcgcaa ttatgcaccg tgccatataa ggcaaataat taatacttgg    1260

cacagggtag ggaaaaacgt atatttgcct cccagggaag gggagttgac ctgcaactca    1320
```

-continued

```
acagtgacca gcataattgc caacattgat acgggagatc aaacagatat tacctttagt   1380

gcagaggtgg cagaactata ccgattggaa ttgggagatt acaaattagt agaaatcaca   1440

ccaattggct tcgcacctac atcagtaaag agatactcct ctgctcacca gagacataca   1500

agaggtgtgt tcgtgctagg gttcttgggt tttctcgcaa cggcaggttc tgcaatgggc   1560

gcggcgtcgt tgacgctgac cgctcagtcc cggacttcat tggctgggat agtgcagcaa   1620

cagcaacagc tgttggatgt ggtcaagaaa caacaagaaa tgttgcgact gaccgtctgg   1680

ggaactaaaa atctccaggc aagagtcact gctatagaga aatacctaaa ggaccaggcg   1740

cagctaaatt catggggatg tgcgtttaga caagtctgcc acacttctgt accatgggta   1800

aatgatagct tgacacctga ttggaacaat atgacgtggc aggaatggga acaaaaagtc   1860

cgctactggg aggcaaatat cagtcaaagt ctagaacaag cacaaattca gcaagaaaag   1920

aatttgtatg agctgcaaaa attaaatagc tggggtgttt ttaccaattg gcttgacttc   1980

acctcctggg tcaggtatat tcaatatgga gtttatgtag tagtaggaat agtagcttta   2040

agaatagtaa tatatatagt acagatgtta agtagactta ggaagggcta taggcctgtt   2100

ttctcctccc cccccggtta tatccaacag atccatatcc acaaggacca ggaacagcca   2160

gccagagaag aaacagaaga agacgttgga agcaacggtg gagacagatc ttggctttag   2220

ccgatagcat atattcattt cctgatccgc ctgctgattc gcctcttgat cgggctatac   2280

aacatctgca gagacttact atccaggatc tccccgatcc tccaaccaat cttccagagt   2340

ctccagagag cactaacagc aatcagagac tggctgaggc ttaaagcagc ctacctgcag   2400

tatgggtgcg agtggatcca agaagcgttc caagcccttg caaggactac aagagagact   2460

cttgcaggcg cgggg                                                     2475
```

<210> SEQ ID NO 2
<211> LENGTH: 1503
<212> TYPE: DNA
<213> ORGANISM: HIV-2/VCP (gp120)

<400> SEQUENCE: 2

```
atgaagggta gtaagaatca actgctgatt gctattgtac tagctagtgc ttacctaaca     60

cattgcaagc aatttgtgac tgttttctat ggcatacccg cgtggaggaa tgcatccatt    120

cccctgtttt gtgcaaccaa aaatagagat acttggggaa ccatacagtg cttgccagac    180

aatgatgatt atcaggaaat agctctaaat gtaacagagg ctttcgatgc atggaataat    240

acagtaacag aacaagcagt ggaggatgtc tggaatctat ttgagacatc aataaaacca    300

tgtgtcaaat taacaccctt atgtgtagca atgaactgta caaggaacat gaccacatcc    360

acagggacca cagacaccca aaatatcaca attataaatg acacttcgcc atgcgtacgt    420

gcagacaact gcacaggatt aaaggaggaa gaaatggtcg actgtcagtt taatatgaca    480

ggattagaga gagacaagag aaaacagtat actgaagcat ggtactcaaa agatgtgatt    540

tgtgacaata acacctcaag tcggagcaag tgttacatga accattgcaa tacatcagtc    600

atcacagagt catgtgataa gcactattgg gatgctatga ggtttagata ctgtgcacca    660

ccgggttttg ccctactaag atgcaatgat actaattatt caggctttgc acctaattgc    720

tctaaagtag tagctgctac atgcaccaga atgatggaaa cgcaatcttc tacatggttt    780

ggctttaatg gcactagagc agaaaataga acatatatct attggcatgg taaaaataac    840

agaactatta tcagcttaaa taacttttat aatctcacta tgcattgtaa gaggccggga    900

aataagacag tgttaccaat aatgtcaggg tttaagtttc actccaagcc ggtcatcaat    960
```

-continued

```
aaaaaaccca ggcaagcatg gtgttggttc aaaggcgaat ggaaggaagc catgcaggag   1020

gtgaaggaga cccttgcgaa acatcccaga tataaaggga acaggagccg cacagagaat   1080

attaaattta aagcaccagg aagaggctca gacccagaag cagcatacat gtggactaac   1140

tgcagagggg aatttctcta ctgcaacatg acttggttcc tcaattgggt agataacagg   1200

acgggtcaga aacagcgcaa ttatgcaccg tgccatataa ggcaaataat taatacttgg   1260

cacagggtag ggaaaaacgt atatttgcct cccagggaag gggagttgac ctgcaactca   1320

acagtgacca gcataattgc caacattgat acgggagatc aaacagatat tacctttagt   1380

gcagaggtgg cagaactata ccgattggaa ttgggagatt acaaattagt agaaatcaca   1440

ccaattggct tcgcacctac atcagtaaag agatactcct ctgctcacca gagacataca   1500

aga                                                                  1503
```

<210> SEQ ID NO 3
<211> LENGTH: 972
<212> TYPE: DNA
<213> ORGANISM: HIV-2/VCP (gp41)

<400> SEQUENCE: 3

```
ggtgtgttcg tgctagggtt cttgggtttt ctcgcaacgg caggttctgc aatgggcgcg     60

gcgtcgttga cgctgaccgc tcagtcccgg acttcattgg ctgggatagt gcagcaacag    120

caacagctgt tggatgtggt caagaaacaa caagaaatgt tgcgactgac cgtctgggga    180

actaaaaatc tccaggcaag agtcactgct atagagaaat acctaaagga ccaggcgcag    240

ctaaattcat ggggatgtgc gtttagacaa gtctgccaca cttctgtacc atgggtaaat    300

gatagcttga cacctgattg gaacaatatg acgtggcagg aatgggaaca aaaagtccgc    360

tactgggagg caaatatcag tcaaagtcta gaacaagcac aaattcagca agaaaagaat    420

ttgtatgagc tgcaaaaatt aaatagctgg ggtgttttta ccaattggct tgacttcacc    480

tcctgggtca ggtatattca atatggagtt tatgtagtag taggaatagt agctttaaga    540

atagtaatat atatagtaca gatgttaagt agacttagga agggctatag gcctgttttc    600

tcctcccccc ccggttatat ccaacagatc catatccaca aggaccagga acagccagcc    660

agagaagaaa cagaagaaga cgttggaagc aacggtggag acagatcttg gctttagccg    720

atagcatata ttcatttcct gatccgcctg ctgattcgcc tcttgatcgg gctatacaac    780

atctgcagag acttactatc caggatctcc ccgatcctcc aaccaatctt ccagagtctc    840

cagagagcac taacagcaat cagagactgg ctgaggctta aagcagccta cctgcagtat    900

gggtgcgagt ggatccaaga agcgttccaa gcccttgcaa ggactacaag agagactctt    960

gcaggcgcgg gg                                                        972
```

<210> SEQ ID NO 4
<211> LENGTH: 739
<212> TYPE: PRT
<213> ORGANISM: HIV-2/VCP (env)

<400> SEQUENCE: 4

```
Met Lys Gly Ser Lys Asn Gln Leu Leu Ile Ala Ile Val Leu Ala Ser
1               5                   10                  15

Ala Tyr Leu Thr His Cys Lys Gln Phe Val Thr Val Phe Tyr Gly Ile
            20                  25                  30

Pro Ala Trp Arg Asn Ala Ser Ile Pro Leu Phe Cys Ala Thr Lys Asn
        35                  40                  45
```

-continued

```
Arg Asp Thr Trp Gly Thr Ile Gln Cys Leu Pro Asp Asn Asp Asp Tyr
    50                  55                  60

Gln Glu Ile Ala Leu Asn Val Thr Glu Ala Phe Asp Ala Trp Asn Asn
65                  70                  75                  80

Thr Val Thr Glu Gln Ala Val Glu Asp Val Trp Asn Leu Phe Glu Thr
                85                  90                  95

Ser Ile Lys Pro Cys Val Lys Leu Thr Pro Leu Cys Val Ala Met Asn
            100                 105                 110

Cys Thr Arg Asn Met Thr Thr Ser Thr Gly Thr Thr Asp Thr Gln Asn
        115                 120                 125

Ile Thr Ile Ile Asn Asp Thr Ser Pro Cys Val Arg Ala Asp Asn Cys
    130                 135                 140

Thr Gly Leu Lys Glu Glu Glu Met Val Asp Cys Gln Phe Asn Met Thr
145                 150                 155                 160

Gly Leu Glu Arg Asp Lys Arg Lys Gln Tyr Thr Glu Ala Trp Tyr Ser
                165                 170                 175

Lys Asp Val Ile Cys Asp Asn Asn Thr Ser Ser Arg Ser Lys Cys Tyr
            180                 185                 190

Met Asn His Cys Asn Thr Ser Val Ile Thr Glu Ser Cys Asp Lys His
        195                 200                 205

Tyr Trp Asp Ala Met Arg Phe Arg Tyr Cys Ala Pro Pro Gly Phe Ala
    210                 215                 220

Leu Leu Arg Cys Asn Asp Thr Asn Tyr Ser Gly Phe Ala Pro Asn Cys
225                 230                 235                 240

Ser Lys Val Val Ala Ala Thr Cys Thr Arg Met Met Glu Thr Gln Ser
                245                 250                 255

Ser Thr Trp Phe Gly Phe Asn Gly Thr Arg Ala Glu Asn Arg Thr Tyr
            260                 265                 270

Ile Tyr Trp His Gly Lys Asn Asn Arg Thr Ile Ile Ser Leu Asn Asn
        275                 280                 285

Phe Tyr Asn Leu Thr Met His Cys Lys Arg Pro Gly Asn Lys Thr Val
    290                 295                 300

Leu Pro Ile Met Ser Gly Phe Lys Phe His Ser Lys Pro Val Ile Asn
305                 310                 315                 320

Lys Lys Pro Arg Gln Ala Trp Cys Trp Phe Lys Gly Glu Trp Lys Glu
                325                 330                 335

Ala Met Gln Glu Val Lys Glu Thr Leu Ala Lys His Pro Arg Tyr Lys
            340                 345                 350

Gly Asn Arg Ser Arg Thr Glu Asn Ile Lys Phe Lys Ala Pro Gly Arg
        355                 360                 365

Gly Ser Asp Pro Glu Ala Ala Tyr Met Trp Thr Asn Cys Arg Gly Glu
    370                 375                 380

Phe Leu Tyr Cys Asn Met Thr Trp Phe Leu Asn Trp Val Asp Asn Arg
385                 390                 395                 400

Thr Gly Gln Lys Gln Arg Asn Tyr Ala Pro Cys His Ile Arg Gln Ile
                405                 410                 415

Ile Asn Thr Trp His Arg Val Gly Lys Asn Val Tyr Leu Pro Pro Arg
            420                 425                 430

Glu Gly Glu Leu Thr Cys Asn Ser Thr Val Thr Ser Ile Ile Ala Asn
        435                 440                 445

Ile Asp Thr Gly Asp Gln Thr Asp Ile Thr Phe Ser Ala Glu Val Ala
    450                 455                 460
```

-continued

Glu Leu Tyr Arg Leu Glu Leu Gly Asp Tyr Lys Leu Val Glu Ile Thr
465 470 475 480

Pro Ile Gly Phe Ala Pro Thr Ser Val Lys Arg Tyr Ser Ser Ala His
485 490 495

Gln Arg His Thr Arg Gly Val Phe Val Leu Gly Phe Leu Gly Phe Leu
500 505 510

Ala Thr Ala Gly Ser Ala Met Gly Ala Ala Ser Leu Thr Leu Thr Ala
515 520 525

Gln Ser Arg Thr Ser Leu Ala Gly Ile Val Gln Gln Gln Gln Gln Leu
530 535 540

Leu Asp Val Val Lys Lys Gln Gln Glu Met Leu Arg Leu Thr Val Trp
545 550 555 560

Gly Thr Lys Asn Leu Gln Ala Arg Val Thr Ala Ile Glu Lys Tyr Leu
565 570 575

Lys Asp Gln Ala Gln Leu Asn Ser Trp Gly Cys Ala Phe Arg Gln Val
580 585 590

Cys His Thr Ser Val Pro Trp Val Asn Asp Ser Leu Thr Pro Asp Trp
595 600 605

Asn Asn Met Thr Trp Gln Glu Trp Glu Gln Lys Val Arg Tyr Trp Glu
610 615 620

Ala Asn Ile Ser Gln Ser Leu Glu Gln Ala Gln Ile Gln Gln Glu Lys
625 630 635 640

Asn Leu Tyr Glu Leu Gln Lys Leu Asn Ser Trp Gly Val Phe Thr Asn
645 650 655

Trp Leu Asp Phe Thr Ser Trp Val Arg Tyr Ile Gln Tyr Gly Val Tyr
660 665 670

Val Val Val Gly Ile Val Ala Leu Arg Ile Val Ile Tyr Ile Val Gln
675 680 685

Met Leu Ser Arg Leu Arg Lys Gly Tyr Arg Pro Val Phe Ser Ser Pro
690 695 700

Pro Gly Tyr Ile Gln Gln Ile His Ile His Lys Asp Gln Glu Gln Pro
705 710 715 720

Ala Arg Glu Glu Thr Glu Glu Asp Val Gly Ser Asn Gly Gly Asp Arg
725 730 735

Ser Trp Leu

<210> SEQ ID NO 5
<211> LENGTH: 501
<212> TYPE: PRT
<213> ORGANISM: HIV-2/VCP (gp120)

<400> SEQUENCE: 5

Met Lys Gly Ser Lys Asn Gln Leu Leu Ile Ala Ile Val Leu Ala Ser
1 5 10 15

Ala Tyr Leu Thr His Cys Lys Gln Phe Val Thr Val Phe Tyr Gly Ile
20 25 30

Pro Ala Trp Arg Asn Ala Ser Ile Pro Leu Phe Cys Ala Thr Lys Asn
35 40 45

Arg Asp Thr Trp Gly Thr Ile Gln Cys Leu Pro Asp Asn Asp Asp Tyr
50 55 60

Gln Glu Ile Ala Leu Asn Val Thr Glu Ala Phe Asp Ala Trp Asn Asn
65 70 75 80

Thr Val Thr Glu Gln Ala Val Glu Asp Val Trp Asn Leu Phe Glu Thr
85 90 95

-continued

```
Ser Ile Lys Pro Cys Val Lys Leu Thr Pro Leu Cys Val Ala Met Asn
            100                 105                 110

Cys Thr Arg Asn Met Thr Thr Ser Thr Gly Thr Thr Asp Thr Gln Asn
        115                 120                 125

Ile Thr Ile Ile Asn Asp Thr Ser Pro Cys Val Arg Ala Asp Asn Cys
    130                 135                 140

Thr Gly Leu Lys Glu Glu Glu Met Val Asp Cys Gln Phe Asn Met Thr
145                 150                 155                 160

Gly Leu Glu Arg Asp Lys Arg Lys Gln Tyr Thr Glu Ala Trp Tyr Ser
                165                 170                 175

Lys Asp Val Ile Cys Asp Asn Asn Thr Ser Ser Arg Ser Lys Cys Tyr
            180                 185                 190

Met Asn His Cys Asn Thr Ser Val Ile Thr Glu Ser Cys Asp Lys His
        195                 200                 205

Tyr Trp Asp Ala Met Arg Phe Arg Tyr Cys Ala Pro Pro Gly Phe Ala
    210                 215                 220

Leu Leu Arg Cys Asn Asp Thr Asn Tyr Ser Gly Phe Ala Pro Asn Cys
225                 230                 235                 240

Ser Lys Val Val Ala Ala Thr Cys Thr Arg Met Met Glu Thr Gln Ser
                245                 250                 255

Ser Thr Trp Phe Gly Phe Asn Gly Thr Arg Ala Glu Asn Arg Thr Tyr
            260                 265                 270

Ile Tyr Trp His Gly Lys Asn Asn Arg Thr Ile Ile Ser Leu Asn Asn
        275                 280                 285

Phe Tyr Asn Leu Thr Met His Cys Lys Arg Pro Gly Asn Lys Thr Val
    290                 295                 300

Leu Pro Ile Met Ser Gly Phe Lys Phe His Ser Lys Pro Val Ile Asn
305                 310                 315                 320

Lys Lys Pro Arg Gln Ala Trp Cys Trp Phe Lys Gly Glu Trp Lys Glu
                325                 330                 335

Ala Met Gln Glu Val Lys Glu Thr Leu Ala Lys His Pro Arg Tyr Lys
            340                 345                 350

Gly Asn Arg Ser Arg Thr Glu Asn Ile Lys Phe Lys Ala Pro Gly Arg
        355                 360                 365

Gly Ser Asp Pro Glu Ala Ala Tyr Met Trp Thr Asn Cys Arg Gly Glu
    370                 375                 380

Phe Leu Tyr Cys Asn Met Thr Trp Phe Leu Asn Trp Val Asp Asn Arg
385                 390                 395                 400

Thr Gly Gln Lys Gln Arg Asn Tyr Ala Pro Cys His Ile Arg Gln Ile
                405                 410                 415

Ile Asn Thr Trp His Arg Val Gly Lys Asn Val Tyr Leu Pro Pro Arg
            420                 425                 430

Glu Gly Glu Leu Thr Cys Asn Ser Thr Val Thr Ser Ile Ile Ala Asn
        435                 440                 445

Ile Asp Thr Gly Asp Gln Thr Asp Ile Thr Phe Ser Ala Glu Val Ala
    450                 455                 460

Glu Leu Tyr Arg Leu Glu Leu Gly Asp Tyr Lys Leu Val Glu Ile Thr
465                 470                 475                 480

Pro Ile Gly Phe Ala Pro Thr Ser Val Lys Arg Tyr Ser Ser Ala His
                485                 490                 495

Gln Arg His Thr Arg
            500
```

-continued

<210> SEQ ID NO 6
<211> LENGTH: 323
<212> TYPE: PRT
<213> ORGANISM: HIV-2/VCP (gp41)

<400> SEQUENCE: 6

```
Gly Val Phe Val Leu Gly Phe Leu Gly Phe Leu Ala Thr Ala Gly Ser
1               5                   10                  15

Ala Met Gly Ala Ala Ser Leu Thr Leu Thr Ala Gln Ser Arg Thr Ser
            20                  25                  30

Leu Ala Gly Ile Val Gln Gln Gln Gln Gln Leu Leu Asp Val Val Lys
        35                  40                  45

Lys Gln Gln Glu Met Leu Arg Leu Thr Val Trp Gly Thr Lys Asn Leu
    50                  55                  60

Gln Ala Arg Val Thr Ala Ile Glu Lys Tyr Leu Lys Asp Gln Ala Gln
65                  70                  75                  80

Leu Asn Ser Trp Gly Cys Ala Phe Arg Gln Val Cys His Thr Ser Val
                85                  90                  95

Pro Trp Val Asn Asp Ser Leu Thr Pro Asp Trp Asn Asn Met Thr Trp
            100                 105                 110

Gln Glu Trp Glu Gln Lys Val Arg Tyr Trp Glu Ala Asn Ile Ser Gln
        115                 120                 125

Ser Leu Glu Gln Ala Gln Ile Gln Gln Glu Lys Asn Leu Tyr Glu Leu
    130                 135                 140

Gln Lys Leu Asn Ser Trp Gly Val Phe Thr Asn Trp Leu Asp Phe Thr
145                 150                 155                 160

Ser Trp Val Arg Tyr Ile Gln Tyr Gly Val Tyr Val Val Val Gly Ile
                165                 170                 175

Val Ala Leu Arg Ile Val Ile Tyr Ile Val Gln Met Leu Ser Arg Leu
            180                 185                 190

Arg Lys Gly Tyr Arg Pro Val Phe Ser Ser Pro Pro Gly Tyr Ile Gln
        195                 200                 205

Gln Ile His Ile His Lys Asp Gln Glu Gln Pro Ala Arg Glu Glu Thr
    210                 215                 220

Glu Glu Asp Val Gly Ser Asn Gly Gly Asp Arg Ser Trp Leu Pro Ile
225                 230                 235                 240

Ala Tyr Ile His Phe Leu Ile Arg Leu Leu Ile Arg Leu Leu Ile Gly
                245                 250                 255

Leu Tyr Asn Ile Cys Arg Asp Leu Leu Ser Arg Ile Ser Pro Ile Leu
            260                 265                 270

Gln Pro Ile Phe Gln Ser Leu Gln Arg Ala Leu Thr Ala Ile Arg Asp
        275                 280                 285

Trp Leu Arg Leu Lys Ala Ala Tyr Leu Gln Tyr Gly Cys Glu Trp Ile
    290                 295                 300

Gln Glu Ala Phe Gln Ala Leu Ala Arg Thr Thr Arg Glu Thr Leu Ala
305                 310                 315                 320

Gly Ala Gly
```

<210> SEQ ID NO 7
<211> LENGTH: 2181
<212> TYPE: DNA
<213> ORGANISM: HIV-2/VCP Clone p16.5 (env)

<400> SEQUENCE: 7

```
atgaagggta gtaagaatca actgctgatt gctattgtac tagctagtgc ttacctaaca     60
```

-continued

```
cattgcaagc aatttgtgac tgttttctat ggcatacccg cgtggaggaa tgcatccatt    120

cccctgtttt gtgcaaccaa aaatagagat acttggggaa ctgtacagtg cttgccagac    180

aatgatgatt atcaggaaat agctttaaat gtaacagagg ctttcgatgc atgggataat    240

acagtaacag aacaagcagt ggaggatgtc tggaatctat ttgagacatc aataaaacca    300

tgtgtcaaat taacaccctt atgtgtaggt gccggccatt gcaatacatc agtcatcaaa    360

gagtcatgtg ataagcacta ttgggatgct atgaggttta gatactgtgc accaccgggt    420

tttgccctac taagatgcaa tgatattaat tattcaggct ttgcacctaa ttgctctaaa    480

gtagtagctg ctacatgcac cagaatgatg gaaacgcaat cttctacatg gtttggcttt    540

aatggcacta gaacagaaaa tagaacatat atctattggc atggtaaaaa taacagaact    600

attatcagct taaataactt ttataatctc actatgcatt gtaagaggcc gggaaataag    660

ggtgccggca aacccaggca agcatggtgt tggttcaaag gcgaatggaa ggaagccatg    720

caggaggtga aggagaccct tgcgaaacat cccagatata aagggaacag gagccgcaca    780

gagaatatta aatttaaagc accaggaaga ggctcagacc cagaagcagc atacatgtgg    840

actaactgca gaggggaatt tctctactgc gacatgactt ggttcctcaa ttgggtagat    900

aacaggacgg gtcagaaaca gcgcaattat gcaccgtgcc atataagaca aataattaat    960

acttggcaca gggtagggaa aaacgtatat ttgcctccca gggaagggga gttgacctgc   1020

aactcaacag tgaccagcat aattgccaac attgatacgg gagatcaaac agatattacc   1080

tttagtgcag aggtggcaga actataccga ttggaattgg gagattacaa attagtagaa   1140

atcacaccaa ttggcttcgc acctacatca gtaaagagat actcctctgc tcaccagaga   1200

catacaagag gtgtgttcgt gctagggttc ttgggttttc tcgcaacggc aggttctgca   1260

atgggcgcgg cgtcggtgac gctgaccgct cagtcccgga cttcattgac tgggatagtg   1320

cagcaacagc aacagctgtt ggatgtggtc aagaaacaac aagaaatgtt gcgactgacc   1380

gtctggggaa ctaaaaatct ccaggcaaga gtcactgcta tagagaaata cctaaaggac   1440

caggcgcagc taaattcatg ggatgtgcg tttagacaag tctgccacac ttctgtacca   1500

tgggtaaatg atagcttgac acctgattgg aacaatatga cgtggcagga atgggaacaa   1560

aaagtccgct actgggaggc aaatatcagt caaagtctag aacaagcaca aattcagcaa   1620

gaaaagaatt tgtatgagct gcaaaaatta aatagctggg gtgtttttac caattggctt   1680

gacttcacct cctgggtcag gtatattcaa tatggagttt acgtagtagt aggaatagta   1740

gctttaagaa tagtaatata tatagtacag atgttaagta gacttaggaa gggctatagg   1800

cctgttttct cctccccccc cggttatatc caacagatcc atatccacaa ggaccaggaa   1860

cagccagcca gagaagaaac agaagaagac gttggaagca acggtggaga cagatcttgg   1920

ctttagccga tagcatatat tcatttcctg atccgcctgc tgattcgcct cttgatcggg   1980

ctatacaaca tctgcagaga cttactatcc aggatctccc cgatcctcca accaatcttc   2040

cagagtctcc agagagcact aacagcaatc agagactggc tgaggcttaa agcagcctac   2100

ctgcagtatg ggtgcgagtg gatccaagaa gcgttccaag cccttgcaag gactacaaga   2160

gagactcttg caggcgcggg g                                              2181
```

<210> SEQ ID NO 8
<211> LENGTH: 1209
<212> TYPE: DNA
<213> ORGANISM: HIV-2/VCP Clone p16.5 (gp120)

<400> SEQUENCE: 8

-continued

```
atgaagggta gtaagaatca actgctgatt gctattgtac tagctagtgc ttacctaaca     60

cattgcaagc aatttgtgac tgttttctat ggcataccgg cgtggaggaa tgcatccatt    120

cccctgtttt gtgcaaccaa aaatagagat acttggggaa ctgtacagtg cttgccagac    180

aatgatgatt atcaggaaat agctttaaat gtaacagagg ctttcgatgc atgggataat    240

acagtaacag aacaagcagt ggaggatgtc tggaatctat ttgagacatc aataaaacca    300

tgtgtcaaat taacaccctt atgtgtaggt gccggccatt gcaatacatc agtcatcaaa    360

gagtcatgtg ataagcacta ttgggatgct atgaggttta gatactgtgc accaccgggt    420

tttgccctac taagatgcaa tgatattaat tattcaggct ttgcacctaa ttgctctaaa    480

gtagtagctg ctacatgcac cagaatgatg gaaacgcaat cttctacatg gtttggcttt    540

aatggcacta gaacagaaaa tagaacatat atctattggc atggtaaaaa taacagaact    600

attatcagct taaataactt ttataatctc actatgcatt gtaagaggcc gggaaataag    660

ggtgccggca aacccaggca agcatggtgt tggttcaaag gcgaatggaa ggaagccatg    720

caggaggtga aggagaccct tgcgaaacat cccagatata aagggaacag gagccgcaca    780

gagaatatta aatttaaagc accaggaaga ggctcagacc cagaagcagc atacatgtgg    840

actaactgca gaggggaatt tctctactgc gacatgactt ggttcctcaa ttgggtagat    900

aacaggacgg gtcagaaaca gcgcaattat gcaccgtgcc atataagaca aataattaat    960

acttggcaca gggtagggaa aaacgtatat ttgcctccca gggaagggga gttgacctgc   1020

aactcaacag tgaccagcat aattgccaac attgatacgg gagatcaaac agatattacc   1080

tttagtgcag aggtggcaga actataccga ttggaattgg gagattacaa attagtagaa   1140

atcacaccaa ttggcttcgc acctacatca gtaaagagat actcctctgc tcaccagaga   1200

catacaaga                                                           1209
```

<210> SEQ ID NO 9
<211> LENGTH: 972
<212> TYPE: DNA
<213> ORGANISM: HIV-2/VCP Clone p16.5 (gp41)

<400> SEQUENCE: 9

```
ggtgtgttcg tgctagggtt cttgggtttt ctcgcaacgg caggttctgc aatgggcgcg     60

gcgtcggtga cgctgaccgc tcagtcccgg acttcattga ctgggatagt gcagcaacag    120

caacagctgt tggatgtggt caagaaacaa caagaaatgt tgcgactgac cgtctgggga    180

actaaaaatc tccaggcaag agtcactgct atagagaaat acctaaagga ccaggcgcag    240

ctaaattcat ggggatgtgc gtttagacaa gtctgccaca cttctgtacc atgggtaaat    300

gatagcttga cacctgattg gaacaatatg acgtggcagg aatgggaaca aaaagtccgc    360

tactgggagg caaatatcag tcaaagtcta gaacaagcac aaattcagca agaaaagaat    420

ttgtatgagc tgcaaaaatt aaatagctgg ggtgttttta ccaattggct tgacttcacc    480

tcctgggtca ggtatattca atatggagtt tacgtagtag taggaatagt agctttaaga    540

atagtaatat atatagtaca gatgttaagt agacttagga agggctatag gcctgttttc    600

tcctcccccc ccggttatat ccaacagatc catatccaca aggaccagga acagccagcc    660

agagaagaaa cagaagaaga cgttggaagc aacggtggag acagatcttg gctttagccg    720

atagcatata ttcatttcct gatccgcctg ctgattcgcc tcttgatcgg gctatacaac    780

atctgcagag acttactatc caggatctcc ccgatcctcc aaccaatctt ccagagtctc    840
```

-continued

```
cagagagcac taacagcaat cagagactgg ctgaggctta aagcagccta cctgcagtat    900

gggtgcgagt ggatccaaga agcgttccaa gcccttgcaa ggactacaag agagactctt    960

gcaggcgcgg gg                                                        972


<210> SEQ ID NO 10
<211> LENGTH: 726
<212> TYPE: PRT
<213> ORGANISM: HIV-2/VCP Clone p16.5 (env)

<400> SEQUENCE: 10

Met Lys Gly Ser Lys Asn Gln Leu Leu Ile Ala Ile Val Leu Ala Ser
1               5                   10                  15

Ala Tyr Leu Thr His Cys Lys Gln Phe Val Thr Val Phe Tyr Gly Ile
            20                  25                  30

Pro Ala Trp Arg Asn Ala Ser Ile Pro Leu Phe Cys Ala Thr Lys Asn
        35                  40                  45

Arg Asp Thr Trp Gly Thr Val Gln Cys Leu Pro Asp Asn Asp Asp Tyr
    50                  55                  60

Gln Glu Ile Ala Leu Asn Val Thr Glu Ala Phe Asp Ala Trp Asp Asn
65                  70                  75                  80

Thr Val Thr Glu Gln Ala Val Glu Asp Val Trp Asn Leu Phe Glu Thr
                85                  90                  95

Ser Ile Lys Pro Cys Val Lys Leu Thr Pro Leu Cys Val Gly Ala Gly
            100                 105                 110

His Cys Asn Thr Ser Val Ile Lys Glu Ser Cys Asp Lys His Tyr Trp
        115                 120                 125

Asp Ala Met Arg Phe Arg Tyr Cys Ala Pro Pro Gly Phe Ala Leu Leu
    130                 135                 140

Arg Cys Asn Asp Ile Asn Tyr Ser Gly Phe Ala Pro Asn Cys Ser Lys
145                 150                 155                 160

Val Val Ala Ala Thr Cys Thr Arg Met Met Glu Thr Gln Ser Ser Thr
                165                 170                 175

Trp Phe Gly Phe Asn Gly Thr Arg Thr Glu Asn Arg Thr Tyr Ile Tyr
            180                 185                 190

Trp His Gly Lys Asn Asn Arg Thr Ile Ile Ser Leu Asn Asn Phe Tyr
        195                 200                 205

Asn Leu Thr Met His Cys Lys Arg Pro Gly Asn Lys Gly Ala Gly Lys
    210                 215                 220

Pro Arg Gln Ala Trp Cys Trp Phe Lys Gly Glu Trp Lys Glu Ala Met
225                 230                 235                 240

Gln Glu Val Lys Glu Thr Leu Ala Lys His Pro Arg Tyr Lys Gly Asn
                245                 250                 255

Arg Ser Arg Thr Glu Asn Ile Lys Phe Lys Ala Pro Gly Arg Gly Ser
            260                 265                 270

Asp Pro Glu Ala Ala Tyr Met Trp Thr Asn Cys Arg Gly Glu Phe Leu
        275                 280                 285

Tyr Cys Asp Met Thr Trp Phe Leu Asn Trp Val Asp Asn Arg Thr Gly
    290                 295                 300

Gln Lys Gln Arg Asn Tyr Ala Pro Cys His Ile Arg Gln Ile Ile Asn
305                 310                 315                 320

Thr Trp His Arg Val Gly Lys Asn Val Tyr Leu Pro Pro Arg Glu Gly
                325                 330                 335

Glu Leu Thr Cys Asn Ser Thr Val Thr Ser Ile Ile Ala Asn Ile Asp
            340                 345                 350
```

-continued

Thr Gly Asp Gln Thr Asp Ile Thr Phe Ser Ala Glu Val Ala Glu Leu
        355                 360                 365

Tyr Arg Leu Glu Leu Gly Asp Tyr Lys Leu Val Glu Ile Thr Pro Ile
    370                 375                 380

Gly Phe Ala Pro Thr Ser Val Lys Arg Tyr Ser Ser Ala His Gln Arg
385                 390                 395                 400

His Thr Arg Gly Val Phe Val Leu Gly Phe Leu Gly Phe Leu Ala Thr
                405                 410                 415

Ala Gly Ser Ala Met Gly Ala Ala Ser Val Thr Leu Thr Ala Gln Ser
            420                 425                 430

Arg Thr Ser Leu Thr Gly Ile Val Gln Gln Gln Gln Gln Leu Leu Asp
        435                 440                 445

Val Val Lys Lys Gln Gln Glu Met Leu Arg Leu Thr Val Trp Gly Thr
    450                 455                 460

Lys Asn Leu Gln Ala Arg Val Thr Ala Ile Glu Lys Tyr Leu Lys Asp
465                 470                 475                 480

Gln Ala Gln Leu Asn Ser Trp Gly Cys Ala Phe Arg Gln Val Cys His
                485                 490                 495

Thr Ser Val Pro Trp Val Asn Asp Ser Leu Thr Pro Asp Trp Asn Asn
            500                 505                 510

Met Thr Trp Gln Glu Trp Glu Gln Lys Val Arg Tyr Trp Glu Ala Asn
        515                 520                 525

Ile Ser Gln Ser Leu Glu Gln Ala Gln Ile Gln Gln Glu Lys Asn Leu
    530                 535                 540

Tyr Glu Leu Gln Lys Leu Asn Ser Trp Gly Val Phe Thr Asn Trp Leu
545                 550                 555                 560

Asp Phe Thr Ser Trp Val Arg Tyr Ile Gln Tyr Gly Val Tyr Val Val
                565                 570                 575

Val Gly Ile Val Ala Leu Arg Ile Val Ile Tyr Ile Val Gln Met Leu
            580                 585                 590

Ser Arg Leu Arg Lys Gly Tyr Arg Pro Val Phe Ser Ser Pro Pro Gly
        595                 600                 605

Tyr Ile Gln Gln Ile His Ile His Lys Asp Gln Glu Gln Pro Ala Arg
    610                 615                 620

Glu Glu Thr Glu Glu Asp Val Gly Ser Asn Gly Gly Asp Arg Ser Trp
625                 630                 635                 640

Leu Pro Ile Ala Tyr Ile His Phe Leu Ile Arg Leu Leu Ile Arg Leu
                645                 650                 655

Leu Ile Gly Leu Tyr Asn Ile Cys Arg Asp Leu Leu Ser Arg Ile Ser
            660                 665                 670

Pro Ile Leu Gln Pro Ile Phe Gln Ser Leu Gln Arg Ala Leu Thr Ala
        675                 680                 685

Ile Arg Asp Trp Leu Arg Leu Lys Ala Ala Tyr Leu Gln Tyr Gly Cys
    690                 695                 700

Glu Trp Ile Gln Glu Ala Phe Gln Ala Leu Ala Arg Thr Thr Arg Glu
705                 710                 715                 720

Thr Leu Ala Gly Ala Gly
                725

<210> SEQ ID NO 11
<211> LENGTH: 403
<212> TYPE: PRT
<213> ORGANISM: HIV-2/VCP Clone p16.5 (gp120)

-continued

<400> SEQUENCE: 11

```
Met Lys Gly Ser Lys Asn Gln Leu Leu Ile Ala Ile Val Leu Ala Ser
1               5                   10                  15

Ala Tyr Leu Thr His Cys Lys Gln Phe Val Thr Val Phe Tyr Gly Ile
            20                  25                  30

Pro Ala Trp Arg Asn Ala Ser Ile Pro Leu Phe Cys Ala Thr Lys Asn
        35                  40                  45

Arg Asp Thr Trp Gly Thr Val Gln Cys Leu Pro Asp Asn Asp Asp Tyr
    50                  55                  60

Gln Glu Ile Ala Leu Asn Val Thr Glu Ala Phe Asp Ala Trp Asp Asn
65                  70                  75                  80

Thr Val Thr Glu Gln Ala Val Glu Asp Val Trp Asn Leu Phe Glu Thr
                85                  90                  95

Ser Ile Lys Pro Cys Val Lys Leu Thr Pro Leu Cys Val Gly Ala Gly
            100                 105                 110

His Cys Asn Thr Ser Val Ile Lys Glu Ser Cys Asp Lys His Tyr Trp
        115                 120                 125

Asp Ala Met Arg Phe Arg Tyr Cys Ala Pro Pro Gly Phe Ala Leu Leu
    130                 135                 140

Arg Cys Asn Asp Ile Asn Tyr Ser Gly Phe Ala Pro Asn Cys Ser Lys
145                 150                 155                 160

Val Val Ala Ala Thr Cys Thr Arg Met Met Glu Thr Gln Ser Ser Thr
                165                 170                 175

Trp Phe Gly Phe Asn Gly Thr Arg Thr Glu Asn Arg Thr Tyr Ile Tyr
            180                 185                 190

Trp His Gly Lys Asn Asn Arg Thr Ile Ile Ser Leu Asn Asn Phe Tyr
        195                 200                 205

Asn Leu Thr Met His Cys Lys Arg Pro Gly Asn Lys Gly Ala Gly Lys
    210                 215                 220

Pro Arg Gln Ala Trp Cys Trp Phe Lys Gly Glu Trp Lys Glu Ala Met
225                 230                 235                 240

Gln Glu Val Lys Glu Thr Leu Ala Lys His Pro Arg Tyr Lys Gly Asn
                245                 250                 255

Arg Ser Arg Thr Glu Asn Ile Lys Phe Lys Ala Pro Gly Arg Gly Ser
            260                 265                 270

Asp Pro Glu Ala Ala Tyr Met Trp Thr Asn Cys Arg Gly Glu Phe Leu
        275                 280                 285

Tyr Cys Asp Met Thr Trp Phe Leu Asn Trp Val Asp Asn Arg Thr Gly
    290                 295                 300

Gln Lys Gln Arg Asn Tyr Ala Pro Cys His Ile Arg Gln Ile Ile Asn
305                 310                 315                 320

Thr Trp His Arg Val Gly Lys Asn Val Tyr Leu Pro Pro Arg Glu Gly
                325                 330                 335

Glu Leu Thr Cys Asn Ser Thr Val Thr Ser Ile Ile Ala Asn Ile Asp
            340                 345                 350

Thr Gly Asp Gln Thr Asp Ile Thr Phe Ser Ala Glu Val Ala Glu Leu
        355                 360                 365

Tyr Arg Leu Glu Leu Gly Asp Tyr Lys Leu Val Glu Ile Thr Pro Ile
    370                 375                 380

Gly Phe Ala Pro Thr Ser Val Lys Arg Tyr Ser Ser Ala His Gln Arg
385                 390                 395                 400

His Thr Arg
```

-continued

<210> SEQ ID NO 12
<211> LENGTH: 323
<212> TYPE: PRT
<213> ORGANISM: HIV-2/VCP Clone p16.5 (gp41)

<400> SEQUENCE: 12

```
Gly Val Phe Val Leu Gly Phe Leu Gly Phe Leu Ala Thr Ala Gly Ser
1               5                   10                  15

Ala Met Gly Ala Ala Ser Val Thr Leu Thr Ala Gln Ser Arg Thr Ser
            20                  25                  30

Leu Thr Gly Ile Val Gln Gln Gln Gln Gln Leu Leu Asp Val Val Lys
        35                  40                  45

Lys Gln Gln Glu Met Leu Arg Leu Thr Val Trp Gly Thr Lys Asn Leu
    50                  55                  60

Gln Ala Arg Val Thr Ala Ile Glu Lys Tyr Leu Lys Asp Gln Ala Gln
65                  70                  75                  80

Leu Asn Ser Trp Gly Cys Ala Phe Arg Gln Val Cys His Thr Ser Val
                85                  90                  95

Pro Trp Val Asn Asp Ser Leu Thr Pro Asp Trp Asn Asn Met Thr Trp
            100                 105                 110

Gln Glu Trp Glu Gln Lys Val Arg Tyr Trp Glu Ala Asn Ile Ser Gln
        115                 120                 125

Ser Leu Glu Gln Ala Gln Ile Gln Gln Glu Lys Asn Leu Tyr Glu Leu
    130                 135                 140

Gln Lys Leu Asn Ser Trp Gly Val Phe Thr Asn Trp Leu Asp Phe Thr
145                 150                 155                 160

Ser Trp Val Arg Tyr Ile Gln Tyr Gly Val Tyr Val Val Val Gly Ile
                165                 170                 175

Val Ala Leu Arg Ile Val Ile Tyr Ile Val Gln Met Leu Ser Arg Leu
            180                 185                 190

Arg Lys Gly Tyr Arg Pro Val Phe Ser Ser Pro Pro Gly Tyr Ile Gln
        195                 200                 205

Gln Ile His Ile His Lys Asp Gln Glu Gln Pro Ala Arg Glu Glu Thr
    210                 215                 220

Glu Glu Asp Val Gly Ser Asn Gly Gly Asp Arg Ser Trp Leu Pro Ile
225                 230                 235                 240

Ala Tyr Ile His Phe Leu Ile Arg Leu Leu Ile Arg Leu Leu Ile Gly
                245                 250                 255

Leu Tyr Asn Ile Cys Arg Asp Leu Leu Ser Arg Ile Ser Pro Ile Leu
            260                 265                 270

Gln Pro Ile Phe Gln Ser Leu Gln Arg Ala Leu Thr Ala Ile Arg Asp
        275                 280                 285

Trp Leu Arg Leu Lys Ala Ala Tyr Leu Gln Tyr Gly Cys Glu Trp Ile
    290                 295                 300

Gln Glu Ala Phe Gln Ala Leu Ala Arg Thr Thr Arg Glu Thr Leu Ala
305                 310                 315                 320

Gly Ala Gly
```

<210> SEQ ID NO 13
<211> LENGTH: 1926
<212> TYPE: DNA
<213> ORGANISM: HIV-2/VCP Clone p16.7 (env)

<400> SEQUENCE: 13

```
atgaagggta gtaagaatca accgctgatt gctattgtac tagctagtgc ttacctaaca      60
```

-continued

```
cattgcaagc aatttgtgac tgttttctat ggcatacccg cgtggaggaa tgcatccatt    120

cccctgtttt gtgcaaccaa aaatagagat acttggggaa ccgtacagtg cttgccagac    180

aatgatgatt atcaggaaat agctttaaat gtaacagagg ctttcgatgc atgggataat    240

acagtaacag aacaagcagt ggaggatgtc tggaatctat ctgagacatc aataaaacca    300

tgtgtcaaat taacaccctt atgtgtaggt gccggccatt gcaatacatc agtcatcaca    360

gagtcatgtg ataagcacta ttgggatgct atgaggttta gatactgtgc accaccgggt    420

tttgccttac taagatgcaa tgatactaat tattcaggct ttgcacctaa ttgctctaaa    480

gtagtagctg ctacatgcac cagaatgatg gaaacgcaat cttctacatg gtttggcttt    540

aatggcacta gagcagaaaa tagaacatat atctattggc atggtaaaaa tgacagaact    600

attatcagct taaataactt ttataatctc actatgcatt gtaagaggcc gggaaataag    660

ggtgccggca aacccaggca agcatggtgt tggttcaaag gcgaatggaa ggaagccatg    720

caggaggtga aggagaccct tgcgaaacat cctagatata aagggaacag gagccgcaca    780

gagaatatta aatttaaagc accaggaaga ggctcagacc cagaagcagc atacatgtgg    840

actaactgca gaggggaatt tctctactgc gacatgactt ggttcctcaa ttgggtagaa    900

aacaggacgg gtcagaaaca gcgtaattat gcaccgtgcc atataaggca aataattaat    960

acttggcaca gggtagggaa aaacgtatat ttgcctccca gggaagggga gttaacctgc   1020

aactcaacag tgaccagcat aattgccaac attgatacgg gagatcaaac agatattacc   1080

tttagtgcag aggtggcaga actataccgg ttggaattgg gagattacaa attagtagaa   1140

atcacaccaa ttggcttcgc acctacatca gtaaagagat actcctctgc tcaccagaga   1200

catacaagag gtgtgttcgt gctagggttc ttgggttttc tcgcaacggc aggttctgca   1260

atgggcgcgg cgtcggtgac gctgaccgct cagtcccgga cttcattgac tggggtagtg   1320

cagcaacagc aacagctgtt ggatgtggtc aagaaacaac aagaaatgtt gcgactgacc   1380

gtctggggaa ctaaaaatct ccaggcaaga gtcactgcta tagagaaata cctaaaggac   1440

caggcgcagc taaattcatg ggatgtgcg tttagacaag tctgccacac ttctgtacca    1500

tgggtaaatg atagcttgac acctgattgg aacaatatga cgtggcagga atgggaacaa   1560

aaagtccgct actgggaggc aaatatcagt caaagtctag aacaagcaca aattcagcaa   1620

gaaaagaatt tgtatgagct gcaaaaatta aatagctggg gtgtttttac caattggctt   1680

gacttcacct cctgggtcag gtatattcaa tatggagttt atgtagtagt aggaatagta   1740

gctttaagaa tagtaatata tatagtacag atgttgagta gacttaggaa gggctatagg   1800

cctgttttct cctccccccc cggttatatc caacagatcc atatccacaa ggaccaggaa   1860

cagccagcca gagaagaaac agaagaagac gttggaagca acggtggaga caaatcttgg   1920

ctttag                                                              1926
```

<210> SEQ ID NO 14
<211> LENGTH: 1209
<212> TYPE: DNA
<213> ORGANISM: HIV-2/VCP Clone p16.7 (gp120)

<400> SEQUENCE: 14

```
atgaagggta gtaagaatca accgctgatt gctattgtac tagctagtgc ttacctaaca     60

cattgcaagc aatttgtgac tgttttctat ggcatacccg cgtggaggaa tgcatccatt    120

cccctgtttt gtgcaaccaa aaatagagat acttggggaa ccgtacagtg cttgccagac    180
```

-continued

```
aatgatgatt atcaggaaat agctttaaat gtaacagagg ctttcgatgc atgggataat     240

acagtaacag aacaagcagt ggaggatgtc tggaatctat ctgagacatc aataaaacca     300

tgtgtcaaat taacaccctt atgtgtaggt gccggccatt gcaatacatc agtcatcaca     360

gagtcatgtg ataagcacta ttgggatgct atgaggttta gatactgtgc accaccgggt     420

tttgccttac taagatgcaa tgatactaat tattcaggct ttgcacctaa ttgctctaaa     480

gtagtagctg ctacatgcac cagaatgatg gaaacgcaat cttctacatg gtttggcttt     540

aatggcacta gagcagaaaa tagaacatat atctattggc atggtaaaaa tgacagaact     600

attatcagct taaataactt ttataatctc actatgcatt gtaagaggcc gggaaataag     660

ggtgccggca aacccaggca agcatggtgt tggttcaaag gcgaatggaa ggaagccatg     720

caggaggtga aggagaccct tgcgaaacat cctagatata aagggaacag gagccgcaca     780

gagaatatta aatttaaagc accaggaaga ggctcagacc cagaagcagc atacatgtgg     840

actaactgca gaggggaatt tctctactgc gacatgactt ggttcctcaa ttgggtagaa     900

aacaggacgg gtcagaaaca gcgtaattat gcaccgtgcc atataaggca aataattaat     960

acttggcaca gggtagggaa aaacgtatat ttgcctccca gggaagggga gttaacctgc    1020

aactcaacag tgaccagcat aattgccaac attgatacgg gagatcaaac agatattacc    1080

tttagtgcag aggtggcaga actataccgg ttggaattgg gagattacaa attagtagaa    1140

atcacaccaa ttggcttcgc acctacatca gtaaagagat actcctctgc tcaccagaga    1200

catacaaga                                                            1209
```

<210> SEQ ID NO 15
<211> LENGTH: 717
<212> TYPE: DNA
<213> ORGANISM: HIV-2/VCP Clone p16.7 (gp41)

<400> SEQUENCE: 15

```
ggtgtgttcg tgctagggtt cttgggtttt ctcgcaacgg caggttctgc aatgggcgcg      60

gcgtcggtga cgctgaccgc tcagtcccgg acttcattga ctggggtagt gcagcaacag     120

caacagctgt tggatgtggt caagaaacaa caagaaatgt tgcgactgac cgtctgggga     180

actaaaaatc tccaggcaag agtcactgct atagagaaat acctaaagga ccaggcgcag     240

ctaaattcat ggggatgtgc gtttagacaa gtctgccaca cttctgtacc atgggtaaat     300

gatagcttga cacctgattg gaacaatatg acgtggcagg aatgggaaca aaaagtccgc     360

tactgggagg caaatatcag tcaaagtcta gaacaagcac aaattcagca agaaaagaat     420

ttgtatgagc tgcaaaaatt aaatagctgg ggtgttttta ccaattggct tgacttcacc     480

tcctgggtca ggtatattca atatggagtt tatgtagtag taggaatagt agctttaaga     540

atagtaatat atatagtaca gatgttgagt agacttagga agggctatag gcctgttttc     600

tcctcccccc ccggttatat ccaacagatc catatccaca aggaccagga acagccagcc     660

agagaagaaa cagaagaaga cgttggaagc aacggtggag acaaatcttg gctttag       717
```

<210> SEQ ID NO 16
<211> LENGTH: 641
<212> TYPE: PRT
<213> ORGANISM: HIV-2/VCP Clone p16.7 (env)

<400> SEQUENCE: 16

```
Met Lys Gly Ser Lys Asn Gln Pro Leu Ile Ala Ile Val Leu Ala Ser
1               5                   10                  15
```

-continued

```
Ala Tyr Leu Thr His Cys Lys Gln Phe Val Thr Val Phe Tyr Gly Ile
            20                  25                  30

Pro Ala Trp Arg Asn Ala Ser Ile Pro Leu Phe Cys Ala Thr Lys Asn
        35                  40                  45

Arg Asp Thr Trp Gly Thr Val Gln Cys Leu Pro Asp Asn Asp Asp Tyr
    50                  55                  60

Gln Glu Ile Ala Leu Asn Val Thr Glu Ala Phe Asp Ala Trp Asp Asn
65                  70                  75                  80

Thr Val Thr Glu Gln Ala Val Glu Asp Val Trp Asn Leu Ser Glu Thr
                85                  90                  95

Ser Ile Lys Pro Cys Val Lys Leu Thr Pro Leu Cys Val Gly Ala Gly
            100                 105                 110

His Cys Asn Thr Ser Val Ile Thr Glu Ser Cys Asp Lys His Tyr Trp
        115                 120                 125

Asp Ala Met Arg Phe Arg Tyr Cys Ala Pro Pro Gly Phe Ala Leu Leu
    130                 135                 140

Arg Cys Asn Asp Thr Asn Tyr Ser Gly Phe Ala Pro Asn Cys Ser Lys
145                 150                 155                 160

Val Val Ala Ala Thr Cys Thr Arg Met Met Glu Thr Gln Ser Ser Thr
                165                 170                 175

Trp Phe Gly Phe Asn Gly Thr Arg Ala Glu Asn Arg Thr Tyr Ile Tyr
            180                 185                 190

Trp His Gly Lys Asn Asp Arg Thr Ile Ile Ser Leu Asn Asn Phe Tyr
        195                 200                 205

Asn Leu Thr Met His Cys Lys Arg Pro Gly Asn Lys Gly Ala Gly Lys
    210                 215                 220

Pro Arg Gln Ala Trp Cys Trp Phe Lys Gly Glu Trp Lys Glu Ala Met
225                 230                 235                 240

Gln Glu Val Lys Glu Thr Leu Ala Lys His Pro Arg Tyr Lys Gly Asn
                245                 250                 255

Arg Ser Arg Thr Glu Asn Ile Lys Phe Lys Ala Pro Gly Arg Gly Ser
            260                 265                 270

Asp Pro Glu Ala Ala Tyr Met Trp Thr Asn Cys Arg Gly Glu Phe Leu
        275                 280                 285

Tyr Cys Asp Met Thr Trp Phe Leu Asn Trp Val Glu Asn Arg Thr Gly
    290                 295                 300

Gln Lys Gln Arg Asn Tyr Ala Pro Cys His Ile Arg Gln Ile Ile Asn
305                 310                 315                 320

Thr Trp His Arg Val Gly Lys Asn Val Tyr Leu Pro Pro Arg Glu Gly
                325                 330                 335

Glu Leu Thr Cys Asn Ser Thr Val Thr Ser Ile Ile Ala Asn Ile Asp
            340                 345                 350

Thr Gly Asp Gln Thr Asp Ile Thr Phe Ser Ala Glu Val Ala Glu Leu
        355                 360                 365

Tyr Arg Leu Glu Leu Gly Asp Tyr Lys Leu Val Glu Ile Thr Pro Ile
    370                 375                 380

Gly Phe Ala Pro Thr Ser Val Lys Arg Tyr Ser Ser Ala His Gln Arg
385                 390                 395                 400

His Thr Arg Gly Val Phe Val Leu Gly Phe Leu Gly Phe Leu Ala Thr
                405                 410                 415

Ala Gly Ser Ala Met Gly Ala Ala Ser Val Thr Leu Thr Ala Gln Ser
            420                 425                 430

Arg Thr Ser Leu Thr Gly Val Val Gln Gln Gln Gln Gln Leu Leu Asp
```

-continued

```
        435                 440                 445

Val Val Lys Lys Gln Gln Glu Met Leu Arg Leu Thr Val Trp Gly Thr
    450                 455                 460

Lys Asn Leu Gln Ala Arg Val Thr Ala Ile Glu Lys Tyr Leu Lys Asp
465                 470                 475                 480

Gln Ala Gln Leu Asn Ser Trp Gly Cys Ala Phe Arg Gln Val Cys His
                485                 490                 495

Thr Ser Val Pro Trp Val Asn Asp Ser Leu Thr Pro Asp Trp Asn Asn
            500                 505                 510

Met Thr Trp Gln Glu Trp Glu Gln Lys Val Arg Tyr Trp Glu Ala Asn
        515                 520                 525

Ile Ser Gln Ser Leu Glu Gln Ala Gln Ile Gln Gln Glu Lys Asn Leu
    530                 535                 540

Tyr Glu Leu Gln Lys Leu Asn Ser Trp Gly Val Phe Thr Asn Trp Leu
545                 550                 555                 560

Asp Phe Thr Ser Trp Val Arg Tyr Ile Gln Tyr Gly Val Tyr Val Val
                565                 570                 575

Val Gly Ile Val Ala Leu Arg Ile Val Ile Tyr Ile Val Gln Met Leu
            580                 585                 590

Ser Arg Leu Arg Lys Gly Tyr Arg Pro Val Phe Ser Ser Pro Pro Gly
        595                 600                 605

Tyr Ile Gln Gln Ile His Ile His Lys Asp Gln Glu Gln Pro Ala Arg
    610                 615                 620

Glu Glu Thr Glu Glu Asp Val Gly Ser Asn Gly Gly Asp Lys Ser Trp
625                 630                 635                 640

Leu


<210> SEQ ID NO 17
<211> LENGTH: 403
<212> TYPE: PRT
<213> ORGANISM: HIV-2/VCP Clone p16.7 (gp120)

<400> SEQUENCE: 17

Met Lys Gly Ser Lys Asn Gln Pro Leu Ile Ala Ile Val Leu Ala Ser
1               5                   10                  15

Ala Tyr Leu Thr His Cys Lys Gln Phe Val Thr Val Phe Tyr Gly Ile
            20                  25                  30

Pro Ala Trp Arg Asn Ala Ser Ile Pro Leu Phe Cys Ala Thr Lys Asn
        35                  40                  45

Arg Asp Thr Trp Gly Thr Val Gln Cys Leu Pro Asp Asn Asp Asp Tyr
    50                  55                  60

Gln Glu Ile Ala Leu Asn Val Thr Glu Ala Phe Asp Ala Trp Asp Asn
65                  70                  75                  80

Thr Val Thr Glu Gln Ala Val Glu Asp Val Trp Asn Leu Ser Glu Thr
                85                  90                  95

Ser Ile Lys Pro Cys Val Lys Leu Thr Pro Leu Cys Val Gly Ala Gly
            100                 105                 110

His Cys Asn Thr Ser Val Ile Thr Glu Ser Cys Asp Lys His Tyr Trp
        115                 120                 125

Asp Ala Met Arg Phe Arg Tyr Cys Ala Pro Pro Gly Phe Ala Leu Leu
    130                 135                 140

Arg Cys Asn Asp Thr Asn Tyr Ser Gly Phe Ala Pro Asn Cys Ser Lys
145                 150                 155                 160

Val Val Ala Ala Thr Cys Thr Arg Met Met Glu Thr Gln Ser Ser Thr
```

-continued

```
                165                 170                 175

Trp Phe Gly Phe Asn Gly Thr Arg Ala Glu Asn Arg Thr Tyr Ile Tyr
            180                 185                 190

Trp His Gly Lys Asn Asp Arg Thr Ile Ile Ser Leu Asn Asn Phe Tyr
        195                 200                 205

Asn Leu Thr Met His Cys Lys Arg Pro Gly Asn Lys Gly Ala Gly Lys
    210                 215                 220

Pro Arg Gln Ala Trp Cys Trp Phe Lys Gly Glu Trp Lys Glu Ala Met
225                 230                 235                 240

Gln Glu Val Lys Glu Thr Leu Ala Lys His Pro Arg Tyr Lys Gly Asn
                245                 250                 255

Arg Ser Arg Thr Glu Asn Ile Lys Phe Lys Ala Pro Gly Arg Gly Ser
            260                 265                 270

Asp Pro Glu Ala Ala Tyr Met Trp Thr Asn Cys Arg Gly Glu Phe Leu
        275                 280                 285

Tyr Cys Asp Met Thr Trp Phe Leu Asn Trp Val Glu Asn Arg Thr Gly
    290                 295                 300

Gln Lys Gln Arg Asn Tyr Ala Pro Cys His Ile Arg Gln Ile Ile Asn
305                 310                 315                 320

Thr Trp His Arg Val Gly Lys Asn Val Tyr Leu Pro Pro Arg Glu Gly
                325                 330                 335

Glu Leu Thr Cys Asn Ser Thr Val Thr Ser Ile Ile Ala Asn Ile Asp
            340                 345                 350

Thr Gly Asp Gln Thr Asp Ile Thr Phe Ser Ala Glu Val Ala Glu Leu
        355                 360                 365

Tyr Arg Leu Glu Leu Gly Asp Tyr Lys Leu Val Glu Ile Thr Pro Ile
    370                 375                 380

Gly Phe Ala Pro Thr Ser Val Lys Arg Tyr Ser Ser Ala His Gln Arg
385                 390                 395                 400

His Thr Arg


<210> SEQ ID NO 18
<211> LENGTH: 238
<212> TYPE: PRT
<213> ORGANISM: HIV-2/VCP Clone p16.7 (gp41)

<400> SEQUENCE: 18

Gly Val Phe Val Leu Gly Phe Leu Gly Phe Leu Ala Thr Ala Gly Ser
1               5                   10                  15

Ala Met Gly Ala Ala Ser Val Thr Leu Thr Ala Gln Ser Arg Thr Ser
            20                  25                  30

Leu Thr Gly Val Val Gln Gln Gln Gln Gln Leu Leu Asp Val Val Lys
        35                  40                  45

Lys Gln Gln Glu Met Leu Arg Leu Thr Val Trp Gly Thr Lys Asn Leu
    50                  55                  60

Gln Ala Arg Val Thr Ala Ile Glu Lys Tyr Leu Lys Asp Gln Ala Gln
65                  70                  75                  80

Leu Asn Ser Trp Gly Cys Ala Phe Arg Gln Val Cys His Thr Ser Val
                85                  90                  95

Pro Trp Val Asn Asp Ser Leu Thr Pro Asp Trp Asn Asn Met Thr Trp
            100                 105                 110

Gln Glu Trp Glu Gln Lys Val Arg Tyr Trp Glu Ala Asn Ile Ser Gln
        115                 120                 125

Ser Leu Glu Gln Ala Gln Ile Gln Gln Glu Lys Asn Leu Tyr Glu Leu
```

-continued

```
    130                 135                 140

Gln Lys Leu Asn Ser Trp Gly Val Phe Thr Asn Trp Leu Asp Phe Thr
145                 150                 155                 160

Ser Trp Val Arg Tyr Ile Gln Tyr Gly Val Tyr Val Val Val Gly Ile
                165                 170                 175

Val Ala Leu Arg Ile Val Ile Tyr Ile Val Gln Met Leu Ser Arg Leu
            180                 185                 190

Arg Lys Gly Tyr Arg Pro Val Phe Ser Ser Pro Pro Gly Tyr Ile Gln
        195                 200                 205

Gln Ile His Ile His Lys Asp Gln Glu Gln Pro Ala Arg Glu Glu Thr
    210                 215                 220

Glu Glu Asp Val Gly Ser Asn Gly Gly Asp Lys Ser Trp Leu
225                 230                 235


<210> SEQ ID NO 19
<211> LENGTH: 2427
<212> TYPE: DNA
<213> ORGANISM: HIV-2/VCP Clone p16.9 (env)

<400> SEQUENCE: 19

atgaagggta gtaagaatca actgctgatt gctattatac tagctagtgc ttacctaaca      60

cattgcaagc aatttgtgac tgttttctat ggcatacccg cgtggaggaa tgcatccatt     120

cccctgtttt gtgcaaccaa aaatagagat acttggggaa ccatacagtg cttgccagac     180

aatgatgatt atcaggaaat agctctaaat gtaacagagg ctttcgatgc atggaataat     240

acagtaacag aacaagcagt ggaggatgtc tggaatctat ttgagacatc aataaaacca     300

tgtgtcaaat taacaccctt atgtgtagca atgaactgta caaggaacat gaccacatcc     360

acagggacca cagacaccca aaatatcaca attataaatg acacttcgcc atgcgtacgt     420

gcagacaact gcacaggatt aaaggaggaa gaaatggtcg actgtcagtt taatatgaca     480

ggattagaga gagacaagag aaaacagtat actggagcat ggtactcaaa agatgtgatt     540

tgtgacaata acacctcaag tcggagcaag tgttacatga accattgcaa tacatcagtc     600

atcacagagt catgtgataa gcactattgg gatgctatga ggtttagata ctgtgcacca     660

ccgggttttg ccctactaag atgcaatgat actaattatt caggctttgc acctaattgc     720

tctaaagtag tagctgctac atgcaccaga atgatggaaa cgcaatcttc tacatggttt     780

ggatttaatg gcactagagc agaaaataga acatatatct attggcatgg taaaaataac     840

agaactatta tcagcttaaa taacttttat aatctcacta tgcattgtaa gaggccggga     900

aataagggtg ccggcaaacc caggcaagca tggtgttggt tcaaaggcga atggaaggaa     960

gccatgcagg aggtgaagga gacccttgcg aaacatccca gatataaagg gaacaggagc    1020

cgcacagaga atattaaatt taaagcacca ggaagaggct cagacccaga agcagcatac    1080

atgtggacta actgcagagg ggaatttctc tactgcaaca tggcttggtt cctcaattgg    1140

gtagataaca ggacgggtca gaaacagcgc aattatgcac cgtgccatat aaggcaaata    1200

attaatactt ggcacagggt agggaaaaac atatatttgc ctcccaggga aggggagttg    1260

acctgcaact caacagtgac cagcataatt gccaacattg atacgggaga tcaaacagat    1320

attaccttta gtgcagaggt ggcagaacta taccgattgg aattgggaga ttacaaatta    1380

gtagaaatca caccaattgg cttcgcacct acatcagtaa agagatactc ctctgctcac    1440

cagagacata caagaggtgt gttcgtgcta gggttcttgg gttttctcgc aacggcaggt    1500

tctgcaatgg gcgcggcgtc ggtgacgctg accgcccagt cccggacttc attggctggg    1560
```

-continued

```
atagtgcagc aacagcaaca gctgttggac gtggtcaaga aacaacaaga aatgttgcga   1620

ctgaccgtct ggggaactaa aaatctccag acaagagtca ctgctataga gaaataccta   1680

aaggaccagg cgcagttaaa ttcatgggga tgtgcgttta gacaagtctg ccacacttct   1740

gtaccatggg taaatgatag cttgacacct gattggaaca atatgacgtg gcaggaatgg   1800

gaacagaaag tccgctactg ggaggcaaat atcagtcaaa gtctagaaca agcacaaatt   1860

cagcaagaaa agaatttgta tgagctgcaa aaattaaata gctggggtgt ttttaccaat   1920

tggcttgact tcacctcctg ggtcaggtat attcaatatg gagtttatgt agtagtagga   1980

atagtaactt taagaatagt aatatatata gtacagatgt taagtagact taggaagggc   2040

tataggcctg ttttctcctc cccccccggt tatatccaac agatccatat ccacaaggac   2100

caggaacagc cagccagaga agaaacagaa gaagacgttg gaagcaacgg tggagacaga   2160

tcttggcttt agccgatagc atatattcat ttcctgatcc gcctgctgat tcgcctcttg   2220

atcgggctat acaacatctg cagagactta ctatccagga tctccccgat cctccaacca   2280

atcttccaga gtctccagag agcactaaca gcaatcagag actggctgag gcttaaagca   2340

gcctacctgc agtatgggtg cgagtggatc caagaagcgt tccaagccct tgcaaggact   2400

acaagagaga ctcttgcagg cgcgggg                                       2427
```

<210> SEQ ID NO 20
<211> LENGTH: 1455
<212> TYPE: DNA
<213> ORGANISM: HIV-2/VCP Clone p16.9 (gp120)

<400> SEQUENCE: 20

```
atgaagggta gtaagaatca actgctgatt gctattatac tagctagtgc ttacctaaca     60

cattgcaagc aatttgtgac tgttttctat ggcatacccg cgtggaggaa tgcatccatt    120

cccctgtttt gtgcaaccaa aaatagagat acttggggaa ccatacagtg cttgccagac    180

aatgatgatt atcaggaaat agctctaaat gtaacagagg ctttcgatgc atggaataat    240

acagtaacag aacaagcagt ggaggatgtc tggaatctat ttgagacatc aataaaacca    300

tgtgtcaaat taacaccctt atgtgtagca atgaactgta caaggaacat gaccacatcc    360

acagggacca cagacaccca aaatatcaca attataaatg acacttcgcc atgcgtacgt    420

gcagacaact gcacaggatt aaaggaggaa gaaatggtcg actgtcagtt taatatgaca    480

ggattagaga gagacaagag aaaacagtat actggagcat ggtactcaaa agatgtgatt    540

tgtgacaata acacctcaag tcggagcaag tgttacatga accattgcaa tacatcagtc    600

atcacagagt catgtgataa gcactattgg gatgctatga ggtttagata ctgtgcacca    660

ccgggttttg ccctactaag atgcaatgat actaattatt caggctttgc acctaattgc    720

tctaaagtag tagctgctac atgcaccaga atgatggaaa cgcaatcttc tacatggttt    780

ggatttaatg gcactagagc agaaaataga acatatatct attggcatgg taaaaataac    840

agaactatta tcagcttaaa taacttttat aatctcacta tgcattgtaa gaggccggga    900

aataagggtg ccggcaaacc caggcaagca tggtgttggt tcaaaggcga atggaaggaa    960

gccatgcagg aggtgaagga gacccttgcg aaacatccca gatataaagg gaacaggagc   1020

cgcacagaga atattaaatt taaagcacca ggaagaggct cagacccaga agcagcatac   1080

atgtggacta actgcagagg ggaatttctc tactgcaaca tggcttggtt cctcaattgg   1140

gtagataaca ggacgggtca gaaacagcgc aattatgcac cgtgccatat aaggcaaata   1200
```

-continued

```
attaatactt ggcacagggt agggaaaaac atatatttgc ctcccaggga aggggagttg   1260

acctgcaact caacagtgac cagcataatt gccaacattg atacgggaga tcaaacagat   1320

attaccttta gtgcagaggt ggcagaacta taccgattgg aattgggaga ttacaaatta   1380

gtagaaatca caccaattgg cttcgcacct acatcagtaa agagatactc ctctgctcac   1440

cagagacata caaga                                                    1455
```

```
<210> SEQ ID NO 21
<211> LENGTH: 717
<212> TYPE: DNA
<213> ORGANISM: HIV-2/VCP Clone p16.9 (gp41)

<400> SEQUENCE: 21

ggtgtgttcg tgctagggtt cttgggtttt ctcgcaacgg caggttctgc aatgggcgcg     60

gcgtcggtga cgctgaccgc ccagtcccgg acttcattgg ctgggatagt gcagcaacag    120

caacagctgt tggacgtggt caagaaacaa caagaaatgt tgcgactgac cgtctgggga    180

actaaaaatc tccagacaag agtcactgct atagagaaat acctaaagga ccaggcgcag    240

ttaaattcat ggggatgtgc gtttagacaa gtctgccaca cttctgtacc atgggtaaat    300

gatagcttga cacctgattg gaacaatatg acgtggcagg aatgggaaca gaaagtccgc    360

tactgggagg caaatatcag tcaaagtcta gaacaagcac aaattcagca agaaaagaat    420

ttgtatgagc tgcaaaaatt aaatagctgg ggtgttttta ccaattggct tgacttcacc    480

tcctgggtca ggtatattca atatggagtt tatgtagtag taggaatagt aactttaaga    540

atagtaatat atatagtaca gatgttaagt agacttagga agggctatag gcctgttttc    600

tcctcccccc ccggttatat ccaacagatc catatccaca aggaccagga acagccagcc    660

agagaagaaa cagaagaaga cgttggaagc aacggtggag acagatcttg gctttag      717
```

```
<210> SEQ ID NO 22
<211> LENGTH: 723
<212> TYPE: PRT
<213> ORGANISM: HIV-2/VCP Clone p16.9 (env)

<400> SEQUENCE: 22

Met Lys Gly Ser Lys Asn Gln Leu Leu Ile Ala Ile Ile Leu Ala Ser
1               5                   10                  15

Ala Tyr Leu Thr His Cys Lys Gln Phe Val Thr Val Phe Tyr Gly Ile
            20                  25                  30

Pro Ala Trp Arg Asn Ala Ser Ile Pro Leu Phe Cys Ala Thr Lys Asn
        35                  40                  45

Arg Asp Thr Trp Gly Thr Ile Gln Cys Leu Pro Asp Asn Asp Asp Tyr
    50                  55                  60

Gln Glu Ile Ala Leu Asn Val Thr Glu Ala Phe Asp Ala Trp Asn Asn
65                  70                  75                  80

Thr Val Thr Glu Gln Ala Val Glu Asp Val Trp Asn Leu Phe Glu Thr
                85                  90                  95

Ser Ile Lys Pro Cys Val Lys Leu Thr Pro Leu Cys Val Ala Met Asn
            100                 105                 110

Cys Thr Arg Asn Met Thr Thr Ser Thr Gly Thr Thr Asp Thr Gln Asn
        115                 120                 125

Ile Thr Ile Ile Asn Asp Thr Ser Pro Cys Val Arg Ala Asp Asn Cys
    130                 135                 140

Thr Gly Leu Lys Glu Glu Glu Met Val Asp Cys Gln Phe Asn Met Thr
145                 150                 155                 160
```

-continued

```
Gly Leu Glu Arg Asp Lys Arg Lys Gln Tyr Thr Gly Ala Trp Tyr Ser
                165                 170                 175

Lys Asp Val Ile Cys Asp Asn Asn Thr Ser Ser Arg Ser Lys Cys Tyr
            180                 185                 190

Met Asn His Cys Asn Thr Ser Val Ile Thr Glu Ser Cys Asp Lys His
        195                 200                 205

Tyr Trp Asp Ala Met Arg Phe Arg Tyr Cys Ala Pro Pro Gly Phe Ala
    210                 215                 220

Leu Leu Arg Cys Asn Asp Thr Asn Tyr Ser Gly Phe Ala Pro Asn Cys
225                 230                 235                 240

Ser Lys Val Val Ala Ala Thr Cys Thr Arg Met Met Glu Thr Gln Ser
                245                 250                 255

Ser Thr Trp Phe Gly Phe Asn Gly Thr Arg Ala Glu Asn Arg Thr Tyr
            260                 265                 270

Ile Tyr Trp His Gly Lys Asn Asn Arg Thr Ile Ile Ser Leu Asn Asn
        275                 280                 285

Phe Tyr Asn Leu Thr Met His Cys Lys Arg Pro Gly Asn Lys Gly Ala
    290                 295                 300

Gly Lys Pro Arg Gln Ala Trp Cys Trp Phe Lys Gly Glu Trp Lys Glu
305                 310                 315                 320

Ala Met Gln Glu Val Lys Glu Thr Leu Ala Lys His Pro Arg Tyr Lys
                325                 330                 335

Gly Asn Arg Ser Arg Thr Glu Asn Ile Lys Phe Lys Ala Pro Gly Arg
            340                 345                 350

Gly Ser Asp Pro Glu Ala Ala Tyr Met Trp Thr Asn Cys Arg Gly Glu
        355                 360                 365

Phe Leu Tyr Cys Asn Met Ala Trp Phe Leu Asn Trp Val Asp Asn Arg
    370                 375                 380

Thr Gly Gln Lys Gln Arg Asn Tyr Ala Pro Cys His Ile Arg Gln Ile
385                 390                 395                 400

Ile Asn Thr Trp His Arg Val Gly Lys Asn Ile Tyr Leu Pro Pro Arg
                405                 410                 415

Glu Gly Glu Leu Thr Cys Asn Ser Thr Val Thr Ser Ile Ile Ala Asn
            420                 425                 430

Ile Asp Thr Gly Asp Gln Thr Asp Ile Thr Phe Ser Ala Glu Val Ala
        435                 440                 445

Glu Leu Tyr Arg Leu Glu Leu Gly Asp Tyr Lys Leu Val Glu Ile Thr
    450                 455                 460

Pro Ile Gly Phe Ala Pro Thr Ser Val Lys Arg Tyr Ser Ser Ala His
465                 470                 475                 480

Gln Arg His Thr Arg Gly Val Phe Val Leu Gly Phe Leu Gly Phe Leu
                485                 490                 495

Ala Thr Ala Gly Ser Ala Met Gly Ala Ala Ser Val Thr Leu Thr Ala
            500                 505                 510

Gln Ser Arg Thr Ser Leu Ala Gly Ile Val Gln Gln Gln Gln Gln Leu
        515                 520                 525

Leu Asp Val Val Lys Lys Gln Gln Glu Met Leu Arg Leu Thr Val Trp
    530                 535                 540

Gly Thr Lys Asn Leu Gln Thr Arg Val Thr Ala Ile Glu Lys Tyr Leu
545                 550                 555                 560

Lys Asp Gln Ala Gln Leu Asn Ser Trp Gly Cys Ala Phe Arg Gln Val
                565                 570                 575
```

-continued

```
Cys His Thr Ser Val Pro Trp Val Asn Asp Ser Leu Thr Pro Asp Trp
            580                 585                 590

Asn Asn Met Thr Trp Gln Glu Trp Glu Gln Lys Val Arg Tyr Trp Glu
        595                 600                 605

Ala Asn Ile Ser Gln Ser Leu Glu Gln Ala Gln Ile Gln Gln Glu Lys
    610                 615                 620

Asn Leu Tyr Glu Leu Gln Lys Leu Asn Ser Trp Gly Val Phe Thr Asn
625                 630                 635                 640

Trp Leu Asp Phe Thr Ser Trp Val Arg Tyr Ile Gln Tyr Gly Val Tyr
                645                 650                 655

Val Val Val Gly Ile Val Thr Leu Arg Ile Val Ile Tyr Ile Val Gln
            660                 665                 670

Met Leu Ser Arg Leu Arg Lys Gly Tyr Arg Pro Val Phe Ser Ser Pro
        675                 680                 685

Pro Gly Tyr Ile Gln Gln Ile His Ile His Lys Asp Gln Glu Gln Pro
    690                 695                 700

Ala Arg Glu Glu Thr Glu Glu Asp Val Gly Ser Asn Gly Gly Asp Arg
705                 710                 715                 720

Ser Trp Leu


<210> SEQ ID NO 23
<211> LENGTH: 485
<212> TYPE: PRT
<213> ORGANISM: HIV-2/VCP Clone p16.9 (gp120)

<400> SEQUENCE: 23

Met Lys Gly Ser Lys Asn Gln Leu Leu Ile Ala Ile Ile Leu Ala Ser
1               5                   10                  15

Ala Tyr Leu Thr His Cys Lys Gln Phe Val Thr Val Phe Tyr Gly Ile
            20                  25                  30

Pro Ala Trp Arg Asn Ala Ser Ile Pro Leu Phe Cys Ala Thr Lys Asn
        35                  40                  45

Arg Asp Thr Trp Gly Thr Ile Gln Cys Leu Pro Asp Asn Asp Asp Tyr
    50                  55                  60

Gln Glu Ile Ala Leu Asn Val Thr Glu Ala Phe Asp Ala Trp Asn Asn
65                  70                  75                  80

Thr Val Thr Glu Gln Ala Val Glu Asp Val Trp Asn Leu Phe Glu Thr
                85                  90                  95

Ser Ile Lys Pro Cys Val Lys Leu Thr Pro Leu Cys Val Ala Met Asn
            100                 105                 110

Cys Thr Arg Asn Met Thr Thr Ser Thr Gly Thr Thr Asp Thr Gln Asn
        115                 120                 125

Ile Thr Ile Ile Asn Asp Thr Ser Pro Cys Val Arg Ala Asp Asn Cys
    130                 135                 140

Thr Gly Leu Lys Glu Glu Glu Met Val Asp Cys Gln Phe Asn Met Thr
145                 150                 155                 160

Gly Leu Glu Arg Asp Lys Arg Lys Gln Tyr Thr Gly Ala Trp Tyr Ser
                165                 170                 175

Lys Asp Val Ile Cys Asp Asn Asn Thr Ser Ser Arg Ser Lys Cys Tyr
            180                 185                 190

Met Asn His Cys Asn Thr Ser Val Ile Thr Glu Ser Cys Asp Lys His
        195                 200                 205

Tyr Trp Asp Ala Met Arg Phe Arg Tyr Cys Ala Pro Pro Gly Phe Ala
    210                 215                 220
```

-continued

```
Leu Leu Arg Cys Asn Asp Thr Asn Tyr Ser Gly Phe Ala Pro Asn Cys
225                 230                 235                 240

Ser Lys Val Val Ala Ala Thr Cys Thr Arg Met Met Glu Thr Gln Ser
                245                 250                 255

Ser Thr Trp Phe Gly Phe Asn Gly Thr Arg Ala Glu Asn Arg Thr Tyr
            260                 265                 270

Ile Tyr Trp His Gly Lys Asn Asn Arg Thr Ile Ile Ser Leu Asn Asn
        275                 280                 285

Phe Tyr Asn Leu Thr Met His Cys Lys Arg Pro Gly Asn Lys Gly Ala
    290                 295                 300

Gly Lys Pro Arg Gln Ala Trp Cys Trp Phe Lys Gly Glu Trp Lys Glu
305                 310                 315                 320

Ala Met Gln Glu Val Lys Glu Thr Leu Ala Lys His Pro Arg Tyr Lys
                325                 330                 335

Gly Asn Arg Ser Arg Thr Glu Asn Ile Lys Phe Lys Ala Pro Gly Arg
            340                 345                 350

Gly Ser Asp Pro Glu Ala Ala Tyr Met Trp Thr Asn Cys Arg Gly Glu
        355                 360                 365

Phe Leu Tyr Cys Asn Met Ala Trp Phe Leu Asn Trp Val Asp Asn Arg
    370                 375                 380

Thr Gly Gln Lys Gln Arg Asn Tyr Ala Pro Cys His Ile Arg Gln Ile
385                 390                 395                 400

Ile Asn Thr Trp His Arg Val Gly Lys Asn Ile Tyr Leu Pro Pro Arg
                405                 410                 415

Glu Gly Glu Leu Thr Cys Asn Ser Thr Val Thr Ser Ile Ile Ala Asn
            420                 425                 430

Ile Asp Thr Gly Asp Gln Thr Asp Ile Thr Phe Ser Ala Glu Val Ala
        435                 440                 445

Glu Leu Tyr Arg Leu Glu Leu Gly Asp Tyr Lys Leu Val Glu Ile Thr
    450                 455                 460

Pro Ile Gly Phe Ala Pro Thr Ser Val Lys Arg Tyr Ser Ser Ala His
465                 470                 475                 480

Gln Arg His Thr Arg
                485


<210> SEQ ID NO 24
<211> LENGTH: 238
<212> TYPE: PRT
<213> ORGANISM: HIV-2/VCP Clone p16.9 (gp41)

<400> SEQUENCE: 24

Gly Val Phe Val Leu Gly Phe Leu Gly Phe Leu Ala Thr Ala Gly Ser
1               5                   10                  15

Ala Met Gly Ala Ala Ser Val Thr Leu Thr Ala Gln Ser Arg Thr Ser
            20                  25                  30

Leu Ala Gly Ile Val Gln Gln Gln Gln Gln Leu Leu Asp Val Val Lys
        35                  40                  45

Lys Gln Gln Glu Met Leu Arg Leu Thr Val Trp Gly Thr Lys Asn Leu
    50                  55                  60

Gln Thr Arg Val Thr Ala Ile Glu Lys Tyr Leu Lys Asp Gln Ala Gln
65                  70                  75                  80

Leu Asn Ser Trp Gly Cys Ala Phe Arg Gln Val Cys His Thr Ser Val
                85                  90                  95

Pro Trp Val Asn Asp Ser Leu Thr Pro Asp Trp Asn Asn Met Thr Trp
            100                 105                 110
```

-continued

```
Gln Glu Trp Glu Gln Lys Val Arg Tyr Trp Glu Ala Asn Ile Ser Gln
        115                 120                 125

Ser Leu Glu Gln Ala Gln Ile Gln Gln Glu Lys Asn Leu Tyr Glu Leu
    130                 135                 140

Gln Lys Leu Asn Ser Trp Gly Val Phe Thr Asn Trp Leu Asp Phe Thr
145                 150                 155                 160

Ser Trp Val Arg Tyr Ile Gln Tyr Gly Val Tyr Val Val Val Gly Ile
                165                 170                 175

Val Thr Leu Arg Ile Val Ile Tyr Ile Val Gln Met Leu Ser Arg Leu
            180                 185                 190

Arg Lys Gly Tyr Arg Pro Val Phe Ser Ser Pro Pro Gly Tyr Ile Gln
        195                 200                 205

Gln Ile His Ile His Lys Asp Gln Glu Gln Pro Ala Arg Glu Glu Thr
    210                 215                 220

Glu Glu Asp Val Gly Ser Asn Gly Gly Asp Arg Ser Trp Leu
225                 230                 235


<210> SEQ ID NO 25
<211> LENGTH: 2142
<212> TYPE: DNA
<213> ORGANISM: HIV-2/VCP Clone 8c.3 (env)

<400> SEQUENCE: 25

atgaagggta gtaagaatca actgctgatt gctattatac tagctagtgc ttacctaaca     60

cattgcaagc aatttgtgac tgttttctat ggcatacccg cgtggaggaa tgcatccatt    120

cccctgtttt gtgcaaccaa aaatagagat acttggggaa ccatacagtg cttgccagac    180

aatgatgatt atcaggaaat agctctaaat gtaacagagg ctttcgatgc atggaataat    240

acagtaacag aacaagcagt ggaggatgtc tggaatctat ttgagacatc aataaaacca    300

tgtgtcaaat taacaccctt atgtgtagca atgaactgta caaggaacat gaccacatcc    360

acagggacca cagacaccca aaatatcaca attataaatg acacttcgcc atgcgtacgt    420

gcagacaact gcacaggatt aaaggaggaa gaaatggtcg actgtcagtt taatatgaca    480

ggattagaga gagacaagag aaaacagtat actggaacat ggtactcaaa agatgtgatt    540

tgtgacaata acacctcaag tcggagcaag tgttacatga accattgcaa tacatcagtc    600

atcacaaagt catgtgataa gcactattgg gatgctatga ggtttagata ctgtgcacca    660

ccgggttttg ccctactaag atgcaatgat actaattatt caggctttgc acctaattgc    720

tctaaagtag tagctgctac atgcaccaga atgatggaaa cgcaatcttc tacatggttt    780

ggatttaatg gcactagagc agaaaataga acatatatat attggcatgg taaaaataac    840

agaactatta tcagcttaaa taacttttat aatctcacta tgcattgtaa gggtgccggc    900

tggtgttggt tcaaaggcga atggaaggaa gccatgcagg aggtgaagga gacccttgcg    960

aaacatccca gatataaagg gaacaggagc cgcacagaga atattaaatt taaagcacca   1020

ggaagaggct cagacccaga agcagcatac atgtggacta actgcagagg ggaatttctc   1080

tactgcaaca tggcttggtt cctcaactgg gtagataaca ggacgggtcg gaaacagcgc   1140

aattatgcac cgtgccatat aaggcaaata attaatactt ggcacagggt agggaaaaac   1200

atatatttgc ctcccaggga aggggagttg gcctgcaact caacagtgac cagcataatt   1260

gccaacattg atacgggaga tcaaacagat attaccttta gtgcagaggt ggcagaacta   1320

taccgattgg aattgggaga ttacaaatta gtagaaatca caccaattgg cttcgcacct   1380
```

-continued acatcagtaa agagatactc ctctgctcac cagagacata caagaggtgt gttcgtgcta 1440
gggttcttgg gttttctcgc aacggcaggt tctgcaatgg gcgcggcgtc ggtgacgctg 1500
accgcccagt cccggacttc attggctggg atagtgcagc aacagcaaca gctgttggac 1560
gtggtcaaga aacaacaaga aatgttgcga ctgaccgtct ggggaactaa aaatctccag 1620
acaagagtca ctgctataga gaaataccta aaggaccagg cgcagttaaa ttcatgggga 1680
tgtgcgttta gacaagtctg ccacacttct gtaccatggg taaatgatag cttgacacct 1740
gattggaaca atatgacgtg gcaggaatgg gaacagaaag tccgctactg ggaggcaaat 1800
atcagtcaaa gtctagaaca agcacaaatt cagcaagaaa agaatttgta tgagctgcaa 1860
aaattaaata gctggggtgt ttttaccaat tggcttgact tcacctcctg ggtcaggtat 1920
attcaatatg gagcatatgt agtagtagga atagtaactt taagaatagt aatatatata 1980
gtacagatgt taagtagact taggaagggc tataggcctg ttttctcctc cccccccggt 2040
tatatccaac agatccatat ccacaaggac caggaacagc cagccagaga agaaacagaa 2100
gaagacgttg gaagcaacgg tggagacaga tcttggcttt ag 2142

<210> SEQ ID NO 26
<211> LENGTH: 1425
<212> TYPE: DNA
<213> ORGANISM: HIV-2/VCP Clone 8c.3 (gp120)

<400> SEQUENCE: 26
atgaagggta gtaagaatca actgctgatt gctattatac tagctagtgc ttacctaaca 60
cattgcaagc aatttgtgac tgttttctat ggcatacccg cgtggaggaa tgcatccatt 120
cccctgtttt gtgcaaccaa aaatagagat acttggggaa ccatacagtg cttgccagac 180
aatgatgatt atcaggaaat agctctaaat gtaacagagg ctttcgatgc atggaataat 240
acagtaacag aacaagcagt ggaggatgtc tggaatctat ttgagacatc aataaaacca 300
tgtgtcaaat taacaccctt atgtgtagca atgaactgta caaggaacat gaccacatcc 360
acagggacca cagacaccca aaatatcaca attataaatg acacttcgcc atgcgtacgt 420
gcagacaact gcacaggatt aaaggaggaa gaaatggtcg actgtcagtt taatatgaca 480
ggattagaga gagacaagag aaaacagtat actggaacat ggtactcaaa agatgtgatt 540
tgtgacaata acacctcaag tcggagcaag tgttacatga accattgcaa tacatcagtc 600
atcacaaagt catgtgataa gcactattgg gatgctatga ggtttagata ctgtgcacca 660
ccgggttttg ccctactaag atgcaatgat actaattatt caggctttgc acctaattgc 720
tctaaagtag tagctgctac atgcaccaga atgatggaaa cgcaatcttc tacatggttt 780
ggatttaatg gcactagagc agaaaataga acatatatat attggcatgg taaaaataac 840
agaactatta tcagcttaaa taacttttat aatctcacta tgcattgtaa gggtgccggc 900
tggtgttggt tcaaaggcga atggaaggaa gccatgcagg aggtgaagga gacccttgcg 960
aaacatccca gatataaagg gaacaggagc cgcacagaga atattaaatt taaagcacca 1020
ggaagaggct cagacccaga agcagcatac atgtggacta actgcagagg ggaatttctc 1080
tactgcaaca tggcttggtt cctcaactgg gtagataaca ggacgggtcg gaaacagcgc 1140
aattatgcac cgtgccatat aaggcaaata attaatactt ggcacagggt agggaaaaac 1200
atatatttgc ctcccaggga aggggagttg gcctgcaact caacagtgac cagcataatt 1260
gccaacattg atacgggaga tcaaacagat attaccttta gtgcagaggt ggcagaacta 1320
taccgattgg aattgggaga ttacaaatta gtagaaatca caccaattgg cttcgcacct 1380

-continued

```
acatcagtaa agagatactc ctctgctcac cagagacata caaga                 1425


<210> SEQ ID NO 27
<211> LENGTH: 717
<212> TYPE: DNA
<213> ORGANISM: HIV-2/VCP Clone 8c.3 (gp41)

<400> SEQUENCE: 27

ggtgtgttcg tgctagggtt cttgggtttt ctcgcaacgg caggttctgc aatgggcgcg     60

gcgtcggtga cgctgaccgc ccagtcccgg acttcattgg ctgggatagt gcagcaacag    120

caacagctgt tggacgtggt caagaaacaa caagaaatgt tgcgactgac cgtctgggga    180

actaaaaatc tccagacaag agtcactgct atagagaaat acctaaagga ccaggcgcag    240

ttaaattcat ggggatgtgc gtttagacaa gtctgccaca cttctgtacc atgggtaaat    300

gatagcttga cacctgattg gaacaatatg acgtggcagg aatgggaaca gaaagtccgc    360

tactgggagg caaatatcag tcaaagtcta gaacaagcac aaattcagca agaaaagaat    420

ttgtatgagc tgcaaaaatt aaatagctgg ggtgttttta ccaattggct tgacttcacc    480

tcctgggtca ggtatattca atatggagca tatgtagtag taggaatagt aactttaaga    540

atagtaatat atatagtaca gatgttaagt agacttagga agggctatag gcctgttttc    600

tcctcccccc ccggttatat ccaacagatc catatccaca aggaccagga acagccagcc    660

agagaagaaa cagaagaaga cgttggaagc aacggtggag acagatcttg gctttag      717


<210> SEQ ID NO 28
<211> LENGTH: 713
<212> TYPE: PRT
<213> ORGANISM: HIV-2/VCP Clone 8c.3 (env)

<400> SEQUENCE: 28

Met Lys Gly Ser Lys Asn Gln Leu Leu Ile Ala Ile Ile Leu Ala Ser
1               5                   10                  15

Ala Tyr Leu Thr His Cys Lys Gln Phe Val Thr Val Phe Tyr Gly Ile
            20                  25                  30

Pro Ala Trp Arg Asn Ala Ser Ile Pro Leu Phe Cys Ala Thr Lys Asn
        35                  40                  45

Arg Asp Thr Trp Gly Thr Ile Gln Cys Leu Pro Asp Asn Asp Asp Tyr
    50                  55                  60

Gln Glu Ile Ala Leu Asn Val Thr Glu Ala Phe Asp Ala Trp Asn Asn
65                  70                  75                  80

Thr Val Thr Glu Gln Ala Val Glu Asp Val Trp Asn Leu Phe Glu Thr
                85                  90                  95

Ser Ile Lys Pro Cys Val Lys Leu Thr Pro Leu Cys Val Ala Met Asn
            100                 105                 110

Cys Thr Arg Asn Met Thr Thr Ser Thr Gly Thr Thr Asp Thr Gln Asn
        115                 120                 125

Ile Thr Ile Ile Asn Asp Thr Ser Pro Cys Val Arg Ala Asp Asn Cys
    130                 135                 140

Thr Gly Leu Lys Glu Glu Glu Met Val Asp Cys Gln Phe Asn Met Thr
145                 150                 155                 160

Gly Leu Glu Arg Asp Lys Arg Lys Gln Tyr Thr Gly Thr Trp Tyr Ser
                165                 170                 175

Lys Asp Val Ile Cys Asp Asn Asn Thr Ser Ser Arg Ser Lys Cys Tyr
            180                 185                 190
```

-continued

```
Met Asn His Cys Asn Thr Ser Val Ile Thr Lys Ser Cys Asp Lys His
        195                 200                 205

Tyr Trp Asp Ala Met Arg Phe Arg Tyr Cys Ala Pro Pro Gly Phe Ala
    210                 215                 220

Leu Leu Arg Cys Asn Asp Thr Asn Tyr Ser Gly Phe Ala Pro Asn Cys
225                 230                 235                 240

Ser Lys Val Val Ala Ala Thr Cys Thr Arg Met Met Glu Thr Gln Ser
                245                 250                 255

Ser Thr Trp Phe Gly Phe Asn Gly Thr Arg Ala Glu Asn Arg Thr Tyr
            260                 265                 270

Ile Tyr Trp His Gly Lys Asn Asn Arg Thr Ile Ile Ser Leu Asn Asn
        275                 280                 285

Phe Tyr Asn Leu Thr Met His Cys Lys Gly Ala Gly Trp Cys Trp Phe
    290                 295                 300

Lys Gly Glu Trp Lys Glu Ala Met Gln Glu Val Lys Glu Thr Leu Ala
305                 310                 315                 320

Lys His Pro Arg Tyr Lys Gly Asn Arg Ser Arg Thr Glu Asn Ile Lys
                325                 330                 335

Phe Lys Ala Pro Gly Arg Gly Ser Asp Pro Glu Ala Ala Tyr Met Trp
            340                 345                 350

Thr Asn Cys Arg Gly Glu Phe Leu Tyr Cys Asn Met Ala Trp Phe Leu
        355                 360                 365

Asn Trp Val Asp Asn Arg Thr Gly Arg Lys Gln Arg Asn Tyr Ala Pro
    370                 375                 380

Cys His Ile Arg Gln Ile Ile Asn Thr Trp His Arg Val Gly Lys Asn
385                 390                 395                 400

Ile Tyr Leu Pro Pro Arg Glu Gly Glu Leu Ala Cys Asn Ser Thr Val
                405                 410                 415

Thr Ser Ile Ile Ala Asn Ile Asp Thr Gly Asp Gln Thr Asp Ile Thr
            420                 425                 430

Phe Ser Ala Glu Val Ala Glu Leu Tyr Arg Leu Glu Leu Gly Asp Tyr
        435                 440                 445

Lys Leu Val Glu Ile Thr Pro Ile Gly Phe Ala Pro Thr Ser Val Lys
    450                 455                 460

Arg Tyr Ser Ser Ala His Gln Arg His Thr Arg Gly Val Phe Val Leu
465                 470                 475                 480

Gly Phe Leu Gly Phe Leu Ala Thr Ala Gly Ser Ala Met Gly Ala Ala
                485                 490                 495

Ser Val Thr Leu Thr Ala Gln Ser Arg Thr Ser Leu Ala Gly Ile Val
            500                 505                 510

Gln Gln Gln Gln Gln Leu Leu Asp Val Val Lys Lys Gln Gln Glu Met
        515                 520                 525

Leu Arg Leu Thr Val Trp Gly Thr Lys Asn Leu Gln Thr Arg Val Thr
    530                 535                 540

Ala Ile Glu Lys Tyr Leu Lys Asp Gln Ala Gln Leu Asn Ser Trp Gly
545                 550                 555                 560

Cys Ala Phe Arg Gln Val Cys His Thr Ser Val Pro Trp Val Asn Asp
                565                 570                 575

Ser Leu Thr Pro Asp Trp Asn Asn Met Thr Trp Gln Glu Trp Glu Gln
            580                 585                 590

Lys Val Arg Tyr Trp Glu Ala Asn Ile Ser Gln Ser Leu Glu Gln Ala
        595                 600                 605

Gln Ile Gln Gln Glu Lys Asn Leu Tyr Glu Leu Gln Lys Leu Asn Ser
```

-continued

```
    610                 615                 620

Trp Gly Val Phe Thr Asn Trp Leu Asp Phe Thr Ser Trp Val Arg Tyr
625                 630                 635                 640

Ile Gln Tyr Gly Ala Tyr Val Val Val Gly Ile Val Thr Leu Arg Ile
                645                 650                 655

Val Ile Tyr Ile Val Gln Met Leu Ser Arg Leu Arg Lys Gly Tyr Arg
            660                 665                 670

Pro Val Phe Ser Ser Pro Pro Gly Tyr Ile Gln Gln Ile His Ile His
        675                 680                 685

Lys Asp Gln Glu Gln Pro Ala Arg Glu Glu Thr Glu Glu Asp Val Gly
    690                 695                 700

Ser Asn Gly Gly Asp Arg Ser Trp Leu
705                 710


<210> SEQ ID NO 29
<211> LENGTH: 475
<212> TYPE: PRT
<213> ORGANISM: HIV-2/VCP Clone 8c.3 (gp120)

<400> SEQUENCE: 29

Met Lys Gly Ser Lys Asn Gln Leu Leu Ile Ala Ile Ile Leu Ala Ser
1               5                   10                  15

Ala Tyr Leu Thr His Cys Lys Gln Phe Val Thr Val Phe Tyr Gly Ile
            20                  25                  30

Pro Ala Trp Arg Asn Ala Ser Ile Pro Leu Phe Cys Ala Thr Lys Asn
        35                  40                  45

Arg Asp Thr Trp Gly Thr Ile Gln Cys Leu Pro Asp Asn Asp Asp Tyr
    50                  55                  60

Gln Glu Ile Ala Leu Asn Val Thr Glu Ala Phe Asp Ala Trp Asn Asn
65                  70                  75                  80

Thr Val Thr Glu Gln Ala Val Glu Asp Val Trp Asn Leu Phe Glu Thr
                85                  90                  95

Ser Ile Lys Pro Cys Val Lys Leu Thr Pro Leu Cys Val Ala Met Asn
            100                 105                 110

Cys Thr Arg Asn Met Thr Thr Ser Thr Gly Thr Thr Asp Thr Gln Asn
        115                 120                 125

Ile Thr Ile Ile Asn Asp Thr Ser Pro Cys Val Arg Ala Asp Asn Cys
    130                 135                 140

Thr Gly Leu Lys Glu Glu Glu Met Val Asp Cys Gln Phe Asn Met Thr
145                 150                 155                 160

Gly Leu Glu Arg Asp Lys Arg Lys Gln Tyr Thr Gly Thr Trp Tyr Ser
                165                 170                 175

Lys Asp Val Ile Cys Asp Asn Asn Thr Ser Ser Arg Ser Lys Cys Tyr
            180                 185                 190

Met Asn His Cys Asn Thr Ser Val Ile Thr Lys Ser Cys Asp Lys His
        195                 200                 205

Tyr Trp Asp Ala Met Arg Phe Arg Tyr Cys Ala Pro Pro Gly Phe Ala
    210                 215                 220

Leu Leu Arg Cys Asn Asp Thr Asn Tyr Ser Gly Phe Ala Pro Asn Cys
225                 230                 235                 240

Ser Lys Val Val Ala Ala Thr Cys Thr Arg Met Met Glu Thr Gln Ser
                245                 250                 255

Ser Thr Trp Phe Gly Phe Asn Gly Thr Arg Ala Glu Asn Arg Thr Tyr
            260                 265                 270
```

-continued

```
Ile Tyr Trp His Gly Lys Asn Asn Arg Thr Ile Ile Ser Leu Asn Asn
        275                 280                 285

Phe Tyr Asn Leu Thr Met His Cys Lys Gly Ala Gly Trp Cys Trp Phe
    290                 295                 300

Lys Gly Glu Trp Lys Glu Ala Met Gln Glu Val Lys Glu Thr Leu Ala
305                 310                 315                 320

Lys His Pro Arg Tyr Lys Gly Asn Arg Ser Arg Thr Glu Asn Ile Lys
                325                 330                 335

Phe Lys Ala Pro Gly Arg Gly Ser Asp Pro Glu Ala Ala Tyr Met Trp
            340                 345                 350

Thr Asn Cys Arg Gly Glu Phe Leu Tyr Cys Asn Met Ala Trp Phe Leu
        355                 360                 365

Asn Trp Val Asp Asn Arg Thr Gly Arg Lys Gln Arg Asn Tyr Ala Pro
    370                 375                 380

Cys His Ile Arg Gln Ile Ile Asn Thr Trp His Arg Val Gly Lys Asn
385                 390                 395                 400

Ile Tyr Leu Pro Pro Arg Glu Gly Glu Leu Ala Cys Asn Ser Thr Val
                405                 410                 415

Thr Ser Ile Ile Ala Asn Ile Asp Thr Gly Asp Gln Thr Asp Ile Thr
            420                 425                 430

Phe Ser Ala Glu Val Ala Glu Leu Tyr Arg Leu Glu Leu Gly Asp Tyr
        435                 440                 445

Lys Leu Val Glu Ile Thr Pro Ile Gly Phe Ala Pro Thr Ser Val Lys
    450                 455                 460

Arg Tyr Ser Ser Ala His Gln Arg His Thr Arg
465                 470                 475


<210> SEQ ID NO 30
<211> LENGTH: 238
<212> TYPE: PRT
<213> ORGANISM: HIV-2/VCP Clone 8c.3 (gp41)

<400> SEQUENCE: 30

Gly Val Phe Val Leu Gly Phe Leu Gly Phe Leu Ala Thr Ala Gly Ser
1               5                   10                  15

Ala Met Gly Ala Ala Ser Val Thr Leu Thr Ala Gln Ser Arg Thr Ser
            20                  25                  30

Leu Ala Gly Ile Val Gln Gln Gln Gln Gln Leu Leu Asp Val Val Lys
        35                  40                  45

Lys Gln Gln Glu Met Leu Arg Leu Thr Val Trp Gly Thr Lys Asn Leu
    50                  55                  60

Gln Thr Arg Val Thr Ala Ile Glu Lys Tyr Leu Lys Asp Gln Ala Gln
65                  70                  75                  80

Leu Asn Ser Trp Gly Cys Ala Phe Arg Gln Val Cys His Thr Ser Val
                85                  90                  95

Pro Trp Val Asn Asp Ser Leu Thr Pro Asp Trp Asn Asn Met Thr Trp
            100                 105                 110

Gln Glu Trp Glu Gln Lys Val Arg Tyr Trp Glu Ala Asn Ile Ser Gln
        115                 120                 125

Ser Leu Glu Gln Ala Gln Ile Gln Gln Glu Lys Asn Leu Tyr Glu Leu
    130                 135                 140

Gln Lys Leu Asn Ser Trp Gly Val Phe Thr Asn Trp Leu Asp Phe Thr
145                 150                 155                 160

Ser Trp Val Arg Tyr Ile Gln Tyr Gly Ala Tyr Val Val Val Gly Ile
                165                 170                 175
```

-continued

```
Val Thr Leu Arg Ile Val Ile Tyr Ile Val Gln Met Leu Ser Arg Leu
            180                 185                 190

Arg Lys Gly Tyr Arg Pro Val Phe Ser Ser Pro Pro Gly Tyr Ile Gln
        195                 200                 205

Gln Ile His Ile His Lys Asp Gln Glu Gln Pro Ala Arg Glu Glu Thr
    210                 215                 220

Glu Glu Asp Val Gly Ser Asn Gly Gly Asp Arg Ser Trp Leu
225                 230                 235
```